US008685960B2

(12) United States Patent
Hartmann et al.

(10) Patent No.: US 8,685,960 B2
(45) Date of Patent: Apr. 1, 2014

(54) 6-PYRIDIN-3-YL-3,4-DIHYDRO-1H-QUINOLIN-2-ONE DERIVATIVES AND RELATED COMPOUNDS AS INHIBITORS OF THE HUMAN ALDOSTERONE SYNTHASE CYP11B2

(75) Inventors: Rolf W. Hartmann, Saarbrücken (DE); Ralf Heim, Wiesbaden (DE); Simon Lucas, Aachen (DE)

(73) Assignee: Elexopharm GmbH (DE)

( * ) Notice: Subject to any disclaimer, the term of this patent is extended or adjusted under 35 U.S.C. 154(b) by 172 days.

(21) Appl. No.: 12/990,909

(22) PCT Filed: May 5, 2009

(86) PCT No.: PCT/EP2009/003217
§ 371 (c)(1),
(2), (4) Date: Jan. 28, 2011

(87) PCT Pub. No.: WO2009/135651
PCT Pub. Date: Nov. 12, 2009

(65) Prior Publication Data
US 2011/0118241 A1 May 19, 2011

Related U.S. Application Data

(60) Provisional application No. 61/051,437, filed on May 8, 2008.

(30) Foreign Application Priority Data

May 6, 2008 (DE) .......................... 10 2008 022 221

(51) Int. Cl.
C07D 401/04 (2006.01)
A61K 31/4745 (2006.01)

(52) U.S. Cl.
USPC ............ 514/211.06; 514/211.08; 514/212.07; 514/294; 514/307; 514/312; 514/338; 514/339; 540/491; 540/523; 540/545; 546/94; 546/144; 546/158; 546/270.1; 546/271.7; 546/273.7; 546/277.7

(58) Field of Classification Search
None
See application file for complete search history.

(56) References Cited

U.S. PATENT DOCUMENTS

| 330,502 | A | 11/1885 | McFarland |
|---|---|---|---|
| 2,525,515 | A | 10/1950 | Bean |
| 2,533,203 | A | 12/1950 | Bean |
| 3,980,650 | A | 9/1976 | Nauta |
| 4,482,560 | A | 11/1984 | Banno et al. |
| 4,582,898 | A | 4/1986 | Hamprecht |
| 4,677,219 | A | 6/1987 | Berman et al. |
| 4,710,507 | A | 12/1987 | Campbell et al. |
| 4,792,561 | A | 12/1988 | Walker et al. |
| 4,845,254 | A | 7/1989 | Norman et al. |
| 4,898,872 | A | 2/1990 | Campbell et al. |
| 4,921,862 | A | 5/1990 | Walker et al. |
| 5,028,606 | A | 7/1991 | Venet et al. |
| 5,057,521 | A * | 10/1991 | Hausler et al. ................ 514/300 |
| 5,147,883 | A | 9/1992 | Aichaioui et al. |
| 5,256,799 | A | 10/1993 | Field et al. |
| 5,342,957 | A | 8/1994 | Van Wauwe et al. |
| 5,358,949 | A | 10/1994 | Tabusa et al. |
| 5,365,088 | A | 11/1994 | Myrosznyk |
| 5,380,857 | A | 1/1995 | Roduit et al. |
| 5,504,080 | A | 4/1996 | Karanewsky |
| 5,597,924 | A | 1/1997 | Marmor et al. |
| 5,696,130 | A | 12/1997 | Jones et al. |
| 5,696,133 | A | 12/1997 | Jones et al. |
| 5,792,767 | A | 8/1998 | Meyer et al. |
| 5,798,365 | A | 8/1998 | Kirsch et al. |
| 6,150,347 | A | 11/2000 | Weber |
| 6,207,664 | B1 | 3/2001 | Hayward et al. |
| 6,258,824 | B1 | 7/2001 | Yang |
| 6,444,668 | B1 | 9/2002 | Grubb et al. |

(Continued)

FOREIGN PATENT DOCUMENTS

| DE | 1 289 051 | 2/1969 |
|---|---|---|
| DE | 2 137 719 | 2/1973 |

(Continued)

OTHER PUBLICATIONS

Christian Berrier, J.C. et al., "Hydrozylation of indulines and indoles by hydrogen peroxide in superacids," Tetrahedron Letters, vol. 27(38) (1986) pp. 4565-4568.
Courturier, M. et al., "The use of borane-amine adducts as versatile palladium-catalyzed hydrogen-transfer reagents in methanol," Tetrahedron Letters, vol. 42 (Apr. 9, 2001) pp. 2763-2766 (Abstract).
Fache, F., "Solvent Dependent Regioselective Hydrogenation of Substituted Quinolines," Synlett, vol. 15 (2004) pp. 2827-2829 (Abstract).

(Continued)

Primary Examiner — Zinna Northington Davis
(74) Attorney, Agent, or Firm — Riverside Law LLP

(57) ABSTRACT

The invention provides compounds of the general formula (I) which are inhibitors of the human aldosterone synthase, and also pharmaceutical compositions containing these compounds, and the use of these compounds and other heteroaryl substituted quinolinone derivatives for the treatment of hyperaldosteronism and/or disorders or diseases that are mediated by 11 β-hydroxylase (CYP11 B1).

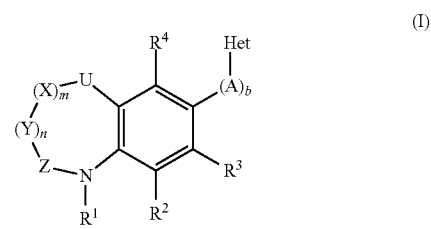

(I)

17 Claims, No Drawings

(56) References Cited

U.S. PATENT DOCUMENTS

| | | | |
|---|---|---|---|
| 6,548,517 B2 | 4/2003 | Marlowe et al. | |
| 6,566,390 B2 | 5/2003 | Petry et al. | |
| 6,579,887 B2 | 6/2003 | Lyssikatos et al. | |
| 6,608,047 B2 | 8/2003 | MacLaughlan et al. | |
| 6,713,468 B2 | 3/2004 | Hardy et al. | |
| 6,765,013 B2 | 7/2004 | Pfahl et al. | |
| 7,056,918 B2 | 6/2006 | Dombroski et al. | |
| 7,067,531 B2 | 6/2006 | Angibaud et al. | |
| 7,078,525 B2 | 7/2006 | Guzi et al. | |
| 7,129,356 B2 | 10/2006 | Angibaud et al. | |
| 7,137,040 B2 | 11/2006 | Bae et al. | |
| 7,192,956 B2 | 3/2007 | Fensome et al. | |
| 7,196,111 B2 | 3/2007 | Shipps et al. | |
| 7,211,585 B2 | 5/2007 | Jover et al. | |
| 7,235,547 B2 | 6/2007 | Ballard et al. | |
| 7,241,777 B2 | 7/2007 | Angibaud et al. | |
| 7,250,442 B2 | 7/2007 | Brown et al. | |
| 7,268,149 B2 | 9/2007 | Fensome et al. | |
| 7,282,511 B2 | 10/2007 | Gronborg et al. | |
| 7,365,061 B2 | 4/2008 | Sher et al. | |
| 7,365,088 B2 | 4/2008 | Nazare et al. | |
| 7,419,996 B2 | 9/2008 | Chow et al. | |
| 7,429,593 B2 | 9/2008 | Yamamori et al. | |
| 7,429,604 B2 | 9/2008 | Corte et al. | |
| 2002/0013303 A1 | 1/2002 | Weber | |
| 2002/0123485 A1 | 9/2002 | Alexander et al. | |
| 2003/0220310 A1 | 11/2003 | Schuh | |
| 2003/0220312 A1 | 11/2003 | Schuh | |
| 2004/0110770 A1* | 6/2004 | Riou et al. | 514/256 |
| 2004/0116388 A1 | 6/2004 | Armistead et al. | |
| 2006/0069098 A1 | 3/2006 | Miyoshi et al. | |
| 2007/0032469 A1 | 2/2007 | Isaac et al. | |
| 2007/0072897 A1 | 3/2007 | Mahaney et al. | |
| 2007/0249605 A1 | 10/2007 | Allen et al. | |
| 2008/0280891 A1 | 11/2008 | Kelly et al. | |
| 2009/0105278 A1 | 4/2009 | Hartmann et al. | |
| 2010/0137264 A1 | 6/2010 | Nickisch et al. | |

FOREIGN PATENT DOCUMENTS

| | | |
|---|---|---|
| DE | 2 825 048 | 12/1978 |
| DE | 2 843 192 | 7/1979 |
| DE | 2 912 105 | 10/1979 |
| DE | 3 034 237 | 4/1981 |
| DE | 3 220 117 | 12/1983 |
| EP | 0 146 370 | 6/1985 |
| EP | 0 148 623 | 7/1985 |
| EP | 0 257 583 | 3/1988 |
| EP | 0 527 534 | 2/1993 |
| EP | 0 602 851 | 6/1994 |
| EP | 0 635 498 | 1/1995 |
| FR | 1 531 330 | 7/1968 |
| FR | 2 675 801 | 10/1992 |
| GB | 1 046 226 | 10/1966 |
| GB | 1 411 913 | 10/1975 |
| JP | 51 016679 | 2/1976 |
| JP | 53 062829 | 6/1978 |
| JP | 54 032481 | 3/1979 |
| JP | 54 132597 | 10/1979 |
| JP | 55 040616 | 3/1980 |
| JP | 59 134770 | 8/1984 |
| JP | 2007 204458 | 8/2007 |
| WO | WO 98/40383 * | 9/1988 |
| WO | WO 94/18980 | 9/1994 |
| WO | WO 95/18097 | 7/1995 |
| WO | WO 95/23141 | 8/1995 |
| WO | WO 95/32205 | 11/1995 |
| WO | WO 96/22991 | 8/1996 |
| WO | WO 96/40255 | 12/1996 |
| WO | WO 99/02502 | 1/1999 |
| WO | WO 99/15524 | 4/1999 |
| WO | WO 01/32631 | 5/2001 |
| WO | WO 01/34132 | 5/2001 |
| WO | WO 01/57019 | 8/2001 |
| WO | WO 01/62756 | 8/2001 |
| WO | WO 01/72725 | 10/2001 |
| WO | WO 02/04440 | 1/2002 |
| WO | WO 02/04445 | 1/2002 |
| WO | WO 02/36588 | 5/2002 |
| WO | WO 02/50067 | 6/2002 |
| WO | WO 02/100327 | 12/2002 |
| WO | WO 03/011862 | 2/2003 |
| WO | WO 03/022785 | 3/2003 |
| WO | WO 03/027090 | 4/2003 |
| WO | WO 03/069245 | 8/2003 |
| WO | WO 03/103398 | 12/2003 |
| WO | WO 2004/018419 | 3/2004 |
| WO | WO 2004/019933 | 3/2004 |
| WO | WO 2004/033419 | 4/2004 |
| WO | WO 2004/048365 | 6/2004 |
| WO | WO 2004/108672 | 12/2004 |
| WO | WO 2004/110986 | 12/2004 |
| WO | WO 2005/018623 | 3/2005 |
| WO | WO 2005/060967 | 7/2005 |
| WO | WO 2005/113509 | 12/2005 |
| WO | WO 2005/118555 | 12/2005 |
| WO | WO 2006/002422 | 1/2006 |
| WO | WO 2006/027684 | 3/2006 |
| WO | WO 2006/030031 | 3/2006 |
| WO | WO 2006/040182 | 4/2006 |
| WO | WO 2006/086705 | 8/2006 |
| WO | WO 2006/088919 | 8/2006 |
| WO | WO 2006/092430 | 9/2006 |
| WO | WO 2006/099379 | 9/2006 |
| WO | WO 2006/113432 | 10/2006 |
| WO | WO 2006/129120 | 12/2006 |
| WO | WO 2007/005668 | 1/2007 |
| WO | WO 2007/020936 | 2/2007 |
| WO | WO 2007/022241 | 2/2007 |
| WO | WO 2007/024600 | 3/2007 |
| WO | WO 2007/028789 | 3/2007 |
| WO | WO 2007/032469 | 3/2007 |
| WO | WO 2007/032936 | 3/2007 |
| WO | WO 2007/052843 | 5/2007 |
| WO | WO 2007/056214 | 5/2007 |
| WO | WO 2007/070359 | 6/2007 |
| WO | WO 2007/097937 | 8/2007 |
| WO | WO 2007/134169 | 11/2007 |
| WO | WO 2007/148093 | 12/2007 |
| WO | WO 2008/011032 | 1/2008 |
| WO | WO 2008/014822 | 2/2008 |
| WO | WO 2008/019372 | 2/2008 |
| WO | WO 2008/021456 | 2/2008 |
| WO | WO 2008/051493 | 5/2008 |
| WO | WO 2008/060578 | 5/2008 |
| WO | WO 2008/069242 | 6/2008 |
| WO | WO 2008/137692 | 11/2008 |

OTHER PUBLICATIONS

Harris, C.S. et al., "Facile synthesis of 7-amino anilinoquinazolines via direct amination of the quinazoline core," Tetrahedron Letters, vol. 46(43) (Oct. 24, 2005) pp. 7381-7384.

Ishiyama, K. et al., "Convenient synthesis of 7-hydroxyindole," Tetrahedron Letters, vol. 46(6) (Feb. 7, 2005) pp. 1021-1022 (Abstract).

Ohno, M. et al., "Development of 3,4-dihydro-2$H$-benzo[1,4] oxazine derivatives as dual thromboxane $A_2$ receptor antagonists and prostacycline receptor agonists," Bioorganic & Medicinal Chemistry, vol. 14(6) (Mar. 15, 2006) pp. 2005-2021.

Torisawa, Y. et al., "Interesting Reaction of the Indanone Oximes under Beckmann Rearrangement Conditions," Bioorganic & Medicinal Chemistry Letters, vol. 12(3) (Feb. 11, 2000) pp. 387-390 (Abstract).

Wang, G.T. et al., "Lead optimization of methionine aminopeptidase-2 (MetAP2) inhibitors containing sulfonamides of 5,6-disubstituted anthranilic acids," Bioorganic & Medicinal Chemistry Letters, vol. 17(10) (May 15, 2007) pp. 2817-2822.

Westaway, S.M. et al., "$N$-Tetrahydroquinolinyl, $N$-quinolinyl and $N$-isoquinolinyl biaryl carboxamides as antagonists of TRPV1," Bioorganic & Medicinal Chemistry Letters, vol. 16(17) (Sep. 1, 2006) pp. 4533-4636 (Abstract).

Zhao, H. et al., "Design synthesis, and discovery of 5-piperazinyl-1,2,6,7-tetrahydro-5$H$-azepino[3,2,1-hi]indol-4-one derivatives: A

(56) References Cited

OTHER PUBLICATIONS novel series of mixed dopamine $D_2/D_4$ receptor antagonist," Bioorganic & Medicinal Chemistry Letters, vol. 13(4) (Feb. 4, 2003) pp, 701-704.

Zhao, H. et al, "Indoline and piperazine containing derivatives as a novel class of mixed $D_2/D_4$ receptor antagonists. Part 1: Identification and structure-activity relationships," Bioorganic & Medicinal Chemistry Letters, vol. 12(21) (Nov. 4, 2002) pp. 3105-3109 (Abstract).

Agarwal, M.K. et al., "Antimineralocorticoids," Renal Physiology and Biochemistry, vol. 14(6) (1991) pp. 217-223 (Abstract).

Alabaster, et al., "2(1H)-Quinolinones with cardiac stimulant activity. 1. Synthesis and biological activities of (six-membered hereroaryl)-substituted derivatives," Journal of Medicinal Chemistry, vol. 31(1) (1988) pp. 2048-2056 (Abstract).

Bell et al., "A Direct Synthesis of 6-Pyridinyl-2(1H)-quinolinones via Palladium-Catalysed Cross-Coupling Reaction," Synthesis, vol. 9 (1987) pp. 843-844 (Abstract).

Blondet, D. et al., "Convenient Synthesis of 6-Methyl, 8-Methyl and 6,8-Dimethyl Derivatives of 5-Hydroxy-1,2,3,4-Tetrahydro-2-Quinolinone," Organic Preparations & Procedures International, vol. 25(2) (1993) pp. 223-228.

Brilla, C.G., "Renin-angiotensin-aldosterone system and myocardial fibrosis," Cardiovasc. Res., vol. 47 (2000) pp. 1-3.

Brilla, C.G. "Aldosterone and myocardial fibrosis in heart failure," Herz, vol. 25(3) (2000) pp. 299-306 (Abstract).

Denner, K. et al., "Cloning and stable expression of the human mitochondrial cytochrome P450 11B1 cDNA in V79 Chinese hamster cells and their application for testing of potential inhibitors," Pharmacogenetics, vol. 5(2) (Apr. 1995) pp. 89-96 (Abstract).

Ehmer, P.B. et al., "Development of a test system for inhibitors of human aldosterone synthase (CYP11B2): screening in fission yeast and evaluation of selectivity in V79 cells," J. Steroid Biochem. Mol. Biol., vol. 81(2) (Jun. 2002) pp. 173-179.

Fernández-Rodriguez, M.A., "A General and Long-Lived Catalyst for the Palladium-Catalyzed Coupling of Aryl Halides with Thiols," J. Am. Chem. Soc., vol. 128(7) (2006) pp. 2180-2181 (Abstract).

Gazdar, A.F. et al., "Establishment and Characterization of a Human Adrenocortical Carcinoma Cell Line That expresses Multiple Pathways of Steroid Biosyntheses," Cancer Research vol. 50 (Sep. 1, 1990) pp. 5488-5496.

International Search Report and Written Opinion dated Jul. 30, 2009 for Application No. PCT/EP2009/003217.

Iyobe, A. et al., "Studies on New Platelet Aggregation Inhibitors 1. Synthesis of 7-Nitro-3,4-dihydroquinoline-2(1H)-one Derivatives," Chem. Pharm. Bull., vol. 49(7) (2001) pp. 822-829.

Kawamoto, T. et al., "Role of steroid 11β-hydroxylase and steroid 18-hydroxylase in the biosynthesis of glucocorticoids and mineralocorticoids in humans," Proc. Natl. Acad. Sci. USA, vol. 89 (1992) pp. 1458-1462.

Knefeli, F. et al., "Electron Impact Induced Loss of C-5/C-8 Substituents of 1,2,3,4-Tetrahydroisoquinolines,VI[1]: Synthesis and Mass Spectrometric Fragmentation of Dihydroindole Derivatives," Archiv der Pharmazie, vol. 323 (1990) pp. 145-155 (Abstract).

Lijnen, P. et al., "Induction of Cardiac Fibrosis by Aldosterone," J. Mol. Cell. Cardiol., vol. 32 (2000) pp. 865-879.

MacFadyen, R.J. et al., "Aldosterone blockade reduces vascular collagen turnover, improves heart rate variability and reduces early morning rise in heart rate n heart failure patients," Cardiovascular Research, vol. 35 (1997) pp. 30-34.

Martinez, et al., "3,4-Dihydroquinolin-2(1H)-ones as combined inhibitors of thromboxane A2 synthase and cAMP phosphodiesterase," Journal of Medicinal Chemistry, vol. 35(4) (1992) pp. 620-628 (Abstract).

Okamoto, K. et al., "Formation of Nanoarchitectures Including Subnanometer Palladium Clusters and Their Use as Highly Active Catalysts," J. Am. Chem. Soc., vol. 127(7) (2005) pp. 2125-2135 (Abstract).

Pitt, B. et al., "Eplerenone, a Selective Aldosterone Blocker, in Patients with Left Ventricular Dysfunction after Myocardial Infarction," N. Eng. J. Med., vol. 348 (2003) pp. 1309-1321.

Pitt, B. et al., "The Effect of Spironolactone on Morbidity and Mortality in Patients with Severe Heart Failure. Randomized Aldactone Evaluation Study," New England J. Med., vol. 341 (1999) pp. 709-717 (Abstract).

Quiroz, A. et al., "Reaction of 7-Substituted 4-Hydroxyl-1,4-Benzoxazin-3-Ones in Strongly Acidic Media," Heterocycles, vol, 32(9) (1991) pp. 1681-1685.

Taymans, S.E. et al., "Human CYP11B2 (Aldosterone Synthase) Maps to Chromosome 8q24.3," J. Clin. Endocrinol. Metab., vol. 83(3) (1998) pp. 1033-1036.

Tomita, M, et al., "Synthesis of Phenoxyquinoline Derivatives," Yakugaku Zasshi, vol. 72 (7) (1952) pp. 905-908 (Abstract).

Weber, K.T. et al., "Pathological hypertrophy and cardiac interstitium. Fibrosis and reninangiotensin-adlosterone system," Circulation, vol. 83 (1991) pp. 1849-1865 (Abstract).

Weindel, K. et al., "Interference of C17-spirosteroids with late steps of aldostrone biosynthesis. Structure-activity studies," Arzneimittelforschung, vol. 41(9) (1991) pp. 1082-1091. (Abstract).

Yamada, K. et al., "Nucleophilic Substitution Reaction of 1-Methoxy-6-nitroindole," Heterocycles, vol. 55(6) (2001) pp. 1151-1159.

Young, M. et al., "Aldosterone and the Heart," Trends Endocrinol. Metab., vol. 11(6) (2000) pp. 224-226 (Abstract).

\* cited by examiner

6-PYRIDIN-3-YL-3,4-DIHYDRO-1H-QUINOLIN-2-ONE DERIVATIVES AND RELATED COMPOUNDS AS INHIBITORS OF THE HUMAN ALDOSTERONE SYNTHASE CYP11B2

CONTINUING DATA

This application is a 371 of PCT/EP2009/003217 filed May 5, 2009 which claims benefit of 61/051,437 filed May 8, 2008.

The invention relates to heteroaryl substituted derivatives of quinolinones and related compounds that inhibit the human aldosterone synthase CYP11B2, to pharmaceutical compositions containing these derivatives, and to the use of these derivatives and other heteroaryl substituted quinolinone derivatives for the treatment of hyperaldosteronism and/or disorders or diseases mediated by 11β-hydroxylase (CYP11B1).

The adrenal glands of humans are divided into two regions, the adrenal medulla and the adrenal cortex. The latter secretes a number of hormones which are known as corticoids and fall under two categories. Glucocorticoids (chiefly hydrocortisone and cortisol) primarily act on hydrocarbon and glucose metabolism, and they can secondarily retard the healing of wounds by interference with the inflammatory process and the formation of fibrous tissue. The second category, the mineralocorticoids, primarily participates in the retention of sodium and the excretion of potassium. The most important and most effective mineralocorticoid is aldosterone.

The aldosterone secretion is regulated by a large number of signals: the plasma concentrations of sodium and potassium and the renin-angiotensin-aldosterone system (RAAS) extending over a number of stages. In this system, renin is secreted by the kidneys in response to low blood pressure and the renin liberates angiotensin I from a precursor peptide. Angiotensin I is in turn dissociated to angiotensin II, which comprises 8 amino acids and is a potent vasoconstrictor. In addition, it acts as a hormone for stimulation of the release of aldosterone (Weber, K. T. & Brilla, C. G., *Circulation* 83, 1849-1865 (1991).

The key enzyme of the mineralocorticoid biosynthesis, CYP11B2 (aldosterone synthase), a mitochondrial cytochrome P450 enzyme, catalyzes the formation of the most potent mineralocorticoid aldosterone from its steroidal substrate 11-deoxycorticosterone (Kawamoto, T. et al., *Proc. Natl. Acad. Sci. USA* 89:1458-1462 (1992). Hyperaldosteronism (excessive plasma aldosterone concentrations) can participate in the cause and progression of clinical pictures such as congestive heart failure, myocardial fibrosis, ventricular arrhythmia, and the stimulation of cardiac fibroblasts, cardiac hypertrophy, renal underperfusion and hypertension (Brilla, C. G., *Herz* 25, 299-306 (2000). In particular, in the case of patients having chronic heart failure or renal underperfusion or renal artery stenoses, the physiological action of the renin angiotensin system (RAAS) is replaced by pathophysiological activation thereof (Young, M., Funder, J. W., *Trends Endocrinol. Metab.* 11, 224-226 (2000). Angiotensin II mediated vasoconstriction and the water and sodium restriction caused by the increased aldosterone level creates an additional stress on the already insufficient myocardium. In the sense of a "*Circulus vitiosus*" there results further reduction in renal perfusion and an increased renin secretion. Additionally, both the increased plasma aldosterone and angiotensin II levels and locally secreted aldosterone in the heart induce fibrotic structural changes in the myocardium, resulting in the formation of a myocardial fibrosis leading to further reduction of the cardiac performance (Brilla, C. G., *Cardiovasc. Res.* 47, 1-3 (2000); Lijnen, P. & Petrov, V. J. *Mol. Cell. Cardiol.* 32, 865-879 (2000).

Fibrotic structural changes are characterized by the formation of tissue distinguished by an abnormally high amount of fibrotic material (primarily collagen strings). Such fibroses are helpful in some situations, such as the healing of wounds, but can be damaging, for example, when they interfere with the function of internal organs. In the case of myocardial fibrosis, fibrotic strings are present in the cardiac muscle and cause the muscle to become stiff and inflexible with consequent impairment of the function thereof.

Since the mortality rate of patients suffering from only slight cardiac insufficiency is from 10% to 20%, it is highly necessary to combat this by means of a suitable pharmacotherapy. Despite long-term therapy using digitalis glycosides, diuretics, ACE inhibitors, or AT II antagonists, the plasma aldosterone levels of the patients remain high, and the medication has no effect on the fibrotic structural changes.

Mineralocorticoid antagonists, particularly aldosterone blocking agents, already form the subject matter of numerous patents. Thus the steroidal mineralocorticoid antagonist spironolactone (17-hydroxy-7-α-mercapto-3-oxo-17-α-pregn-4-ene-21-carboxylic acid γ-lactone acetate) (Aldactone®) blocks aldosterone receptors competitively with aldosterone and thus impedes the receptor mediated aldosterone action. US 2002/0013303, U.S. Pat. No. 6,150,347, and U.S. Pat. No. 6,608,047 describe the administration of spironolactone for the treatment or prophylaxis of cardiovascular disorders and myocardial fibrosis whilst maintaining the normal electrolyte and water balance of the patients.

The "Randomized Aldactone Evaluation Study" (RALES) (Pitt, B. et al., *New Engl. J. Med.* 341, 709-717 (1999) has impressively shown that the administration of the aldosterone receptor antagonist spironolactone (Aldactone®), when used as a supplement to the basic treatment with ACE inhibitors and loop diuretics, was capable of causing a significant improvement in the survival rate of severely cardially insufficient patients, since it inhibited the action of aldosterone to an adequate extent (Kulbertus, H., *Rev. Med. Liege* 54, 770-772 (1999). However, the application of spironolactone was accompanied by serious side effects such as gynaecomastia, dysmenorrhoea, and pectoral pain, caused by the steroidal structure of the substance and the resultant reciprocal actions thereof with other steroid receptors (Pitt, B. et al., *New Eng. J. Med.* 341, 709-717 (1999); MacFadyen, R. J. et al., *Cardiovasc. Res.* 35, 30-34 (1997); Soberman, J. E. & Weber, K. T., *Curr. Hypertens. Rep.* 2, 451-456 (2000).

Mespirenone (15,16-methylene-17-spirolactone) and its derivatives have been regarded as a promising alternative to spironolactone since they show only a low percentage of the anti-androgen action of spironolactone (Losert, W. et al., *Drug Res.* 36, 1583-1600 (1986); Nickisch, K. et al., *J. Med. Chem.* 30(8), 1403-1409 (1987); Nickisch, K. et al., *J. Med. Chem.* 34, 2464-2468 (1991); Agarwal, M. K., Lazar, G., *Renal Physiol. Biochem.* 14, 217-223 (1991). Mespirenone blocks the aldosterone biosynthesis as part of an overall mineralocorticoid biosynthesis inhibition (Weindel, K. et al., *Arzneimittelforschung* 41(9), 946-949 (1991). However mespirenone, like spironolactone, inhibits the aldosterone biosynthesis only at very high concentrations.

WO 01/34132 describes methods for the treatment, prophylaxis or blocking of pathogenic changes resulting from vascular lesions (restenoses) in mammals by administration of an aldosterone antagonist, namely eplerenone (an aldosterone receptor antagonist) or related structures, which are partially epoxysteroidal and can all be derived from 20-spiroxanes.

WO 96/40255, US 2002/0123485, US 2003/0220312, and US 2003/0220310 describe therapeutic methods for the treatment of cardiovascular disorders, myocardial fibrosis or cardiac hypertrophy by the use of a combination therapy with an angiotensine II antagonist and an epoxysteroidal aldosterone receptor antagonist such as eplerenone or epoxymexrenone.

The recently published study EPHESUS (*"Eplerenone's Heart Failure Efficacy and Survival Study"*, 2003) was able to substantiate the results of RALES. Supplementarily to the basic therapy applied, the first selective steroidal mineralocorticoid receptor antagonist eplerenone (Inspras®) distinctly reduces morbidity and mortality in the case of patients having acute myocardial infarction and also reduces the occurrence of complications, eg, decrease of the left ventricular ejection fraction and cardiac failure (Pitt, B. et al., *N. Eng. J. Med.* 348, 1390-1382 (2003).

RALES and EPHESUS have clearly shown that aldosterone antagonists provide a therapy option which should not be underestimated. However, their side effect profile demands a search for substances which differ from spironolactone in structure and action mechanism. A very promising alternative is given in this case by non-steroid inhibitors of the mineralocorticoid biosynthesis, for it is better to reduce the pathologically increased aldosterone concentration than merely to block the mineralocorticoid receptors. CYP11B2, as key enzyme, could in this context be a starting point for achieving specific inhibitors. An excessive generalized liberation of aldosterone and, in particular, the cardiac production of aldosterone could be reduced by specific inhibition of the biosynthesis, which might in turn reduce pathological structural changes in the myocardium.

Selective aldosterone synthase inhibitors might be a promising class of substances which, following a myocardial infarction, might promote healing of the impaired myocardium tissue with reduced cicatrization and thus diminish the occurrence of serious complications.

The human steroid-11β-hydroxylase CYP11B1, the key enzyme for biosynthesis of glucocorticoids in humans, shows a homology of more than 93% with human CYP11B2 (Kawamoto, T. et al., *Proc. Natl. Acad. Sci. USA* 89, 1458-1462 (1992); Taymans, S. E. et al., *J. Clin. Endocrinol. Metab.* 83, 1033-1036 (1998). Despite the high structural and functional similarities of these two enzymes it would be desirable if strong inhibiting substances of the aldosterone synthase did not influence steroid-11β-hydroxylase. Moreover, preferably non-steroid inhibitors of the aldosterone synthase should be used as therapeutic agents, since fewer side effects on the endocrine system are to be expected than with steroid inhibitors. The development of selective CYP11B2 inhibitors that do not influence the CYP11B1 is hampered by the high homology of CYP11B1 with CYP11B2.

Also, the inhibitors should not interfere with other P450 (CYP) enzymes to any great extent.

SUMMARY OF THE INVENTION

It has been found that certain heteroaryl substituted derivatives of quinolinones and related compounds are suitable for selective inhibition of the aldosterone synthase CYP11B2.

The invention thus relates to a compound of the general formula (I)

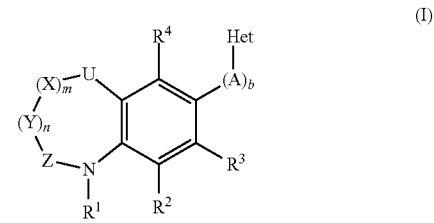

in which
Z stands for C=O, C=S, or SO$_2$;
U stands independently for CR$^5$R$^6$, NR$^7$, O, S, SO, or SO$_2$;
X stands independently for CR$^5$R$^6$, NR$^7$, O, or S;
Y stands independently for CR$^5$R$^6$, NR$^7$, O, or S;
A stands for CR$^8$R$^9$, C=O, C=S, NR$^{10}$, O, S, or SO$_2$;
b is 0 or 1;
n is 0 or 1;
m is 0 or 1;
provided that not more than one of U, X, and Y stands for NR$^7$, O, or S; and X and Y do not stand for O or S, and X or Y only stands for NR$^7$ in a position vicinal to U, when U stands for SO or SO$_2$,
wherein, when at least one of n or m is not equal to zero, the bond between U and X or U and Y, respectively, or X and Y can be a C=C or C=N double bond;
Het is a ring system containing 1 or 2 rings, and at least one of the rings is aromatic and contains 5 or 6 ring atoms, of which at least one is nitrogen, and the other ring can be saturated or unsaturated and comprises from 5 to 7 ring atoms; while the ring system can contain additional 1 to 5 heteroatoms selected from the group consisting of N, S, and O, provided that not more than two heteroatoms are selected from the group consisting of S and O; and the ring system can be substituted by from one to four substituents R$^{11}$, with the following provisos:
when R$^1$ and R$^2$ do not together form part of a ring system,
1) 3-pyridyl has at position 6 no substituents other than H, when Het stands for 3-pyridyl; and
2) Het is not a substituted or unsubstituted pyridyl or pyrimidyl when Z stands for C=O, n is 0, m is 1, and X stands for CR$^5$R$^6$, U stands for CR$^5$R$^6$, and R$^2$ is not NO$_2$;
R$^1$ is selected from the group consisting of H; C$_{1-4}$ alkyl, C$_{2-4}$ alkenyl, C$_{3-7}$ cycloalkyl, C$_{1-4}$ alkylcarbonyl, and C$_{1-4}$ alkoxycarbonyl, each of which can be substituted by from one to three substituents R$^a$, wherein R$^a$ is independently selected from the group consisting of optionally partially or completely halogenated C$_{1-4}$ alkyl, C$_{1-4}$ alkoxy, C$_{1-4}$ alkylthio, and C$_{1-4}$ alkylcarbonyl and also hydroxyl, nitro, and cyano, or can be partially or completely halogenated with independent halogen atoms; aryl C$_{1-4}$ alkyl and heterocyclyl C$_{1-4}$ alkyl, which can in each case be substituted on the ring or at least on one ring by from one to four substituents R$^b$, wherein R$^b$ is selected from the group consisting of C$_{1-4}$ alkyl, C$_{1-4}$ alkoxy, C$_{1-4}$ alkylthio, C$_{1-4}$ alkylcarbonyl, C$_{1-4}$ alkylsulfonyl, whose alkyl moieties may be partially or completely halogenated with independent halogen atoms, halogen, hydroxyl, nitro, cyano, —NR$^c_2$, —CONR$^c_2$, and SO$_2$NR$^c_2$, wherein R$^c$ is independently selected from the group consisting of H and C$_{1-4}$ alkyl;
R$^2$ is selected from the group consisting of H; C$_{1-4}$ alkyl, C$_{2-4}$ alkenyl, C$_{2-4}$ alkynyl, C$_{3-7}$ cycloalkyl, C$_{5-7}$ cycloalkenyl, C$_{1-4}$ alkoxy, C$_{1-4}$ alkylcarbonyl, C$_{1-4}$ alkoxycarbonyl, C$_{1-4}$ alkylsulfonyl, which in each case can be substituted by from one to three substituents $R^a$, wherein $R^a$ has the meanings stated above, or can be partially or completely halogenated with independent halogen atoms; aryl $C_{1-4}$ alkyl, aryl $C_{0-4}$ alkylsulfonyl, heterocyclyl $C_{1-4}$ alkyl, which can in each case be substituted on the ring or at least on one ring by from one to four substituents $R^b$, wherein $R^b$ has the meanings stated above; halogen, hydroxyl, nitro, cyano, —$NR^c_2$, —$CONR^c_2$, and —$SO_2NR^c_2$, wherein $R^c$ has the meanings stated above;

or $R^1$ and $R^2$ form, together with the atoms to which they are bonded, an unsaturated nitrogen-containing five membered to seven membered ring comprising 1 or 2 unsaturated bonds and may, in addition to the nitrogen atom to which the $R^1$ group is bonded, also contain a hetero atom or a heteroatom-containing group selected from the group consisting of O, S and $NR^7$, and can be substituted by from one to four substituents $R^{12}$;

$R^3$ and $R^4$ independently have the meanings stated for $R^2$;

$R^5$ and $R^6$ are independently selected from the group consisting of H; $C_{1-4}$ alkyl, $C_{3-7}$ cycloalkyl, hydroxyl $C_{1-4}$ alkyl, $C_{1-4}$ alkoxy, $C_{1-4}$ alkoxycarbonyl, $C_{1-4}$ alkylthio, whose alkyl moieties can be partially or completely halogenated with independent halogen atoms; halogen, hydroxyl, nitro, cyano, —$NR^c_2$, and $NR^cCOR^d$, wherein $R^c$ has the meanings stated above and $R^d$ is selected from the group consisting of $C_{1-4}$ alkyl, $C_{3-7}$ cycloalkyl, $C_{1-4}$ alkoxy, whose alkyl moieties can be partially or completely halogenated with independent halogen atoms, and wherein $R^5$ or $R^6$ may be bonded to a carbon atom forming part of a double bond, $R^7$ is selected from the group consisting of H; $C_{1-4}$ alkyl, and $C_{3-7}$ cycloalkyl, which in each case can be substituted by from one to three substituents $R^a$, wherein $R^a$ has the meanings stated above, or can be partially or completely halogenated with independent halogen atoms; and aryl $C_{1-4}$ alkyl, which can be substituted on the ring or at least on one ring by from one to four substituents $R^b$, wherein $R^b$ has the meanings stated above;

$R^8$ and $R^9$ are independently selected from the group consisting of H; $C_{1-4}$ alkyl, $C_{3-7}$ cycloalkyl, $C_{1-4}$ alkoxy, $C_{1-4}$ alkylthio, $C_{1-4}$ alkylcarbonyl, $C_{1-4}$ alkoxycarbonyl, which can in each case be substituted by from one to three substituents $R^a$, wherein $R^a$ has the meanings stated above, or can be partially or completely halogenated with independent halogen atoms; halogen, hydroxyl; aryl, aryl $C_{1-4}$ alkyl, heterocyclyl, heterocyclyl $C_{1-4}$ alkyl, which can be substituted on the ring or at least on one ring by from one to four substituents $R^b$, wherein $R^b$ has the meanings stated above;

or $R^8$ and $R^9$ form, together with the carbon atom to which they are bonded, a cyclopropane ring;

$R^{10}$ is selected from the group consisting of H; $C_{1-4}$ alkyl, $C_{3-7}$ cycloalkyl, which in each case can be substituted by from one to three substituents $R^a$, wherein $R^a$ has the meanings stated above, or can be partially or completely halogenated with independent halogen atoms; aryl, aryl $C_{1-4}$ alkyl, heterocyclyl, and heterocyclyl $C_{1-4}$ alkyl, each of which can be substituted on the or at least one ring by from one to four substituents $R^b$, wherein $R^b$ has the meanings stated above;

$R^{11}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylthio, $C_{1-4}$ alkylcarbonyl, $C_{1-4}$ alkoxycarbonyl, $C_{1-4}$ alkylsulfonyl, which can in each case be substituted by from one to three substituents $R^a$, wherein $R^a$ has the meanings stated above, or can be partially or completely halogenated with independent halogen atoms; aryl, heterocyclyl, aryl $C_{0-4}$ alkylsulfonyl, aryl $C_{1-4}$ alkyl, and heterocyclyl $C_{1-4}$ alkyl, which can in each case be substituted on the ring or at least on one ring by from one to four substituents $R^b$, wherein $R^b$ has the meanings stated above, halogen, hydroxyl, nitro, cyano, —$NR^c_2$, —$CONR^c_2$, and —$SO_2NR^c_2$, wherein $R^c$ has the meanings stated above; and $R^{12}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, which can in each case be substituted by from one to three substituents $R^a$, wherein $R^a$ has the meanings stated above, or can be partially or completely halogenated with independent halogen atoms; aryl, heterocyclyl, aryl $C_{1-4}$ alkyl, and heterocyclyl $C_{1-4}$ alkyl, which can in each case be substituted on the ring or at least on one ring by from one to four substituents $R^b$, wherein $R^b$ has the meanings stated above, and is also selected from the group consisting of optionally partially or completely halogenated $C_{1-4}$ alkoxy, hydroxyl, halogen, nitro, cyano, and $NR^c_2$ when $R^{12}$ is bonded to a carbon atom, wherein $R^c$ has the meanings stated above;

or a pharmaceutically acceptable salt thereof.

The invention further relates to said compounds of formula (I) and the pharmaceutically acceptable salts thereof as a medicinal substance and pharmaceutical composition containing said compounds or pharmaceutically acceptable salts thereof and a pharmaceutically acceptable vehicle or adjuvant.

Furthermore, the invention relates to the use of the compounds of formula (I) or a pharmaceutical composition containing the same for the treatment of hyperaldosteronism.

Furthermore, the invention relates to the use of compounds of the general formula (II)

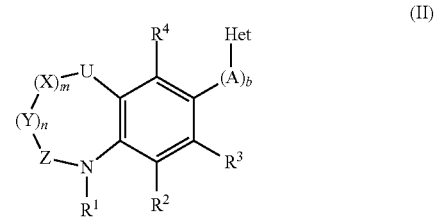

(II)

in which

Z stands for C=O, C=S, or $SO_2$;

U stands independently for $CR^5R^6$, $NR^7$, O, S, SO, or $SO_2$;

X stands independently for $CR^5R^6$, $NR^7$, O, or S;

Y stands independently for $CR^5R^6$, $NR^7$, O, or S;

A stands for $CR^8R^9$, C=O, C=S, $NR^{10}$, O, S, or $SO_2$;

b is 0 or 1;

n is 0 or 1;

m is 0 or 1;

provided that not more than one of U, X, and Y stands for $NR^7$, O, or S; and X and Y do not stand for O or S, and X or Y only stands for $NR^7$ in a position vicinal to U, when U stands for SO or $SO_2$, wherein, when at least one of n or m is not equal to zero, the bond between U and X or U and Y, respectively, or X and Y can be a C=C or C=N double bond;

Het is a saturated or unsaturated ring system containing 1 or 2 rings, and at least one of the rings is aromatic and contains 5 or 6 ring atoms, of which at least one is nitrogen, and the other ring can be saturated or unsaturated and comprises from 5 to 7 ring atoms; wherein the ring system can contain additional 1 to 5 heteroatoms selected from the group consisting of N, S, and O, provided that not more than two heteroatoms are selected from the group consisting of S and O; and the ring system can be substituted by from one to four substituents $R^{11}$;

$R^1$ is selected from the group consisting of H; $C_{1-4}$ alkyl, $C_{2-4}$ alkenyl, $C_{3-7}$ cycloalkyl, $C_{1-4}$ alkylcarbonyl, and $C_{1-4}$ alkoxycarbonyl, each of which can be substituted by from one to three substituents $R^a$, wherein $R^a$ is independently selected from the group consisting of optionally partially or completely halogenated $C_{1-4}$ alkyl, $C_{1-4}$ alkoxy, $C_{1-4}$ alkylthio, $C_{1-4}$ alkylcarbonyl and hydroxyl, nitro, and cyano, or can be partially or completely halogenated with independent halogen atoms; aryl $C_{1-4}$ alkyl and heterocyclyl $C_{1-4}$ alkyl, which can in each case be substituted on the ring or at least on one ring by from one to four substituents $R^b$, $R^b$ being selected from the group consisting of $C_{1-4}$ alkyl, $C_{1-4}$ alkoxy, $C_{1-4}$ alkylthio, $C_{1-4}$ alkylcarbonyl, $C_{1-4}$ alkylsulfonyl, whose alkyl moieties may be partially or completely halogenated with independent halogen atoms, halogen, hydroxyl, nitro, cyano, —$NR^c_2$, —$CONR^c_2$, and $SO_2NR^c_2$, wherein $R^c$ is independently selected from the group consisting of H and $C_{1-4}$ alkyl;

$R^2$ is selected from the group consisting of H; $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylcarbonyl, $C_{1-4}$ alkoxycarbonyl, $C_{1-4}$ alkylsulfonyl, which can in each case be substituted by from one to three substituents $R^a$, wherein $R^a$ has the meanings stated above, or can be partially or completely halogenated with independent halogen atoms; aryl $C_{1-4}$ alkyl, aryl $C_{0-4}$ alkylsulfonyl, heterocyclyl $C_{1-4}$ alkyl, which can in each case be substituted on the ring or at least on one ring with from one to four substituents $R^b$, wherein $R^b$ has the meanings stated above; halogen, hydroxyl, nitro, cyano, —$NR^c_2$, —$CONR^c_2$, and —$SO_2NR^c_2$, wherein $R^c$ has the meanings stated above;

or $R^1$ and $R^2$ form, together with the atoms to which they are bonded, an unsaturated nitrogen-containing five membered to seven membered ring which contains 1 or 2 unsaturated bonds and, in addition to the nitrogen atom to which the $R^1$ group is bonded, can also contain a hetero atom or a heteroatom-containing group selected from the group consisting of O, S, and $NR^7$ and can be substituted by from one to four substituents $R^{12}$;

$R^3$ and $R^4$ independently have the meanings stated for $R^2$;

$R^5$ and $R^6$ are independently selected from the group consisting of H; $C_{1-4}$ alkyl, $C_{3-7}$ cycloalkyl, hydroxyl $C_{1-4}$ alkyl, $C_{1-4}$ alkoxy, $C_{1-4}$ alkoxycarbonyl, $C_{1-4}$ alkylthio, whose alkyl moieties can be partially or completely halogenated with independent halogen atoms; halogen, hydroxyl, nitro, cyano, —$NR^c_2$, and $NR^cCOR^d$, wherein $R^c$ has the meanings stated above and $R^d$ is selected from the group consisting of $C_{1-4}$ alkyl, $C_{3-7}$ cycloalkyl, $C_{1-4}$ alkoxy, whose alkyl moieties can be partially or completely halogenated with independent halogen atoms, and $R^5$ or $R^6$ may be bonded to a carbon atom forming part of a double bond, $R^7$ is selected from the group consisting of H; $C_{1-4}$ alkyl, $C_{3-7}$ cycloalkyl, which in each case can be substituted by from one to three substituents $R^a$, wherein $R^a$ has the meanings stated above, or can be partially or completely halogenated with independent halogen atoms; and aryl $C_{1-4}$ alkyl, which can be substituted on the ring or at least on one ring by from one to four substituents $R^b$, wherein $R^b$ has the meanings stated above;

$R^8$ and $R^9$ are independently selected from the group consisting of H; $C_{1-4}$ alkyl, $C_{3-7}$ cycloalkyl, $C_{1-4}$ alkoxy, $C_{1-4}$ alkylthio, $C_{1-4}$ alkylcarbonyl, and $C_{1-4}$ alkoxycarbonyl, which can in each case be substituted by from one to three substituents $R^a$, wherein $R^a$ has the meanings stated above, or can be partially or completely halogenated with independent halogen atoms; halogen, hydroxyl; aryl, aryl $C_{1-4}$ alkyl, heterocyclyl, heterocyclyl $C_{1-4}$ alkyl, which can be substituted on the ring or at least on one ring by from one to four substituents $R^b$, wherein $R^b$ has the meanings stated above;

or $R^8$ and $R^9$ form, together with the carbon atom to which they are bonded, a cyclopropane ring;

$R^{10}$ is selected from the group consisting of H; $C_{1-4}$ alkyl, $C_{3-7}$ cycloalkyl, which in each case can be substituted by from one to three substituents $R^a$, wherein $R^a$ has the meanings stated above, or can be partially or completely halogenated with independent halogen atoms; aryl, aryl $C_{1-4}$ alkyl, heterocyclyl, and heterocyclyl $C_{1-4}$ alkyl, each of which can be substituted on the ring by from one to four substituents $R^b$, wherein $R^b$ has the meanings stated above;

$R^{11}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylthio, $C_{1-4}$ alkylcarbonyl, $C_{1-4}$ alkoxycarbonyl, $C_{1-4}$ alkylsulfonyl, which can in each case be substituted by from one to three substituents $R^a$, wherein $R^a$ has the meanings stated above, or can be partially or completely halogenated with independent halogen atoms; aryl, heterocyclyl, aryl $C_{0-4}$ alkylsulfonyl, aryl $C_{1-4}$ alkyl, and heterocyclyl $C_{1-4}$ alkyl, which can in each case be substituted on the ring or at least on one ring by from one to four substituents $R^b$, wherein $R^b$ has the meanings stated above, halogen, hydroxyl, nitro, cyano, —$NR^c_2$, —$CONR^c_2$, and —$SO_2NR^c_2$, wherein $R^c$ has the meanings stated above; and $R^{12}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, which can in each case be substituted by from one to three substituents $R^a$, wherein $R^a$ has the meanings stated above, or can be partially or completely halogenated with independent halogen atoms; aryl, heterocyclyl, aryl $C_{1-4}$ alkyl, and heterocyclyl $C_{1-4}$ alkyl, which can in each case be substituted on the ring or at least on one ring by from one to four substituents $R^b$, wherein $R^b$ has the meanings stated above, and, when $R^{12}$ is bonded to a carbon atom, is further selected from the group consisting of optionally partially or completely halogenated $C_{1-4}$ alkoxy, hydroxyl, halogen, nitro, cyano, and $NR^c_2$, wherein $R^c$ has the meanings stated above;

or a pharmaceutically acceptable salt thereof for the treatment of hyperaldosteronism.

There follow definitions of the chemical expressions used in the formulas and formula schemes. In general, the expressions used have the meanings normally accorded thereto by the person skilled in the art.

"$C_{1-4}$ alkyl" stands for methyl, ethyl, n-propyl, isopropyl, n-butyl, sec-butyl, isobutyl, or tert-butyl.

"$C_{2-4}$ alkenyl" stands for an alkenyl radical containing from 2 to 4 carbon atoms, such as vinyl, prop-1-en-1-yl, allyl, isopropenyl, but-(1, 2, or 3)-en-1-yl or 1-methyl-1-propenyl, 1-methyl-2-propenyl, or 2-methyl-2-propen-1-yl.

"$C_{2-4}$ alkynyl" stands for ethynyl, prop-(1 or 2)-yn-1-yl, but-(1, 2, or 3)-yn-1-yl and 1-methyl-2-propyn-1-yl.

"$C_{3-7}$ cycloalkyl" stands for cyclopropyl, cyclobutyl, cyclopentyl, cyclohexyl, and cycloheptyl.

"$C_{5-7}$ cycloalkenyl" stands for the various isomers of cyclopentenyl, cyclohexenyl, and cycloheptenyl.

"$C_{1-4}$ alkoxy" stands for methyl, ethyl, propyl, isopropyl, butyl, isobutyl, sec-butyl, or tert-butyl, which is bonded to the rest of the molecule via an oxygen atom. Examples thereof are methoxy (methyloxy), ethoxy (ethyloxy), n-propoxy (n-propyloxy), and n-butoxy (n-butyloxy).

"$C_{1-4}$ alkylthio" stands for methyl, ethyl, propyl, isopropyl, butyl, isobutyl, sec-butyl, or tert-butyl, which is bonded to the rest of the molecule via a sulfur atom. Examples thereof are methylthio, ethylthio, n-propylthio, and n-butylthio.

"$C_{1-4}$ alkylcarbonyl" stands for methyl, ethyl, propyl, isopropyl, butyl, isobutyl, sec-butyl, or tert-butyl, which is bonded to the rest of the molecule via a carbonyl group. Examples thereof are acetyl, propionyl, 2-methylpropanoyl, butanoyl, and pentanoyl.

"$C_{1-4}$ alkoxycarbonyl" stands for a $C_{1-4}$ alkoxy radical (or alkyloxy radical) having the meanings stated above, which is bonded to the rest of the molecule via a carbonyl group. Examples thereof are methoxycarbonyl, ethoxycarbonyl, and propyloxycarbonyl.

"$C_{1-4}$ alkylsulfonyl" stands for methyl, ethyl, n-propyl, isopropyl, n-butyl, isobutyl, sec-butyl, or tert-butyl, which is bonded to the rest of the molecule via a sulfonyl group ($-SO_2-$).

"Aryl", as used herein, stands for carbocyclic radicals containing from 6 to 13 carbons and having one or two rings, at least one ring being an aromatic six membered ring linked to the rest of the molecule. Examples thereof are phenyl, 1 and 2-naphthyl, biphenylyl, indanyl, indenyl, 5,6,7,8-tetrahydronaphth-(1 or 2)-yl. Phenyl is preferred.

"Aryl $C_{1-4}$ alkyl" stands for aryl having the meanings stated above which is joined to a $C_{1-4}$ alkyl group having the meanings stated above which is in turn bonded to the rest of the molecule. Examples thereof are benzyl, phenethyl, and phenylpropyl.

"Aryl $C_{0-4}$ alkylsulfonyl" stands for aryl having the meanings stated above, which is either directly bonded to a sulfonyl group ($-SO_2-$) (C is zero, ie there is no alkyl present), or is joined to $C_{1-4}$ alkyl, which is bonded to the rest of the molecule via a sulfonyl group.

"Heterocyclyl", as used herein, stands for saturated, partially unsaturated, maximally unsaturated, and fully aromatic heterocyclic ring systems having one or two rings each having from 5 to 7 ring members, which are directly linked to the rest of the molecule via a carbon or nitrogen atom. The heterocyclic compounds can contain N, O, and S as hetero atoms. The number of hetero atoms varies, but there are usually not more than one or two oxygen or sulfur atoms within, the ring system, while there can be up to 8 nitrogen atoms.

Example of saturated heterocyclyl having the meanings stated above are pyrrolidinyl, pyrazolidinyl, imidazolidinyl, piperidyl, piperazinyl, morpholino, tetrahydrofuryl, tetrahydrothienyl, homopiperidinyl, isoxazolidinyl, oxazolidinyl, 1,3-diazepanyl, and 1,3-thiazolidynyl.

Examples of partially unsaturated heterocyclyl having the meanings stated above are 2,3-dihydropyridyl, 1,2-dihydrofuryl, 1,2-dihydrothienyl, 2,3-dihydrothiazolyl, 2,3-dihydropyrrol, 2,3-dihydropyridine, 2,3-dihydropyrimidine, 5,6,7,8-tetrahydroquinoline, 5,6,7,8-tetrahydro-isoquinoline, indolinyl, chromanyl, 2,3-dihydroindolyl, 5,6,7,8-tetrahydroquinoxalinyl, 4H-2,3-dihydropyrido[3,2-b][1,4]oxazynyl, and 5,6-dihydroimidazo[1,5-a]pyridyl.

Examples of maximally unsaturated heterocyclyl having the meanings stated above are 2H-pyrane, 4H-thiopyrane, 2H-chromene, 4H-1,3-benzothiazine, 4H-pyrido[3,2-b][1,4] oxazine, and 2H-quinolizinyl.

Examples of fully aromatic heterocyclyl are furyl, thienyl, 1,3-thiazolyl, 1H-benzimidazolyl, 1- and 2-benzofuranyl, benzothiazolyl, benzoxazolyl, 2,3-bipyridyl, quinazolinyl, quinolyl, quinoxalinyl, cinnolinyl, dithiazolyl, imidazolidinyl, imidazolinyl, imidazolyl, indazolyl, indolyl, isoquinolyl, isoindolyl, isothiazolidinyl, isothiazolyl, isoxazolyl, naphthyridinyl, oxadiazolyl, oxazolyl, phthalazinyl, pteridinyl, purinyl, pyridazinyl, pyrazinyl, pyrazolyl, pyrazolinyl, pyridazinyl, pyridyl, pyrimido[4,5-c]pyridazine, pyrimidyl, pyrrolinyl, pyrrolyl, tetrazinyl, tetrazolyl, thiadiazolyl, thiazinyl, thiazolyl, triazinyl, and triazolyl.

The heterocyclyl groups having one ring, such as pyridyl, piperidyl, or morpholino, are particularly preferred.

"Heterocyclyl $C_{1-4}$ alkyl" is a heterocyclyl having the meanings stated above, which is bonded to $C_{1-4}$ alkyl having the meanings stated above via a carbon or nitrogen atom, which in turn is bonded to the rest of the molecule.

"Halogen" stands for fluorine, chlorine, bromine, and iodine.

A partially or completely halogenated alkyl, alkenyl, cycloalkyl, alkythio, alkyl carbonyl, alkysulfonyl, and alkoxycarbonyl can be, for example, a $CF_3$ group, a $CF_3CF_2O$ group, a $CF_3CO$ group, a $ClCH_2$ group, or a $Cl_3CCH_2O$ group.

"Het" in formulas (I) and (II) is a ring system including 1 or 2 rings, and at least one of the rings is aromatic and contains 5 or 6 ring atoms, of which at least one is nitrogen, and the other ring can be saturated or unsaturated and comprises from 5 to 7 ring atoms; wherein the ring system can further contain from 1 to 5 heteroatoms selected from the group consisting of N, S, and O provided that not more than two heteroatoms are selected from the group consisting of S and O; and the ring system can be substituted by from one to four substituents $R^{11}$, wherein $R^{11}$ has the meanings stated with reference to the compounds of formula (I) or (II).

Examples of such ring systems are 1H-benzimidazolyl, benzothiazolyl, benzoxazolyl, 2,3-bipyridyl, quinazolinyl, quinolyl, quinoxalinyl, quinolinyl, dithiazolyl, imidazolidinyl, imidazolinyl, imidazolyl, indazolyl, indolyl, isoquinolyl, isoindolyl, isothiazolidinyl, isothiazolyl, isoxazolyl, naphthyridinyl, oxadiazolyl, oxazolyl, phthalazinyl, pteridinyl, purinyl, pyridazinyl, pyrazinyl, pyrazolyl, pyrazolinyl, pyridazinyl, pyridyl, pyrimido[4,5-c]pyridazine, pyrimidyl, pyrrolinyl, pyrrolyl, tetrazinyl, tetrazolyl, thiadiazolyl, thiazinyl, thiazolyl, triazinyl, and triazolyl.

In all embodiments of the invention, preference is given to 3-pyridyl, 4-substituted and/or 5-substituted 3-pyridyl, 4-pyridyl, 4-isoquinolyl, 1-imidazolyl, 4-imidazolyl, and 5-pyrimidyl.

The unsaturated nitrogen-containing five membered to seven membered ring, which can be formed by $R^1$ and $R^2$ together with the atoms to which they are bonded, has 1 or 2 unsaturated bonds, namely the unsaturated bond of the benzene ring to which it is added by condensation, and optionally another unsaturated bond which, by reason of the bonding geometry, cannot be a triple bond. The five membered to seven membered ring can further contain another hetero atom or group of hetero atoms selected from the group consisting of O, S, N, and $NR^7$, which atoms can be substituted by from one to three substituents $R^{12}$, wherein $R^{12}$ has the meanings stated with reference to formulas (I) or (II).

The ring is preferably a five membered or six membered ring having one or two unsaturated bonds and not containing any further hetero atoms.

The compounds of the formulas (I) and (H) can exhibit chirality centers (eg, the carbons substituted by $R^5$ and $R^6$ or $R^8$ and $R^9$ or $R^{12}$). In this case, both the mixtures of isomers and the isolated single compounds are within the scope of the invention.

Preferred embodiments of the invention are mentioned below. Reference to the compounds of formula (I) and/or formula (II) should always be taken to include the pharmaceutically acceptable salts thereof.

In a first preferred embodiment of the invention, the bond between U and X or U and Y or X and Y in the compounds of formulas (I) and (II) is a single bond.

In a second preferred embodiment, n is 0 or m is 0 in the compounds of formulas (I) and (II) or in the compounds of the first preferred embodiment.

In a third preferred embodiment, both n and m are equal to 0.

In a fourth preferred embodiment, Z denotes C=O in the compounds of formulas (I) and (II) or in the compounds of the first three preferred embodiments.

In a fifth preferred embodiment, Z stands for C=S or —SO$_2$— in the compounds of formulas (I) and (II) or in the compounds of the first four preferred embodiments.

In a sixth preferred embodiment, $R^1$ stands for H or $C_{1-4}$ alkyl, $C_{3-7}$ cycloalkyl, or $C_{1-4}$ alkylcarbonyl in the compounds of the formulas (I) and (II) or in the compounds of the first five preferred embodiments, and these groups can be partially or completely halogenated with independent halogen atoms;

In a seventh preferred embodiment, $R^1$ and $R^2$ in the compounds of formulas (I) and (II) or in the compounds of the first six preferred embodiments form, together with the atoms to which they are bonded, an unsaturated nitrogen-containing five membered to seven membered ring having 1 or 2 unsaturated bonds and, in addition to the nitrogen atom to which $R^1$ is bonded, can also contain a hetero atom or a group of hetero atoms selected from the group consisting of O, S and $NR^7$ and can be substituted by from one to four substituents $R^{12}$, wherein $R^{12}$ has the meanings stated with reference to the compounds of formula (I) or (II).

In an eighth preferred embodiment, the unsaturated nitrogen-containing ring in the seventh preferred embodiment is a five membered or six membered ring having one or two unsaturated bonds and not containing any further hetero atoms.

In a ninth preferred embodiment, the ring in the seventh or eighth embodiment is unsubstituted or substituted by a substituent $R^{12}$, wherein $R^{12}$ has the meanings stated above.

A tenth preferred embodiment of the compounds of formulas (I) and (II) or the compounds of the first, second, and fourth to ninth preferred embodiment are compounds in which U stands for S or $CR^5R^6$, wherein $R^5$ and $R^6$ are independently selected from the group consisting of H and $C_{1-4}$ alkyl, X stands for $CH_2$ and n is 0.

An eleventh preferred embodiment of the compounds of formulas (I) and (II) or the compounds of the first ten preferred embodiments comprises compounds in which A stands for C=O or $CR^8R^9$, wherein $R^8$ and $R^9$ independently stand for the group consisting of H, $C_{1-4}$ alkyl, $C_{3-7}$ cycloalkyl, and aryl, which can be substituted by from 1 to 4 substituents $R^b$, wherein $R^b$ has the meanings stated above; or $R^8$ and $R^9$ form, together with the carbon atom to which they are bonded, a cyclopropane ring, or A is non-existent, ie b is zero.

A twelfth preferred embodiment of the compounds of formulas (I) and (II) or the compounds of the first ten preferred embodiments comprises compounds in which Het stands for optionally $R^{11}$-substituted 3-pyridyl, 4-pyridyl, 4-isoquinolinyl, 5-pyrimidyl, 1-imidazolyl, or 4-imidazolyl, wherein $R^{11}$ has the meanings stated above with reference to the compounds of formula (I) or (II).

In a thirteenth preferred embodiment, $R^2$ in the compounds of the formulas (I) and (II) or the compounds of the first six and the tenth to twelfth preferred embodiments, if not joined to $R^1$ to form a ring, stands for H; $C_{1-4}$ alkyl or $C_{1-4}$ alkoxy optionally partially or completely substituted by fluorine or chlorine; halogen; or nitro.

In a fourteenth preferred embodiment, $R^3$ and $R^4$ in the compounds of the formulas (I) and (II) or the compounds of the first thirteen preferred embodiments independently stand for H; $C_{1-4}$ alkyl or $C_{1-4}$ alkoxy optionally partially or completely substituted by fluorine or chlorine; halogen; or nitro.

In a fifteenth preferred embodiment, one of $R^5$ and $R^6$ in the compounds of formulas (I) and (II) or the compounds of the first fourteen preferred embodiments stands for H and the other for H; $C_{1-4}$ alkyl or $C_{1-4}$ alkoxy optionally partially or completely substituted by fluorine or chlorine; halogen; hydroxyl; or nitro.

In a sixteenth preferred embodiment, $R^7$ in the compounds of formulas (I) and (II) or the compounds of the first fifteen preferred embodiments stands for H; $C_{1-4}$ alkyl, $C_{3-7}$ cycloalkyl or $C_{1-4}$ alkyl optionally partially or completely substituted by fluorine.

In a seventeenth preferred embodiment, one of $R^8$ and $R^9$ in the compounds of the formulas (I) and (II) or the compounds of the first sixteen preferred embodiments stands for H and the other stands for H, $C_{1-4}$ alkyl or $C_{1-4}$ alkoxy optionally partially or completely substituted by fluorine or chlorine; halogen or hydroxyl; or $R^8$ and $R^9$ form, together with the carbon atom to which they are bonded, cyclopropane In an eighteenth preferred embodiment, $R^{10}$ in the compounds of formulas (I) and (II) or the compounds of the above preferred embodiments one to ten and twelve to seventeen stands for H; $C_{1-4}$ alkyl, $C_{3-7}$ cycloalkyl that may be partially or completely substituted by fluorine; aryl, aryl $C_{1-4}$ alkyl, which can in each case be substituted on the ring or at least on one ring by from one to four substituents $R^b$, wherein $R^b$ has the meanings stated above.

In a nineteenth preferred embodiment, Het in the compounds of formulas (I) and (II) or the compounds of the above preferred embodiments one to eighteen is either unsubstituted or is substituted by a substituent $R^{11}$, which stands for $C_{1-4}$ alkyl or $C_{1-4}$ alkoxy optionally partially or completely substituted by fluorine or chlorine; halogen, hydroxyl, or phenyl, optionally substituted by one or two substituents independently selected from the group consisting of $C_{1-4}$ alkyl, $C_{1-4}$ alkoxy, $C_{1-4}$ alkylthio, $C_{1-4}$ alkylcarbonyl, $C_{1-4}$ alkylsulfonyl, whose alkyl moieties can be partially or completely halogenated with independent halogen atoms, halogen, hydroxyl, nitro, cyano, —$NR^c{}_2$, —$CONR^c{}_2$, and $SO_2NR^c{}_2$, wherein $R^c$ is independently selected from the group consisting of H and $C_{1-4}$ alkyl.

In a twentieth preferred embodiment, the substituent $R^{12}$ in the compounds of formulas (I) and (II) or the compounds of the above preferred embodiments seven to eighteen in which $R^1$ and $R^2$ form, together with the atoms to which they are bonded, an unsaturated nitrogen-containing ring having the meanings stated above, stands for $C_{1-4}$ alkyl optionally partially or completely substituted by fluorine or chlorine and also for $C_{1-4}$ alkoxy optionally partially or completely substituted by fluorine or chlorine, halogen, or hydroxyl when $R^{12}$ is bonded to a carbon atom.

Particularly preferred compounds of the invention are:
5-Pyridin-3-yl-1,3-dihydroindol-2-one
6-Isoquinolin-4-yl-3,4-dihydro-1H-quinolin-2-one
6-Isoquinolin-4-yl-1-methyl-3,4-dihydro-1H-quinolin-2-one
6-Pyridin-3-yl-3,4-dihydro-1H-quinoline-2-thione
8-Pyridin-3-yl-1,2,5,6-tetrahydropyrrolo[3,2,1-ij]quinolin-4-one 8-Nitro-6-pyridin-3-yl-3,4-dihydro-1H-quinolin-2-one
7-Pyridin-3-yl-4H-benzo[1,4]thiazin-3-one
8-Chloro-6-pyridin-3-yl-3,4-dihydro-1H-quinolin-2-thione
9-Pyridin-3-yl-1,2,6,7-tetrahydro-5H-pyrido[3,2,1-ij]quinolin-3-one
8-(5-Methoxypyridin-3-yl)-1,2,5,6-tetrahydropyrrolo[3,2,1-ij]quinolin-4-one
8-Isoquinolin-4-yl-1,2,5,6-tetrahydropyrrolo[3,2,1-ij]quinolin-4-one
9-(5-Methoxypyridin-3-yl)-1,2,6,7-tetrahydro-5H-pyrido[3,2,1-ij]quinolin-3-one
9-Isoquinolin-4-yl-1,2,6,7-tetrahydro-5H-pyrido[3,2,1-ij]quinolin-3-one
8-Pyridin-3-yl-1,2,5,6-tetrahydropyrrolo[3,2,1-ij]quinoline-4-thione
6,6-Dimethyl-8-pyridin-3-yl-1,2,5,6-tetrahydropyrrolo[3,2,1-ij]quinolin-4-one
8-(5-Ethoxypyridin-3-yl)-1,2,5,6-tetrahydropyrrolo[3,2,1-ij]quinolin-4-one
8-(5-Trifluoromethylpyridin-3-yl)-1,2,5,6-tetrahydropyrrolo[3,2,1-ij]quinolin-4-one
8-(5-Fluoropyridin-3-yl)-1,2,5,6-tetrahydropyrrolo[3,2,1-ij]quinolin-4-one
8-Imidazol-1-yl-1,2,5,6-tetrahydropyrrolo[3,2,1-ij]quinolin-4-one.
8-Pyridin-4-yl-1,2,5,6-tetrahydropyrrolo[3,2,1-ij]quinolin-4-one
8-Pyrimidin-5-yl-1,2,5,6-tetrahydropyrrolo[3,2,1-ij]quinolin-4-one
8-(Pyridin-4-carbonyl)-1,2,5,6-tetrahydropyrrolo[3,2,1-ij]quinolin-4-one
8-(Pyridin-3-carbonyl)-1,2,5,6-tetrahydropyrrolo[3,2,1-ij]quinolin-4-one
8-(5-Phenylpyridin-3-yl)-1,2,5,6-tetrahydropyrrolo[3,2,1-ij]quinolin-4-one
8-(5-Isopropoxypyridin-3-yl)-1,2,5,6-tetrahydropyrrolo[3,2,1-ij]quinolin-4-one
8-(1-Imidazol-1-yl-ethyl)-1,2,5,6-tetrahydropyrrolo[3,2,1-ij]quinolin-4-one
8-[5-(4-Fluorophenyl)pyridin-3-yl]-1,2,5,6-tetrahydropyrrolo[3,2,1-ij]quinolin-4-one
8-[5-(3-Fluorophenyl)pyridin-3-yl]-1,2,5,6-tetrahydropyrrolo[3,2,1-ij]quinolin-4-one
8-[5-(4-Methoxyphenyl)pyridin-3-yl]-1,2,5,6-tetrahydropyrrolo[3,2,1-ij]quinolin-4-one
8-[5-(3-Methoxyphenyl)pyridin-3-yl]-1,2,5,6-tetrahydropyrrolo[3,2,1-ij]quinolin-4-one
8-[5-(2-Fluorophenyl)pyridin-3-yl]-1,2,5,6-tetrahydropyrrolo[3,2,1-ij]quinolin-4-one
8-[5-(3-Trifluoromethylphenyl)pyridin-3-yl]-1,2,5,6-tetrahydropyrrolo[3,2,1-ij]quinolin-4-one
8-[5-(3,4-Difluorophenyl)pyridin-3-yl]-1,2,5,6-tetrahydropyrrolo[3,2,1-ij]quinolin-4-one
8-[5-(3-Trifluoromethoxyphenyl)pyridin-3-yl]-1,2,5,6-tetrahydropyrrolo[3,2,1-ij]quinolin-4-one
8-[5-(2-Methoxyphenyl)pyridin-3-yl]-1,2,5,6-tetrahydropyrrolo[3,2,1-ij]quinolin-4-one
or a pharmaceutically acceptable salt thereof.

Preferably used compounds include the following:
6-Pyridin-3-yl-3,4-dihydro-1H-quinolin-2-one
1-Methyl-6-pyridin-3-yl-3,4-dihydro-1H-quinolin-2-one
6-(5-Methoxypyridin-3-yl)-3,4-dihydro-1H-quinolin-2-one
6-(5-Methoxypyridin-3-yl)-1-methyl-3,4-dihydro-1H-quinolin-2-one
1-Ethyl-6-pyridin-3-yl-3,4-dihydro-1H-quinolin-2-one
1-Isopropyl-6-pyridin-3-yl-3,4-dihydro-1H-quinolin-2-one
8-Chloro-6-pyridin-3-yl-3,4-dihydro-1H-quinolin-2-one
6-Pyrimidin-5-yl-3,4-dihydro-1H-quinolin-2-one
and the pharmaceutically acceptable salts thereof.

The present invention also provides prodrugs of the compounds of the invention, which are converted in vivo to the latter. A prodrug is an active or inactive compound which, following administration, is modified by a physiological in vivo action, such as hydrolysis and/or metabolism, to form a compound of the invention, as is well known to the person skilled in the art. Prodrugs can be divided into two classes: bioprecursor prodrugs and carrier prodrugs, which classifications do not necessarily exclude each other. An overview is given in *The Practice of Medicinal Chemistry*, Chapters 31 and 32 (Editor: Wermuth, Academic Press, San Diego, Calif., 2001). In general, bioprecursor prodrugs are inactive compounds or show lower activity than the corresponding active medicinal compound, contain one or more protective groups, and are converted to an active form by metabolization or solvolysis (specifically hydrolysis). Formation of the active medicinal compound from the prodrug precursor can be based on a metabolic process or reaction that may fall under:

1. Oxidative reactions, such as the oxidation of alcohol and carbonyl functions leading to acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, and other oxidative reactions.
2. Reductive reactions, such as the reduction of carbonyl groups, reduction of alcoholic groups and carbon-carbon double bonds, reduction of nitrogen-containing functional groups, and other reductive reactions.
3. Reactions that do not change the state of oxidation, such as hydrolysis of esters and ethers, hydrolytic cleavage of carbon-nitrogen single bonds, hydrolytic cleavage of non-aromatic heterocyclic compounds, hydration and dehydration at multiple bonds, new atomic links arising from dehydration reactions, hydrolytic dehalogenation, removal of halogen-hydrogen molecules, and other such reactions.

Carrier prodrugs are medicinal compounds that contain a transport moiety, which improves, for example, absorption and/or localized delivery to a site of action. With such a carrier prodrug, the linkage between the carrier moiety and the transport moiety is preferably a covalent bond if the prodrug is inactive or less active than the medicinal compound and if each liberated transport moiety is not significantly toxic. In the case of prodrugs in which the transport moiety is intended to improve absorption, release of the transport moiety should take place rapidly. In other cases it is desirable to use a moiety that ensures slow release, such as certain polymers or cyclodextrins. Such carrier prodrugs are frequently advantageous in the case of orally administered medicinal substances. Carrier prodrugs can be used, for example, to achieve one or more of the following goals: increased lipophilicity, increased duration of pharmacological actions, increased site specificity, reduced toxicity and fewer side effects and/or an improvement of the medicinal formulation (eg, stability, water solubility, suppression of an undesirable organoleptic or physicochemical property). For example, the lipophilicity can be increased by esterification of hydroxyl groups with lipophilic carboxylic acids or of carboxylic acid groups with alcohols, eg, aliphatic alcohols, as described in Wermuth, *The Practice of Medicinal Chemistry*, Chapters 31 and 32, Editor: Wermuth, Academic Press, San Diego, Calif., 2001.

Examples of prodrugs are, for example, esters of free carboxylic acids and S-acyl and O-acyl derivatives of thiols, alcohols, or phenols, wherein acyl is an R—C(O)— group. Pharmaceutically acceptable ester derivatives that are converted to the parent carboxylic acid under physiological conditions, for example low-alkyl esters, cycloalkyl esters, low-alkenyl esters, benzyl esters, monosubstituted or disubstituted lower alkyl esters, such as the ω-(amino, mono- or di-lower alkylamino, carboxyl, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, are preferred. In addition, amines can be masked as arylcarbonyloxymethyl substituted derivatives, which are cleaved in vivo by esterases to liberate the free medicinal substance and formaldehyde, as described, for example, in Bundgaard, *J. Med. Chem.* 2503 (1989). Furthermore, medicinal substances containing an acid NH group, such as imidazole, imide, and indole, can be masked with, inter alia, N-acyloxymethyl groups (cf Bundgaard, *Design of Prodrugs*, Elsevier (1985). Hydroxyl groups can be masked as esters and ethers.

With regard to the close relationship between the presently described compounds, the compounds in the form of their salts and prodrugs, all references to the compounds of the invention should be taken to include the corresponding prodrugs of said compounds.

Furthermore, the compounds of the present invention, including the salts thereof, may also be obtained in the form of their hydrates or include other solvents as used for crystallization thereof.

The compounds of the invention possess valuable pharmacological properties, because they are aldosterone synthase inhibitors. As mentioned above, the aldosterone synthase (CYP11B2) is a mitochondrial cytochrome P450 enzyme that catalyzes the final three stages of the production of aldosterone in the adrenal cortex, that is to say, the conversion of 11-deoxycorticosterone to aldosterone. It has been shown that aldosterone synthase is expressed in all cardiovascular tissues, such as the heart, in the umbilical cord, in the mesenteric and pulmonary arteries, in the aorta, in the endothelium, and in vascular cells. Furthermore, the expression of the aldosterone synthase is closely correlated with the production of aldosterone in cells. It has been found that increasing the aldosterone activity or aldosterone concentration induces a diversity of diseases, such as congestive heart failure, cardial or myocardial fibrosis, renal failure, hypertension, or ventricular arrhythmia.

Accordingly, the invention relates to the use of a compound of formula I or II for the treatment of hyperaldosteronism.

As aldosterone synthase inhibitors, the compounds of the invention are thus also useful for the prophylaxis of, retardation of the progression of, or therapy of, diseases or clinical pictures which respond to an inhibition of the aldosterone synthase or are characterized by an abnormal aldosterone synthase activity. Included therein are hypokalaemia, hypertension, renal failure, particularly chronic renal failure, restenosis, atherosclerosis, syndrome X, obesity, nephropathy, inflammation, increased collagen formation, fibrosis, such as cardial or myocardial fibrosis, remodeling following hypertension, endothelial dysfunction and/or edema. The compounds of formula (I) are also preferentially considered in the form of medicinal substances for the treatment of congestive heart failure, ventricular fibrillation, postmyocardial infarction syndrome and coronary cardiac diseases.

In addition, the invention provides the use of the compounds of the formulas (I) and (II) for the treatment of hypercortisolismus mediated by 11β-hydroxylase (CYP11B1). This includes the prophylaxis or retardation of the progression of, or the therapy of, diseases or clinical pictures such as Cushing's syndrome, ectopic ACTH formation syndrome, a change in the adrenocortical mass, primary pigmented nodular adrenocortical dysplasia (PPNAD), the Carny complex, Anorexia nervosa, chronic alcoholic intoxication, nicotine and cocaine withdrawal syndromes, post-traumatic stress syndrome, cognitive impairment following apoplectic stroke and cortisol-induced mineralocorticoid excess.

Another aspect of the invention relates to pharmaceutical preparations comprising a compound of the invention and a pharmaceutically acceptable excipient. The pharmaceutical preparation can be formulated for specific administration routes, such as oral administration, parenteral administration, and rectal administration. In addition, the pharmaceutical preparations of the present invention can be prepared in solid form, including capsules, tablets, pellets, granules, powders, and suppositories, or in liquid form, including solutions, suspensions, or emulsions. The pharmaceutical preparations can be subjected to conventional pharmaceutical processes, such as sterilization, and/or can contain conventional inert diluents, slip agents or buffering agents and also adjuvants such as preserving agents, stabilizing agents, wetting agents, emulsifiers, and buffers.

Preferably, the pharmaceutical preparations are in the form of tablets and gelatin capsules, which contain the active ingredient together with diluents, eg, lactose, dextrose, sucrose, mannitol, sorbitol, cellulose and/or glycine; slip agents, eg, silicon dioxide, talc, stearic acid, their magnesium or calcium salts, and/or polyethylene glycol; in the case of tablets, also binding agents, eg, magnesium aluminum silicate, starch paste, gelatine, tragacanth gum, methyl cellulose, sodium carboxymethyl cellulose, and/or polyvinylpyrrolidone, if desired also tablet disintegration agents, eg, starches, agar, alginic acid or its sodium salt, or effervescent mixtures; and/or absorbents, stabilizing agents, preserving agents, coloring agents, flavoring agents, and sweetening agents.

Tablets may be film coated or provided with a gastro-resistant coating and comprise a slow release material, such as glycerol monostearate or glycerol distearate.

Injectable preparations are preferably aqueous isotonic solutions or suspensions, and suppositories are advantageously produced from fatty emulsions or suspensions. These preparations can be sterilized and/or contain adjuvants, such as preserving agents, stabilizing agents, wetting or emulsifying agents, solubilizers, salts for regulation of the osmotic pressure and/or buffers. They contain approximately from 0.1% to 75%, preferably approximately from 1% to 50%, of active ingredient.

Suitable preparations for transdermal application comprise an effective amount of a compound of the invention together with an excipient, preferably an absorbable pharmacologically acceptable solvent, in order to enhance transdermal delivery. Suitable transdermal devices are all types of plaster. Other preparations for topical application to the skin or to the eyes, or to the respiratory passages, comprise aqueous solutions, suspensions, ointments, creams, gels, and sprayable formulations for, say, aerosol delivery.

The compounds of the invention can also be used in anhydrous pharmaceutical preparations, since water can accelerate the degradation of some compounds.

A therapeutically effective amount of the compounds of the invention can range approximately from 0.1 to 500 mg/kg, preferably approximately from 1 to 100 mg/kg, depending on the administration route. The amount of administered active ingredient, ie the dosage used, depends on the type and severity of the disease being treated, on the method of administration and the treatment employed, and on the age and constitutional condition of the patient and will be adjusted by the physician in charge, according to general medical expertise, to accommodate the given situation.

The pharmaceutical preparations of the invention contain a therapeutically effective amount of a compound of the invention either alone or together with another therapeutic agent in suitable dosage. Such therapeutic agents comprise, for example, active ingredients to counteract obesity, such as orlistat, antihypertensive drugs, inotropic agents and hypolipidemic agents, eg, loop diuretics, such as ethacrynic acid, furosemide, and torsemide; angiotensine converting enzyme (ACE) inhibitors, such as benacepril, captopril, enalapril, fosinopril, lisinopril, moexipril, perinodopril, quinapril, ramipril, and trandolapril; inhibitors of the Na—K-ATPase membrane pump, such as digoxin; neutral endopeptidase (NEP) inhibitors; (ACE/NEP inhibitors, such as omapatrilate, sampatrilate, and fasidotril; angiotensin II receptor blockers (ARBs), such as candesartane, eprosartane, irbesartane, losartane, telmisartane, and valsartane, particularly valsartane; β-receptor blockers, such as acebutolol, atenolol, betaxolol, bisoprolol, metoprolol, nadolol, propanolol, sotalol, and timolol; inotropic agents, such as digoxin, dobutamine, and milrinone; renin inhibitors, such as aliskiren and remikiren; calcium channel blockers, such as amlodipine, bepridil, diltiazem, felodipine, nicardipine, nimodipine, nifedipine, nisoldipine, and verapamil; and 3-hydroxyl-3-methylglutaryl coenzyme A (HMG-CoA) reductase inhibitors, such as lovastatine, pitavastatine, simvastatine, pravastatine, cerivastatine, mevastatine, velostatine, fluvastatine, delvastatine, atorvastatine, rosuvastatine, and rivastatine. A compound of the present invention can be administered concurrently with, prior to, or after the other active ingredient, either separately therefrom by, a different administration route or together therewith in the same pharmaceutical formulation.

Furthermore, the administration can take place simultaneously, separately, or consecutively.

The preparation of the compounds of the invention is explained below.

The following abbreviations are used:

| | |
|---|---|
| Ac | acetyl |
| BINAP | 2,2'-bis(diphenylphosphino)-1,1'-binaphthyl |
| Bn | benzyl |
| Boc | tert-butyloxycarbonyl |
| Bz | benzoyl |
| DIBAL | diisobutylaluminum hydride |
| DMF | dimethylformamide |
| DMSO | dimethyl sulfoxide |
| dppf | diphenyl-phosphino ferrocene |
| Et | ethyl |
| h | hours |
| iPr | isopropyl |
| LDA | lithium diisopropylamide |
| LHMDS | lithium hexamethyl disilazane |
| mCPBA | meta-chloroperbenzoic acid |
| Me | methyl |
| min | minutes |
| Ms | methanesulfonyl |
| μw | microwaves |
| NBS | N-bromosuccinimide |
| NMP | N-methyl-2-pyrrolidone |
| Pd$_2$(dba)$_3$ | tris(dibenzylideneacetone)dipalladium(0) |
| Pd(dppf)Cl$_2$ | [1.1'-bis(diphenylphosphino)ferrocene]dichloropalladium(II) |
| Pd(PPh$_3$)$_4$ | tetrakis(triphenylphosphine)palladium(0) |
| PG | protective group |
| Ph | phenyl |
| Pr | propyl |
| R$_f$ | retention factor |
| RT | room temperature |
| mp | melting point |
| Tf | trifluoromethanesulfonyl |
| Tf$_2$NPh | N-phenyltrifluoromethanesulfonimide |
| THF | tetrahydrofuran |
| W | Watts |

In Schemes 1-19, R stands collectively for the meanings of $R^3$ and $R^4$ in the above formula (I) at the positions indicated therein. R' stands collectively for $R^5$ and $R^6$ in the meaning of $CR^5R^6$ in U, X, and Y in formula (I). R''' in Het-B(OR''') preferably stands for H. $R^1$ and $R^2$ have the same meanings as stated with reference to formula (I). Het in Schemes 1-19 is as defined in formula (I).

Compounds of the general structure (I) having a quinolinone or quinoline thione skeletal structure can be produced from anilines according to Scheme 1. For this purpose, acylation is first carried out using an ω-chlorocarboxylic acid chloride in acetone (Step a) followed by an intramolecular Friedel Crafts alkylation in an AlCl$_3$/NaCl melt at 150° C. (Step b). The introduction of a suitable leaving group is then carried out either via the formation of a triflate (Step c) or by regioselective bromination by means of NBS (Step d). The resulting central intermediate stage can be derivatized by N-alkylation (Step g) and/or electrophilic substitution on the aromatic compound (Step e). The target compounds are obtained via transition metal catalyzed cross coupling (for example Suzuki coupling) (Step f) and can be derivatized with Lawesson's reagent (Step h) to form the corresponding thio analogues.

The substituted 4-aminophenols used for the syntheses according to Scheme 1 are commercially available when R denotes 2-Me [CAS: 2835-96-3], 3-Me [CAS: 2835-99-6], 2-iPr [CAS: 16750-66-6], 3-iPr [CAS: 82744-61-6], 3-Pr [CAS: 226084-99-7], 3-Et [CAS: 61638-00-4], 2-F [CAS: 399-96-2], 3-F [CAS: 399-95-1], 2-Cl [CAS: 3964-52-1], 3-Cl [CAS: 17609-80-2], 2-OH [CAS: 13047-04-6], 3-OH [CAS: 34781-86-7], 2-OMe [CAS: 52200-90-5], 3-OMe [CAS: 61638-01-5].

Other substituted 4-aminophenols can be synthesized according to synthesis instructions described in the literature when R denotes 3-Et [CAS: 61638-00-4], J. Am. Chem. Soc. 1941, 63, 308-11; 2-Et [CAS: 178698-88-9], 2-Pr [CAS: 855397-55-6], U.S. Pat. No. 2,533,203; 2-CF$_3$ [CAS: 1535-76-8], 3-CF$_3$ [CAS: 445-04-5], WO 2007097937, J. Org. Chem. 1962, 27, 4660-2; 2-OEt [CAS: 55483-70-0], 3-OEt [CAS: 139444-58-9], J. Am. Chem. Soc. 1919, 41, 1450-72; 2-OPh [CAS: 669092-25-5], J. Org. Chem. 1950, 15, 1108-12; 3-OPh [CAS: 669092-27-7], U.S. Pat. No. 2,525,515; 2-OBn [CAS: 106131-28-6], J. Med. Chem. 1995, 38, 4157-60; 2-Cyclopropyl [CAS: 947607-29-6], WO2007097937.

The substituted anilines used for the syntheses according to Scheme 1 are commercially available when R denotes 2-Me [CAS: 95-53-4], 3-Me [CAS: 108-44-1], 2-Et [CAS: 578-54-1], 3-Et [CAS: 587-02-0], 2-Pr [CAS: 1821-39-2], 2-iPr [CAS: 649-28-7], 3-iPr [CAS: 5369-16-4], 2-CF$_3$ [CAS: 88-17-5], 3-CF$_3$ [CAS: 98-16-8], 2-Bn [CAS: 28059-64-5], 3-Bn [CAS: 61424-26-8], 2-Cyclopropyl [CAS: 3158-73-4], 3-Cyclopropyl [CAS: 485402-64-0], 2-F [CAS: 348-54-9], 3-F [CAS: 372-19-0], 2-Cl [CAS: 95-51-2], 3-Cl [CAS: 108-42-9], 2-OH [CAS: 95-55-6], 3-OH [CAS: 591-27-5], 2-OMe [CAS: 90-04-0], 3-OMe [CAS: 536-90-3], 2-OEt [CAS: 94-70-2], 3-OEt [CAS: 621-33-0], 2-OPh [CAS: 2688-84-8], 3-OPh [CAS: 3586-12-7], 2-SPh [CAS: 1134-94-7], 2-NH$_2$ [CAS: 95-54-5], 3-NH$_2$ [CAS: 108-45-2]. Other substituted anilines can be synthesized according to synthesis instructions described in the literature when R denotes, for example, 3-SPh [CAS: 3985-12-4], J. Am. Chem. Soc. 2006, 128, 2180-81.

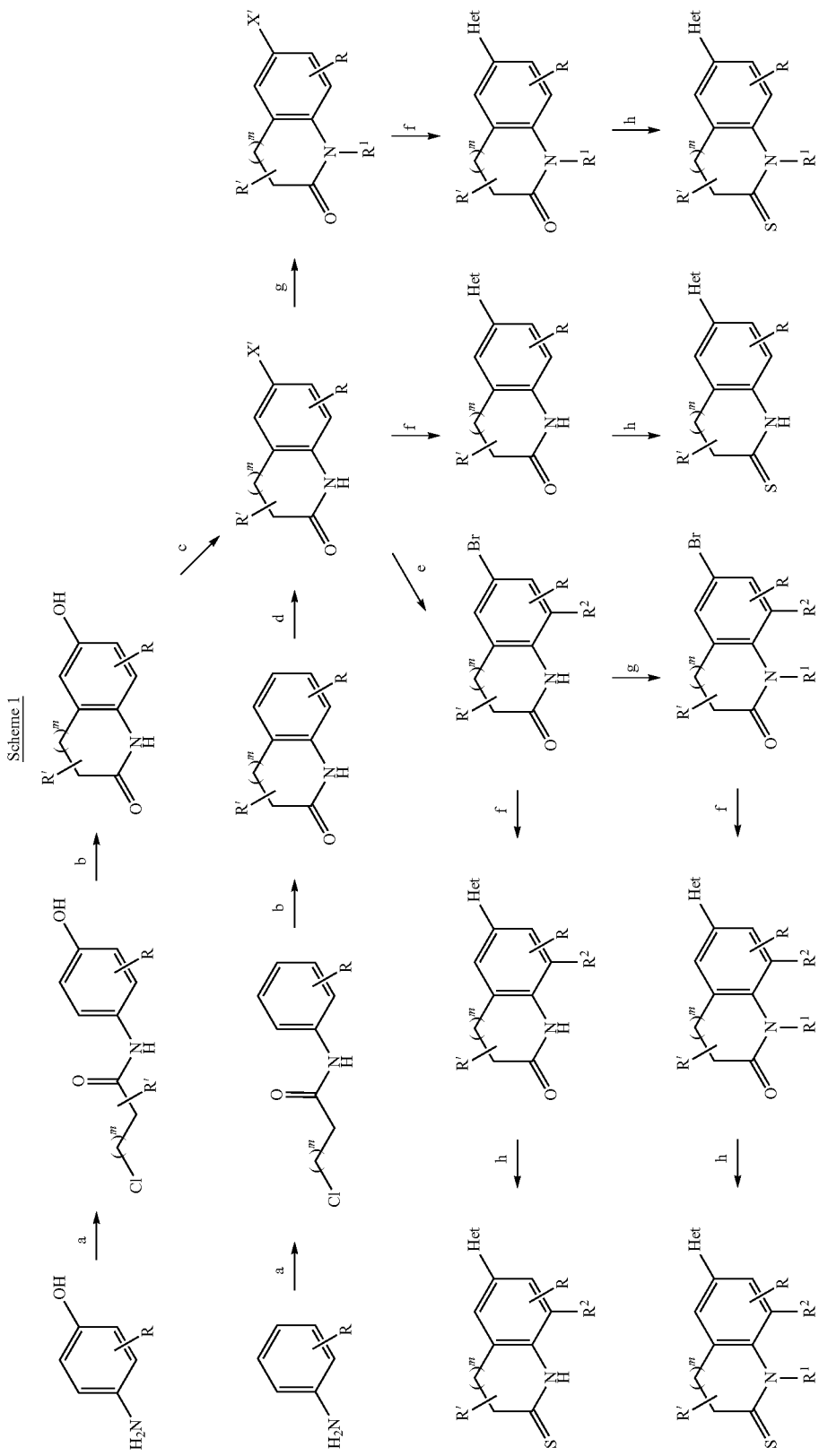

The synthesis of the pyrrolo or pyrido quinolinones or pyrrolo or pyrido thiones (Scheme 2) starting from indolines (n=1) or tetrahydroquinolines (n=2) is carried out in an analogous manner. For this purpose, in this case also, acylation is first carried out using an ω-chlorocarboxylic acid chloride in acetone (Step a) followed by an intramolecular Friedel Crafts alkylation in an AlCl$_3$/NaCl melt at 150° C. (Step b). Bromination with NBS in DMF at 0° C. yields selectively the para-substituted product (Step c). This can be converted to a boronic-acid ester by reaction with bis(pinacolato)diborone under palladium catalysis (Step d). The heterocycle is then introduced via Suzuki coupling (Het) (Step e), either by reaction of the bromide with a heterocyclic boronic acid or by reaction of the boronic acid ester with a heterocyclic halide or triflate. The resulting oxo compounds can be derivatized to the corresponding thio analogues with Lawesson's reagent (Step f).

The substituted indolines used for the syntheses according to Scheme 2 (n=1) are commercially available when R denotes H [CAS: 496-15-1], 4-Me [CAS: 62108-16-1], 4-CF$_3$ [CAS: 905274-07-9], 4-F [CAS: 552866-98-5], 4-CN [CAS: 885278-80-8], 4-Cl [CAS: 41910-64-9], 4-Br [CAS: 86626-38-2], 4-OH [CAS: 85926-99-4], 4-OMe [CAS: 7555-94-4], 4-OEt [CAS: 220657-56-7], 4-OPh [CAS: 930790-14-0], 4-NH$_2$ [CAS: 52537-01-6], 4-CO$_2$H [CAS: 175647-03-7], 4-NO$_2$ [CAS: 84807-26-1], 6-Me [CAS: 86911-82-2], 6-Et [CAS: 162716-49-6], 6-Pr [CAS: 172078-24-6], 6-CF$_3$ [CAS: 181513-29-1], 6-F [CAS: 2343-23-9], 6-CN [CAS: 15861-35-5], 6-Cl [CAS: 52537-00-5], 6-Br [CAS: 63839-24-7], 6-OMe [CAS: 7556-47-0], 6-OPh [CAS: 930791-17-6], 6-NH$_2$ [CAS: 15918-79-3], 6-CO$_2$H [CAS: 15861-37-7], 6-NO$_2$ [CAS: 19727-83-4], or 6-iPr [CAS: 122299-59-6].

Other substituted indolines (n=1) can be synthesized according to synthesis instructions described in the literature when R denotes, for example, 4-Et [CAS: 127693-34-9], *Arch. Pharm.* 1990, 323, 145-155; 6-Pr [CAS: 172078-24-9], WO 9523141; 6-OH [CAS: 4770-37-0], U.S. Pat. No. 5,256,799, *Tetrahedron Lett.* 1986, 27, 4565-68; 6-OEt [CAS: 37865-90-0], *Heterocycles* 1998, 48, 2481-84; 6-OiPr [CAS: 37865-92-2], DE 2843192; 4-F [CAS: 552866-98-5], *Bioorg. Med. Chem. Lett.* 2002, 12, 3105-09; 4-OPh [CAS: 930790-14-0], US 2007072897; or 6-OPh [CAS: 930791-17-6], US 2007072897.

Other substituted indolines (n=1) can be produced by regioselective reduction of the heterocyclic five membered ring of the correspondingly substituted indoles with boron hydride reagents such as NaBH$_4$ or NaBH$_4$CN according to synthesis instructions described in the literature (*Bioorg. Med. Chem. Lett.* 2002, 12, 3105-09; *J. Med. Chem.* 2004, 47, 5451-66; *Synth. Commun.* 1983, 13, 489-93; *Bioorg. Med. Chem.* 2006, 14, 2005-21; *Chem. Commun.* (Cambridge, UK) 2005, (29), 3664-66).

The substituted tetrahydroquinolines used for the syntheses according to Scheme 2 (n=2) are commercially available when R denotes H [CAS: 635-46-1], 5-iPr [CAS: 777013-12-4], 5-CN [CAS: 939758-72-2], 5-CF$_3$ [CAS: 939758-74-4], 5-CO$_2$H [CAS: 114527-54-7], 5-NH$_2$ [CAS: 36887-98-6], 5-F [CAS: 345264-61-1], 7-Me [CAS: 58960-03-5], 7-iPr [CAS: 746560-03-5], 7-CF$_3$ [CAS: 450-62-4], 7-CN [CAS: 939758-76-6], 7-CO$_2$H [22048-88-0], 7-NO$_2$ [CAS: 30450-62-5], 7-NH$_2$ [CAS: 153856-89-4], 7-OH [CAS: 58196-33-1], 7-F [CAS: 939758-75-5].

Other substituted tetrahydroquinolines (n=2) can be synthesized according to synthesis instructions described in the literature when R denotes, for example, 5-NO$_2$ [CAS: 39217-91-9], WO 2007052843, *Bioorg. Med. Chem. Lett.* 2006, 16, 4533-36; 5-OH [CAS: 61468-43-7], WO 2003011862, *Tetrahedron Lett.* 1986, 27, 4565-68; 5-OMe [CAS: 30389-37-8], JP 55040616, *Chemistry & Industry* (London) 1970, 45, 1435; 5-OPh [CAS: 860204-04-2], *Yakugaku Zasshi* 1952, 72, 905-08; 5-Cl [CAS: 72995-16-5], JP 55040616, US 2004116388; 5-Br [CAS: 114744-50-2], *New Journal of Chemistry* 1987, 11, 605-09; 7-OMe [CAS: 19500-61-9], U.S. Pat. No. 5,696,133, U.S. Pat. No. 5,696,130, *Bioorg. Med. Chem. Lett.* 2002, 12, 387-90; 7-OPh [CAS: 874498-69-8], *Yakugaku Zasshi* 1952, 72, 905-08; 7-Cl [CAS: 90562-35-9], US 2004116388; 7-Br [CAS: 114744-51-3], *New Journal of Chemistry* 1987, 11, 605-09, WO 9902502.

Other substituted tetrahydroquinolines (n=2) can be produced by regioselective reduction of the heterocyclic 6-ring of appropriately substituted quinolines. Preferably used reduction systems for this purpose are elemental hydrogen or boron hydrides used together with a transition metal catalyst such as Pd, Pt, In, Ni, Rh (*Organic & Biomolecular Chemistry* 2006, 4, 2529-31; *J. Am. Chem. Soc.* 2005, 127, 2125-35; *Synlett* 2004, (15), 2827-29; *J. Org. Chem.* 2004, 69, 2871-73; *Advanced Synthesis & Catalysis* 2003, 345, 275-79; *Tetrahedron Lett.* 2001, 42, 2763-66; *Synlett* 1998, (9), 1029-30).

Scheme 2

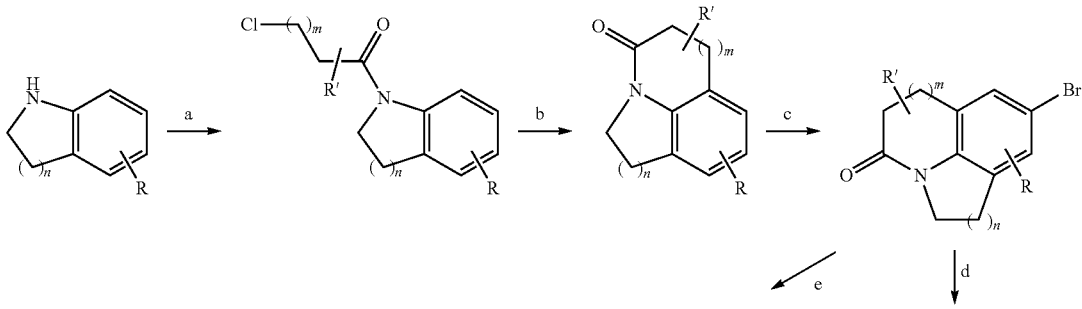

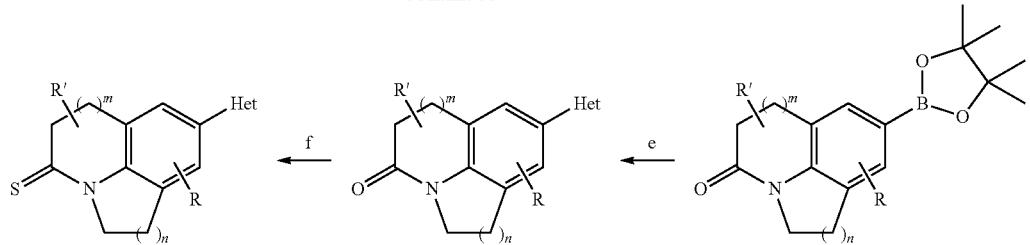

Scheme 2: a) ω-chlorocarboxylic acid chloride, acetone, 60° C.; b) AlCl$_3$, NaCl, 150° C.; c) NBS, DMF, 0° C.; d) bis(pinacolato)diborone, Pd(dppf)Cl$_2$, DMSO, 80° C.; e) Het—B(OH)$_2$ or Het—I or Het—Br or Het—OTf (Het having the meaning stated for formula (I), Pd(PPh$_3$)$_4$, Na$_2$CO$_3$, toluene/ethanol/water, 100° C., or: Pd(PPh$_3$)$_4$, NaHCO$_3$, DMF/water, μw, 150° C.; f) Lawesson's reagent, toluene, 120° C. (m = 0, 1, or 2; n = 1, 2, or 3).

In particular, 3,5-disubstituted pyridines carrying, in addition to the pyrrolo or pyrido quinolinone or pyrrolo or pyrido thione skeletal structure another sp$^2$-hybridized substituent (eg, aryl, heteroaryl) can be produced according to Scheme 3. The reaction sequence takes place in this case via two consecutive Suzuki couplings (Steps a and b). The resulting oxo compounds can be derivatized to the corresponding thio analogues with Lawesson's reagent (Step c).

Pyrrolo or pyrido quinolinones or pyrrolo or pyrido thiones in which the heterocycle is linked to the skeletal structure via an alkyl or alkanoyl linker are produced as depicted in Scheme 4 or Scheme 5. The starting compounds used are the tricyclic intermediate stages described in Scheme 2.

In the case of 1-imidazoles (Scheme 4), an alkylcarbonyl or arylcarbonyl substituent is first of all introduced by selective Friedel Crafts acylation (Step a), followed by reduction with NaBH$_4$ in methanol (Step b). The heterocycle is then introduced by reaction with thionyl-bis-imidazole in THF (Step c). The resulting oxo compounds can be derivatized to the corresponding thio analogues with Lawesson's reagent (Step d). In this scheme, R" stands for R$^8$ or R$^9$ in the meaning of A=CR$^8$R$^9$ in formula (I).

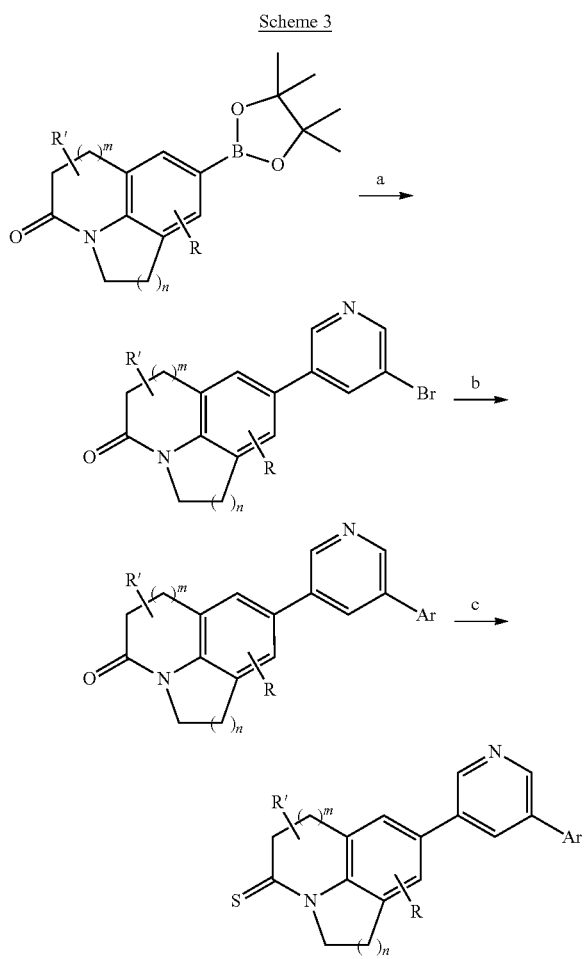

Scheme 3: a) 3,5-dibromopyridine, Pd(PPh$_3$)$_4$, Na$_2$CO$_3$, toluene/ethanol/water, 85° C.; b) Ar—B(OH)$_2$ (wherein Ar denotes a radical bonded to sp$^2$-hybridized carbon), Pd(PPh$_3$)$_4$, Na$_2$CO$_3$, toluene/ethanol/water, 100° C.; c) Lawesson's reagent, toluene, 120° C. (m = 0, 1, or 2; n = 1, 2, or 3).

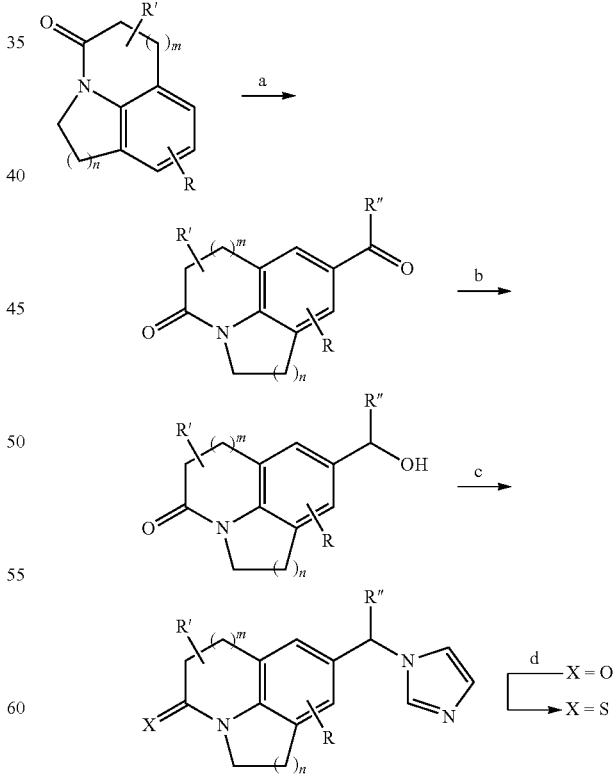

Scheme 4: a) R'—COCl (wherein R' denotes alkyl, aryl, or heteroaryl), CH$_2$Cl$_2$, RT; b) NaBH$_4$, methanol, 0° C.; c) thionyl-bis-imidazole, THF, RT; d) Lawesson's reagent, toluene, 120° C. (m = 0, 1, or 2; n = 1, 2, or 3).

In the synthesis of other heterocyclic compounds of the general structure (I) (Scheme 5), the introduction of the heterocycle is carried out via Friedel Crafts acylation (Step a). The resulting dioxo compounds can be derivatized further to form secondary or tertiary alcohols by reduction or the Grignard reaction (Step b) and subsequent reduction to alkanes (Step d), and also by thionation with Lawesson's reagent (Step c). In this scheme, R' stands for $R^8$ or $R^9$ in the meaning of $A=CR^8R^9$ in formula (I).

The synthesis of other compounds of this invention having a pyrrolo or pyrido quinolinone structure or a pyrrolo or pyrido thione structure and a thiadiazine indole dioxide structure (Scheme 6) starts from cyano or cyanoalkyl substituted indolines (n=1) or tetrahydroquinolines (n=2) via reduction (Step a) followed by cyclization with the introduction of an $SO_2$ group (Step b) or a CO group (Step c). There then follows, for the production of the pyrrolo or pyrido quinolinones

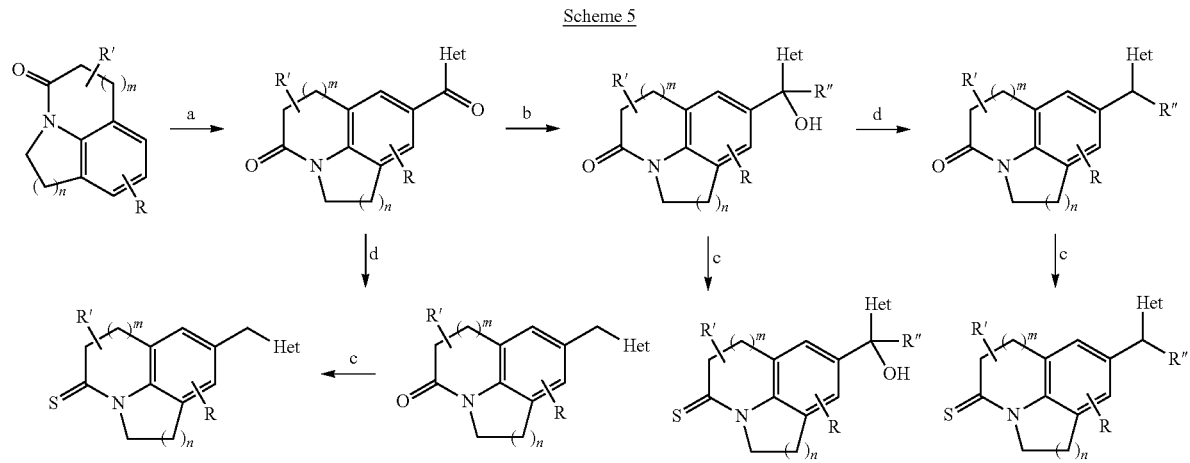

Scheme 5: a) Het-COCl (wherein Het denotes heteroaryl), $CH_2Cl_2$, RT; b) $NaBH_4$, methanol (when R' is H), or R'MgBr, $Et_2O$, 0° C. (when R' denotes alkyl, aryl, or heteroaryl), 0° C.; c) Lawesson's reagent, toluene, 120° C.; d) $NaBH_4$, $AlCl_3$, THF, 60° C., or: $Me_3SiCl$, NaI, $CH_3CN$, 65° C., or: $H_2$, Pd/C, THF, or methanol/$H_2SO_4$, RT to 60° C., or: Zn, $HCO_2H$/ethanol, or HCl, RT to 80° C., or: $N_2H_4$, KOH, diethylene glycol, 170° C. (m = 0, 1, or 2; n = 1, 2, or 3).

The carbonyl compounds obtained after introduction of the heterocycle via Friedel Crafts acylation (Step a, Scheme 5) can be converted to the corresponding cyclopropyl derivatives in another derivatization involving Wittig olefination followed by cyclopropanation via the Simmons Smith reaction (Scheme 5a).

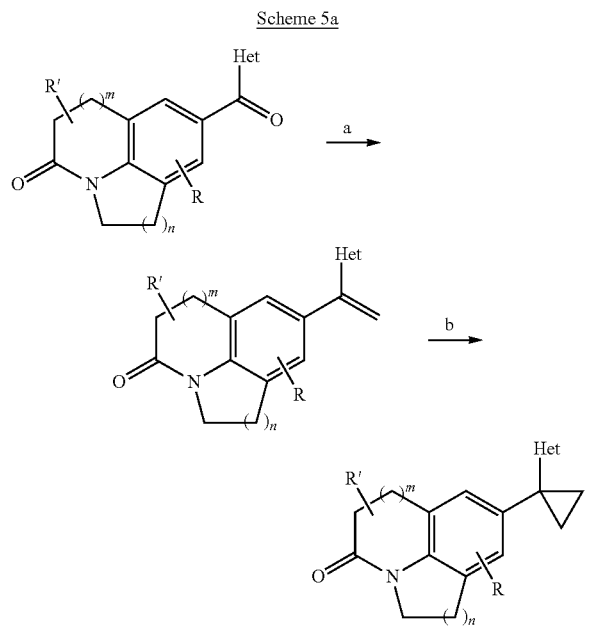

Scheme 5a: a) $Ph_3P=CH_2$ (prepared from $[Ph_3P-CH_3]^+$ Br⁻ and n-BuLi) $CH_2Cl_2$, RT; b) $ZnEt_2$, $CH_2I_2$, toluene, 60° C. (m = 0, 1, or 2).

or pyrrolo or pyrido thiones, the described synthesis sequence consisting of bromination, Suzuki coupling, nucleophilic derivatization of the quinazoline nitrogen, and thionation using Lawesson's reagent (Steps d to g). In this scheme, $R^7$ has the meanings stated with reference to the compounds of formula (I).

The cyano-substituted indoline (n=1, m=0, R'=H, R=H) used for the syntheses according to Scheme 6 is synthesized according to synthesis instructions described in the literature: [CAS: 115661-82-0], U.S. Pat. No. 5,380,857, EP 257583. Other substituted 7-cyanoindolines (n=1, m=0, R'=H) are synthesized according to the syntheses described in the literature for Scheme 2 from the correspondingly substituted indoles when R denotes, for example, 4-OMe [CAS: 389628-45-9], WO 2002004440, US 2003069245; or R denotes 4-F [CAS: 313337-33-6], commercially available; or R denotes 6-$NO_2$ [CAS: 354807-15-1], *Heterocycles* 2001, 55, 1151-59.

Other substituted 7-cyanoalkylindolines (n=1, m=1, R'=0) are synthesized by regioselective reduction of the corresponding commercially available indoles according to the syntheses described in the literature for Scheme 2 when, for example: R denotes H [CAS: 8299-98-2], R denotes 4-F [CAS: 1000516-43-7], or R denotes 4-OMe [CAS: 1000558-59-7]. 7-Aminoindoline [CAS: 2759-12-8] and 7-methylaminoindoline [CAS: 2580-93-0], (*J. Am. Chem. Soc.* 1966, 88, 4061-68), are directly converted according to Steps b and c.

The 8-alkylamino substituted tetrahydroquinolines used in Steps b and c according to Scheme 6 (n=2, R, R'=H, m=0, CAS: 148287-05-2) and (n=2, R, R'=H, m=1, CAS: 148287-05-3) are commercially available or are obtainable by syntheses described in the literature (FR 2675801, *J. Am. Chem. Soc.* 1966, 88, 4061-68).

Scheme 6

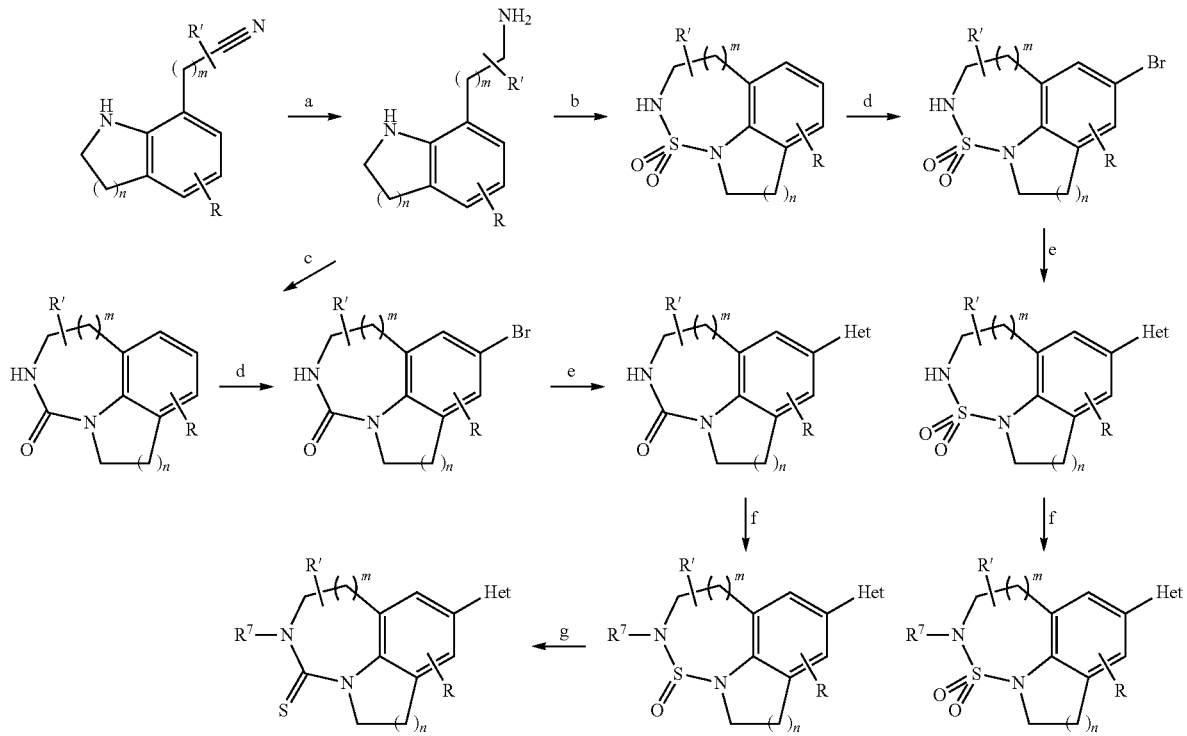

Scheme 6: a) LiAlH₄, THF, or Et₂O, RT to 65° C., or BH₃•THF, THF; b) H₂NSO₇NH₂, pyridine, 50° C. to 150° C.; c) ClCO₂M, or: triphosgene, THF; d) NBS, DMF, 0° C.; e) Het-B(OR)₂, Pd(PPh₃)₄, Na₂CO₃, toluene/ethanol/water, 100° C., or: Pd(PPh₃)₄, NaHCO₃, DMF/water, µw, 150° C.; f) R⁷—Br or R⁷—I (wherein R⁷ is alkyl), DMF or THF, base (eg, K₂CO₃ or NaH), RT to 65° C.; g) Lawesson's reagent, toluene, 120° C., (m = 0 or 1; n = 0, 2, or 3; R⁷ has the meanings stated with reference to formula (I)

The synthesis of oxazino indolones or oxazino quinolinones (Scheme 7) is carried out in a similar manner starting from carboxy substituted indolines (n=1) or tetrahydroquinolines (n=2). Following reduction to the alcohol starting from the carbonyl compound (ketone or aldehyde), wherein R' is alkyl or H respectively) or the carboxyl compound (carboxylic acid or carboxylate wherein R' is OH or OMe or OEt respectively) by means of a suitable reducing agent (eg, NaBH₄, BH₃.THF or LiAlH₄) or a Grignard reaction with a carbonyl compound (ketone or aldehyde, wherein R' is alkyl or H) (all Step a) there follows the aforementioned synthesis sequence (Steps b to e).

The 8-carboxy substituted indolines (n=1, m=0) used for the syntheses according to Scheme 7 are commercially available when R=H, R'=H [143262-21-9], or R=6-F, R'=H [603310-02-7], R=H, R'=Me [104019-19-4], or R=H, R'=OMe [112106-91-9]. The 8-carboxy indoline (R=H, R'=OH, CAS: 15861-40-2) is obtainable according to synthesis instructions described in the literature (WO 2003103398, J. Med. Chem. 1996, 39, 4692-03). The 8-carboxy substituted indolines extended by a methylene group (n=1, m=1) are, in the case of carboxylic acid (R'=OH, R=H, CAS: 2580-92-9) and of the corresponding methyl ester (R'=OMe, R=H, CAS: 7633-52-5), obtained by synthesis described in the literature (J. Am. Chem. Soc. 1966, 88, 4061-68). The corresponding keto compound (R=H, R'=Me, CAS: 7633-52-5) is commercially available.

The 8-carboxy substituted tetrahydroquinolines used for the syntheses according to Scheme 7 (n=2, m=0) are obtainable via syntheses described in the literature: R'=H, R=H [CAS: 69906-07-6], Synthesis 1979, 2, 99-100; R'=OMe, R=H [CAS: 477532-02-8], WO 2003022785, J. Org. Chem. 2002, 67, 7890-93; R'=OMe, R=5-F [CAS: 928839-61-6], WO 2007028789; R'=OMe, R=5-Br [CAS: 928839-65-0], WO 2007028789. The keto compound (R'=Me, R=H, CAS: 890093-80-8) is commercially available, as is the 8-carboxy substituted tetrahydroquinoline extended by a methylene group (n=2, m=1, R'=OH, R=H, CAS: 933727-44-7).

Scheme 7

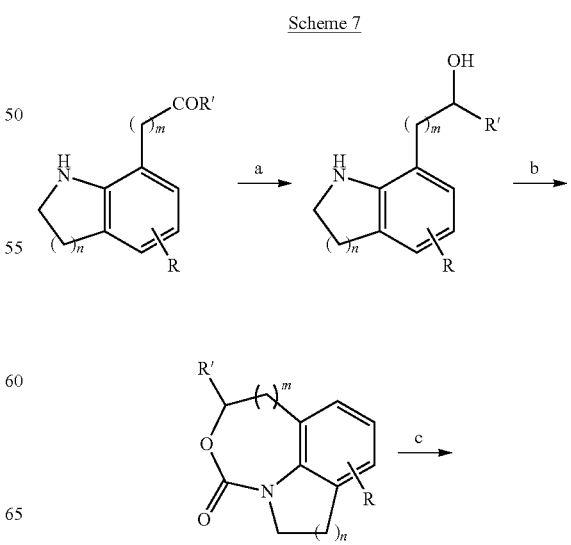

-continued

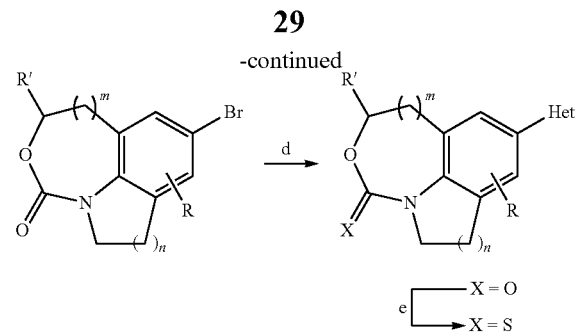

m = 0 or 1; n = 1, 2, or 3

Scheme 7: a) LiAlH₄ or NaBH₄, solvent (eg, THF, Et₂O or MeOH), RT
to 65° C., or BH₃•THF, THF (when R' is H, OH, OMe, or OEt), or: R'MgX, THF, 0° C.
to RT (when R' is alkyl); b) ClCO₂M, or: triphosgene, THF; c) NBS, DMF, 0° C; d) Het-B(OR)₂, Pd(PPh₀)₂, Na₃CO₄, toluene/ethanol/water, 100° C., or: Pd(PPh₃)₄, NaHCO₃, DMF/water, μw, 100° C.; e) Lawesson's reagent, toluene, 120° C.

Pyrroloquinoxalinones and oxazino and thiazino indolones are synthesized starting from U'-functionalized (wherein U' is $NH_2$, $NO_2$, OH, SH) indolines (n=1), or tetrahydroquinolines (n=2) (Scheme 8). For this purpose, acylation with an ω-chlorocarboxylic acid chloride or sulfonic acid chloride (Step a) is first carried out. This is followed by cyclization via an intramolecular $S_N$ reaction (Step b). A heterocycle is then introduced via Pd catalyzed cross coupling (Step c). The groups X', U', U and Z depicted in Scheme 8 can be further modified chemically prior to or after each Step a, b, or c eg, from X'=OH to X'=OTf, from U'=$NO_2$ to U'=$NH_2$, from U=NH to U=$NR^7$, from U=S to U=$SO_{(2)}$, or from Z=CO to Z=CS. Reactive functional groups such as —OH, —$NH_2$, —SH should be optionally protected during the synthesis with suitable protective groups described in the literature and should be deprotected at a suitable moment. U and Z have the meanings stated with reference to formula (I).

The substituted indolines used for the syntheses according to Scheme 8 (n=1) are synthesized according to synthesis instructions described in the literature: (U'=OH, X'=H, R=H, CAS: 4770-38-1, *Tetrahedron Lett.* 2005, 46, 1021-22), (U'=SH, X'=H, R=H, CAS: 72696-18-5, JP 54132597), (U'=$NH_2$, X'=Br, R=H, CAS: 503621-32-7, WO 2003027090) or are commercially available, (U'=OMe, X'=H, R=H, CAS: 334986-38-1), (U'=$NH_2$, X'=H, R=H, CAS: 2759-12-8), (U'=OMe, X'=OMe, R=H, CAS: 82260-13-7). Other substituted indolines (n=1) are synthesized by regioselective reduction of the corresponding commercially available indoles according to the synthesis instructions described in the literature for Scheme 2.

The substituted tetrahydroquinolines used for the syntheses according to Scheme 8 (n=2) are synthesized according to synthesis instructions described in the literature: (U'=SH, X'=H, R=H, CAS: 21570-31-0, *J. Org. Chem.* 1963, 28, 2581-7), (U'=$NH_2$, X'=Br, R=H, CAS: 859959-07-2, *Berichte der Deutschen Pharmazeutischen Gesellschaft* 1911, 20, 183-200), (U'=$NH_2$, X'=OMe, R=H, CAS: 19279-83-5, US 2007032469, EP 146370) or are commercially available (U'=OH, X'=H, R=H, CAS: 6640-50-2), (U'=OMe, X'=OMe, R=H, CAS: 953906-79-1), (U'=OMe, X'=H, R=H, CAS: 53899-17-5).

Scheme 8

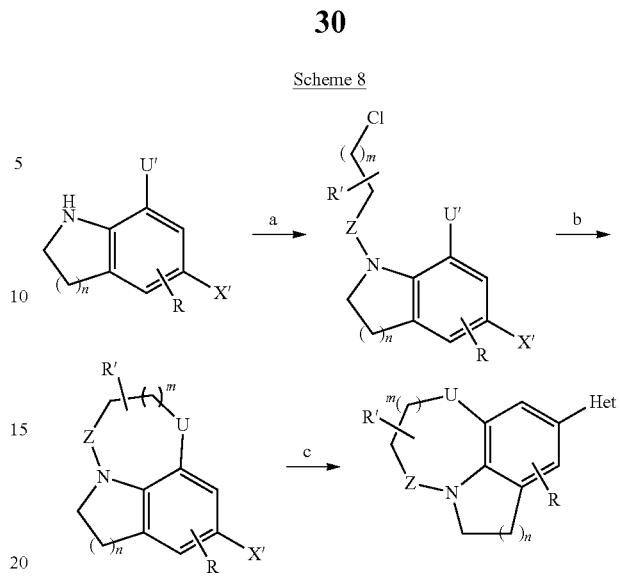

Scheme 8: X' = I, Br, Cl, OH, triflate; U' = $NH_2$ (eg, via reduction of U' = $NO_2$ following Step b), OH, SH; a) ω-Cl-alkyl-ZCl (wherein Z is CO, $SO_2$); b) DMF or THF, base (eg, $K_2CO_3$ or NaH), RT to 65° C.; c) Het-B(OR'')₂, Pd(PPh₃)₄, $Na_2CO_3$, toluene/ethanol/water, 100° C., or: Pd(PPh₃)₄, NaHCO₃, DMF/water, μw, 150° C.; when Z is CO conversion to CA via Lawesson's reagent, toluene, 120° C.; when U is S conversion to SO or $SO_2$ via oxidation, eg, mCPBA, dioxane; when U is NH conversion to $NR^7$ by reaction with $R^7$—I or $R^7Br$ (m = 0 or 1; n = 1, 2, or 3).

The indolines used for the syntheses can be obtained by reduction (eg, with sodium cyanoboron hydride) of the corresponding indoles. Compounds of the general formula (I) can be obtained by methods described in the literature, including in an enantiomerically pure state, for example, by salt formation with optically active acids (eg, (+)- or (−)-mandelic acid followed by separation of the diastereoisomeric salts by fractional crystallization or by derivatization with a chiral auxiliary followed by separation of the diastereoisomeric products by chromatography and/or recrystallization. The absolute configuration of freshly generated stereocenters can be determined by radiographic methods.

Syntheses of other heterocycles of the general structure (I) can be carried out as shown in the schemes listed below (Schemes 9 to 18). In Schemes 9, 10, and 12, R stands collectively for $R^2$, $R^3$, and $R^4$ in formula (I) at the positions stated.

The substituted methyl 2-aminobenzoates (methyl anthranilates) used for the syntheses according to Scheme 9 and having a leaving group at position 5 (X'=Br) are commercially available or are synthesized according to synthesis instructions described in the literature: R=H [CAS: 52727-57-8], commercially available; R=4-iPr [CAS: 1000018-13-2], commercially available; R=3-Me [CAS: 206548-14-3], commercially available; R=3-Br [CAS: 606-00-8], commercially available; R=6-Cl [CAS: 943138-46-3], *Bioorg. Med. Chem. Lett.* 2007, 17, 2817-22; R=6-Me [CAS: 573692-58-7], *Bioorg. Med. Chem. Lett.* 2007, 17, 2817-22; WO 2004108672; R=6-OMe [CAS: 681247-48-3], *Bioorg. Med. Chem. Lett.* 2007, 17, 2817-22; WO2004033419; R=6-OEt [CAS: 681247-12-1], *Bioorg. Med. Chem. Lett.* 2007, 17, 2817-22; WO2004033419; R=6-$NO_2$ [CAS: 90050-54-7], *Tetrahedron* 1963, 19, 1911-17; R=4-$NO_2$ [CAS: 174566-52-0], WO 9532205; R=4-OMe [CAS: 169044-96-6], WO 9518097; R=3-Cl [CAS: 101080-26-6], *Zhurnal Obshchei Khimii* 1957, 27, 1554-57; R=3-$NO_2$ [CAS: 636581-61-8], WO 2007148093; WO 2006099379; R=3-OMe [CAS: 115378-21-7], WO 2008019372; WO 2005113509.

Other substituted methyl anthranilates (X'=OMe) used, which are first of all derivatized by removal of the methyl group and conversion of the hydroxyl function by means of standard methods to the corresponding triflate, are obtainable according to syntheses described in the literature when R is 4-F [CAS: 159768-51-1], *Tetrahedron Lett.* 2005, 46, 7381-84; EP 635498; EP 602851; or R is 4-Cl [CAS: 181434-36-8], WO 9622991; U.S. Pat. No. 5,792,767.

Scheme 9

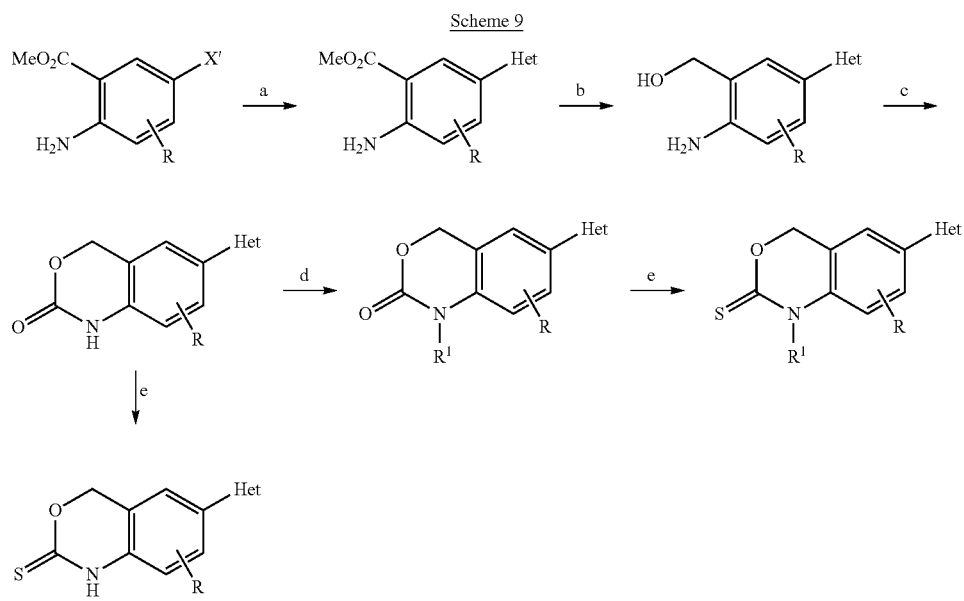

Scheme 9: a) Het-B(OR")$_2$, Pd(PPh$_3$)$_4$, Na$_2$CO$_3$, toluene/ethanol/water, 100° C., or: Pd(PPh$_3$)$_4$, NaHCO$_3$, DMF/water, μw, 150° C.; b) DIBAL, THF; c) triphosgene, THF; d) R$^1$—Br or R$^1$—I (wherein R$^1$ is alkyl or cycloalkyl), DMF or THF, base (eg, K$_2$CO$_3$ or NaH), RT to 65° C.; e) Lawesson's reagent, toluene, 120° C. X' stands for halogen (particularly Br) or triflate (OTf, produced from OH or OMe).

The substituted 2-nitrobenzonitriles used for the syntheses according to Scheme 10 and having a leaving group in position 5 (X'=Br, Cl, OTf) are commercially available or are synthesized according to synthesis instructions described in the literature: X'=Br, R=H [CAS: 89642-50-2], *J. Org. Chem.* 1961, 26, 4967-74; *J. Am. Chem. Soc.* 1960, 82, 3152-57; X'=Br, R=4-F [CAS: 927392-00-5], *J. Am. Chem. Soc.* 1960, 82, 3152-57; JP 2007204458; X'=Br, R=6-Me [CAS: 110127-08-7], U.S. Pat. No. 4,677,219; X'=Cl, R=4-F [CAS: 906559-47-5], WO 2006088919; X'=Cl, R=4-Me [CAS: 97113-40-1], *J. Med. Chem.* 1985, 28, 1387-93; X'=OH, R=4-Me [CAS: 873999-89-4], commercially available; X'=OH, R=6-NO$_2$ [CAS: 861604-57-1], commercially available.

Scheme 10

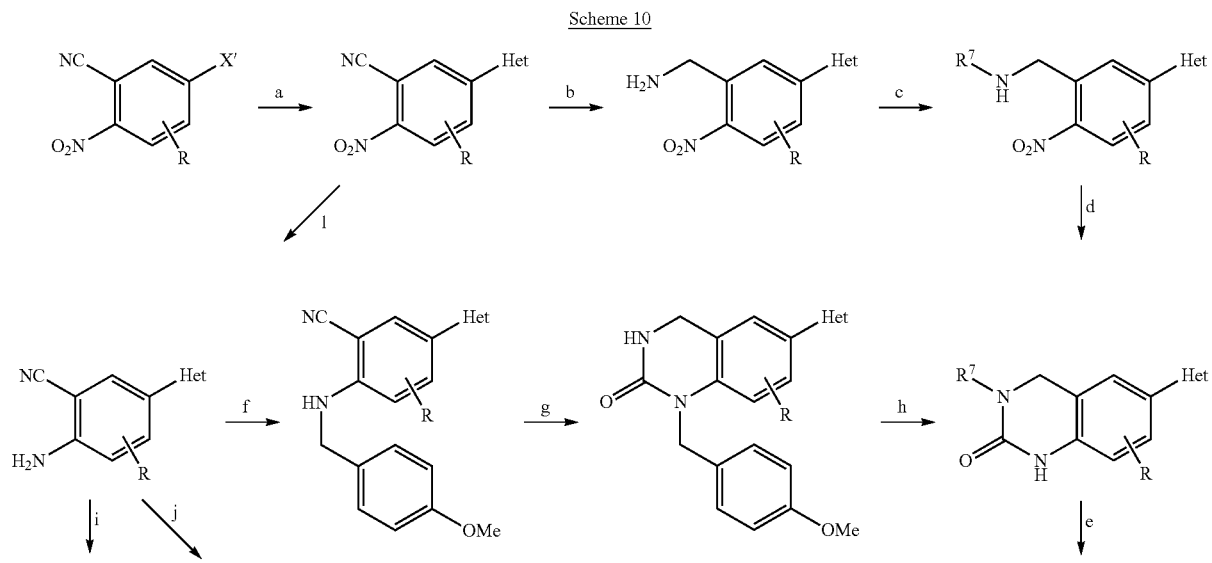

-continued

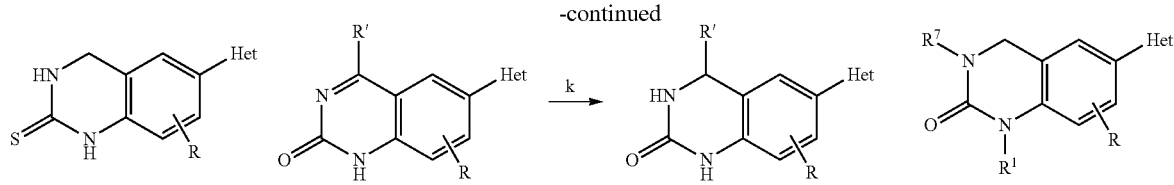

Scheme 10: a) Het-B(OR″)$_2$, Pd(PPh$_3$)$_4$, Na$_2$CO$_3$, toluene/ethanol/water, 100° C., or: Pd(PPh$_3$)$_4$, NaHCO$_3$, DMF/water, μw, 150° C.; b) BH$_3$•THF, THF; c) R$^7$CHO, NaHB(OAc)$_3$, EtOH, RT; d) 1st stage H$_2$ Pd/C, MeOH, 2nd stage triphosgene, THF; e) R$^1$—Br or R$^1$—I (wherein R$^1$ is alkyl), DMF or THF, base (eg, K$_2$CO$_3$ or NaH), RT to 65° C.; f) 4-MeOPhCH$_2$Cl, MeCN, heat; g) 1st stage LiAlH$_4$, THF, 2nd stage triphosgene, THF; h) 1st stage NaH, R$^7$—X, DMF, heat, 2nd stage TFA; i) 1st stage LiAlH$_4$, THF, 2nd stage EtOCS$_2$K, pyridine, heat; j) 1st stage R'MgBr, THF, 2nd stage ClCO$_2$M, THF; k) NaBH$_4$, MeOH, RT; LI) H$_2$ Pd/C, MeOH. R stands collectively for R$^2$, R$^3$, and R$^4$ in formula (I). R' has the meanings stated for R$^5$ or R$^6$ in formula (I). R$^1$ and R$^7$ have the meanings stated with reference to formula (I). X' stands for halogen (particularly I, Br, Cl) or triflate (OTf) or mesylate (OMs).

The ortho-fluoro substituted nitrobenzenes used for the syntheses according to Scheme 11 and having a leaving group in position 4 are commercially available: X'=Br [CAS: 321-23-3]; X'=Cl [CAS: 70037-8]; X'=OH [CAS: 394-41-2].

Scheme 11

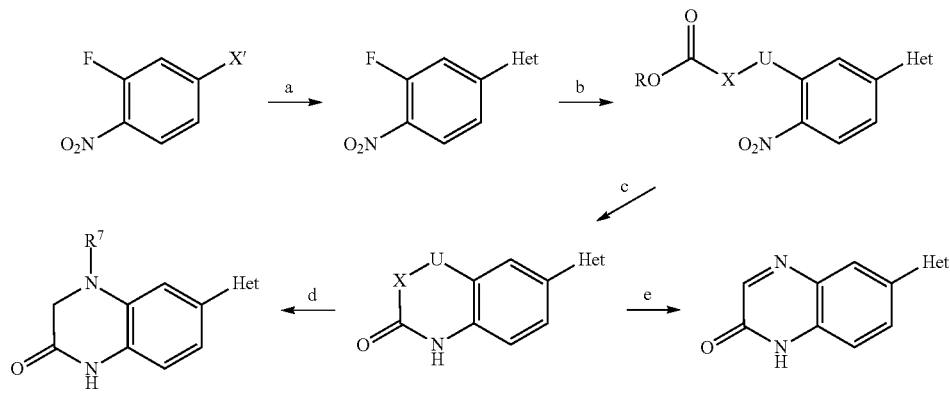

X is, eg, CR$^5$R$^6$ (eg, CH$_2$); U is, eg, NH, S, O; X' is I, Br, Cl, triflate (OTf)
Schema 11: a) Het-B(OR″)$_2$, Pd(PPh$_3$)$_4$, Na$_2$CO$_3$, toluene/ethanol/water, 100° C., or: Pd(PPh$_3$)$_4$, NaHCO$_3$, DMF/water, μw, 150° C.; b) RO$_2$CXUH, base, solvent, heat; c) 1st stage H$_2$ Pd/C, solvent, 2nd stage cyclization; d) R$^7$—Br or R$^7$—I, DMF or THF, base (eg, K$_2$CO$_3$ or NaH), RT or heat; e) H$_2$O$_2$, NaOH (aqeous), heat (when U is NH and X is CH$_2$). X and U have the meanings stated with reference to formula (I). R$^5$ and R$^6$ in the meaning of CR$^5$R$^6$ have the meanings stated for U and X with reference to formula (I).

The substituted 5-bromo-2-aminobenzonitriles used for the syntheses according to Scheme 12 are commercially available or are synthesized according to synthesis instructions described in the literature: R=H [CAS: 39263-32-6]; R=3-Cl [CAS: 914636-86-5]; R=3-Br [CAS: 68385-95-5]; R=3-Cl/6-F [CAS: 1000577-60-5]; R=4-Cl [CAS: 671795-60-1]; R=6-F [CAS: 845866-92-4]; R=3-CF$_3$ [CAS: 1000571-53-8]; all commercially available. R=3-OMe [CAS: 176718-54-0], Chem. Pharm. Bull. 1996, 44, 547-51; R=3-CN [CAS: 40249-43-2], JP 59134770, DE 2137719, GB 1411913; R=3-CN/4-Me [CAS: 88817-30-5], U.S. Pat. No. 4,582,898, DE 3220117; R=4-F/6-Me [CAS: 927392-19-6], WO 2007020936; R=6-Me [CAS: 110127-09-8], WO 9418980; R=6-Cl [CAS: 159020-87-8], WO 9418980.

Scheme 12

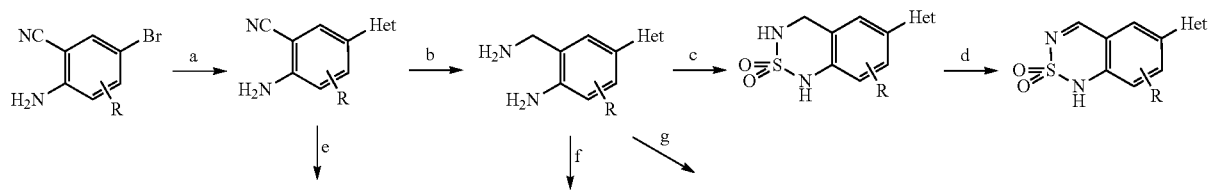

-continued

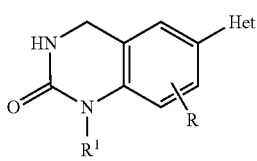
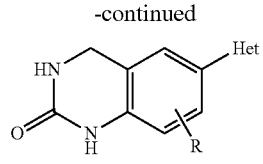
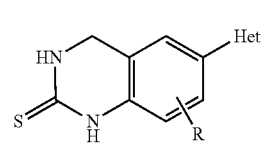

Scheme 12: a) Het-B(OR)$_2$, Pd(PPh$_3$)$_4$, Na$_2$CO$_3$, toluene/ethanol/water, 100° C., or: Pd(PPh$_3$)$_4$, NaHCO$_3$, DMF/water, μw, 150° C.; b) LiAlH$_4$, THF; c) H$_2$NSO$_2$NH$_2$, pyridine, heat; d) KMnO$_4$, base; e) 1st stage R$^1$—Br or R$^1$—I, DMF, or THF, base (eg, K$_2$CO$_3$ or NaH), RT or heat, 2nd stage LiAlH$_4$, THF, 3rd stage triphosgene, THF; f) triphosgene, THF; g) EtOCS$_2$K, pyridine, heat. R stands collectively for R$^2$, R$^3$, and R$^4$ in formula (I). R$^1$ has the meanings stated with reference to formula (I).

The 4-bromo-1-methoxy-2-nitrobenzene [CAS: 771583-12-1] used for the syntheses according to Scheme 13 is synthesized according to synthesis instructions described in the literature (WO 2008014822). 4-Chloro-1-methoxy-2-nitrobenzene [CAS: 109319-85-9] is commercially available.

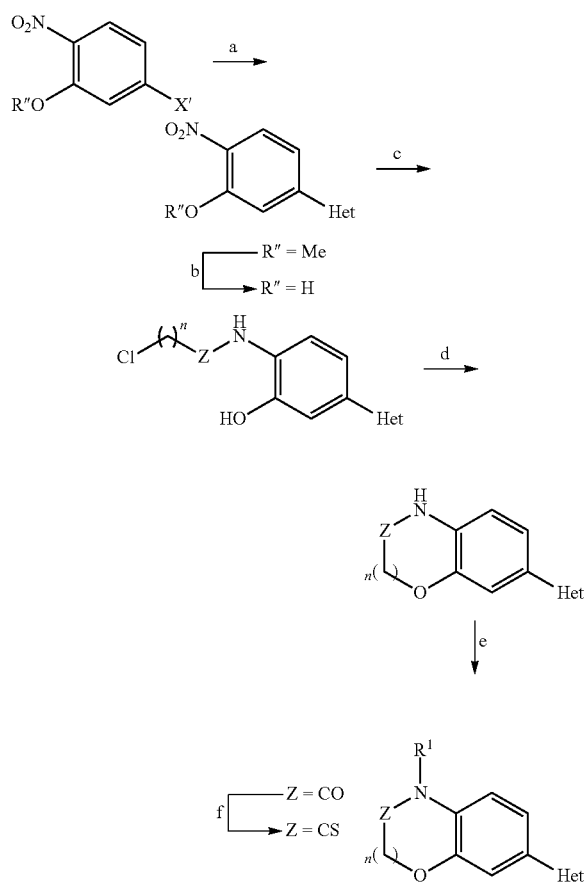

X' = Br, Cl, OTf; Z = CO, SO$_2$, n = 1, 2

Scheme 13: a) Het-B(OR")$_2$, Pd(PPh$_3$)$_4$, Na$_2$CO$_3$, toluene/ethanol/water, 100° C., or: Pd(PPh$_3$)$_4$, NaHCO$_3$, DMF/water, μw, 150° C.;b) LiCl, DMF, reflux, or HBr, AcOH, heat; c) 1st stage Zn, AcOH, 2nd stage Cl(CH$_2$)$_n$ZCl, base, solvent; d) K$_2$CO$_3$, solvent, heat; e)R$^1$—Br or R$^1$—I, DMF, or THF, base (eg, K$_2$CO$_3$ or NaH), RT or heat; f) Lawesson's reagent, toluene, 120° C. R$^1$ and Het have the meanings stated with reference to formula (I).

The substituted 3,4-dihydroquinolinones (U=CH$_2$, Z=CO) used for the syntheses according to Scheme 14 and having a leaving group (X'=OTf, Br, Cl) in position 6 are synthesized according to synthesis instructions described in the literature or are commercially available: (X'=Br, R=H, CAS: 3279-90-1), (X'=OH, R=H, CAS: 54197-66-9), (X'=Br, R=8-NO$_2$, CAS: 858213-76-0), (X'=Cl, R=7-Me, CAS: 116936-84-6), all commercially available; (X'=Br, R=8-Me, CAS: 1872-69-1, FR 1531330, U.S. Pat. No. 330,502, GB1046226); (X'=Br, R=5-OH, CAS: 148934-11-6, *Organic Preparation & Procedures International* 1993, 25, 223-28); (X'=Cl, R=7-OH, CAS: 72565-97-0, U.S. Pat. No. 4,482,560, DE 3034237, DE 2912105); (X'=Cl, R=7-OMe, CAS: 72565-96-9, U.S. Pat. No. 4,482,560, DE 3034237, DE 2912105); (X'=Cl, R=7-NH$_2$, CAS: 813425-54-6, WO 2004110986); (X'=Cl, R=8-Me, CAS: 2004-25-3, FR 1531330, DE 1289051); (X'=OH, R=8-F, CAS: 143268-82-0, *J. Med. Chem.* 1992, 35, 3607-12); (X'=OH, R=8-Cl, CAS: 119729-98-5, *J. Heterocycl. Chem.* 1988, 25, 1279-81); (X'=OH, R=7-Br, CAS: 71100-14-6, JP 54032481); (X'=OH, R=7-OMe, CAS: 68360-27-0, *J. Chem. Soc. Perkin Trans.* 1 1978, 5, 440-46); (X'=OH, R=7-NO$_2$, CAS: 359864-62-3, *Chem. Pharm. Bull.* 2001, 49, 822-29); (X'=OH, R=7-CO$_2$H, CAS: 59865-01-9, JP 51016679); (X'=OH, R=5-Cl, CAS: 69592-12-7, DE 2825048).

The substituted 2H-benzo[b][1,4]-oxazin-3(4H)-ones used for the syntheses according to Scheme 14 (U=O, Z=CO) and having a leaving group (X'=Br, OTf) in position 7 are synthesized according to synthesis instructions described in the literature or are commercially available: (X'=OH, R=H, CAS: 67193-97-9, WO 2006027684); (X'=OMe, R=5-Cl, CAS: 138035-69-5, *Heterocycles* 1991, 32, 1681-85); (X'=OMe, R=H, CAS: 6529-94-8, *J. Med. Chem.* 1987, 30, 580-83);

The substituted 2H-benzo[b][1.4]-thiacin-3(4H)-ones used for the syntheses according to Scheme 14 (U=S, Z=CO) and having a leaving group (X'=Br, OTf) in position 7 are synthesized according to synthesis instructions described in the literature or are commercially available: (X'=Br, R=H, CAS: 90814-91-8), (X'=OH, R=H, CAS: 91375-75-6), (X'=OMe, R=H, CAS: 22726-30-3), all commercially available.

The substituted cyclic sulfonamides (U=CH$_2$, Z=SO$_2$) used for the syntheses according to Scheme 14 and having a leaving group (X'=Br, OTf) in position 6 are synthesized according to synthesis instructions described in the literature: (X'=Br, R=H, CAS: 3279-87-6, U.S. Pat. No. 3,303,190, *J. Org. Chem.* 1965, 30, 3163-66); (X'=OMe, R=H, CAS: 93427-20-4, *J. Org. Chem.* 1984, 49, 9124-39).

Scheme 14

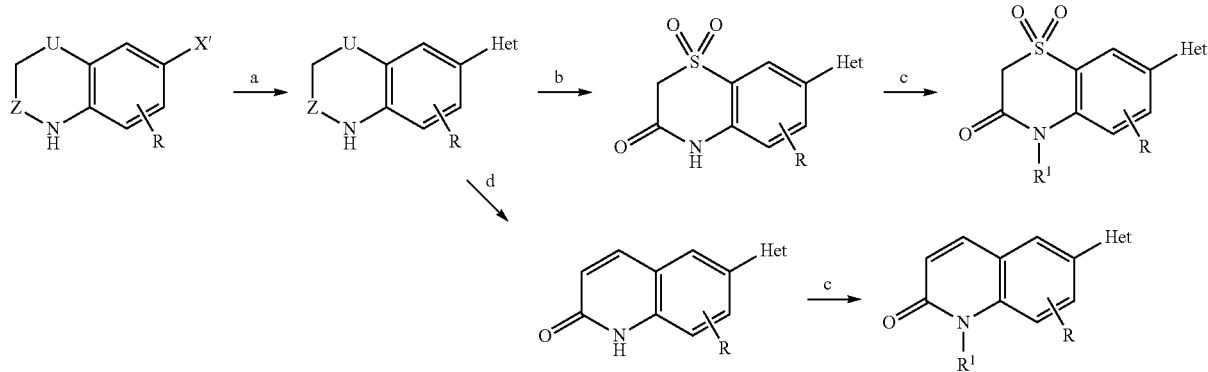

X' = Br, Cl, triflate (OTf); U = CH₂, S, O; Z = CO, SO₂

Scheme 14: a) Het-B(OR")₂, Pd (PPh₃)₄, Na₂CO₃, toluene/ethanol/water, 100° C., or: Pd(PPh₃)₄, NaHCO₃, DMF/water, μw, 150° C.; b) (when U is S and Z is CO) mCPBA, dioxane, heat; c)R¹—Br or R¹—I, DMF, or THF, base (eg, K₂CO₃ or NaH), RT or heat; d) (for U = CH₂, Z = CO) NBS, (BZO)₂, CHCl₃, heat. R¹, U, Z and Het have the meanings stated with reference to formula (I). R stands collectively for R², R³, and R⁴ in formula (I).

The bicyclic starting compounds used for the syntheses according to Scheme 15: 3,4-dihydroquinolinone (U=CH₂), CAS: 553-03-7; 2H-benzo[b][1,4]oxazin-3(4H)-on (U=O), CAS: 5466-88-6; 2H-benzo[b][1,4]thiazin-3(4H)-one (U=S), CAS: 5325-20-2; benzo[e][1,4]oxazepin-2(1H,3H,5H)-on (U=CH₂O), CAS: 3693-08-1; 4,5-dihydro-1H-benzo[b]azepin-2(3H)-on (U=CH₂—CH₂), CAS: 4424-80-0 are commercially available. Benzo[e][1,4]thiazepin-2(1H,3H,5H)-one (U=CH₂S) is synthesized according to synthesis instructions described in the literature (CAS: 1128-46-7, *J. Org. Chem.* 1965, 30, 3111-14).

The tricyclic starting compounds used for the syntheses according to Scheme 15 are synthesized according to synthesis instructions described in the literature or are commercially available: U=CH₂, CAS: 57369-32-1, commercially available; U=O, CAS: 67548-65-6, JP 54132597, JP 53062829; U=S, CAS: 72696-16-3, JP 54132597; (U=CH₂—CH₂), CAS: 221692-31-5, *Bioorg. Med. Chem. Lett.* 2003, 13, 701-04).

Scheme 15

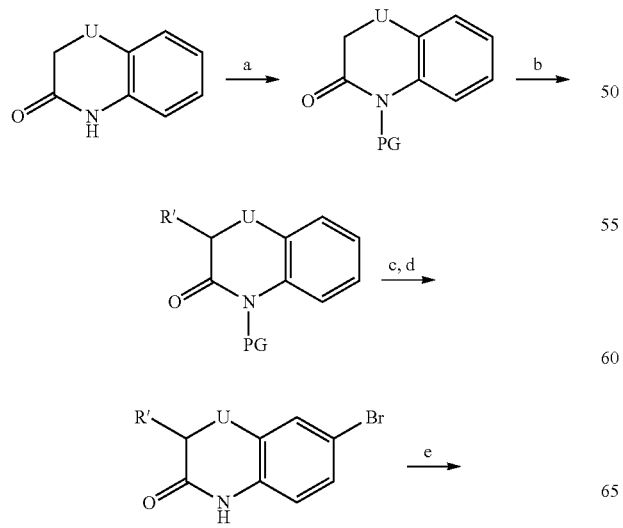

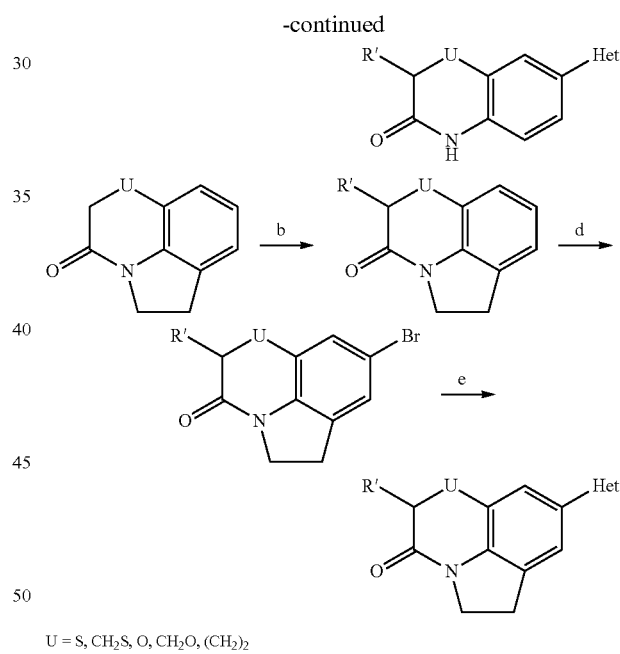

U = S, CH₂S, O, CH₂O, (CH₂)₂

Scheme 15: a) introduction of a protective group (PG) (eg, BoC₂O, base, solvent); b) 1st stage LDA, THF, -78° C., 2nd stage addition of R'—X' (wherein X' = I, Br, Cl, OTf, OM), heat to RT; c) removal of the protective group (eg, TFA, solvent); d) NBS, DMF, 0° C.; e) Het-B(OR")₂, Pd(PPh₃)₄, Na₂CO₃, toluene/ethanol/H₂O, 100° C., or: Pd(PPh₃)₄, NaHCO₃, DMF/water, μw, 150° C. R' stands collectively for R⁵ and R⁶ in the meaning of CR⁵R⁶ in U, X, and Y in formula (I). Het and U have the meanings stated with reference to formula (I).

The 5-bromo-2-nitrobenzaldehyde used for the syntheses according to Scheme 16 (CAS: 20357-20-4) is commercially available or is readily available according to the synthesis described in the literature (*Org. Lett.* 2003, 5, 2251-53). 2-Nitrobenzaldehyde (CAS: 552-89-6) is likewise commercially available.

Scheme 16

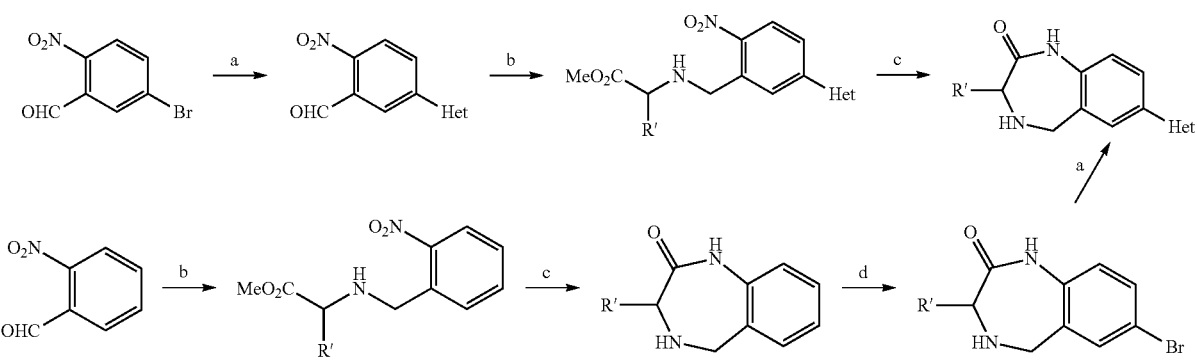

Scheme 16: a) Het-B(OR")₂, Pd(PPh₃)₄, Na₂CO₃, toluene/ethanol/water, 100° C., or: Pd(PPh₃)₄, NaHCO₃, DMF/water, μw, 150° C.; b) RCH(NH₂)CO₂M, MeOH, NaBH₃CN; c) 1st stage H₂, Pd/C, EtOAc, 2nd stage AlMe₃, toluene, 0° C.; d) NBS, DMF, 0° C. R' stands collectively for $R^5$ and $R^6$ in the meaning of $CR^5R^6$ in U, X, and Y in formula (I).

The 4-chloro-2-methoxy-1-nitrobenzene (X'=Cl) used for the syntheses according to Scheme 17, CAS: 6627-53-8 is commercially available. The 4-bromo-2-methoxy-1-nitrobenzene (X'=Br), CAS: 103966-66-1 is synthesized according to synthesis instructions described in the literature (WO 2006040182, WO 2002036588, WO 2001032631), likewise 3-methoxy-4-nitrophenol (X'=OH, CAS: 16292-95-8; *Org. Lett.* 2008, 10, 997-1000).

The starting compounds used for the syntheses according to Scheme 17—4-bromo-2-fluoro-1-nitrobenzene (X'=Br, CAS: 321-23-3), 4-chloro-2-fluoro-1-nitrobenzene (X'=Cl, CAS: 700-37-8), and 3-fluoro-4-nitrophenol (X'=OH, CAS: 394-41-2)—are commercially available.

Scheme 17

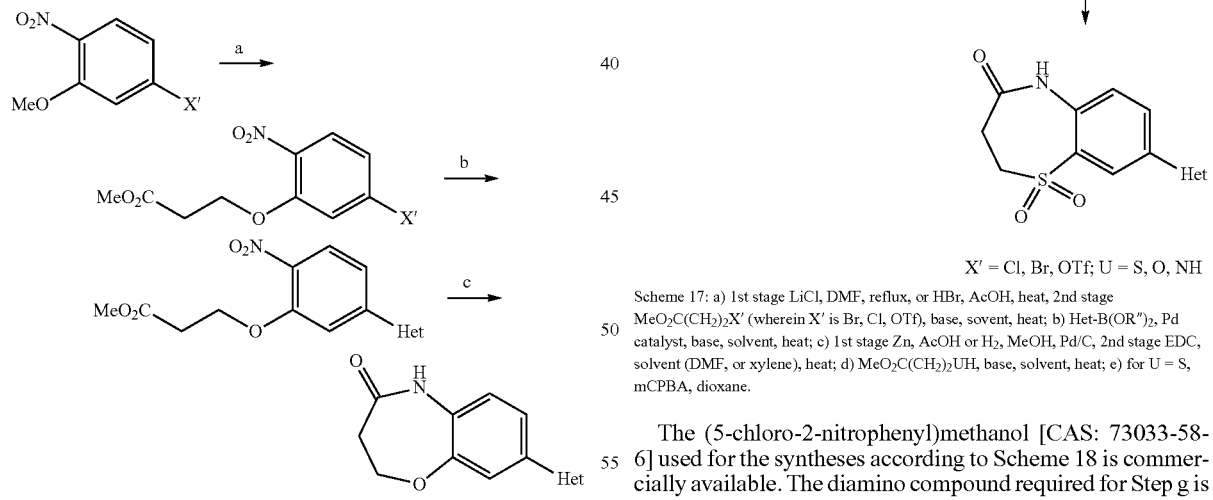

X' = Cl, Br, OTf; U = S, O, NH

Scheme 17: a) 1st stage LiCl, DMF, reflux, or HBr, AcOH, heat, 2nd stage MeO₂C(CH₂)₂X' (wherein X' is Br, Cl, OTf), base, sovent, heat; b) Het-B(OR")₂, Pd catalyst, base, solvent, heat; c) 1st stage Zn, AcOH or H₂, MeOH, Pd/C, 2nd stage EDC, solvent (DMF, or xylene), heat; d) MeO₂C(CH₂)₂UH, base, solvent, heat; e) for U = S, mCPBA, dioxane.

The (5-chloro-2-nitrophenyl)methanol [CAS: 73033-58-6] used for the syntheses according to Scheme 18 is commercially available. The diamino compound required for Step g is synthesized as described in Scheme 12.

Scheme 18

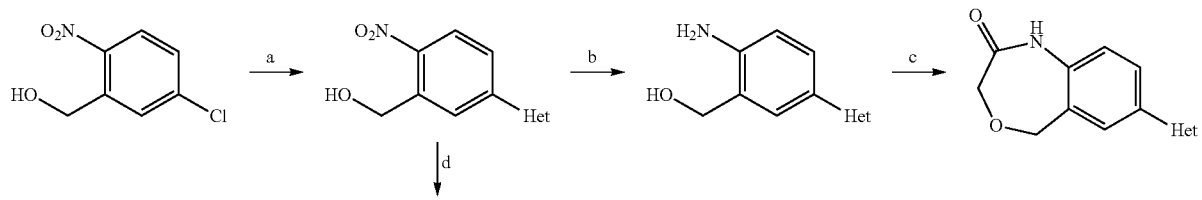

-continued

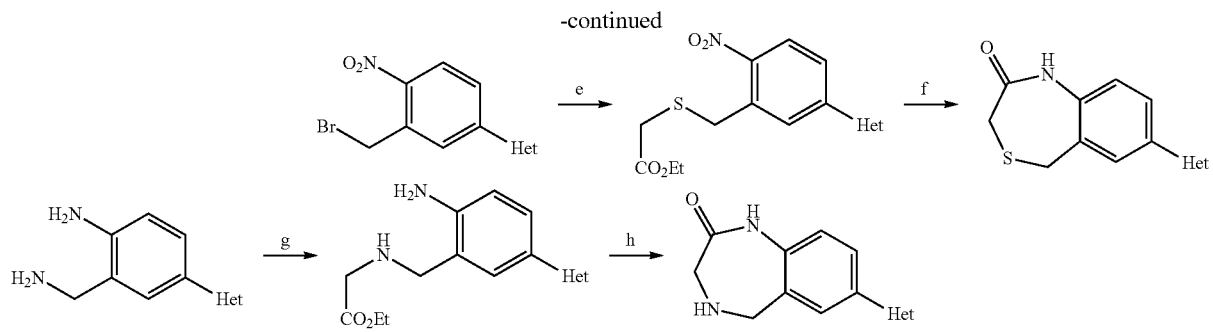

Scheme 18: a) Het-B(OR")$_2$, Pd catalyst, base, solvent, heat; b) Zn, AcOH; c) 1st stage ClCH$_2$COCl, base (eg, NEt$_3$), solvent, 2nd stage NaH, THF; d) PBr$_3$, pyridine; e) 1st stage EtO$_2$CCH$_2$SH, K$_2$CO$_3$, DMF, 2nd stage Zn, AcOH; solvent, reflux.

The starting compounds used for the syntheses according to Scheme 19 are synthetic or commercially available, as described in the syntheses illustrated above (cf Schemes 1, 2, 6, 7, 8, 14, 15 and 16).

The reaction products can be converted, by methods known to the person skilled in the art, to stable salts thereof, preferably HCl salts or other pharmaceutically acceptable salts thereof.

Scheme 19

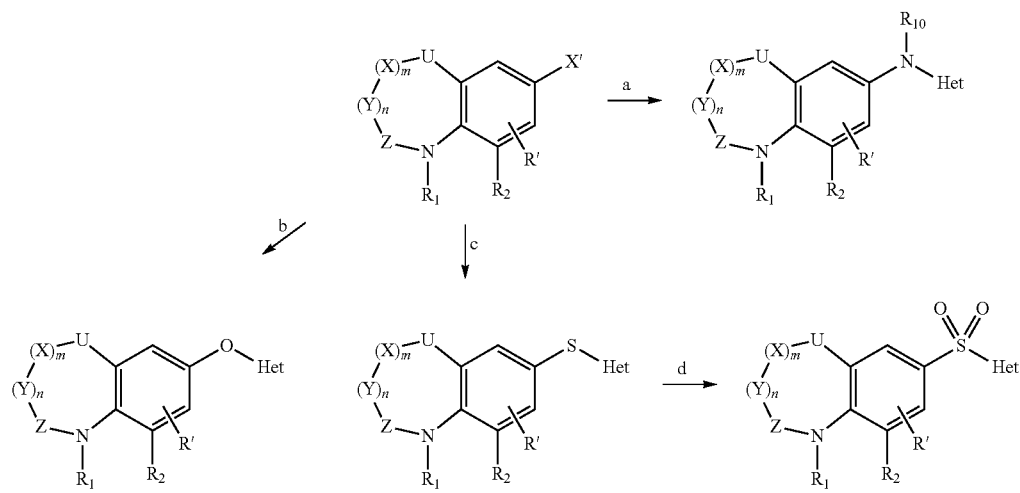

Scheme 19: a) Het-NHR$^{10}$, Pd catalyst (eg, Pd$_2$(dba)$_3$, PdCl$_2$(P-ortho-tolyl$_3$)$_2$) and possibly ligand (eg, BINAP, dppf), base (NaO$^t$O BU or LHMDS), solvent (toluene or dioxane), reflux; b) Het-OH, Cu catalyst (eg, CuCl, CuI, CuO), base (eg, K$_2$CO$_3$, Cs$_2$CO$_3$, pyridine), solvent (eg, NMP, DMSO), 100-150° C., or: Het-OH, Pd(OAc)$_2$, ligand, K$_3$PO$_4$, toluene, reflux; c) Het-SH, Cu catalyst (eg, CuCl, CuI, CuO), base (eg, K$_2$CO$_3$, Cs$_2$CO$_3$, pyridine), solvent (eq, NMP, DMSO), 100-150° C., or: Het-SH, Pd$_2$(dba)$_3$, ligand, KO$t$Bu, toluene, reflux; d) mCPBA, dioxane (m = 0, 1; N = 0, 1; X' = OTf, Br, I, Cl; Het has the meanings stated with reference to formula (I).

Those skilled in the art are conversant with the precise reaction conditions of the reactions illustrated in Schemes 1-19, which are all analogy processes. Further details are disclosed in the following examples.

Reactive functional groups present in the starting compounds or in intermediates formed during the synthesis (inter alia, alcohols, thiols, amines, carboxylic acids) should be protected, depending on the respective reaction conditions, using protective groups that are conventionally used in organic syntheses, as described in the literature. At suitable moments during the syntheses, the introduced protective groups are removed by the use of reaction conditions as described in the literature, (cf, eg, Theodora W. Greene, Peter G. M. Wuts, *Protective Groups in Organic Synthesis* (3rd Edition, John Wiley & Sons Inc. 1999) and Philip J. Kocienski, *Protecting Groups* (3rd Edition, Georg Thieme Verlag Stuttgart, New York 2005).

EXAMPLES

The following examples illustrate the present invention and are not intended to limit the scope thereof.

Chemical and analytical methods. Melting points were measured on a Mettler FP1 melting point apparatus and are uncorrected. $^1$H-NMR and $^{13}$C-NMR were recorded on a Bruker DRX-500 (500 MHz) instrument. Chemical shifts are given in parts per million (ppm), and tetramethylsilane (TMS) was used as internal standard for spectra obtained in DMSO-d$_6$ and CDCl$_3$. All coupling constants (J) are given in hertz. Mass spectra (LC/MS) were measured on a TSQ Quantum (Thermo Electron Corporation, Dreireich, Germany) instrument with a RP18 100-3 column (Macherey Nagel, Düren, Germany) and with water/acetonitrile mixtures as eluents. Reagents were used as obtained from commercial suppliers without further purification. Solvents were distilled before use. Dry solvents were obtained by distillation from appropriate drying reagents and stored over molecular sieves.

Flash chromatography was performed on silica gel 40 (35/40-63/70 μM) with hexane/ethyl acetate or dichloromethane/methanol mixtures as eluents, and the reaction progress was determined by thin-layer chromatography analyses on Alugram SIL G/UV254 (Macherey-Nagel). Visualization was accomplished with UV light and $KMnO_4$ solution. All microwave irradiation experiments were carried out in a CEM-Discover monomode microwave apparatus.

The following are the structural formulae of the compounds synthesized in the Examples:

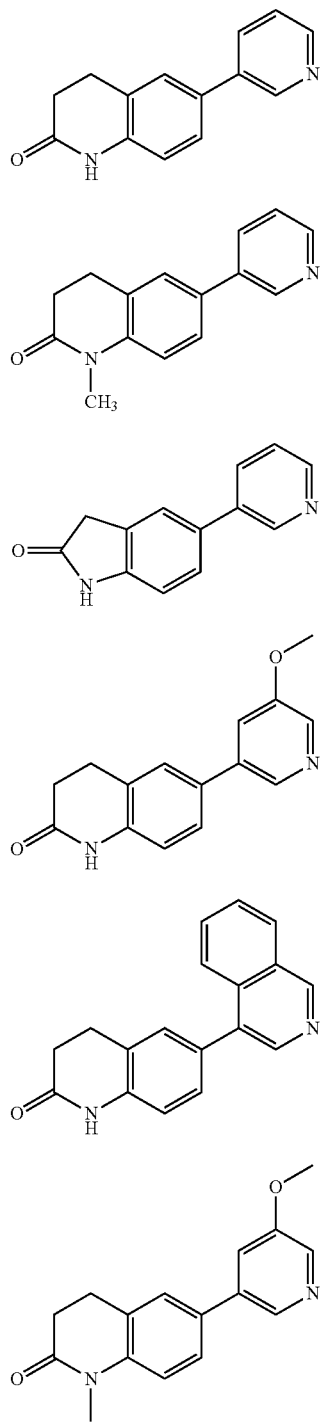
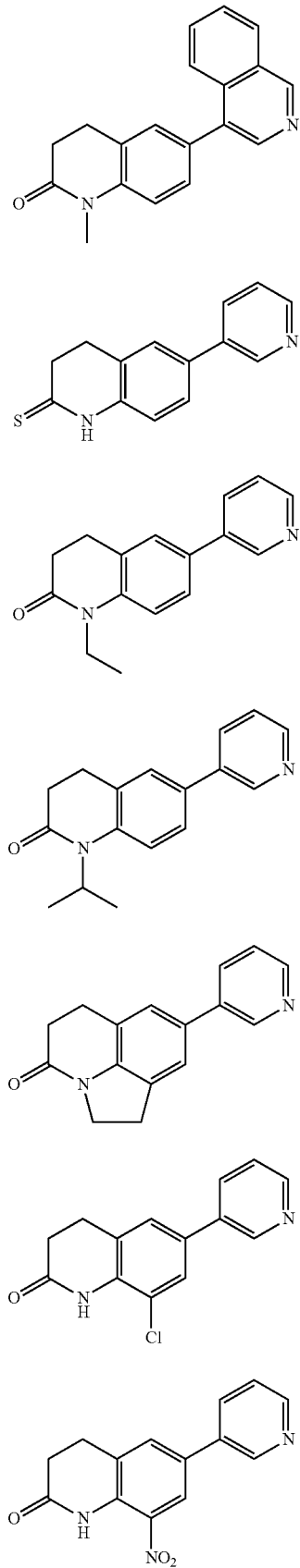

14
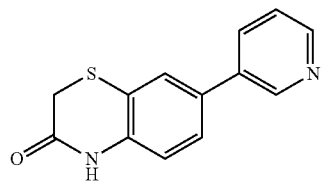
15
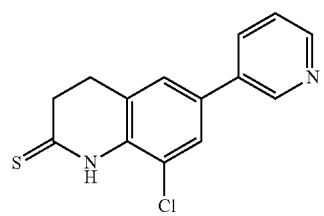
16
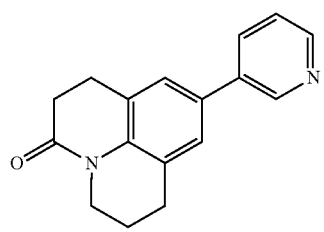
17
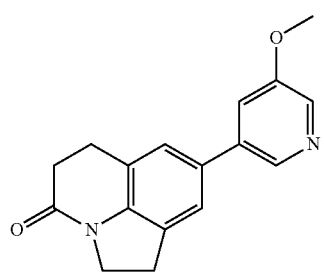
18
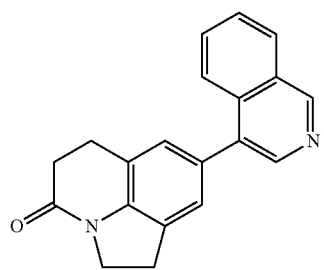
19
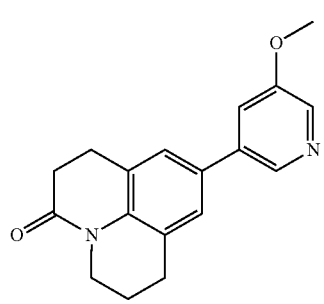
20
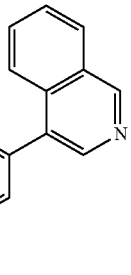
21
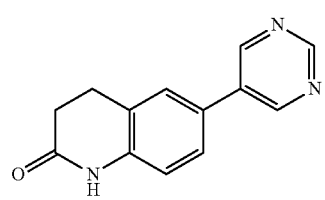
22
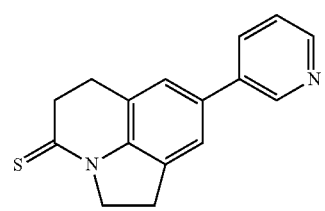
23
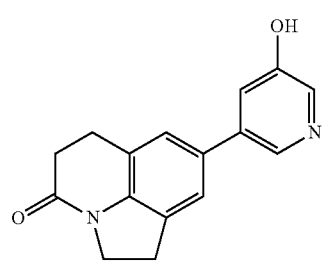
24
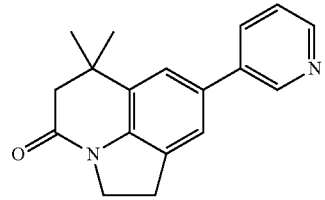
25
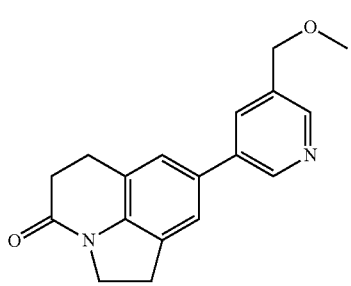

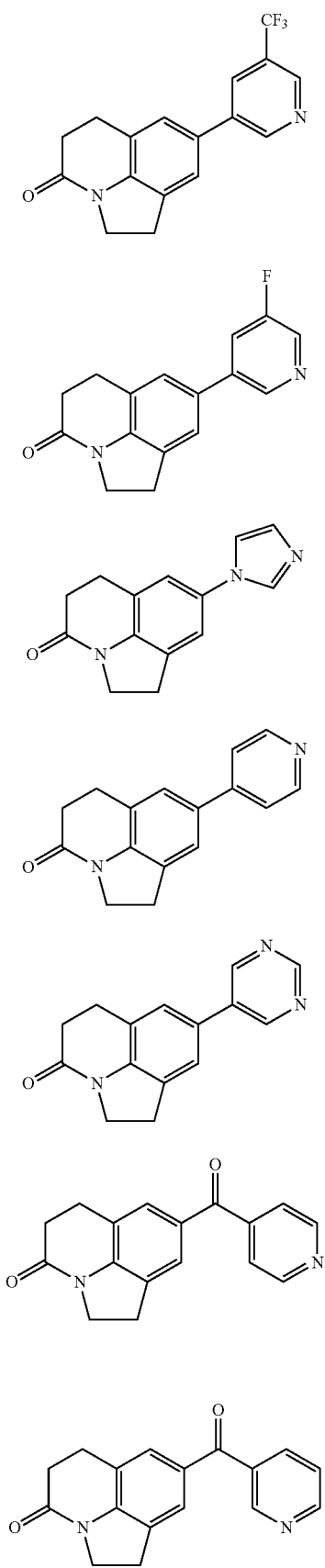
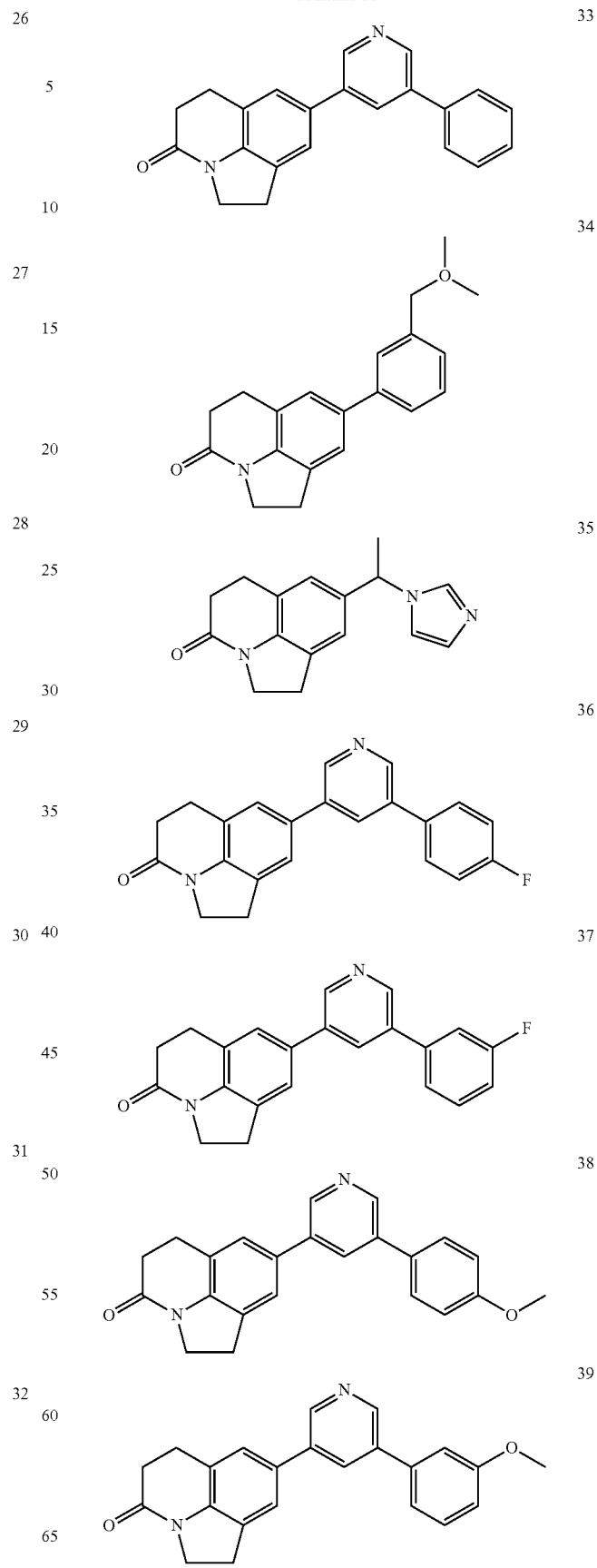

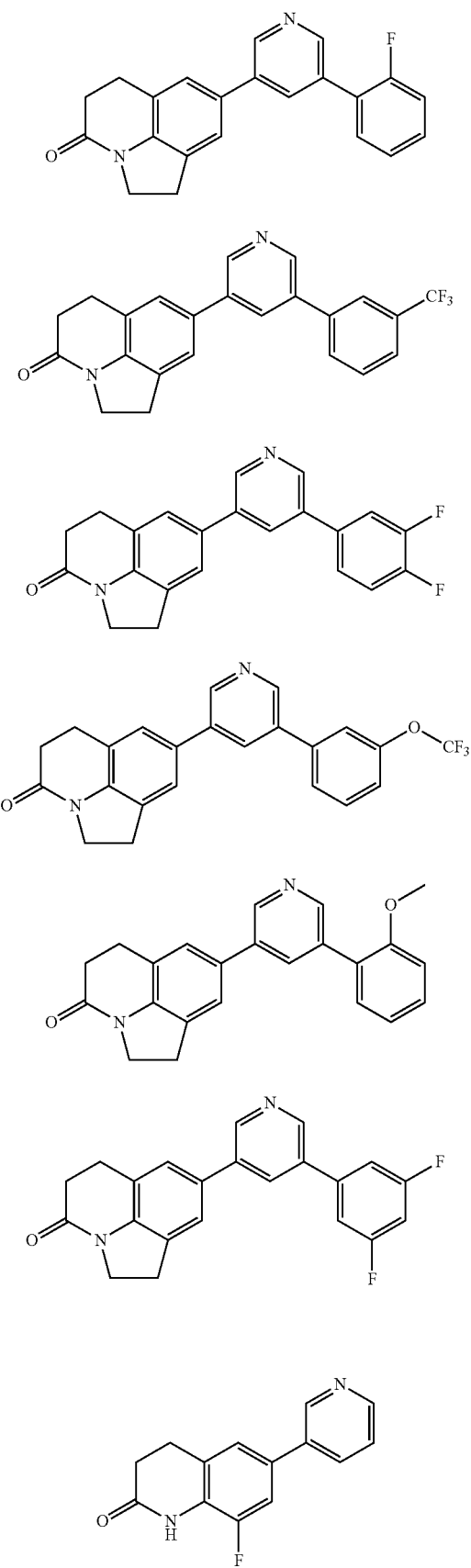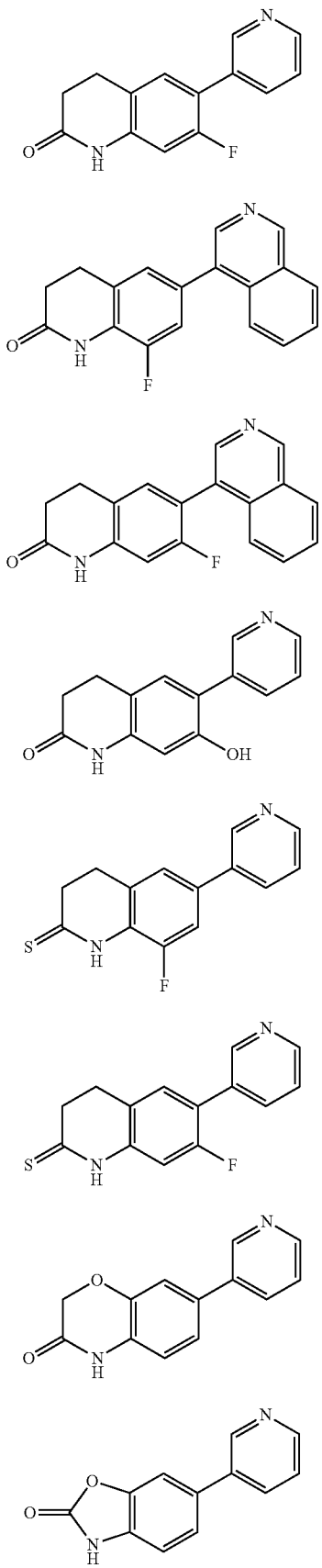

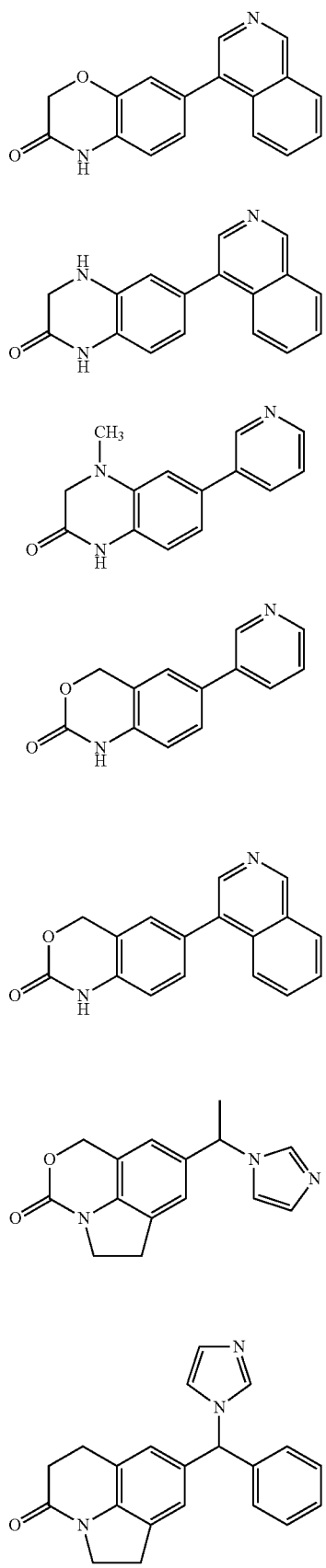
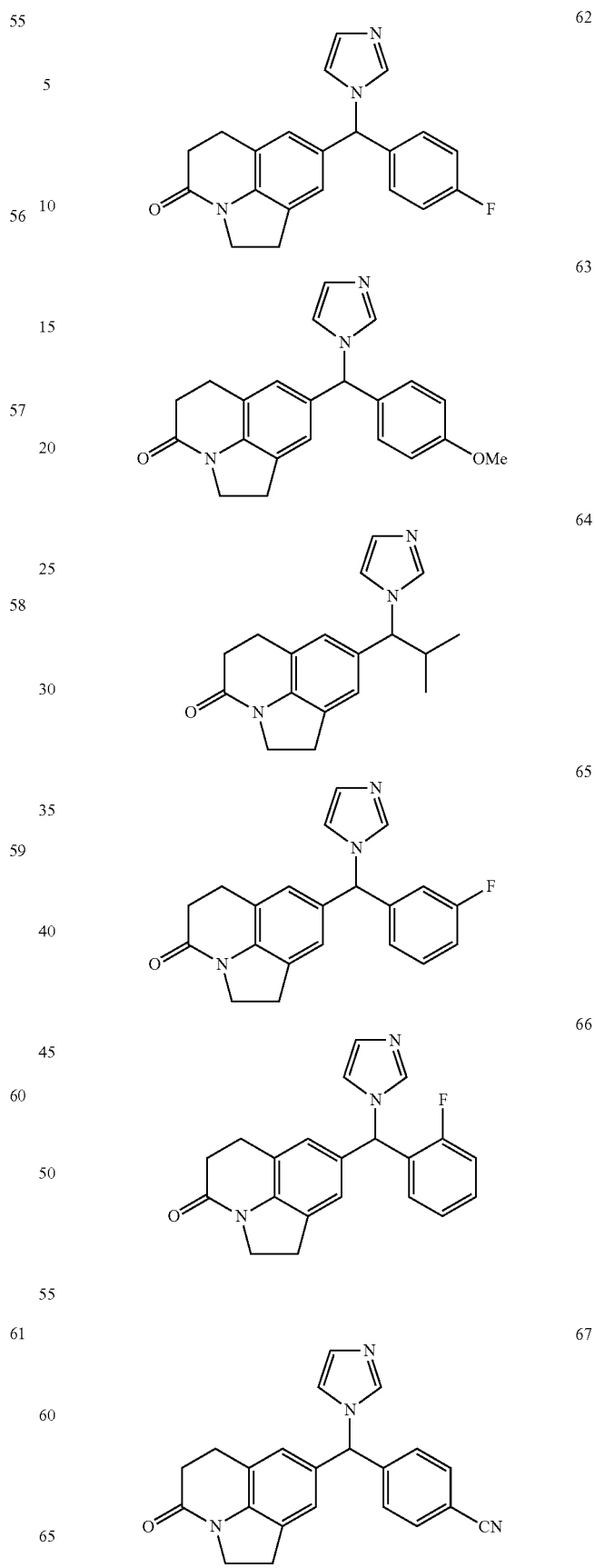

| | |
|---|---|
| 68 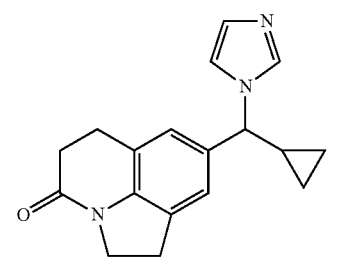 | 74 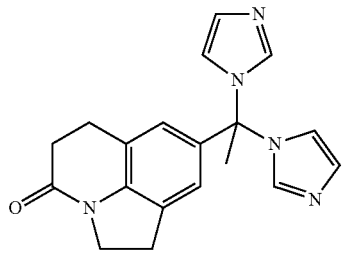 |
| 69 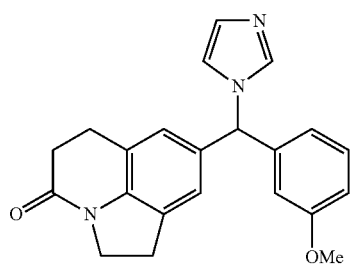 | 75 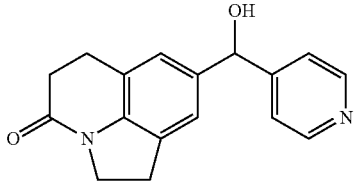 |
| 70 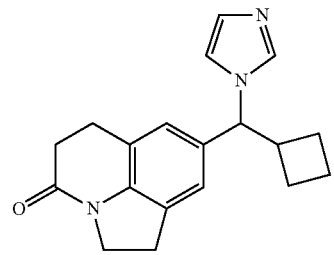 | 76 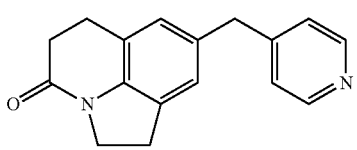 |
| 71 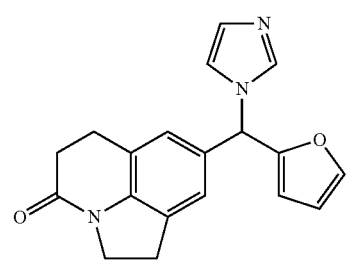 | 77 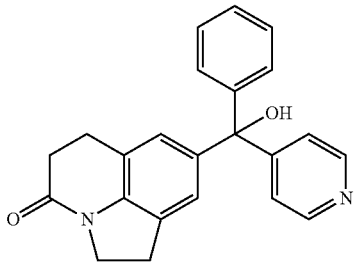 |
| 72 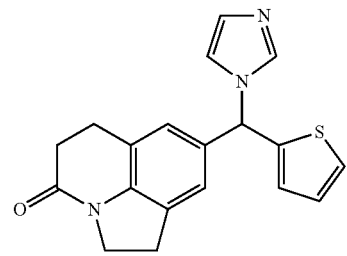 | 78 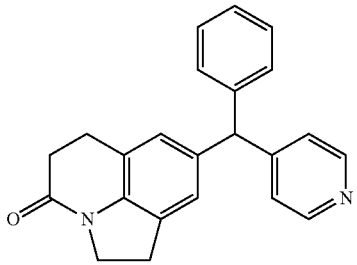 |
| 73 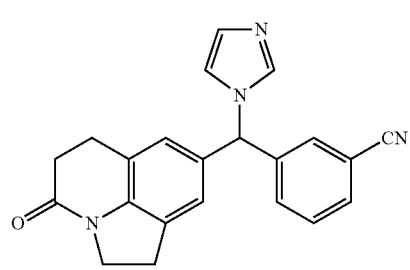 | |

Synthesis of the Starting Materials and Intermediates

General Procedure I: Bromination

To a solution of the corresponding substituted tetrahydro-1H-quinolin-2-one (0.75 mol, 1 equivalent) in DMF (50 mL) was added dropwise a solution of NBS (0.79 mol, 1.05 equivalents) in DMF (20 mL) under $N_2$ in an ice bath. Then the reaction mixture was stirred at 0° C. for 10 to 15 hours before dilution with water. The mixture was extracted 3 times with ethyl acetate, then the combined organic layers were washed with brine, dried over $MgSO_4$ and the solvents were removed in vacuo. The solid residues were purified by flash chromatography on silica gel (hexanes/ethyl acetate) to give the desired product.

Synthesis Example 1

6-Bromo-3,4-dihydro-1H-quinolin-2-one

To a solution of 3,4-dihydro-1H-quinolin-2-one (10.0 g, 67.9 mmol) in 100 ml dry DMF was added dropwise a solution of N-bromosuccinimide (12.7 g, 71.3 mmol) in 150 ml dry DMF at 0° C. The mixture was stirred at 0° C. for 2 h, then 400 ml water was added and the solution was extracted with ethyl acetate (3×150 ml). The organic phase was washed with water (2×200 ml), then dried over $MgSO_4$ and evaporated, affording a yellow solid which was purified by washing with cold ether providing pure 6-bromo-3,4-dihydro-1H-quinolin-2-one (13.6 g, 60.3 mmol, 89%) as colorless needles.

Synthesis Example 2

6-Bromo-1-methyl-3,4-dihydro-1H-quinolin-2-one

To a solution of 6-bromo-3,4-dihydro-1H-quinolin-2-one (339 mg, 1.50 mmol) in 15 ml dry DMF was added potassium tert-butylate (336 mg, 3.0 mmol). After the mixture was stirred for 30 min at room temperature, a solution of methyl iodide (426 mg, 3.0 mmol) in 5 ml dry DMF was added. Following overnight stirring, the mixture was diluted with 100 ml 1 N HCl. Extraction with ethyl acetate (2×100 mL) followed by washing of the organic extracts with water and brine, drying over $MgSO_4$ and removal of the solvent in vacuo gave a light yellow solid. Purification by flash chromatography (hexanes/ethyl acetate, 7/3, $R_f$=0.21) gave 6-bromo-1-methyl-3,4-dihydro-1H-quinolin-2-one (281 mg, 1.17 mmol, 78%) as colorless needles.

Synthesis Example 3

6-Bromo-1-ethyl-3,4-dihydro-1H-quinolin-2-one

To a solution of 6-bromo-3,4-dihydro-1H-quinolin-2-one (750 mg, 3.32 mmol) in 20 ml dry DMF was added potassium tert-butylate (804 mg, 6.64 mmol). After the mixture was stirred for 30 min at room temperature, a solution of ethyl bromide (724 mg, 6.64 mmol) in 10 ml dry DMF was added. Following overnight stirring, the mixture was diluted with 150 ml 1 N HCl. Extraction with ethyl acetate (2×100 mL) followed by washing of the organic extracts with water and brine, drying over $MgSO_4$ and removal of the solvent in vacuo gave a light yellow solid. Purification by flash chromatography (hexanes/ethyl acetate, 1/1, $R_f$=0.52) gave 6-bromo-1-ethyl-3,4-dihydro-1H-quinolin-2-one (583 mg, 2.29 mmol, 59%) as a colorless solid.

Synthesis Example 4

6-Bromo-1-isopropyl-3,4-dihydro-1H-quinolin-2-one

To a solution of 6-bromo-3,4-dihydro-1H-quinolin-2-one (750 mg, 3.32 mmol) in 20 ml dry DMF was added potassium tert-butylate (804 mg, 6.64 mmol). After the mixture was stirred for 30 min at room temperature, a solution of isopropyl bromide (814 mg, 6.64 mmol) in 10 ml dry DMF was added and the mixture heated to 80° C. After stirring for additional 48 h, the mixture was cooled to room temperature and diluted with 150 ml 1 N HCl. Extraction with ethyl acetate (2×100 mL) followed by washing of the organic extracts with water and brine, drying over $MgSO_4$ and removal of the solvent in vacuo gave a light yellow solid. Purification by flash chromatography (hexanes/ethyl acetate, 4/1, $R_f$=0.21) gave 6-bromo-1-isopropyl-3,4-dihydro-1H-quinolin-2-one (347 mg, 1.29 mmol, 33%) as pale yellow solid.

Synthesis Example 5

1,2,5,6-Tetrahydro-pyrrolo[3,2,1-ij]quinolin-4-one

A solution of 3-chloropropanoyl chloride (9.1 ml, 95.0 mmol) in 20 ml dry acetone was added dropwise to a solution of indoline (20.5 g, 0.21 mol) in 80 ml dry acetone and the mixture was refluxed for 1 h. After cooling to ambient temperature the solution was poured into 500 ml stirred 2N HCl and extracted with ethyl acetate (3×150 ml). After washing with 1N HCl and brine and drying over $MgSO_4$ the solvent was removed under reduced pressure and the crude product was obtained as a pale yellow solid. This was added portionwise to a molten mixture of $AlCl_3$ (60.0 g, 0.45 mol) and NaCl (17.5 g, 300 mmol) at 150° C. and stirred for additional 30 min. On cooling, excess aluminum chloride was decomposed by the addition of a chilled mixture of 20 ml concentrated hydrochloric acid and 500 ml water. Extraction with ethyl acetate (3×200 ml), followed by drying over $MgSO_4$ and removal of the solvent gave a yellow solid, which was purified by crystallization from acetone/ether yielding 1,2,5,6-tetrahydro-pyrrolo[3,2,1-ij]quinolin-4-one (11.8 g, 65.8 mmol, 69%) as colorless needles.

Synthesis Example 6

1,2,6,7-Tetrahydro-5H-pyrido[3,2,1-ij]quinolin-3-one

A solution of 3-chloropropanoyl chloride (9.1 ml, 95.0 mmol) in 20 ml dry acetone was added dropwise to a solution of 1,2,3,4-tetrahydroquinoline (26.6 g, 0.20 mol) in 80 ml dry acetone and the mixture was refluxed for 1 h. After cooling to ambient temperature the solution was poured into 500 ml stirred 2N HCl and extracted with ethyl acetate (3×150 ml). After washing with 1N HCl and brine and drying over $MgSO_4$ the solvent was removed under reduced pressure and the crude product was obtained as a pale yellow solid. This was added portionwise to a molten mixture of $AlCl_3$ (60.0 g, 0.45 mol) and NaCl (17.5 g, 300 mmol) at 150° C. and stirred for additional 30 minutes. On cooling, excess aluminum chloride was decomposed by the addition of a chilled mixture of 20 ml concentrated hydrochloric acid and 500 ml water. Extraction with ethyl acetate (3×200 ml), followed by drying over $MgSO_4$ and removal of the solvent gave 1,2,6,7-tetrahydro-5H-pyrido[3,2,1-ij]quinolin-3-one (15.6 g, 83.3 mmol, 88%) as a yellow solid.

Synthesis Example 7

8-Bromo-1,2,5,6-tetrahydro-pyrrolo[3,2,1-ij]quinolin-4-one

To a solution of 1,2,5,6-tetrahydro-pyrrolo[3,2,1-ij]quinolin-4-one (10.0 g, 55.8 mmol) in 100 ml dry DMF was added dropwise a solution of N-bromosuccinimide (10.4 g, 58.6 mmol) in 150 ml dry DMF at 0° C. The mixture was stirred at 0° C. for 2 h, then 400 ml water was added and the solution was extracted with ethyl acetate (3×150 ml). The organic phase was washed with water (2×200 mL), then dried over $MgSO_4$ and evaporated, affording a yellow solid, which was purified by crystallization from acetone/ether providing pure 8-bromo-1,2,5,6-tetrahydro-pyrrolo[3,2,1-ij]-quinolin-4-one (12.8 g, 50.8 mmol, 91%) as pale yellow needles.

Synthesis Example 8

9-Bromo-1,2,6,7-tetrahydro-5H-pyrido[3,2,1-ij]quinolin-3-one

To a solution of 1,2,6,7-tetrahydro-5H-pyrido[3,2,1-ij]quinolin-3-one (9.1 g, 48.6 mmol) in 100 ml dry DMF was added dropwise a solution of N-bromosuccinimide (9.08 g, 51.0 mmol) in 150 ml dry DMF at 0° C. The mixture was stirred at 0° C. for 2 h, then 400 ml water was added and the solution was extracted with ethyl acetate (3×150 ml). The organic phase was washed with water (2×200 ml), then dried over MgSO$_4$ and evaporated, affording a yellow solid, which was purified by crystallization from acetone/ether providing pure 9-bromo-1,2,6,7-tetrahydro-5H-pyrido[3,2,1-ij]quinolin-3-one (6.53, 24.5 mmol, 50%) as pale yellow needles.

Synthesis Example 9

8-(4,4,5,5-Tetramethyl-[1,3,2]dioxaborolan-2-0)-1,2,5,6-tetrahydro-pyrrolo[3,2,1-ij]quinolin-4-one To a solution of bis(pinacolato)diboron (1.75 g, 6.90 mmol), potassium acetate (1.96 g, 20.0 mmol) and [1,1-Bis(diphenylphosphino)ferrocene]dichloropalladium(II) (158 mg, 0.19 mmol) in 50 ml degassed DMSO was added 8-bromo-1,2,5,6-tetrahydro-pyrrolo[3,2,1-ij]quinolin-4-one (1.58 g, 6.30 mmol) under an atmosphere of nitrogen, and the mixture was stirred for 2 h at 80° C. After cooling to ambient temperature the solution was poured into 100 ml water and extracted with ethyl acetate (3×100 ml). The combined organic layers were washed with water (3×100 ml), dried over MgSO$_4$ and concentrated in vacuo to give the crude product which was crystallized from acetone to yield pure 8-(4,4,5,5-tetramethyl-[1,3,2]dioxaborolan-2-yl)-1,2,5,6-tetrahydro-pyrrolo[3,2,1-ij]quinolin-4-one (1.40 g, 4.68 mmol, 74%) as pale yellow plates.

Synthesis Example 10

6-Bromo-8-fluoro-3,4,4a,8a-tetrahydro-1H-quinolin-2-one

This intermediate was obtained according to general procedure I from 8-fluoro-3,4,4a,8a-tetrahydro-1H-quinolin-2-one (515 mg, 3.12 mmol) and NBS (583 mg, 3.27 mmol) after flash chromatography on silica gel (hexanes/ethyl acetate, 5/1, R$_f$=0.32) as white solid (647 mg, 2.65 mmol, 85%).

Synthesis Example 11

6-Bromo-7-fluoro-3,4,4a,8a-tetrahydro-1H-quinolin-2-one

This intermediate was obtained according to general procedure I from 7-fluoro-3,4,4a,8a-tetrahydro-1H-quinolin-2-one (92 mg, 0.56 mmol) and NBS (104 mg, 0.58 mmol) after flash chromatography on silica gel (hexanes/ethyl acetate, 5/1, R$_f$=0.27) as white solid (120 mg, 0.49 mmol, 88%).

Synthesis Example 12

6-Bromo-7-hydroxy-3,4,4a,8a-tetrahydro-1H-quinolin-2-one

This intermediate was obtained according to general procedure I from 7-hydroxy-3,4,4a,8a-tetrahydro-1H-quinolin-2-one (370 mg, 2.27 mmol) and NBS (424 mg, 2.38 mmol) after flash chromatography on silica gel (hexanes/ethyl acetate, 1/1, R$_f$=0.15) as white solid (500 mg, 2.07 mmol, 91%).

Synthesis Example 13

2-(4-Bromo-2-fluorophenylamino)-2-oxoethyl acetate

To a solution of 4-bromo-2-fluoroaniline (9.5 g, 50.0 mmol) in 150 ml dry CHCl$_3$ was added drop wise acetoxyacetyl chloride (7.5 g, 55.0 mmol) under nitrogen. The mixture was stirred at room temperature for 0.5 h, then water was added and the solution was extracted several times with dichloromethane. The combined organic layers were washed with brine, dried over MgSO$_4$ and evaporated, affording 2-(4-bromo-2-fluorophenylamino)-2-oxoethyl acetate (15.2 g) as colorless solid in quantitative yield.

Synthesis Example 14

N-(4-Bromo-2-fluorophenyl)-2-hydroxyacetamide

To a solution of 2-(4-Bromo-2-fluorophenylamino)-2-oxoethyl acetate (14.2 g, 49.0 mmol) in 150 ml ethanol was added a 2 M solution of NaOH (49 ml, 97.9 mmol) at 0° C. The mixture was stirred at room temperature for 0.5 h, then water was added. Acidification of the solution with 3 M HCl afforded after filtration and drying overnight over silica gel N-(4-bromo-2-fluorophenyl)-2-hydroxyacetamide (9.1 g, 36.6 mmol, 75%) as colorless solid.

Synthesis Example 15

7-Bromo-2H-benzo[b][1,4]oxazin-3(4H)-one

A solution of N-(4-bromo-2-fluorophenyl)-2-hydroxyacetamide (8.0 g, 32.3 mmol) in 50 ml dry DMF was added drop wise to a suspension of sodium hydride (5.2 g, 129 mmol) in 30 ml dry DMF and the mixture was stirred for 2 h under an atmosphere of nitrogen at 140° C. After cooling to ambient temperature water was added and the mixture was extracted several times with ethyl acetate. After washing the combined organic layers with brine and drying over MgSO$_4$ the solvent was removed under reduced pressure and the crude product was obtained as a pale yellow solid. Purification by flash chromatography on silica gel (dichloromethane/methanol, 97/3, R$_f$=0.35) yielded 7-bromo-2H-benzo[b][1,4]oxazin-3(4H)-one (2.3 g, 10.1 mmol, 31%) as off-white solid.

Synthesis Example 16

N-(4-Bromo-2-nitrophenyl)-2-chloroacetamide

To a solution of 4-bromo-2-nitroaniline (15.0 g, 69.1 mmol) was added drop wise 2-chloroacetyl chloride (9.4 g, 82.9 mmol) under nitrogen. After refluxing for 1.5 h, the reaction mixture was cooled to ambient temperature and the solvent was removed under reduced pressure. Crystallization from ethyl acetate/hexane afforded N-(4-bromo-2-nitrophenyl)-2-chloroacetamide (19.4 g, 66.1 mmol, 96%) as yellow needles.

Synthesis Example 17

N-(2-Amino-4-bromophenyl)-2-chloroacetamide

Ferrous powder (19.8 g, 354 mmol), ammonium chloride (1.1 g, 19.7 mmol) and acetic acid (4.9 ml, 86.5 mmol) were suspended in 300 ml water and stirred at 50° C. for 15 min. To this mixture, a solution of N-(4-bromo-2-nitrophenyl)-2- chloroacetamide (11.5 g, 39.3 mmol) in 100 ml DMF was added quickly. After stirring for 15 min, the mixture was basified to pH 9 with aqueous sodium carbonate solution. The remaining solids were filtered and washed with water and ethyl acetate. Extraction of the water layer with ethyl acetate, washing of the combined organic layers with brine, drying over $MgSO_4$, removing the solvent under reduced pressure and purification of the crude product by flash chromatography on silica gel (petroleum ether/ethyl acetate, 1/1) yielded N-(2-amino-4-bromophenyl)-2-chloroacetamide (4.5 g, 17.0 mmol, 43%) as an off-white solid.

Synthesis Example 18

6-Bromo-3,4-dihydroquinoxalin-2(1H)-one

A mixture of N-(2-amino-4-bromophenyl)-2-chloroacetamide (4.5 g, 17.0 mmol), sodium iodide (101 mg, 2.0 mmol) and sodium carbonate (3.6 g, 33.8 mmol) in 300 ml acetonitrile was refluxed overnight under an atmosphere of nitrogen. Then the acetonitrile was removed under vacuum. The resulting solid was suspended in 150 ml water acidified to pH 5-6 with 1 N HCl. Extraction with ethyl acetate, washing of the combined organic layers with brine, drying over $MgSO_4$, removing the solvent under reduced pressure and purification of the crude product by flash chromatography on silica gel (petroleum ether/ethyl acetate, 1.5/1) yielded 6-bromo-3,4-dihydroquinoxalin-2(1H)-one (1.3 g, 5.8 mmol, 34%) as yellow solid.

Synthesis Example 19

6-Bromo-4-methyl-3,4-dihydroquinoxalin-2(1H)-one

To a solution of 6-bromo-3,4-dihydroquinoxalin-2(1H)-one (370 mg, 1.63 mmol) in 10 ml methanol was added a solution of 37% formaldehyde in water (59 mg, 1.95 mmol) and acetic acid (196 mg, 3.26 mmol). The mixture was stirred at room temperature for 2 h, then refluxed for 1 h. After addition of $NaBH_3CN$ (307 mg, 4.89 mmol) stirring was continued for 2.5 h at room temperature. Then methanol was removed under vacuum. To the remaining mixture water was added. Then the solution was basified to pH 8-9 with an aqueous solution of sodium hydrogen carbonate and extracted several times with ethyl acetate. The combined organic layers were washed with brine, dried over $MgSO_4$ and evaporated, affording 6-bromo-4-methyl-3,4-dihydroquinoxalin-2(1H)-one (369 mg, 1.53 mmol, 94%) as off-white solid.

Synthesis Example 20

(2-Amino-5-bromophenyl)methanol

To a suspension of lithium aluminium hydride (0.33 g, 8.7 mmol) in THF (10 ml) was added a solution of methyl 2-amino-5-bromobenzoate (2.0 g, 8.7 mmol) in 20 ml THF at 0° C. under nitrogen. Then stirring was continued for 2 h. 0.64 ml water, 2 M solution of sodium hydroxide (0.64 ml) and again 1.28 ml water were added before the resulting mixture was filtered through celite. Evaporation of the solvent and purification of the crude product by flash chromatography on silica gel (dichloromethane/ethyl acetate, 2/1) yielded (2-amino-5-bromophenyl)methanol (1.0 g, 5.2 mmol, 59%) as off-white solid.

Synthesis Example 21

6-Bromo-1H-benzo[d][1,3]oxazin-2(4H)-one

To a solution of (2-amino-5-bromophenyl)methanol (772 mg, 3.8 mmol) in 15 ml THF was added triphosgene (1.03 g, 3.8 mmol) under nitrogen. After precipitation of a colorless solid, stirring was continued for 20 min before water was added. The solution was extracted several times with ethyl acetate. The combined organic layers were washed with brine, dried over $MgSO_4$ and evaporated, affording 6-bromo-1H-benzo[d][1,3]oxazin-2(4H)-one (830 mg, 3.64 mmol, 96%) as colorless solid.

Synthesis Example 22

8-(Tributylstannyl)-1,2,5,6-tetrahydropyrrolo[3,2,1-ij]quinolin-4-one

To a solution of 8-bromo-1,2,5,6-tetrahydro-pyrrolo[3,2,1-ij]quinolin-4-one (9.07 g, 36.0 mmol) and 1,1,1,2,2,2-hexabutyldistannane (29.1 mL, 57.6 mmol) in 40 mL degassed dry toluene was added tetrakis(triphenylphosphine)palladium(0) (4.16 g, 3.60 mmol) under an atmosphere of nitrogen, and the mixture was stirred overnight at 90° C. After cooling to ambient temperature the mixture was concentrated in vacuo. The crude product was purified by flash chromatography on silica gel (hexanes/ethyl acetate, 1/10, $R_f$=0.1) to yield pure 8-(tributylstannyl)-1,2,5,6-tetrahydropyrrolo[3,2,1-ij]quinolin-4-one as a light yellow oil (7.50 g, 16.2 mmol, 45%).

Synthesis Example 23

8-Acetyl-1,2,5,6-tetrahydropyrrolo[3,2,1-ij]quinolin-4-one

To a suspension of 1,2,5,6-tetrahydro-pyrrolo[3,2,1-ij]quinolin-4-one (700 mg, 4.04 mmol) and $AlCl_3$ (3.61 g, 27.0 mmol) in $CS_2$ (20 mL) was added dropwise acetyl chloride (0.34 mL, 6.06 mmol) at 0° C. The mixture was warmed to ambient temperature and refluxed for 18 h before being cooled down to 0° C. A mixture of ice/water was added to quench and a precipitate was formed and filtered to yield a pale yellow solid (802 mg, 3.73 mmol, 92%) which was sufficiently pure for further use.

General Experimental Procedures for the Synthesis of the Compounds of the Examples General Procedure A: Microwave Enhanced Suzuki Coupling.

Pyridine boronic acid (0.75 mol, 1 equivalent), aryl bromide (0.9-1.3 equivalents), and tetrakis(triphenyl-phosphane)palladium(0) (43 mg, 37.5 µmol, 5 mol %) were suspended in 1.5 ml DMF in a 10 mL septum-capped tube containing a tiny stirring magnet. To this was added a solution of $NaHCO_3$ (189 mg, 2.25 mmol, 3 equivalents) in 1.5 ml water and the vial was sealed tightly with an Teflon crimp top. The mixture was irradiated for 15 min at a temperature of 150° C. with an initial irradiation power of 100 W. After the reaction, the vial was cooled to 40° C. by gas jet cooling, the crude mixture was partitioned between ethyl acetate and water and the aqueous layer was extracted three times with ethyl acetate. The combined organic layers were dried over $MgSO_4$ and the solvents were removed in vacuo. The coupling products were obtained after flash chromatography on silica gel and/or crystallization. If an oil was obtained, it was transferred into the hydrochloride salt by addition of 1N HCl solution in diethylether and/or THF.

General Procedure B: Suzuki Coupling with Conventional Heating.

Pyridine boronic acid (1 equivalent), aryl bromide (1.3-1.5 equivalents), and tetrakis(triphenyl-phosphane)palladium(0) (5 mol %) were suspended in toluene/ethanol 4/1 to give a 0.07-0.1 M solution of boronic acid under an atmosphere of nitrogen. To this was added a 1 N aqueous solution of $Na_2CO_3$ (6 equivalents). The mixture was then refluxed for 12-18 h, cooled to room temperature, diluted with water and extracted several times with ethyl acetate. The combined extracts were dried over $MgSO_4$, concentrated and purified by flash chromatography on silica gel and/or crystallization. If an oil was obtained, it was transferred into the hydrochloride salt by addition of 1N HCl solution in diethylether and/or THF.

General Procedure C: Suzuki Coupling Reaction.

To a suspension of aryl bromide (1 equivalent), boronic acid (1.2-1.3 equivalents), $Na_2CO_3$ (5-6 equivalents) in DME/water (3/1) was added tetrakis(triphenylphosphane)palladium(0) (5 mol %) under an atmosphere of nitrogen. The reaction mixture was then refluxed for 3.5-16 h. After being cooled to room temperature, it was diluted with water and extracted several times with ethyl acetate. The combined extracts were washed with brine, dried over $MgSO_4$, concentrated and purified by flash chromatography on silica gel and if necessary crystallization.

General Procedure D: Sulfuration. To a suspension of the corresponding quinolinone (1 equivalent) in dry toluene (50 mL) was added Lawesson's reagent (0.6 equivalents). Then the reaction mixture was heated to reflux over night under $N_2$. After being cooled to room temperature, it was diluted with water and extracted several times with ethyl acetate. The combined extracts were washed with brine, dried over $MgSO_4$, concentrated and purified by flash chromatography on silica gel and/or crystallization.

General procedure E: Imidazolization.

8-(Tributylstannyl)-1,2,5,6-tetrahydro-pyrrolo[3,2,1-ij]quinolin-4-one (1.0 equivalent), dichlorobis(triphenylphosphine)palladium(II) (0.1 equivalents) and an acyl chloride (2.0 equivalents) were suspended in dry toluene under an atmosphere of nitrogen. The mixture was refluxed for 2 h before it was concentrated in vacuo. The resulting residue was purified by flash chromatography on silica gel (hexanes/ethyl acetate) to yield a ketone. This ketone (1.0 equivalent) was dissolved in methanol and sodium boron hydride (1.0 equivalent) was added in several portions at 0° C. After stirring for 1 h, water was added and the mixture was extracted with ethyl acetate. Drying of the combined organic layers over $MgSO_4$ and removal of the solvent gave the alcohol as crude product. The obtained alcohol was added to a solution of thionylbis(imidazole) (4.0 equivalents) in THF at 0° C. After being stirred at ambient temperature for 15-40 h, it was concentrated in vacuo and diluted with water followed by extraction with dichloromethane three times. The combined extracts were washed with brine, dried over $MgSO_4$ and concentrated in vacuo. The product was obtained after flash chromatography on silica gel (methanol/dichloromethane).

Example 1

6-Pyridin-3-yl-3,4-dihydro-1H-quinolin-2-one

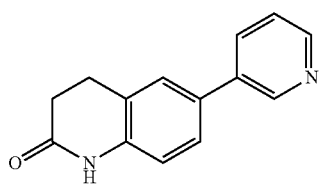 [SMILES: O=C1CCc2cc(-c3cccnc3)ccc2N1]

The title compound was obtained via Suzuki coupling according to general procedure B from 6-bromo-3,4-dihydro-1H-quinolin-2-one (2.71 g, 12.0 mmol) and 3-pyridineboronic acid (1.23 g, 10.0 mmol) after crystallization from acetone/diethylether as colorless needles (2.15 g, 9.59 mmol, 96%), mp (acetone/diethylether) 189° C. $^1$H-NMR (500 MHz, DMSO-$d_6$): δ=2.49 (t, $^3$J=7.3 Hz, 2H), 2.95 (t, $^3$J=7.3 Hz, 2H), 6.95 (d, $^3$J=8.2 Hz, 1H), 7.43 (ddd, $^3$J=7.9 Hz, $^3$J=4.7 Hz, $^5$J=0.6 Hz, 1H), 7.51 (dd, $^3$J=8.2 Hz, $^4$J=2.2 Hz, 1H), 7.56 (d, $^4$J=2.1 Hz, 1H), 8.00 (ddd, $^3$J=7.9 Hz, $^4$J=2.2 Hz, $^4$J=1.6 Hz, 1H), 8.50 (dd, $^3$J=4.7 Hz, $^4$J=1.5 Hz, 1H), 8.84 (d, $^4$J=2.2 Hz, 1H), 10.19 (s, 1H). $^{13}$C-NMR (125 MHz, DMSO-$d_6$): δ=24.8, 30.3, 115.6, 123.8, 124.3, 125.6, 126.2, 130.6, 133.4, 135.2, 138.4, 147.2, 147.8, 170.2. MS m/z 225.25 (MH$^+$).

According to Example 1 using the general experimental procedures A or B and the suitable starting compounds (see Schemes 1-19) the following compounds are synthesized:

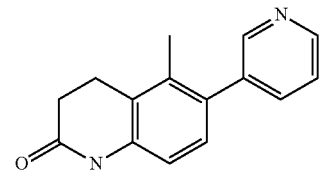

5-Methyl-6-pyridin-3-yl-3,4-dihydroquinolin-2(1H)-one

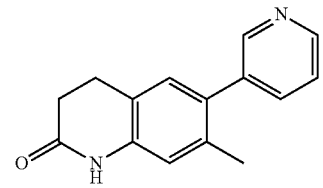

7-Methyl-6-pyridin-3-yl-3,4-dihydroquinolin-2(1H)-one

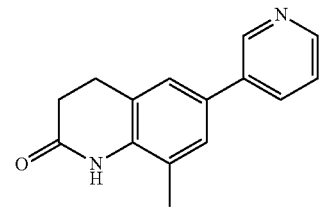

8-Methyl-6-pyridin-3-yl-3,4-dihydroquinolin-2(1H)-one

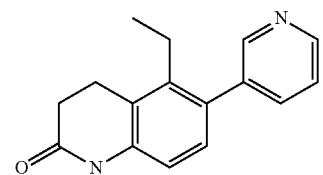

5-Ethyl-6-(pyridin-3-yl)-3,4-dihydroquinolin-2(1H)-one

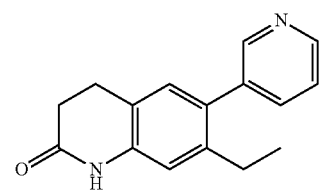

7-Ethyl-6-(pyridin-3-yl)-3,4-dihydroquinolin-2(1H)-one

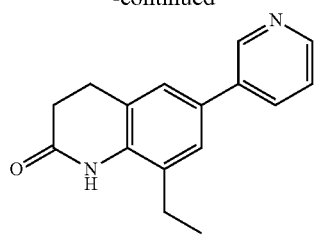

8-Ethyl-6-(pyridin-3-yl)-3,4-dihydroquinolin-2(1H)-one

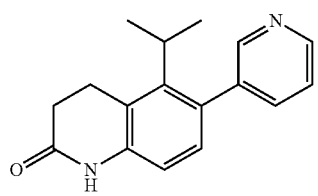

5-Isopropyl-6-(pyridin-3-yl)-3,4-dihydroquinolin-2(1H)-one

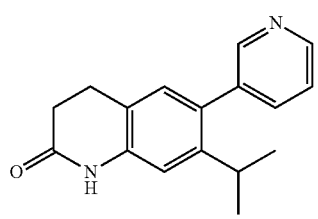

7-Isopropyl-6-(pyridin-3-yl)-3,4-dihydroquinolin-2(1H)-one

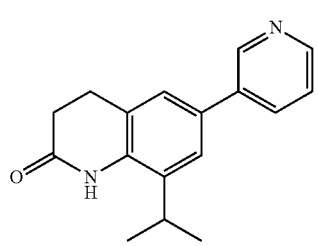

8-Isopropyl-6-(pyridin-3-yl)-3,4-dihydroquinolin-2(1H)-one

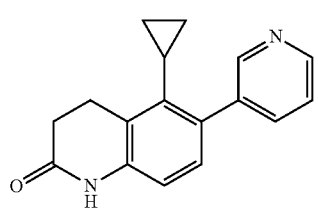

5-Cyclopropyl-6-(pyridin-3-yl)-3,4-dihydroquinolin-2(1H)-one

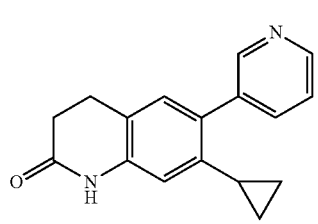

7-Cyclopropyl-6-(pyridin-3-yl)-3,4-dihydroquinolin-2(1H)-one

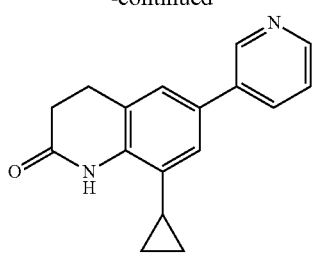

8-Cyclopropyl-6-(pyridin-3-yl)-3,4-dihydroquinolin-2(1H)-one

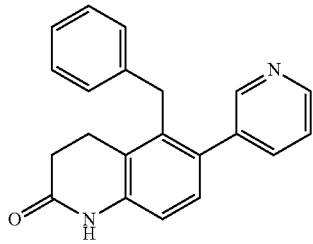

5-Benzyl-6-(pyridin-3-yl)-3,4-dihydroquinolin-2(1H)-one

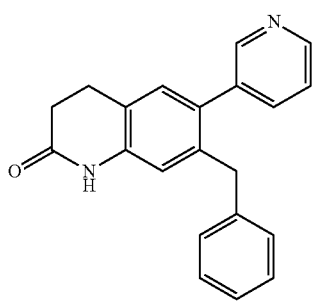

7-Benzyl-6-(pyridin-3-yl)-3,4-dihydroquinolin-2(1H)-one

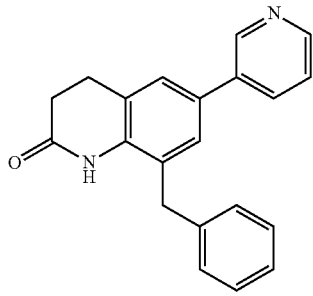

8-Benzyl-6-(pyridin-3-yl)-3,4-dihydroquinolin-2(1H)-one

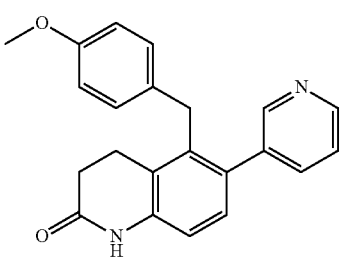

5-(4-Methoxybenzyl)-6-(pyridin-3-yl)-3,4-dihydroquinolin-2(1H)-one

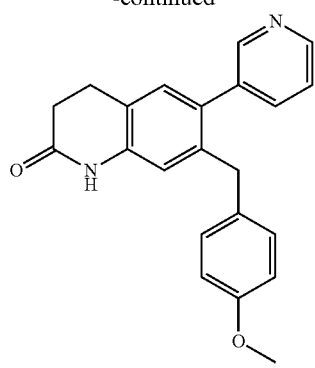

7-(4-Methoxybenzyl)-6-(pyridin-3-yl)-3,4-dihydroquinolin-2(1H)-one

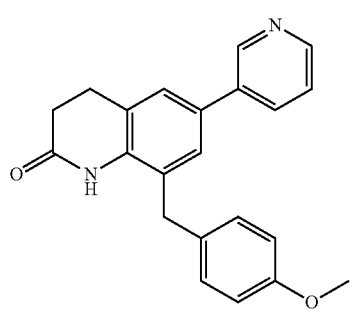

8-(4-Methoxybenzyl)-6-(pyridin-3-yl)-3,4-dihydroquinolin-2(1H)-one

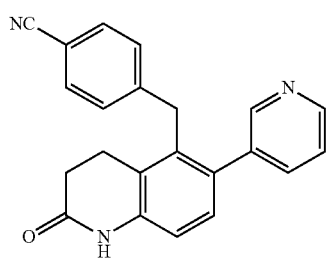

4-((2-Oxo-6-(pyridin-3-yl)-1,2,3,4-tetrahydroquinolin-5-yl)methyl)benzonitrile

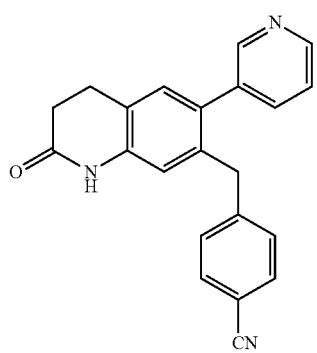

4-((2-Oxo-6-(pyridin-3-yl)-1,2,3,4-tetrahydroquinolin-7-yl)methyl)benzonitrile

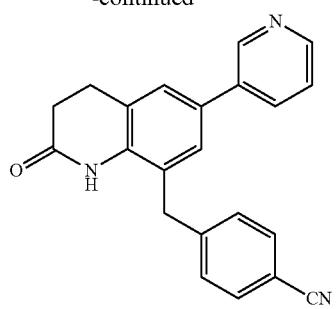

4-((2-Oxo-6-(pyridin-3-yl)-1,2,3,4-tetrahydroquinolin-8-yl)methyl)benzonitrile

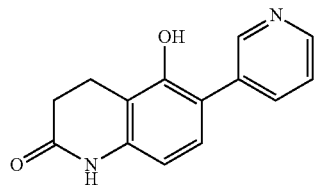

5-Hydroxy-6-(pyridin-3-yl)-3,4-dihydroquinolin-2(1H)-one

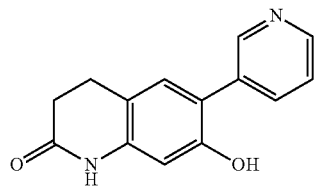

7-Hydroxy-6-(pyridin-3-yl)-3,4-dihydroquinolin-2(1H)-one

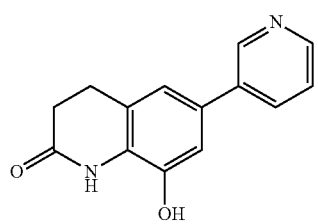

8-Hydroxy-6-(pyridin-3-yl)-3,4-dihydroquinolin-2(1H)-one

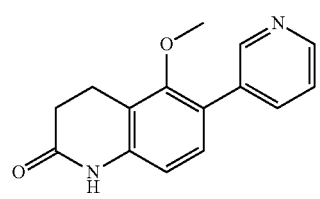

5-Methoxy-6-pyridin-3-yl-3,4-dihydroquinolin-2(1H)-one

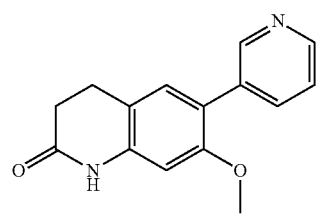

7-Methoxy-6-pyridin-3-yl-3,4-dihydroquinolin-2(1H)-one

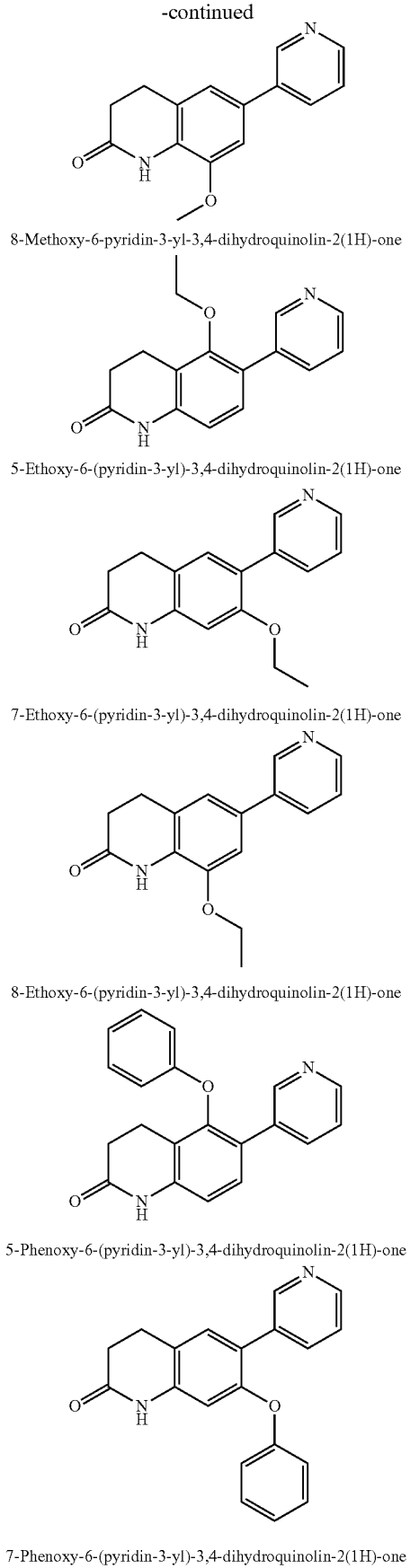

8-Methoxy-6-pyridin-3-yl-3,4-dihydroquinolin-2(1H)-one

5-Ethoxy-6-(pyridin-3-yl)-3,4-dihydroquinolin-2(1H)-one

7-Ethoxy-6-(pyridin-3-yl)-3,4-dihydroquinolin-2(1H)-one

8-Ethoxy-6-(pyridin-3-yl)-3,4-dihydroquinolin-2(1H)-one

5-Phenoxy-6-(pyridin-3-yl)-3,4-dihydroquinolin-2(1H)-one

7-Phenoxy-6-(pyridin-3-yl)-3,4-dihydroquinolin-2(1H)-one

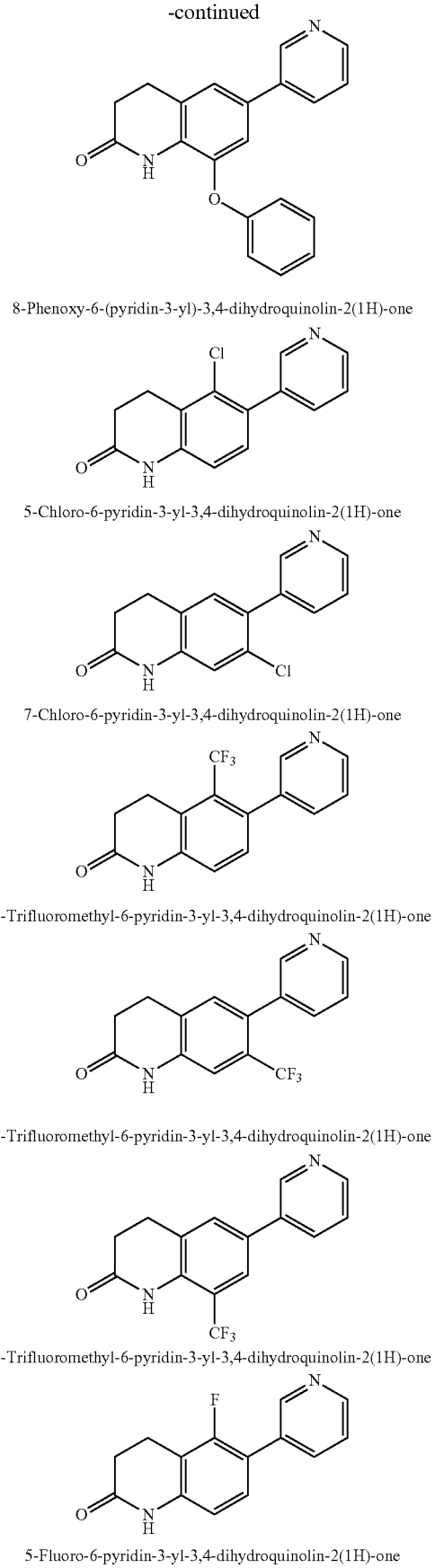

8-Phenoxy-6-(pyridin-3-yl)-3,4-dihydroquinolin-2(1H)-one

5-Chloro-6-pyridin-3-yl-3,4-dihydroquinolin-2(1H)-one

7-Chloro-6-pyridin-3-yl-3,4-dihydroquinolin-2(1H)-one

5-Trifluoromethyl-6-pyridin-3-yl-3,4-dihydroquinolin-2(1H)-one

7-Trifluoromethyl-6-pyridin-3-yl-3,4-dihydroquinolin-2(1H)-one

8-Trifluoromethyl-6-pyridin-3-yl-3,4-dihydroquinolin-2(1H)-one

5-Fluoro-6-pyridin-3-yl-3,4-dihydroquinolin-2(1H)-one

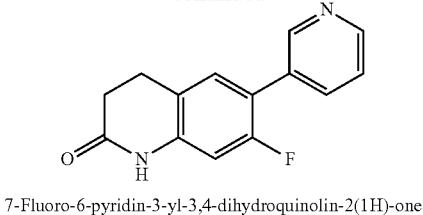

7-Fluoro-6-pyridin-3-yl-3,4-dihydroquinolin-2(1H)-one

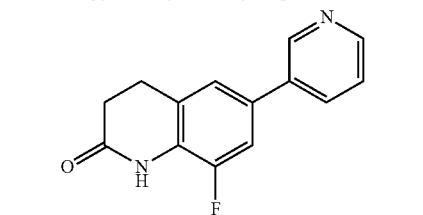

8-Fluoro-6-pyridin-3-yl-3,4-dihydroquinolin-2(1H)-one

Example 2

1-Methyl-6-pyridin-3-yl-3,4-dihydro-1H-quinolin-2-one

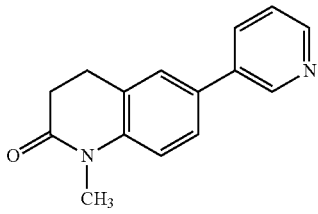 [SMILES: CN1C(=O)CCc2cc(-c3cccnc3)ccc21]

The title compound was obtained via Suzuki coupling according to general procedure A from 6-bromo-1-methyl-3,4-dihydro-1H-quinolin-2-one (110 mg, 0.46 mmol) and 3-pyridineboronic acid (74 mg, 0.6 mmol) after flash chromatography on silica gel (hexanes/ethyl acetate, 2/3, $R_f$=0.07) as colorless needles (83 mg, 0.35 mmol, 75%), mp (hexanes/ethyl acetate) 101° C. $^1$H-NMR (500 MHz, CDCl$_3$): δ=2.68 (t, $^3J$=7.3 Hz, 2H), 2.97 (t, $^3J$=7.3 Hz, 2H), 3.38 (s, 3H), 7.06 (d, $^3J$=8.2 Hz, 1H), 7.33 (ddd, $^3J$=7.9 Hz, $^3J$=4.8 Hz, $^5J$=0.6 Hz, 1H), 7.37 (d, $^4J$=2.1 Hz, 1H), 7.45 (dd, $^3J$=8.3 Hz, $^4J$=2.2 Hz, 1H), 7.82 (ddd, $^3J$=7.9 Hz, $^4J$=2.2 Hz, $^4J$=1.6 Hz, 1H), 8.55 (dd, $^3J$=4.7 Hz, $^4J$=1.6 Hz, 1H), 8.81 (d, $^4J$=2.2 Hz, 1H). $^{13}$C-NMR (125 MHz, CDCl$_3$): δ=25.5, 29.6, 31.6, 115.2, 123.5, 126.0, 126.3, 126.9, 132.2, 133.9, 135.7, 140.6, 147.9, 148.3, 170.2. MS m/z 239.80.

Example 3

5-Pyridin-3-yl-1,3-dihydro-indol-2-one

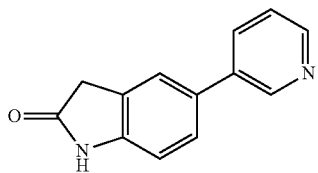 [SMILES: O=C1Cc2cc(-c3cccnc3)ccc2N1]

The title compound was obtained via Suzuki coupling according to general procedure A from 5-Bromo-1,3-dihydro-indol-2-one (159 mg, 0.75 mmol) and 3-pyridineboronic acid (123 mg, 1.0 mmol) after crystallization from acetone/diethylether as pale yellow needles (129 mg, 0.61 mmol, 77%), mp (acetone/diethylether) 220° C. $^1$H-NMR (500 MHz, DMSO-d$_6$): δ=3.53 (s, 2H), 6.91 (d, $^3J$=7.9 Hz, 1H), 7.42 (dd, $^3J$=7.9 Hz, $^3J$=4.7 Hz, 1H), 7.52 (d, $^3J$=7.9 Hz, 1H), 7.56 (s, 1H), 7.97 (m, 1H), 8.49 (dd, $^3J$=4.7 Hz, $^4J$=1.3 Hz, 1H), 8.81 (d, $^4J$=2.2 Hz, 1H), 10.50 (s, 1H). $^{13}$C-NMR (125 MHz, DMSO-d$_6$): δ=35.8, 109.6, 123.0, 123.8, 126.3, 126.9, 130.2, 133.5, 135.8, 143.9, 147.2, 147.7, 176.3. MS m/z 211.01 (MH$^+$).

According to Example 3 using the general experimental procedures A or B and the suitable starting compounds the following compounds are synthesized:

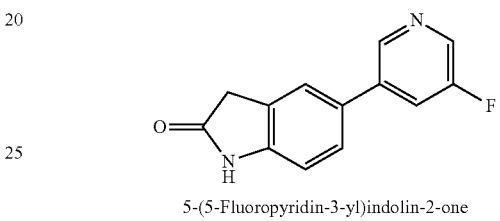

5-(5-Fluoropyridin-3-yl)indolin-2-one

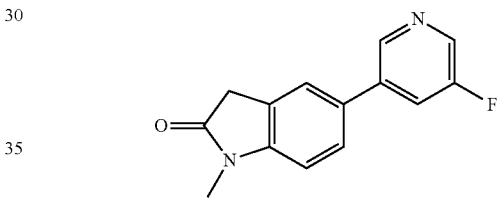

1-Methyl-5-(5-fluoropyridin-3-yl)indolin-2-one

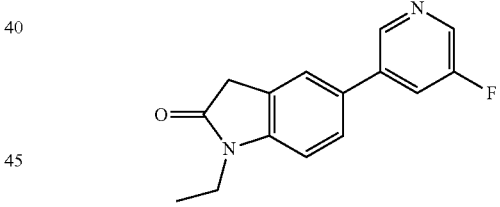

1-Ethyl-5-(5-fluoropyridin-3-yl)indolin-2-one

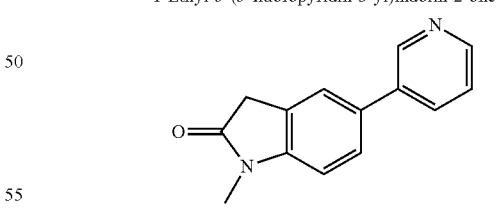

1-Methyl-5-(pyridine-3-yl)indolin-2-one

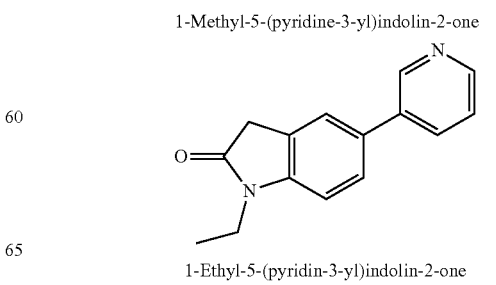

1-Ethyl-5-(pyridine-3-yl)indolin-2-one

-continued

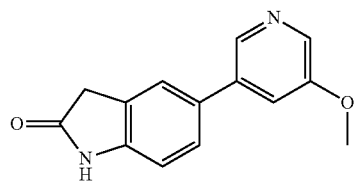

5-(5-Methoxypyridin-3-yl)indolin-2-one

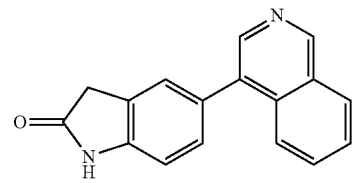

5-(Isoquinolin-4-yl)indolin-2-one

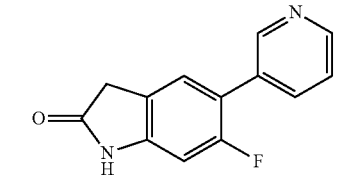

6-Fluoro-5-(pyridin-3-yl)indolin-2-one

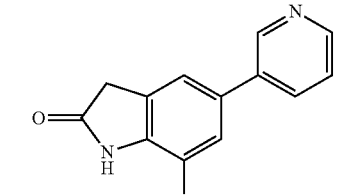

7-Fluoro-5-(pyridin-3-yl)indolin-2-one

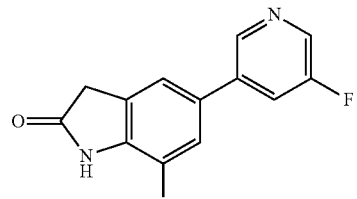

7-Chloro-5-(5-fluoropyridin-3-yl)indolin-2-one

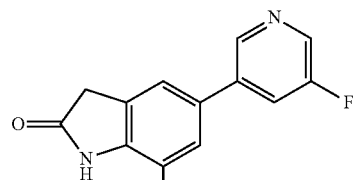

7-Fluoro-5-(5-fluoropyridin-3-yl)indolin-2-one

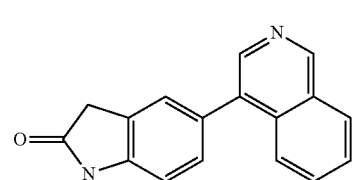

7-Fluoro-5-(isoquinolin-4-yl)indolin-2-one

-continued

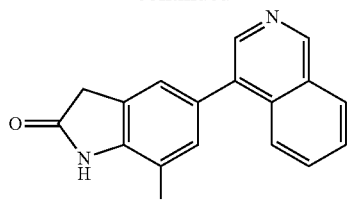

7-Chloro-5-(isoquinolin-4-yl)indolin-2-one

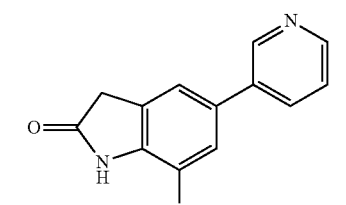

7-Chlor-5-(pyridin-3-yl)indolin-2-on

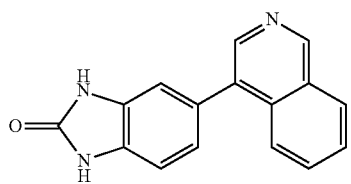

5-(Isoquinolin-4-yl)-1H-benzo[d]imidazol-2(3H)-one

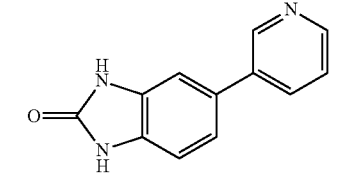

5-(Pyridin-3-yl)-1H-benzo[d]imidazol-2(3H)-one

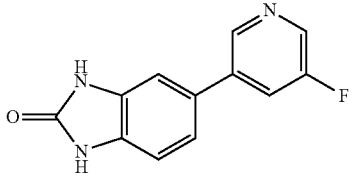

5-(5-Fluoropyridin-3-yl)-1H-benzo[d]imidazol-2(3H)-one

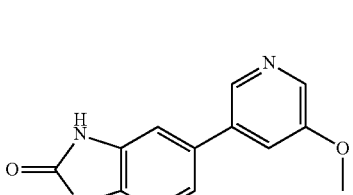

5-(5-Methoxypyridin-3-yl)-1H-benzo[d]imidazol-2(3H)-one

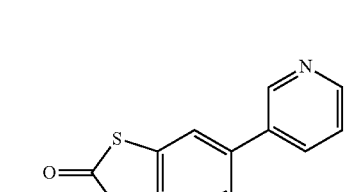

6-(Pyridin-3-yl)benzo[d]thiazol-2(3H)-one

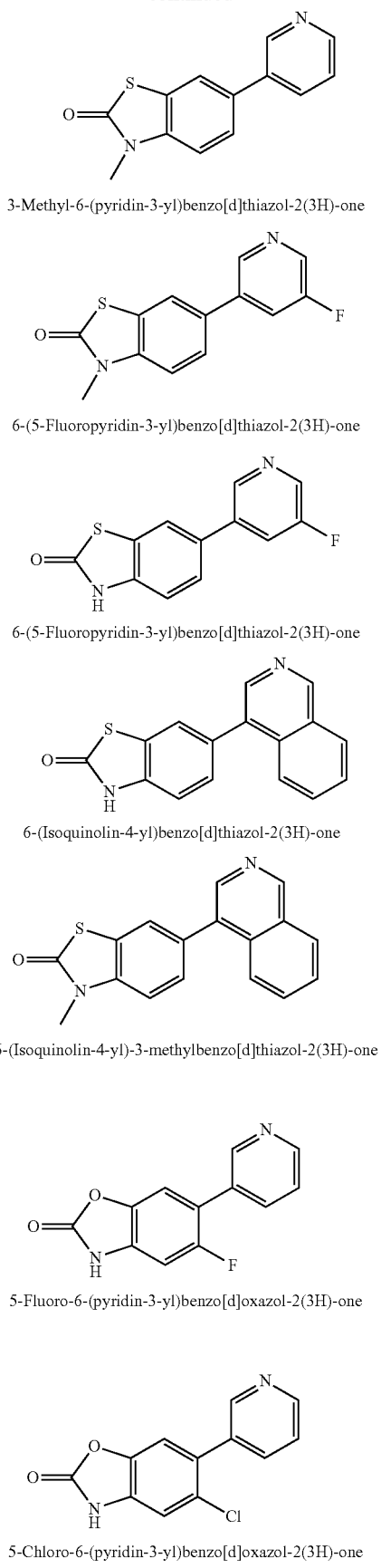

3-Methyl-6-(pyridin-3-yl)benzo[d]thiazol-2(3H)-one 6-(5-Fluoropyridin-3-yl)benzo[d]thiazol-2(3H)-one 6-(5-Fluoropyridin-3-yl)benzo[d]thiazol-2(3H)-one 6-(Isoquinolin-4-yl)benzo[d]thiazol-2(3H)-one 6-(Isoquinolin-4-yl)-3-methylbenzo[d]thiazol-2(3H)-one 5-Fluoro-6-(pyridin-3-yl)benzo[d]oxazol-2(3H)-one 5-Chloro-6-(pyridin-3-yl)benzo[d]oxazol-2(3H)-one

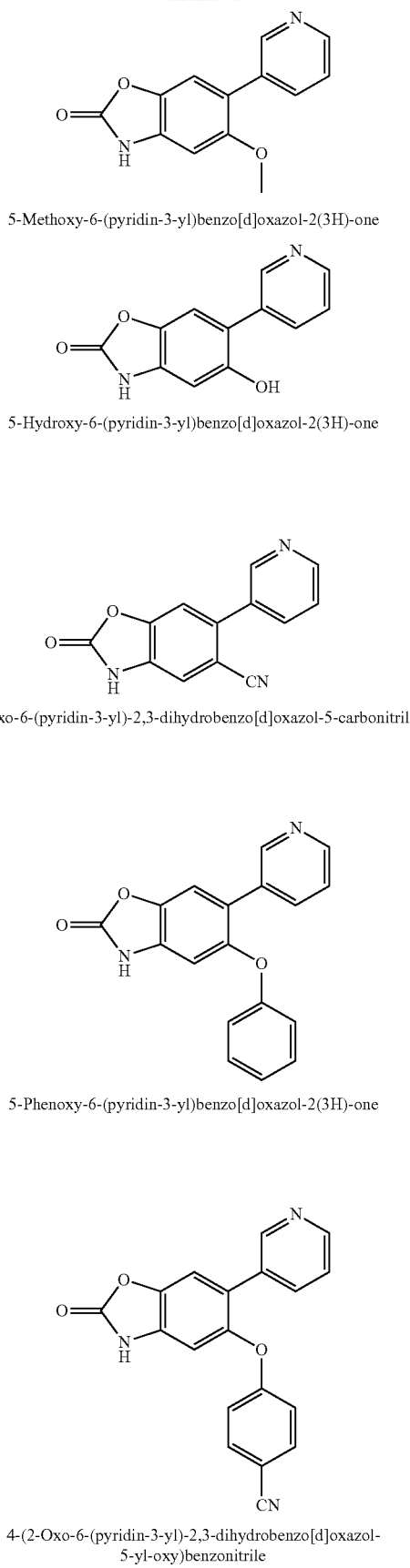

5-Methoxy-6-(pyridin-3-yl)benzo[d]oxazol-2(3H)-one

5-Hydroxy-6-(pyridin-3-yl)benzo[d]oxazol-2(3H)-one

2-Oxo-6-(pyridin-3-yl)-2,3-dihydrobenzo[d]oxazol-5-carbonitrile

5-Phenoxy-6-(pyridin-3-yl)benzo[d]oxazol-2(3H)-one 4-(2-Oxo-6-(pyridin-3-yl)-2,3-dihydrobenzo[d]oxazol-5-yl-oxy)benzonitrile -continued

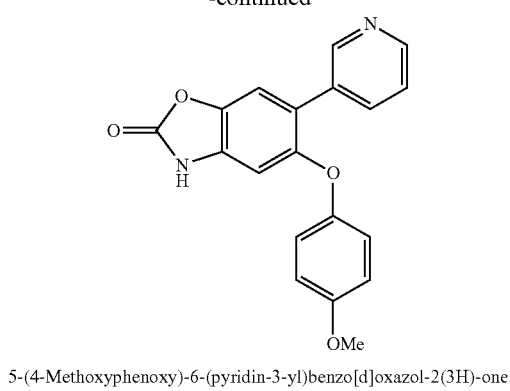
5-(4-Methoxyphenoxy)-6-(pyridin-3-yl)benzo[d]oxazol-2(3H)-one

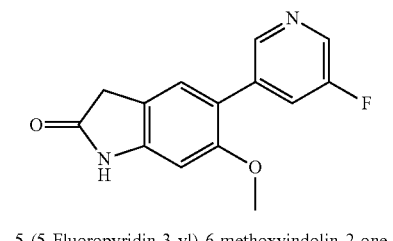
5-(5-Fluoropyridin-3-yl)-6-methoxyindolin-2-one

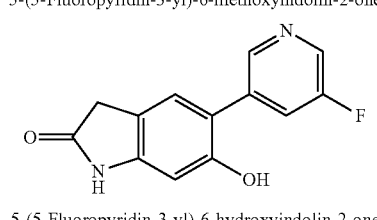
5-(5-Fluoropyridin-3-yl)-6-hydroxyindolin-2-one

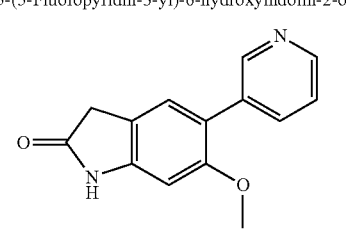
6-Methoxy-5-(pyridin-3-yl)indolin-2-one

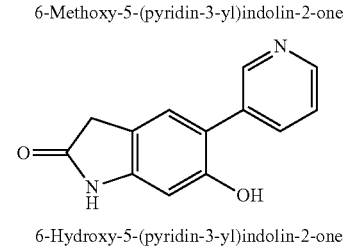
6-Hydroxy-5-(pyridin-3-yl)indolin-2-one

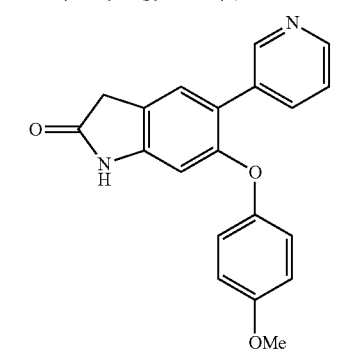
6-(4-Methoxyphenoxy)-5-(pyridin-3-yl)indolin-2-one

-continued

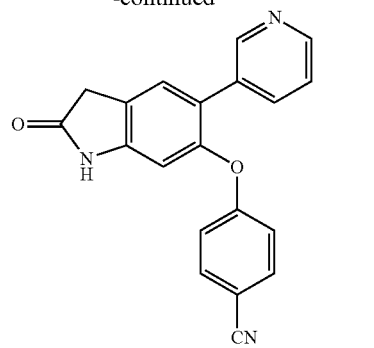
4-(2-Oxo-5-(pyridin-3-yl)indolin-6-yloxy)benzonitrile

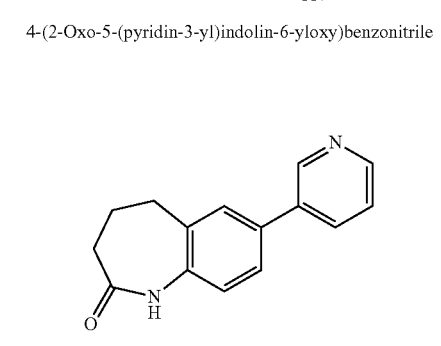
7-(Pyridin-3-yl)-4,5-dihydro-1H-benzo[b]azepin-2(3H)-one

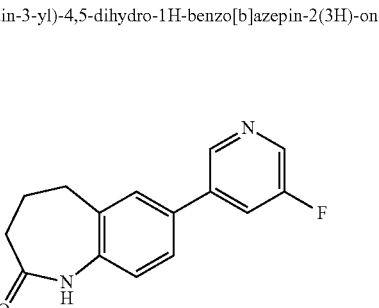
7-(5-Fluoropyridin-3-yl)-4,5-dihydro-1H-benzo[b]azepin-2(3H)-one

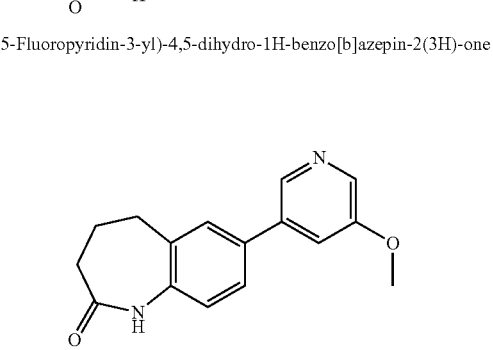
7-(5-Methoxypyridin-3-yl)-4,5-dihydro-1H-benzo[b]azepin-2(3H)-one

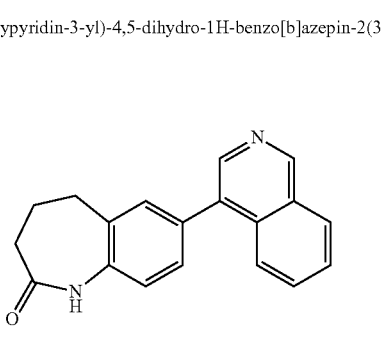
7-(Isoquinolin-4-yl)-4,5-dihydro-1H-benzo[b]azepin-2(3H)-one

Example 4

6-(5-Methoxypyridin-3-yl)-3,4-dihydro-1H-quinolin-2-one

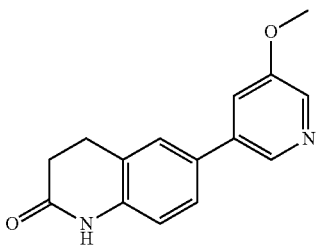 [SMILES: COc1cncc(-c2ccc3c(c2)CCC(=O)N3)c1]

The title compound was obtained via Suzuki coupling according to general procedure A from 6-bromo-3,4-dihydro-1H-quinolin-2-one (170 mg, 0.75 mmol) and 5-methoxy-3-pyridineboronic acid (150 mg, 0.98 mmol) after crystallization from acetone/diethylether as colorless needles (77 mg, 0.30 mmol, 40%), mp (acetone/diethylether) 215° C. $^1$H-NMR (500 MHz, DMSO-$d_6$): δ=2.50 (t, $^3J$=7.6 Hz, 2H), 2.96 (t, $^3J$=7.9 Hz, 2H), 3.89 (s, 3H), 6.95 (d, $^3J$=8.2 Hz, 1H), 7.53 (dd, $^3J$=8.2 Hz, $^4J$=1.9 Hz, 1H), 7.55 (dd, $^4J$=2.8 Hz, $^4J$=1.9 Hz, 1H), 7.59 (d, $^4J$=1.6 Hz, 1H), 8.22 (d, $^4J$=2.5 Hz, 1H), 8.44 (d, $^4J$=1.6 Hz, 1H), 10.20 (s, 1H). $^{13}$C-NMR (125 MHz, DMSO-$d_6$): δ=24.8, 30.3, 55.6, 115.5, 117.7, 124.3, 125.8, 126.4, 130.4, 135.8, 136.1, 138.5, 139.4, 155.6, 170.2. MS m/z 255.02 (MH$^+$).

Example 5

6-Isoquinolin-4-yl-3,4-dihydro-1H-quinolin-2-one

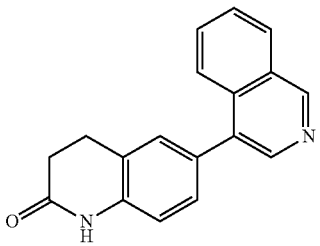 [SMILES: O=C1CCc2cc(-c3cncc4ccccc34)ccc2N1]

The title compound was obtained via Suzuki coupling according to general procedure A from 6-bromo-3,4-dihydro-1H-quinolin-2-one (170 mg, 0.75 mmol) and 4-isoquinolineboronic acid (170 mg, 0.98 mmol) after crystallization from acetone/diethylether as colorless needles (109 mg, 0.40 mmol, 53%), mp (acetone/diethylether) 222° C. $^1$H-NMR (500 MHz, DMSO-$d_6$): δ=2.51 (t, $^3J$=7.3 Hz, 2H), 2.96 (t, $^3J$=7.3 Hz, 2H), 7.02 (d, $^3J$=8.2 Hz, 1H), 7.29 (dd, $^4J$=8.2 Hz, $^4J$=1.9 Hz, 1H), 7.34 (s, 1H) 7.70 (m, 1H), 7.76 (m, 1H) 7.88 (d, $^3J$=8.2 Hz, 1H), 8.17 (d, $^3J$=7.9 Hz, 1H), 8.39 (s, 1H), 9.29 (s, 1H), 10.26 (s, 1H). $^{13}$C-NMR (125 MHz, DMSO-$d_6$): δ=24.8, 30.3, 115.2, 124.0, 124.2, 127.4, 128.0, 128.7, 129.2, 129.9, 130.9, 132.2, 133.3, 138.2, 142.3, 151.6, 170.3. MS m/z 275.04 (MH$^+$).

Example 6

6-(5-Methoxypyridin-3-yl)-1-methyl-3,4-dihydro-1H-quinolin-2-one

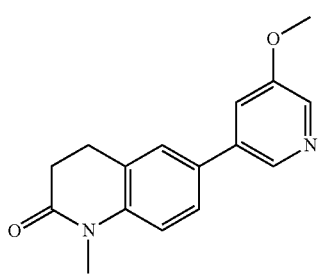 [SMILES: COc1cncc(-c2ccc3c(c2)CCC(=O)N3C)c1]

The title compound was obtained via Suzuki coupling according to general procedure A from 6-bromo-1-methyl-3,4-dihydro-1H-quinolin-2-one (200 mg, 0.83 mmol) and 5-methoxy-3-pyridineboronic acid (115 g, 0.75 mmol) after crystallization from acetone/diethylether as colorless needles (132 mg, 0.50 mmol, 66%), mp (acetone/diethylether) 159° C. $^1$H-NMR (500 MHz, CDCl$_3$): δ=2.69 (t, $^3J$=7.9 Hz, 2H), 2.98 (t, $^3J$=7.9 Hz, 2H), 3.39 (s, 3H), 3.91 (s, 3H), 7.06 (d, $^3J$=8.2 Hz, 1H), 7.33 (dd, $^4J$=2.8 Hz, $^4J$=1.9 Hz, 1H), 7.37 (d, $^4J$=2.2 Hz, 1H), 7.46 (dd, $^3J$=8.5 Hz, $^4J$=2.2 Hz, 1H), 8.27 (d, $^4J$=2.8 Hz, 1H), 8.43 (d, $^4J$=1.9 Hz, 1H). $^{13}$C-NMR (125 MHz, CDCl$_3$): δ=25.5, 29.6, 31.6, 55.7, 115.2, 118.7, 126.2, 126.5, 126.9, 132.1, 135.8, 136.5, 140.4, 140.7, 155.8, 170.3. MS m/z 268.95 (MH$^+$).

Example 7

6-Isoquinolin-4-yl-1-methyl-3,4-dihydro-1H-quinolin-2-one

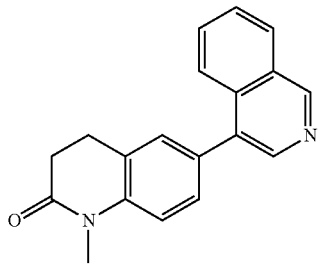 [SMILES: CN1C(=O)CCc2cc(-c3cncc4ccccc34)ccc21]

The title compound was obtained via Suzuki coupling according to general procedure A from 6-bromo-1-methyl-3,4-dihydro-1H-quinolin-2-one (264 mg, 1.10 mmol) and 4-isoquinolineboronic acid (172 mg, 1.0 mmol) after crystallization from acetone/diethylether as colorless needles (163 mg, 0.57 mmol, 57%), mp (acetone/diethylether) 176° C. $^1$H-NMR (500 MHz, CDCl$_3$): δ=2.73 (t, $^3J$=7.6 Hz, 2H), 2.99 (t, $^3J$=7.7 Hz, 2H), 3.43 (s, 3H), 7.12 (d, $^3J$=8.2 Hz, 1H), 7.32 (d, $^4J$=1.9 Hz, 1H), 7.40 (dd, $^3J$=8.2 Hz, $^4J$=2.2 Hz, 1H), 7.63 (m, 1H), 7.68 (m, 1H), 7.91 (d, $^3J$=7.9 Hz, 1H), 8.03 (d, $^3J$=7.6 Hz, 1H), 8.46 (s, 1H), 9.24 (s, 1H). $^{13}$C-NMR (125 MHz, CDCl$_3$): δ=25.4, 29.6, 31.6, 114.8, 124.6, 126.5, 127.2, 128.0, 128.4, 129.1, 129.3, 130.6, 131.5, 132.4, 134.2, 140.4, 142.8, 152.0, 170.4. MS m/z 289.91 (MH$^+$).

Example 8

6-Pyridin-3-yl-3,4-dihydro-1H-quinoline-2-thione

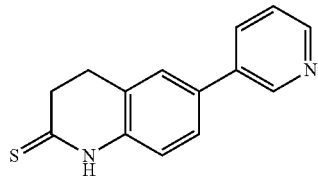 [SMILES: S=C1CCc2cc(-c3cccnc3)ccc2N1]

A mixture of 6-Pyridin-3-yl-3,4-dihydro-1H-quinolin-2-one (395 mg, 1.76 mmol) and Lawessons reagent (356 mg, 0.88 mmol) was refluxed in 30 ml toluene for 2 h. After evaporation of the solvent under reduced pressure, the residue was purified by flash chromatography on silica gel (hexanes/ethyl acetate, 3/7, R$_f$=0.31) which gave 6-Pyridin-3-yl-3,4-dihydro-1H-quinoline-2-thione as yellow plates (63 mg, 0.26 mmol, 15%), mp (hexanes/ethyl acetate) 267° C. $^1$H-NMR (500 MHz, DMSO-d$_6$): δ=2.87 (m, 2H), 2.97 (m, 2H), 7.20 (d, $^3$J=8.2 Hz, 1H), 7.46 (dd, $^3$J=7.9 Hz, $^3$J=4.6 Hz, 1H), 7.59 (dd, $^3$J=8.2 Hz, $^4$J=1.9 Hz, 1H), 7.62 (d, $^4$J=1.9 Hz, 1H), 8.04 (m, 1H), 8.53 (dd, $^3$J=4.7 Hz, $^4$J=1.6 Hz, 1H), 8.87 (d, $^4$J=2.2 Hz, 1H), 12.30 (s, 1H). MS m/z=241.05 (MH$^+$).

According to Example 8 using the suitable substituted 6-pyridin-3-yl-3,4-dihydro-1H-quinolin-2-one derivatives (see Schemes 1-19) the following compounds are synthesized:

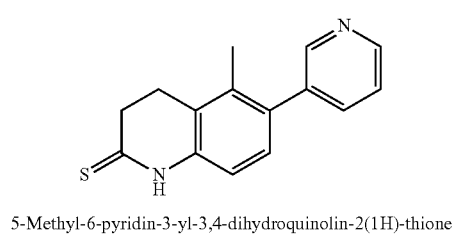

5-Methyl-6-pyridin-3-yl-3,4-dihydroquinolin-2(1H)-thione

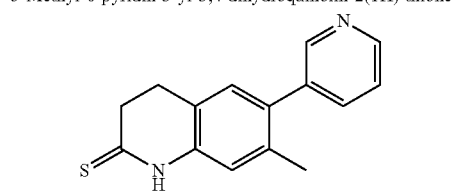

7-Methyl-6-pyridin-3-yl-3,4-dihydroquinolin-2(1H)-thione

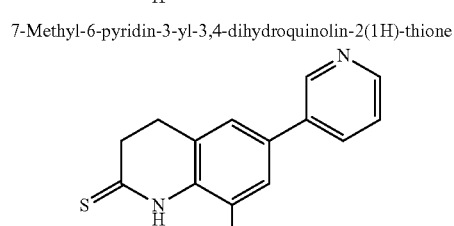

8-Methyl-6-pyridin-3-yl-3,4-dihydroquinolin-2(1H)-thione

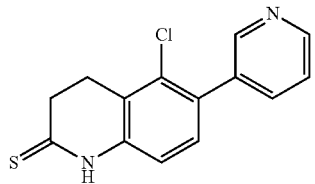

5-Chloro-6-pyridin-3-yl-3,4-dihydroquinolin-2(1H)-thione

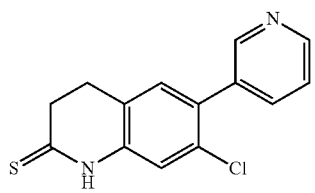

7-Chloro-6-pyridin-3-yl-3,4-dihydroquinolin-2(1H)-thione

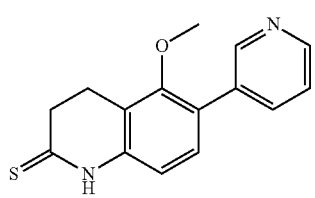

5-Methoxy-6-pyridin-3-yl-3,4-dihydroquinolin-2(1H)-thione

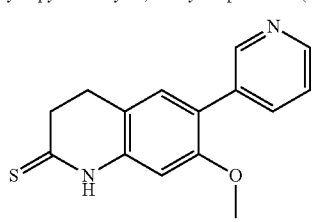

7-Methoxy-6-pyridin-3-yl-3,4-dihydroquinolin-2(1H)-thione

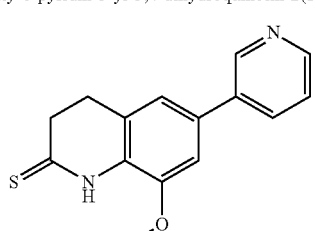

8-Methoxy-6-pyridin-3-yl-3,4-dihydroquinolin-2(1H)-thione

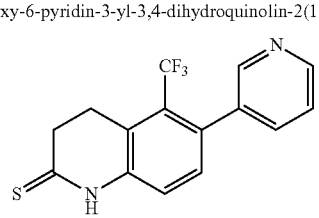

5-Trifluoromethyl-6-pyridin-3-yl-3,4-dihydroquinolin-2(1H)-thione

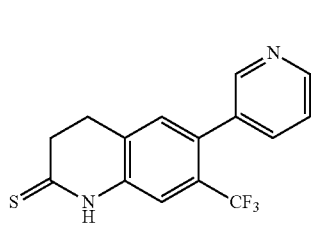

7-Trifluoromethyl-6-pyridin-3-yl-3,4-dihydroquinolin-2(1H)-thione

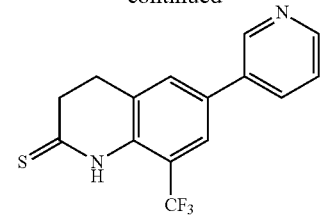

8-Trifluoromethyl-6-pyridin-3-yl-3,4-dihydroquinolin-2(1H)-thione

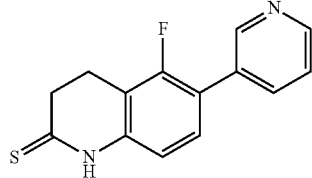

5-Fluoro-6-pyridin-3-yl-3,4-dihydroquinolin-2(1H)-thione

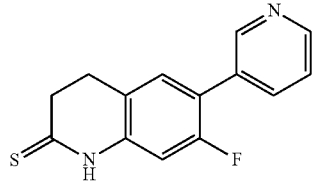

7-Fluoro-6-pyridin-3-yl-3,4-dihydroquinolin-2(1H)-thione

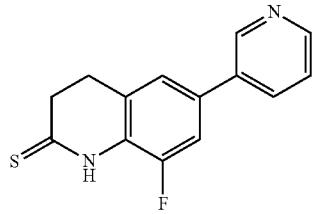

8-Fluoro-6-pyridin-3-yl-3,4-dihydroquinolin-2(1H)-thione

Example 9

1-Ethyl-6-pyridin-3-yl-3,4-dihydro-1H-quinolin-2-one

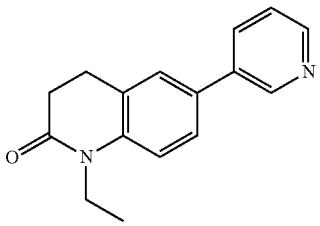 [SMILES: CCN1C(=O)CCc2cc(-c3cccnc3)ccc21]

The title compound was obtained via Suzuki coupling according to general procedure A from 6-bromo-1-ethyl-3,4-dihydro-1H-quinolin-2-one (229 mg, 0.9 mmol) and 3-pyridineboronic acid (92 mg, 0.75 mmol) after flash chromatography on silica gel (hexanes/ethyl acetate, 1/1, $R_f$=0.09) and crystallization from acetone/diethylether as colorless plates (125 mg, 0.50 mmol, 66%), mp (acetone/diethylether) 91° C. $^1$H-NMR (500 MHz, CDCl$_3$): δ=1.30 (t, $^3$J=7.3 Hz, 3H), 2.70 (t, $^3$J=7.6 Hz, 2H), 2.99 (t, $^3$J=7.6 Hz, 2H), 4.04 (q, $^3$J=7.3 Hz, 2H), 7.13 (d, $^3$J=8.2 Hz, 1H), 7.37 (ddd, $^3$J=7.9 Hz, $^3$J=4.7 Hz, $^5$J=0.6 Hz, 1H), 7.41 (d, $^4$J=2.2 Hz, 1H), 7.48 (dd, $^3$J=8.5 Hz, $^4$J=2.2 Hz, 1H), 7.85 (ddd, $^3$J=7.9 Hz, $^4$J=2.2 Hz, $^4$J=1.6 Hz, 1H), 8.58 (dd, $^3$J=5.0 Hz, $^4$J=1.6 Hz, 1H), 8.84 (dd, $^4$J=2.5 Hz, $^5$J=0.6 Hz, 1H). $^{13}$C-NMR (125 MHz, CDCl$_3$): δ=12.8, 25.7, 31.8, 37.4, 115.2, 123.6, 126.1, 126.7, 127.3, 132.2, 133.9, 135.7, 139.6, 148.0, 148.4, 169.7. MS m/z 253.00 (MH$^+$).

Example 10

1-Isopropyl-6-pyridin-3-yl-3,4-dihydro-1H-quinolin-2-one

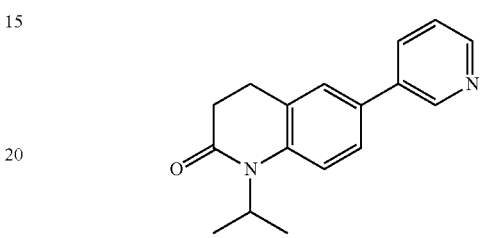

The title compound was obtained via Suzuki coupling according to general procedure A from 6-bromo-1-isopropyl-3,4-dihydro-1H-quinolin-2-one (174 mg, 0.65 mmol) and 3-pyridineboronic acid (74 mg, 0.6 mmol) after flash chromatography on silica gel (hexanes/ethyl acetate, 1/1, $R_f$=0.14) as a colorless solid (74 mg, 0.18 mmol, 29%), mp (hexanes/ethyl acetate) 101° C. $^1$H-NMR (500 MHz, CDCl$_3$): δ=1.54 (d, $^3$J=6.9 Hz, 6H), 2.61 (t, $^3$J=7.3 Hz, 2H), 2.80 (t, $^3$J=7.3 Hz, 2H), 4.73 (sep, $^3$J=6.9 Hz, 1H), 7.23 (d, $^3$J=8.5 Hz, 1H), 7.35 (ddd, $^3$J=7.9 Hz, $^3$J=5.0 Hz, $^5$J=0.9 Hz, 1H), 7.38 (d, $^4$J=2.2 Hz, 1H), 7.43 (dd, $^3$J=8.5 Hz, $^4$J=2.2 Hz, 1H), 7.83 (ddd, $^3$J=7.9 Hz, $^4$J=2.5 Hz, $^4$J=1.9 Hz, 1H), 8.56 (dd, $^3$J=4.7 Hz, $^4$J=1.9 Hz, 1H), 8.84 (dd, $^4$J=2.2 Hz, $^5$J=0.6 Hz, 1H). $^{13}$C-NMR (125 MHz, CDCl$_3$): δ=20.2, 26.0, 33.4, 48.5, 117.0, 123.6, 125.7, 126.4, 129.2, 132.3, 133.9, 135.8, 140.4, 148.0, 148.4, 171.1. MS m/z 267.10 (MH$^+$).

Example 11

8-Pyridin-3-yl-1,2,5,6-tetrahydro-pyrrolo[3,2,1-ij]quinoline-4-one

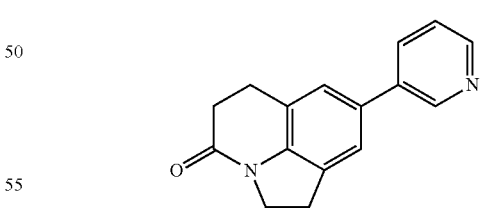

The title compound was obtained via Suzuki coupling according to general procedure A from 8-bromo-1,2,5,6-tetrahydro-pyrrolo[3,2,1-ij]quinolin-4-one (185 mg, 0.73 mmol) and 3-pyridineboronic acid (82 mg, 0.67 mmol) after crystallization from acetone/diethylether as a colorless solid (83 mg, 0.33 mmol, 49%), mp (acetone/diethylether) 152° C. $^1$H-NMR (500 MHz, CDCl$_3$): δ=2.72 (t, $^3$J=7.8 Hz, 2H), 3.03 (t, $^3$J=7.8 Hz, 2H), 3.25 (t, $^3$J=8.5 Hz, 2H), 4.13 (t, $^3$J=8.5 Hz, 2H), 7.20 (s, 1H), 7.28 (s, 1H), 7.32 (ddd, $^3$J=7.8 Hz, $^3$J=4.8 Hz, $^5$J=0.5 Hz, 1H), 7.79 (ddd, $^3$J=7.8 Hz, $^4$J=2.2 Hz, $^4$J=1.6

Hz, 1H), 8.54 (dd, $^3J$=4.7 Hz, $^4J$=1.4 Hz, 1H), 8.59 (d, $^4J$=2.0 Hz, 1H). $^{13}$C-NMR (125 MHz, CDCl$_3$): δ=24.5, 27.7, 31.6, 45.5, 120.7, 122.4, 123.5, 124.7, 129.9, 133.5, 134.0, 136.7, 141.6, 148.1, 167.6. MS m/z 251.00 (MH$^+$).

According to Example 11 using the general experimental procedures A or B and the suitable starting compounds (see Schemes 1-19) the following compounds are synthesized:

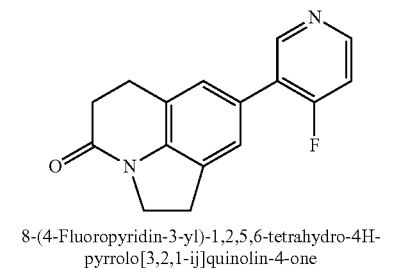

8-(4-Fluoropyridin-3-yl)-1,2,5,6-tetrahydro-4H-pyrrolo[3,2,1-ij]quinolin-4-one

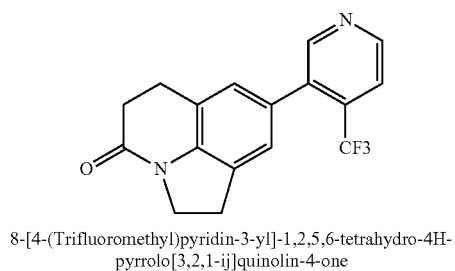

8-[4-(Trifluoromethyl)pyridin-3-yl]-1,2,5,6-tetrahydro-4H-pyrrolo[3,2,1-ij]quinolin-4-one

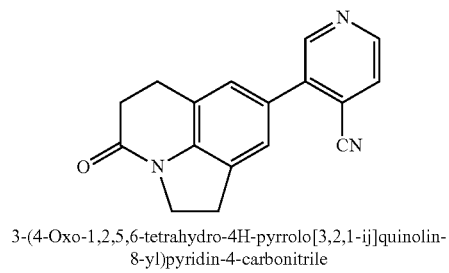

3-(4-Oxo-1,2,5,6-tetrahydro-4H-pyrrolo[3,2,1-ij]quinolin-8-yl)pyridin-4-carbonitrile

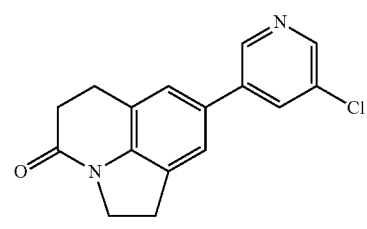

8-(5-Chloropyridin-3-yl)-1,2,5,6-tetrahydro-4H-pyrrolo[3,2,1-ij]quinolin-4-one

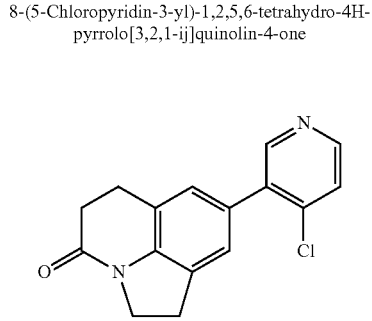

8-(4-Chloropyridin-3-yl)-1,2,5,6-tetrahydro-4H-pyrrolo[3,2,1-ij]quinolin-4-one

-continued

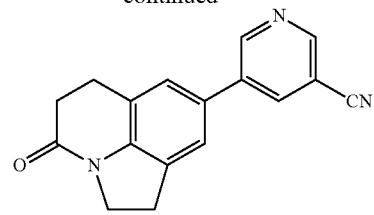

5-(4-Oxo-1,2,5,6-tetrahydro-4H-pyrrolo[3,2,1-ij]quinolin-8-yl)pyridin-3-carbonitrile

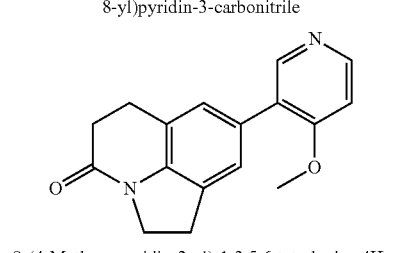

8-(4-Methoxypyridin-3-yl)-1,2,5,6-tetrahydro-4H-pyrrolo[3,2,1-ij]quinolin-4-one

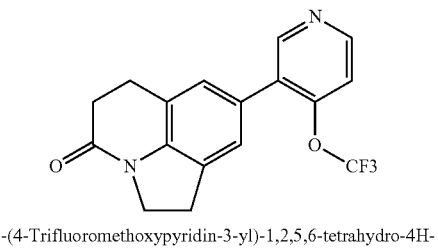

8-(4-Trifluoromethoxypyridin-3-yl)-1,2,5,6-tetrahydro-4H-pyrrolo[3,2,1-ij]quinolin-4-one

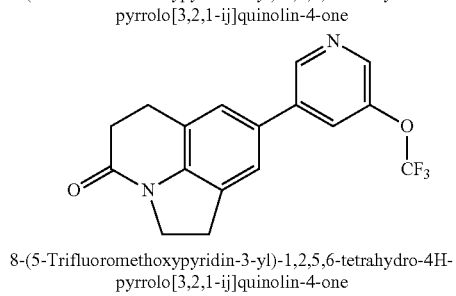

8-(5-Trifluoromethoxypyridin-3-yl)-1,2,5,6-tetrahydro-4H-pyrrolo[3,2,1-ij]quinolin-4-one

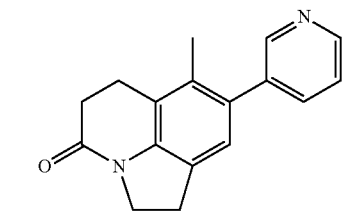

7-Methyl-8-pyridin-3-yl-1,2,5,6-tetrahydro-4H-pyrrolo[3,2,1-ij]quinolin-4-one

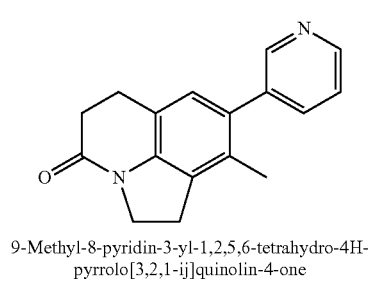

9-Methyl-8-pyridin-3-yl-1,2,5,6-tetrahydro-4H-pyrrolo[3,2,1-ij]quinolin-4-one

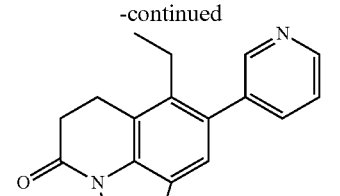

7-Ethyl-8-pyridin-3-yl-1,2,5,6-tetrahydro-4H-
pyrrolo[3,2,1-ij]quinolin-4-one

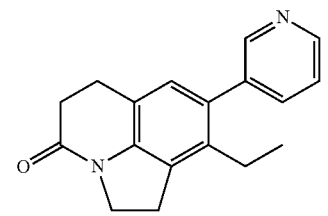

9-Ethyl-8-pyridin-3-yl-1,2,5,6-tetrahydro-4H-
pyrrolo[3,2,1-ij]quinolin-4-one

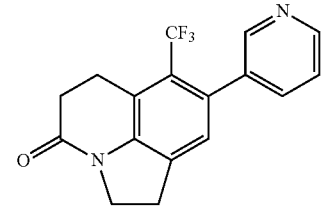

8-(Pyridin-3-yl)-7-(trifluoromethyl)-1,2,5,6-
tetrahydropyrrolo[3,2,1-ij]quinolin-4-one

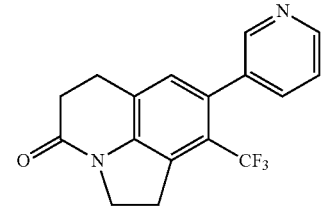

8-(Pyridin-3-yl)-9-(trifluoromethyl)-1,2,5,6-
tetrahydropyrrolo[3,2,1-ij]quinolin-4-one

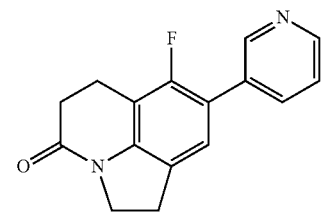

7-Fluoro-8-pyridin-3-yl-1,2,5,6-tetrahydro-4H-
pyrrolo[3,2,1-ij]quinolin-4-one

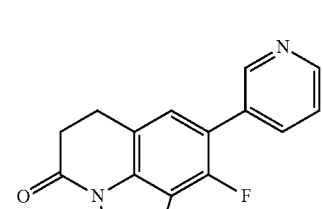

9-Fluoro-8-pyridin-3-yl-1,2,5,6-tetrahydro-4H-
pyrrolo[3,2,1-ij]quinolin-4-one

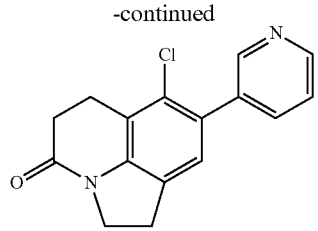

7-Chloro-8-pyridin-3-yl-1,2,5,6-tetrahydro-4H-
pyrrolo[3,2,1-ij]quinolin-4-one

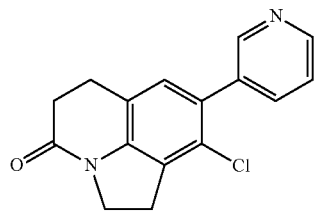

9-Chloro-8-pyridin-3-yl-1,2,5,6-tetrahydro-4H-
pyrrolo[3,2,1-ij]quinolin-4-one

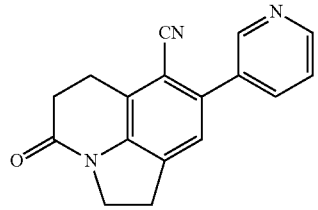

4-Oxo-8-(pyridin-3-yl)-2,4,5,6-tetrahydro-1H-
pyrrolo[3,2,1-ij]quinolin-7-carbonitrile

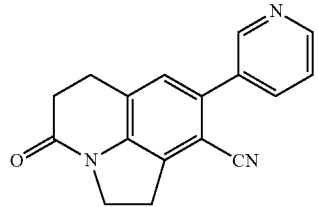

4-Oxo-8-(pyridin-3-yl)-2,4,5,6-tetrahydro-1H-
pyrrolo[3,2,1-ij]quinolin-9-carbonitrile

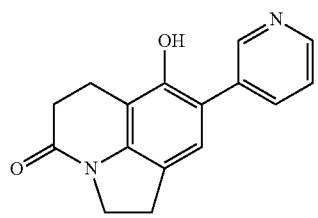

7-Hydroxy-8-(pyridin-3-yl)-1,2,5,6-
tetrahydropyrrolo[3,2,1-ij]quinolin-4-one

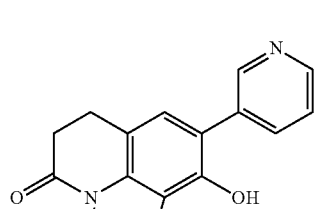

9-Hydroxy-8-(pyridin-3-yl)-1,2,5,6-
tetrahydropyrrolo[3,2,1-ij]quinolin-4-one

-continued

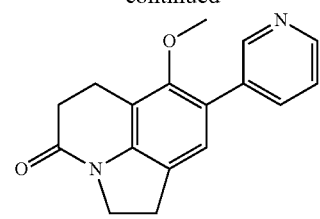

7-Methoxy-8-pyridin-3-yl-1,2,5,6-tetrahydro-4H-
pyrrolo[3,2,1-ij]quinolin-4-one

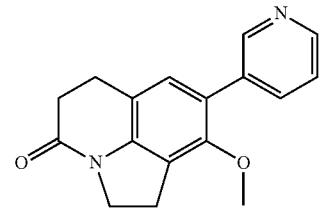

9-Methoxy-8-pyridin-3-yl-1,2,5,6-tetrahydro-4H-
pyrrolo[3,2,1-ij]quinolin-4-one

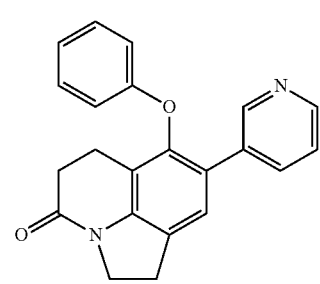

7-Phenoxy-8-pyridin-3-yl-1,2,5,6-tetrahydro-4H-
pyrrolo[3,2,1-ij]quinolin-4-one

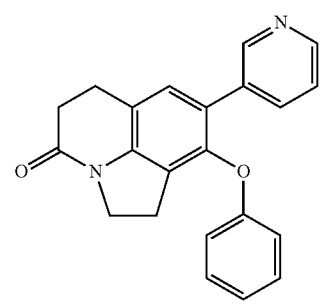

9-Phenoxy-8-pyridin-3-yl-1,2,5,6-tetrahydro-4H-
pyrrolo[3,2,1-ij]quinolin-4-one

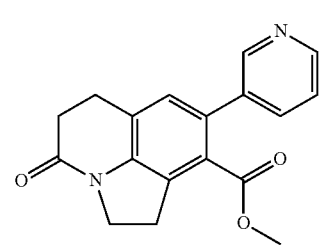

Methyl 4-oxo-8-(pyridin-3-yl)-2,4,5,6-tetrahydro-1H-
pyrrolo[3,2,1-ij]quinoline-9-carboxylate -continued

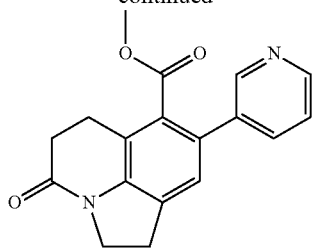

Methyl 4-oxo-8-(pyridin-3-yl)-2,4,5,6-tetrahydro-1H-
pyrrolo[3,2,1-ij]quinoline-7-carboxylate

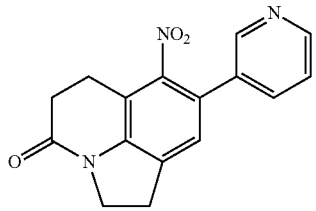

7-Nitro-8-pyridin-3-yl-1,2,,5,6-tetrahydro-4H-
pyrrolo[3,2,1-ij]quinolin-4-one

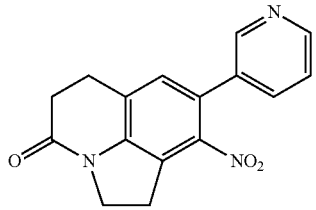

9-Nitro-8-pyridin-3-yl-1,2,,5,6-tetrahydro-4H-
pyrrolo[3,2,1-ij]quinolin-4-one

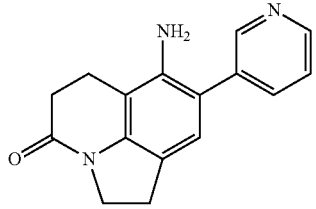

7-Amino-8-pyridin-3-yl-1,2,5,6-tetrahydro-4H-
pyrrolo[3,2,1-ij]quinolin-4-one

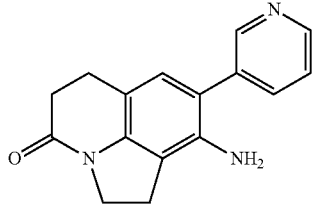

9-Amino-8-pyridin-3-yl-1,2,5,6-tetrahydro-4H-
pyrrolo[3,2,1-ij]quinolin-4-one

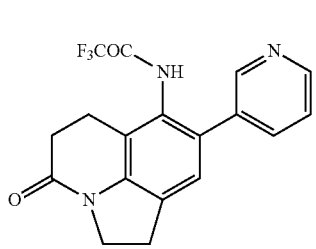

2,2,2-Trifluoro-N-(4-oxo-8-(pyridin-3-yl)-2,4,5,6-tetrahydro-1H-
pyrrolo[3,2,1-ij]quinolin-7-yl)acetamide -continued

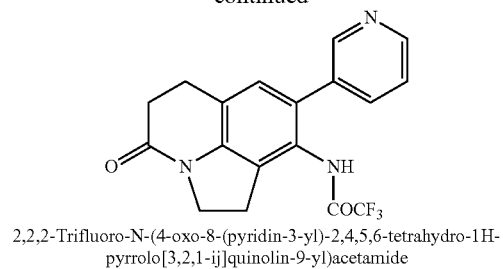

2,2,2-Trifluoro-N-(4-oxo-8-(pyridin-3-yl)-2,4,5,6-tetrahydro-1H-pyrrolo[3,2,1-ij]quinolin-9-yl)acetamide

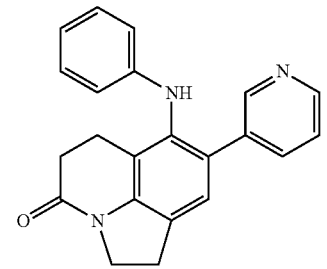

7-(Phenylamino)-8-(pyridin-3-yl)-1,2,5,6-tetrahydropyrrolo[3,2,1-ij]quinolin-4-one

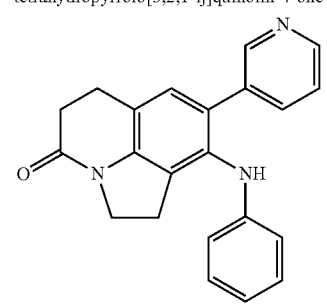

9-(Phenylamino)-8-(pyridin-3-yl)-1,2,5,6-tetrahydropyrrolo[3,2,1-ij]quinolin-4-one

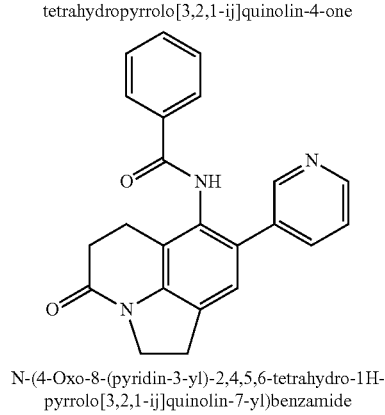

N-(4-Oxo-8-(pyridin-3-yl)-2,4,5,6-tetrahydro-1H-pyrrolo[3,2,1-ij]quinolin-7-yl)benzamide

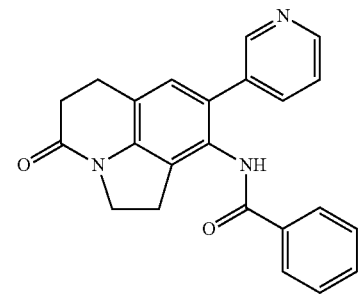

N-(4-Oxo-8-(pyridin-3-yl)-2,4,5,6-tetrahydro-1H-pyrrolo[3,2,1-ij]quinolin-9-yl)benzamide Example 12

8-Chloro-6-pyridin-3-yl-3,4-dihydro-1H-quinolin-2-one

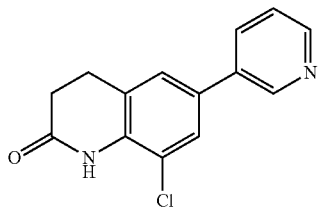 [SMILES: O=C1CCc2cc(-c3cccnc3)cc(Cl)c2N1]

To a solution of 6-Pyridin-3-yl-3,4-dihydro-1H-quinolin-2-one (560 mg, 2.50 mmol) in 5 ml dry DMF was added N-chlorosuccinimide (368 mg, 2.75 mmol) in 5 ml dry DMF over a period 2 h at 65° C. After additional 3 h at 65° C., the mixture was poured into 75 ml ice water and extracted with ethyl acetate (3×50 ml). The combined organic layers were washed with water and brine, dried over MgSO$_4$ and the solvent was evaporated in vacuo. 8-Chloro-6-pyridin-3-yl-3,4-dihydro-1H-quinolin-2-one was obtained after flash chromatography on silica gel (hexanes/ethyl acetate, 3/7, R$_f$=0.15) and crystallization from acetone/diethylether as colorless needles (225 mg, 0.87 mmol, 35%), mp (acetone/diethylether) 178° C. $^1$H-NMR (500 MHz, DMSO-d$_6$): δ=2.54 (m, 2H), 3.01 (m, 2H), 7.45 (ddd, $^3$J=8.0 Hz, $^3$J=4.8 Hz, $^5$J=0.8 Hz, 1H), 7.60 (d, $^4$J=2.0 Hz, 1H), 7.69 (d, $^4$J=2.0 Hz, 1H), 8.06 (ddd, $^3$J=8.0 Hz, $^4$J=2.5 Hz, $^4$J=1.5 Hz, 1H), 8.53 (dd, $^3$J=4.8 Hz, $^4$J=1.5 Hz, 1H), 8.88 (dd, $^4$J=2.5 Hz, $^5$J=0.8 Hz, 1H), 9.64 (s, 1H). $^{13}$C-NMR (125 MHz, DMSO-d$_6$): δ=25.3, 30.3, 119.7, 123.8, 125.0, 125.6, 127.4, 131.7, 133.7, 133.8, 134.8, 147.3, 152.4, 170.3. MS m/z 258.95 (M$^+$).

Example 13

8-Nitro-6-pyridin-3-yl-3,4-dihydro-1H-quinolin-2-one

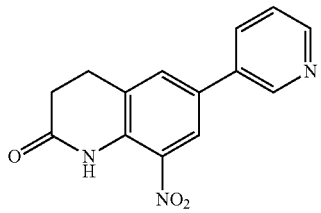 [SMILES: O=C1CCc2cc(-c3cccnc3)cc([N+](=O)[O-])c2N1]

The title compound was obtained via Suzuki coupling according to general procedure B from 6-bromo-8-nitro-3,4-dihydro-1H-quinolin-2-one (1.0 g, 3.70 mmol) (prepared previously by nitration of 6-bromo-3,4-dihydro-1H-quinolin-2-one with concentrated HNO$_3$/H$_2$SO$_4$) and 3-pyridineboronic acid (546 mg, 4.44 mmol) after flash chromatography on silica gel (ethyl acetate, R$_f$=0.15) as yellow needles (311 mg, 1.16 mmol, 31%), mp (ethyl acetate) 189° C. $^1$H-NMR (500 MHz, DMSO-d$_6$): δ=2.64 (t, $^3$J=7.9 Hz, 2H), 3.13 (t, $^3$J=7.9 Hz, 2H), 7.50 (ddd, $^3$J=8.2 Hz, $^3$J=4.9 Hz, $^5$J=0.9 Hz, 1H), 8.09 (d, $^4$J=2.1 Hz, 1H), 8.15 (ddd, $^3$J=7.9 Hz, $^4$J=2.4 Hz, $^4$J=1.5 Hz, 1H), 8.29 (d, $^4$J=2.1 Hz, 1H), 8.59 (dd, $^3$J=4.9 Hz, $^4$J=1.8 Hz, 1H), 8.95 (dd, $^4$J=2.4 Hz, $^5$J=0.8 Hz, 1H), 9.88 (s, 1H). $^{13}$C-NMR (125 MHz, DMSO-$d_6$): δ=25.0, 29.3, 121.4, 123.9, 128.5, 130.6, 132.3, 133.1, 133.2, 134.0, 135.0, 147.4, 149.0, 170.0. MS m/z 269.94 (MH$^+$).

According to Example 13 using the general experimental procedures A or B and the suitable starting compounds (see Schemes 1-19) the following compounds are synthesized:

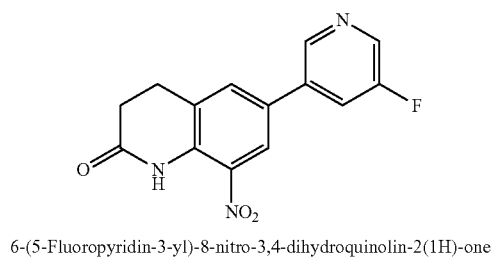

6-(5-Fluoropyridin-3-yl)-8-nitro-3,4-dihydroquinolin-2(1H)-one

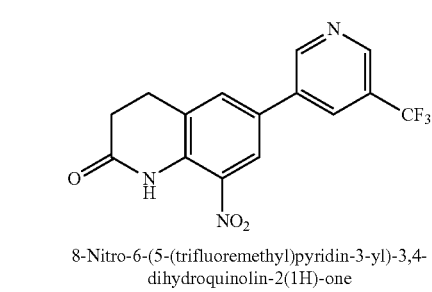

8-Nitro-6-(5-(trifluoremethyl)pyridin-3-yl)-3,4-dihydroquinolin-2(1H)-one

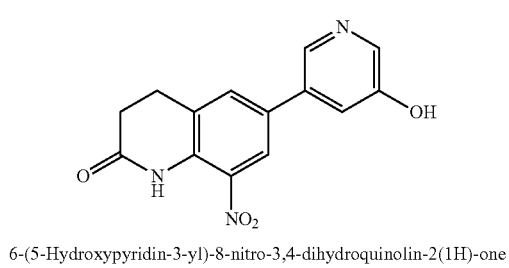

6-(5-Hydroxypyridin-3-yl)-8-nitro-3,4-dihydroquinolin-2(1H)-one

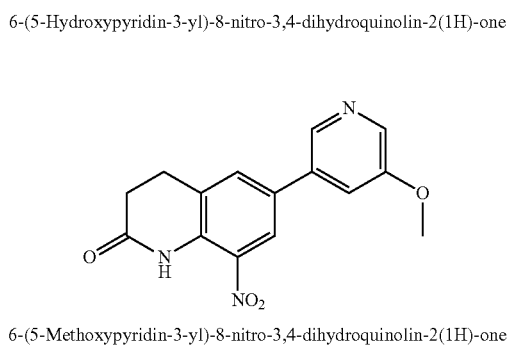

6-(5-Methoxypyridin-3-yl)-8-nitro-3,4-dihydroquinolin-2(1H)-one

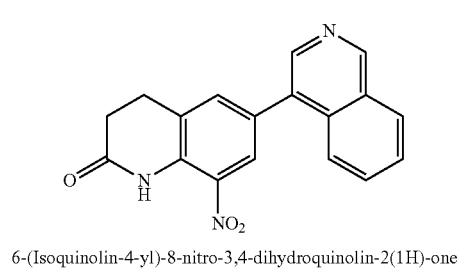

6-(Isoquinolin-4-yl)-8-nitro-3,4-dihydroquinolin-2(1H)-one

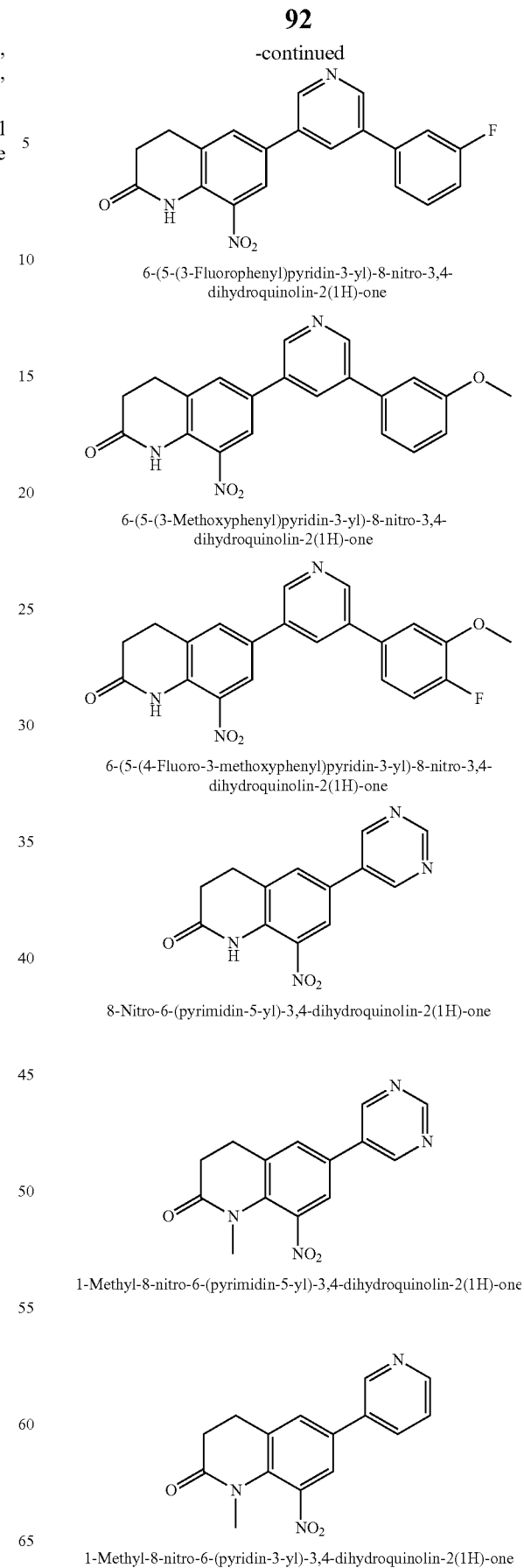

6-(5-(3-Fluorophenyl)pyridin-3-yl)-8-nitro-3,4-dihydroquinolin-2(1H)-one 6-(5-(3-Methoxyphenyl)pyridin-3-yl)-8-nitro-3,4-dihydroquinolin-2(1H)-one 6-(5-(4-Fluoro-3-methoxyphenyl)pyridin-3-yl)-8-nitro-3,4-dihydroquinolin-2(1H)-one 8-Nitro-6-(pyrimidin-5-yl)-3,4-dihydroquinolin-2(1H)-one 1-Methyl-8-nitro-6-(pyrimidin-5-yl)-3,4-dihydroquinolin-2(1H)-one 1-Methyl-8-nitro-6-(pyridin-3-yl)-3,4-dihydroquinolin-2(1H)-one

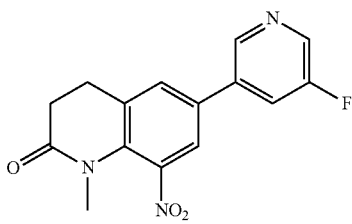

6-(5-Fluoropyridin-3-yl)-1-methyl-8-nitro-3,4-dihydroquinolin-2(1H)-one

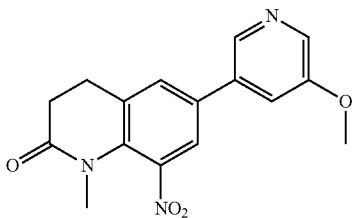

6-(5-Methoxypyridin-3-yl)-1-methyl-8-nitro-3,4-dihydroquinolin-2(1H)-one

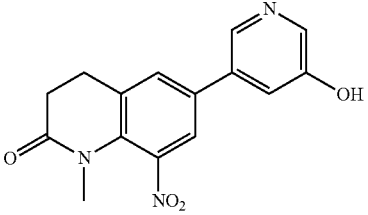

6-(5-Hydroxypyridin-3-yl)-1-methyl-8-nitro-3,4-dihydroquinolin-2(1H)-one

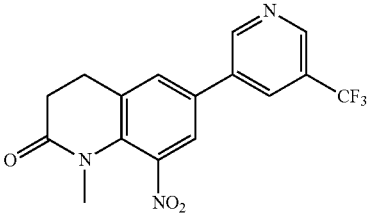

1-Methyl-8-nitro-6-(5-(trifluoromethyl)pyridin-3-yl)-3,4-dihydroquinolin-2(1H)-one

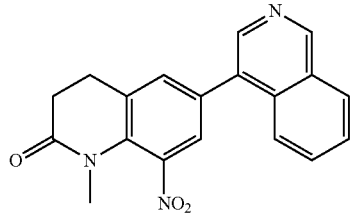

6-(Isoquinolin-4-yl)-1-methyl-8-nitro-3,4-dihydroquinolin-2(1H)-one

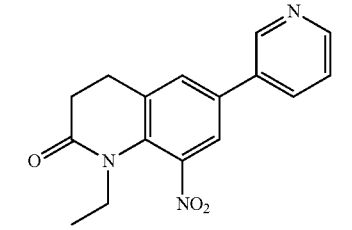

1-Ethyl-8-nitro-6-(pyridin-3-yl)-3,4-dihydroquinolin-2(1H)-one

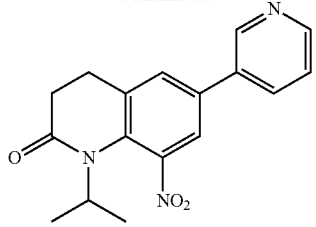

1-Isopropyl-8-nitro-6-(pyridin-3-yl)-3,4-dihydroquinolin-2(1H)-one

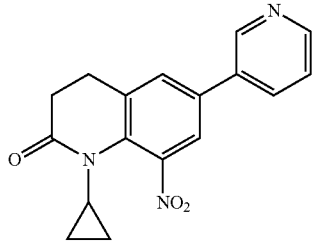

1-Cyclopropyl-8-nitro-6-(pyridin-3-yl)-3,4-dihydroquinolin-2(1H)-one

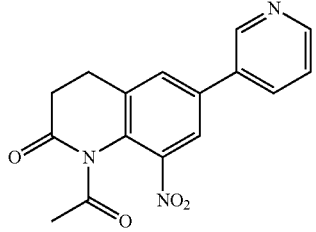

1-Acetyl-8-nitro-6-(pyridin-3-yl)-3,4-dihydroquinolin-2(1H)-one

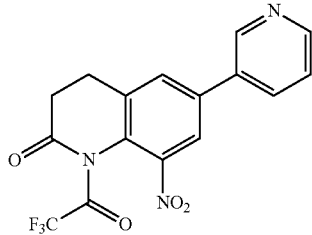

8-Nitro-6-(pyridin-3-yl)-1-(2,2,2-trifluoroacetyl)-3,4-dihydroquinolin-2(1H)-one Example 14

7-Pyridin-3-yl-4H-benzo[1,4]thiazin-3-one

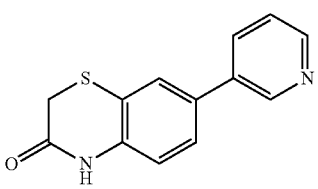

The title compound was obtained via Suzuki coupling according to general procedure B from 7-Bromo-4H-benzo[1,4]thiazin-3-one (1.15 g, 4.71 mmol) and 3-pyridineboronic acid (695 mg, 5.56 mmol) after flash chromatography on silica gel (hexanes/ethyl acetate, 1/1, $R_f$=0.20) and crystallization from ethanol as colorless needles (486 mg, 2.01 mmol, 43%), mp (ethanol) 240° C. $^1$H-NMR (500 MHz, DMSO-d$_6$): δ=3.51 (s, 2H), 7.07 (d, $^3$J=8.5 Hz, 1H), 7.44 (ddd, $^3$J=7.9 Hz, $^3$J=4.9 Hz, $^5$J=0.6 Hz, 1H), 7.54 (dd, $^3$J=8.2 Hz, $^4$J=2.1 Hz, 1H), 7.70 (d, $^4$J=2.1 Hz, 1H), 8.03 (ddd, $^3$J=7.9 Hz, $^4$J=2.4 Hz, $^4$J=1.5 Hz, 1H), 8.52 (dd, $^3$J=4.9 Hz, $^4$J=1.5 Hz, 1H), 8.86 (dd, $^4$J=2.4 Hz, $^5$J=0.6 Hz, 1H), 10.68 (s, 1H). MS m/z 242.99 (MH$^+$).

According to Example 14 using the general experimental procedures A or B and the suitable starting compounds (see Schemes 1-19) the following compounds are synthesized:

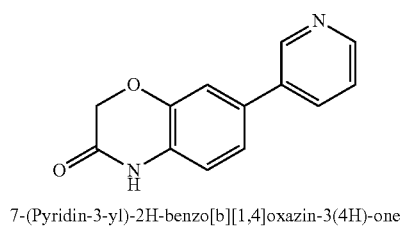

7-(Pyridin-3-yl)-2H-benzo[b][1,4]oxazin-3(4H)-one

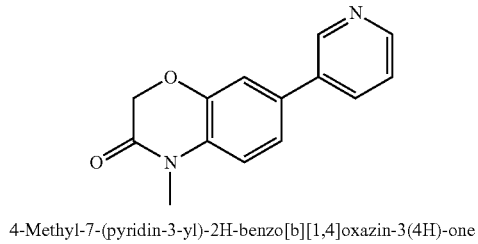

4-Methyl-7-(pyridin-3-yl)-2H-benzo[b][1,4]oxazin-3(4H)-one

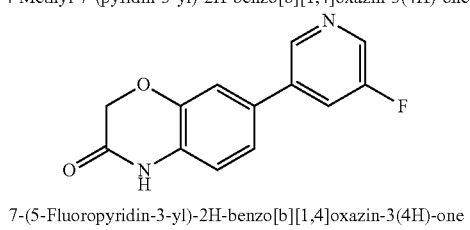

7-(5-Fluoropyridin-3-yl)-2H-benzo[b][1,4]oxazin-3(4H)-one

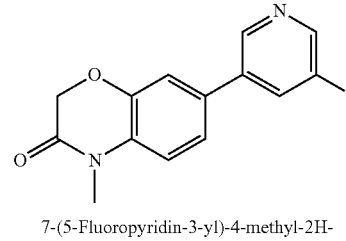

7-(5-Fluoropyridin-3-yl)-4-methyl-2H-benzo[b][1,4]oxazin-3(4H)-one

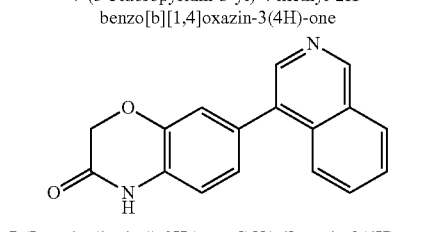

7-(Isoquinolin-4-yl)-2H-benzo[b][1,4]oxazin-3(4H)-one

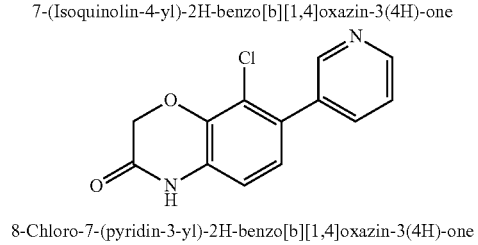

8-Chloro-7-(pyridin-3-yl)-2H-benzo[b][1,4]oxazin-3(4H)-one

-continued

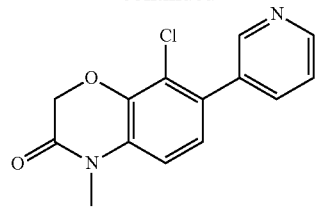

8-Chloro-4-methyl-7-(pyridin-3-yl)-2H-benzo[b][1,4]oxazin-3(4H)-one

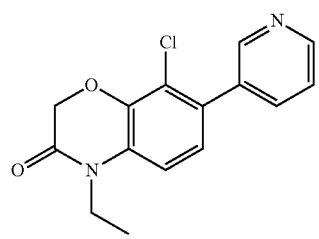

8-Chloro-4-ethyl-7-(pyridin-3-yl)-2H-benzo[b][1,4]oxazin-3(4H)-one

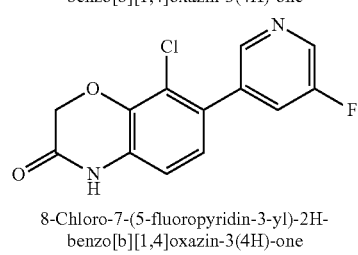

8-Chloro-7-(5-fluoropyridin-3-yl)-2H-benzo[b][1,4]oxazin-3(4H)-one

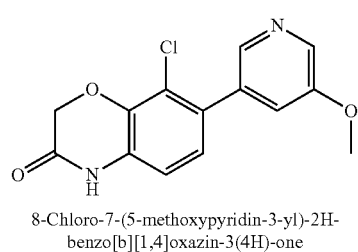

8-Chloro-7-(5-methoxypyridin-3-yl)-2H-benzo[b][1,4]oxazin-3(4H)-one

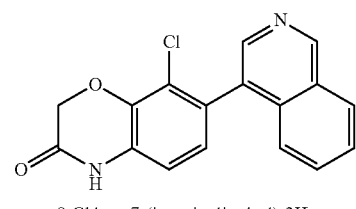

8-Chloro-7-(isoquinolin-4-yl)-2H-benzo[b][1,4]oxazin-3(4H)-one

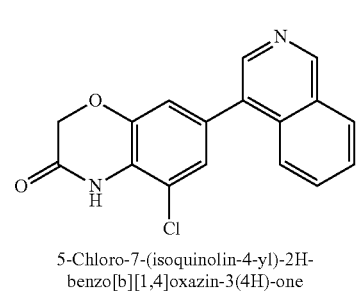

5-Chloro-7-(isoquinolin-4-yl)-2H-benzo[b][1,4]oxazin-3(4H)-one

-continued

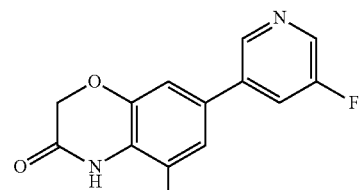

5-Chloro-7-(5-fluorpyridin-3-yl)-2H-benzo[b][1,4]oxazin-3(4H)-one

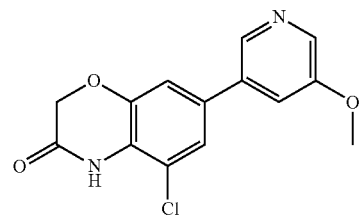

5-Chloro-7-(5-methoxypyridin-3-yl)-2H-benzo[b][1,4]oxazin-3(4H)-one

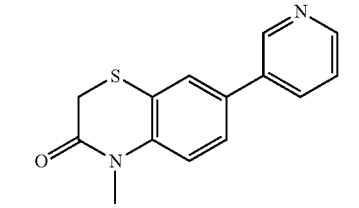

4-Methyl-7-(pyridin-3-yl)-2H-benzo[b][1,4]thiazin-3(4H)-one

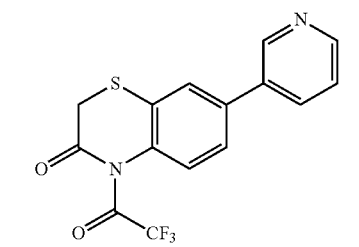

7-(Pyridin-3-yl)-4-(2,2,2-trifluoroacetyl)-2H-benzo[b][1,4]thiazin-3(4H)-one

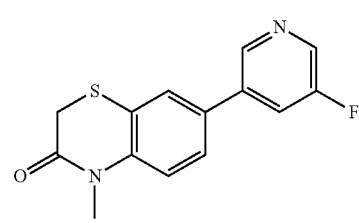

7-(5-Fluoropyridin-3-yl)-4-methyl-2H-benzo[b][1,4]thiazin-3(4H)-one

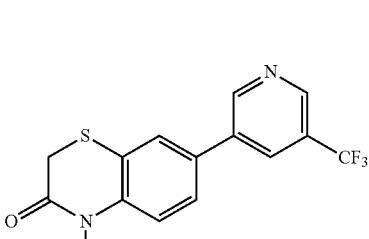

4-Methyl-7-(5-(trifluoromethyl)pyridin-3-yl)-2H-benzo[b][1,4]thiazin-3(4H)-one

-continued

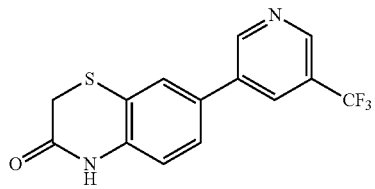

7-(5-(Trifluoromethyl)pyridin-3-yl)-2H-benzo[b][1,4]thiazin-3(4H)-one

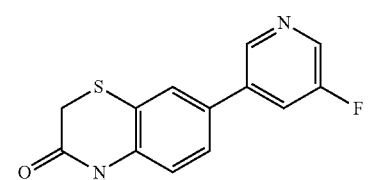

7-(5-Fluoropyridin-3-yl)-2H-benzo[b][1,4]thiazin-3(4H)-one

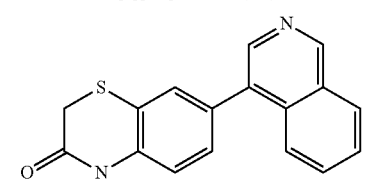

7-(Isoquinolin-4-yl)-2H-benzo[b][1,4]thiazin-3(4H)-one

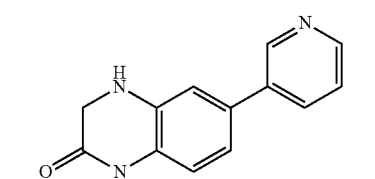

6-(Pyridin-3-yl)-3,4-dihydroquinoxalin-2(1H)-one

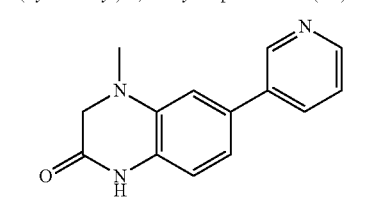

4-Methyl-6-(pyridin-3-yl)-3,4-dihydroquinoxalin-2(1H)-one

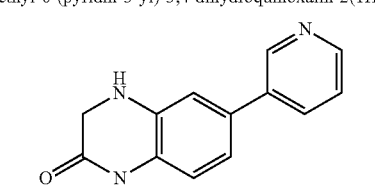

1-Methyl-6-(pyridin-3-yl)-3,4-dihydroqiinoxalin-2(1H)-one

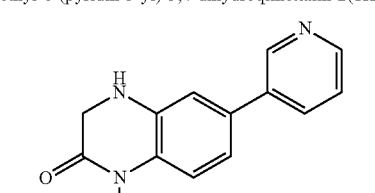

1-Ethyl-6-(pyridin-3-yl)-3,4-dihydroquinoxalin-2(1H)-one

-continued

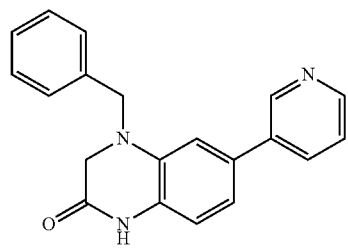

4-Benzyl-6-(pyridin-3-yl)-3,4-dihydroquinoxalin-2(1H)-one

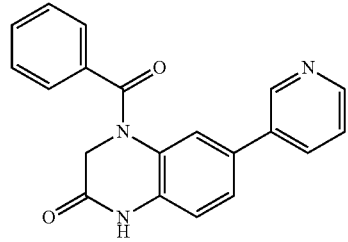

4-Benzoyl-6-(pyridin-3-yl)-3,4-dihydroquinoxalin-2(1H)-one

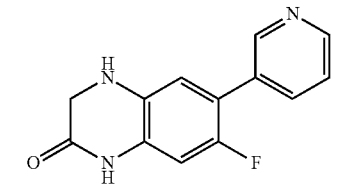

7-Fluoro-6-(pyridin-3-yl)-3,4-dihydroqiinoxalin-2(1H)-one

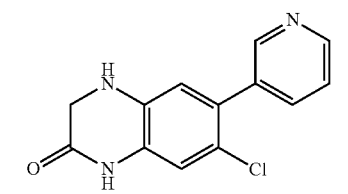

7-Chloro-6-(pyridin-3-yl)-3,4-dihydroquinoxalin-2(1H)-one

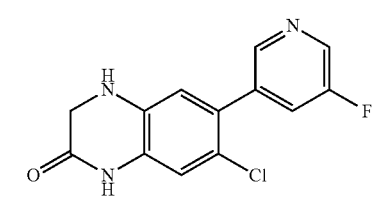

7-Chloro-6-(5-fluoropyridin-3-yl)-3,4-dihydroquinoxalin-2(1H)-one

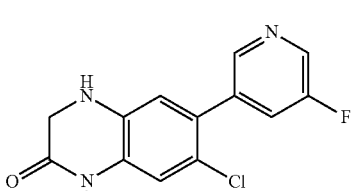

7-Chloro-6-(5-fluoropyridin-3-yl)-1-methyl-3,4-dihydroquinoxalin-2(1H)-one

-continued

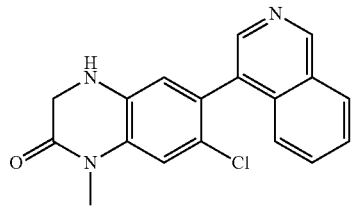

7-Chloro-6-(isoquinolin-4-yl)-1-methyl-3,4-dihydroquinoxalin-2(1H)-one

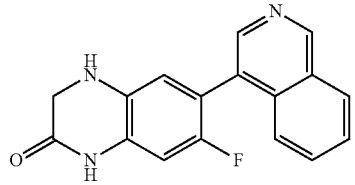

7-Fluoro-6-(isoquinolin-4-yl)-3,4-dihydroquinoxalin-2(1H)-one

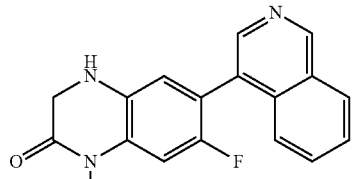

7-Fluoro-6-(isoquinolin-4-yl)-1-methyl-3,4-dihydroquinoxalin-2(1H)-one

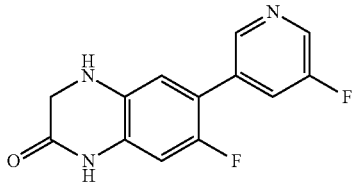

7-Fluoro-6-(5-fluoropyridin-3-yl)-3,4-dihydroquinoxalin-2(1H)-one

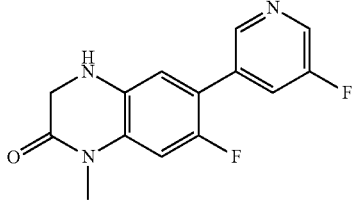

7-Fluoro-6-(5-fluoropyridin-3-yl)-1-methyl-3,4-dihydroquinoxalin-2(1H)-one

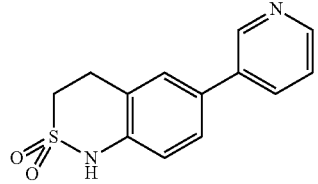

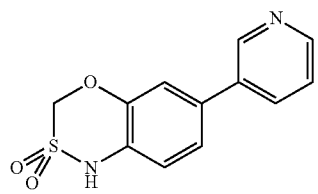

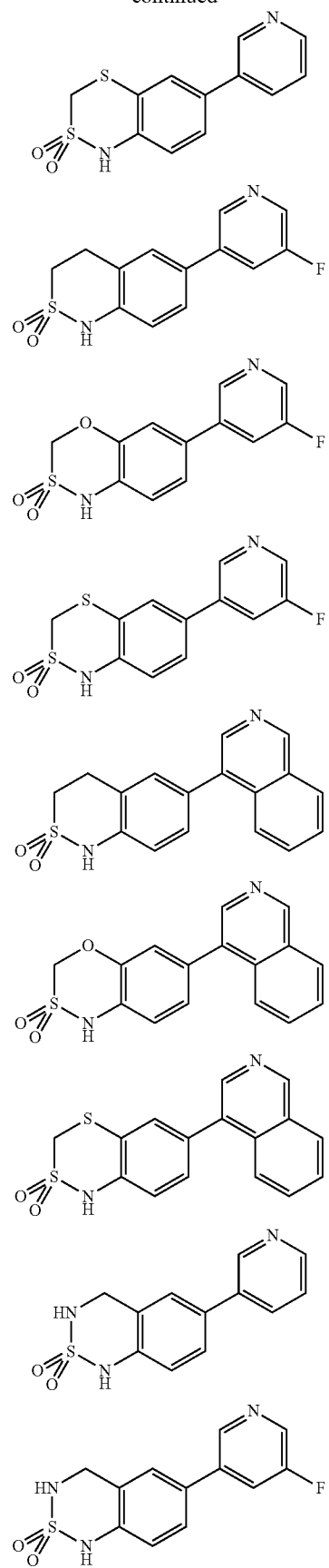
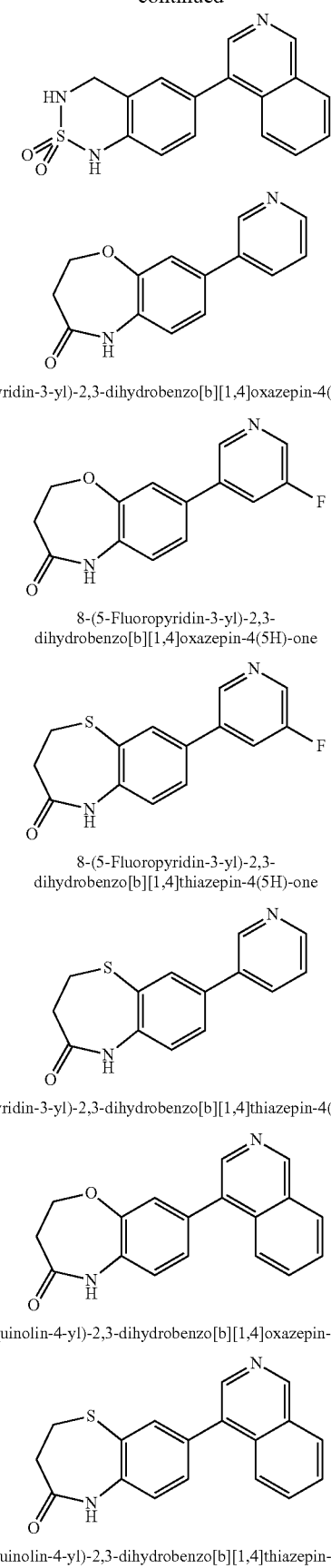
8-(Pyridin-3-yl)-2,3-dihydrobenzo[b][1,4]oxazepin-4(5H)-one
8-(5-Fluoropyridin-3-yl)-2,3-dihydrobenzo[b][1,4]oxazepin-4(5H)-one
8-(5-Fluoropyridin-3-yl)-2,3-dihydrobenzo[b][1,4]thiazepin-4(5H)-one
8-(Pyridin-3-yl)-2,3-dihydrobenzo[b][1,4]thiazepin-4(5H)-one
8-(Isoquinolin-4-yl)-2,3-dihydrobenzo[b][1,4]oxazepin-4(5H)-one
8-(Isoquinolin-4-yl)-2,3-dihydrobenzo[b][1,4]thiazepin-4(5H)-one -continued

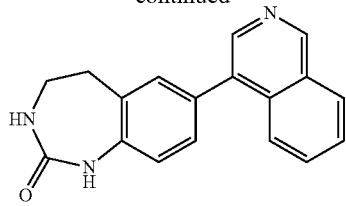

7-(Isoquinolin-4-yl)-4,5-dihydro-1H-benzo[d][1,3]diazepin-2(3H)-one

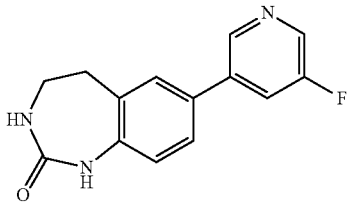

7-(5-Fluoropyridin-3-yl)-4,5-dihydro-1H-benzo[d][1,3]diazepin-2(3H)-one

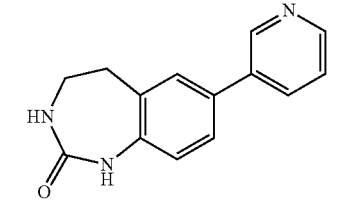

7-(Pyridin-3-yl)-4,5-dihydro-1H-benzo[d][1,3]diazepin-2(3H)-one

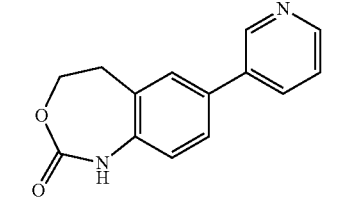

7-(Pyridin-3-yl)-4,5-dihydrobenzo[d][1,3]oxazepin-2(1H)-one

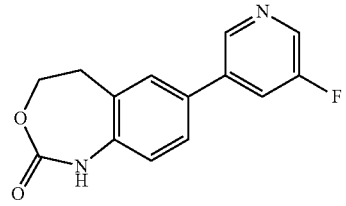

7-(5-Fluoropyridin-3-yl)-4,5-dihydrobenzo[d][1,3]oxazepin-2(1H)-one

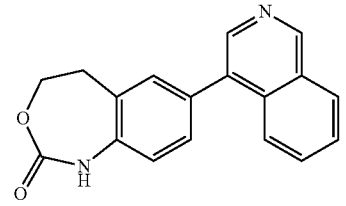

7-(Isoquinolin-4-yl)-4,5-dihydrobenzo[d][1,3]oxazepin-2(1H)-one

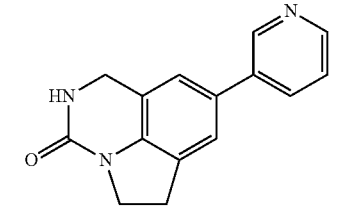

8-Pyridin-3-yl-1,2,5,6-tetrahydro-3H-pyrrolo[3,2,1-ij]quinazolin-3-one

-continued

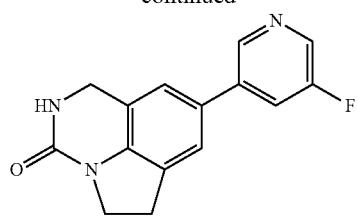

8-(5-Fluoropyridin-3-yl)-1,2,5,6-tetrahydro-3H-pyrrolo[3,2,1-ij]chinazolin-3-on

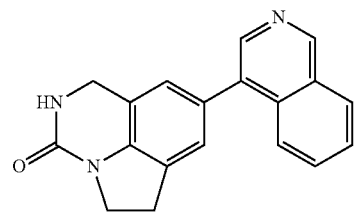

8-Isoquinolin-4-yl-1,2,5,6-tetrahydro-3H-pyrrolo[3,2,1-ij]chinazolin-3-one

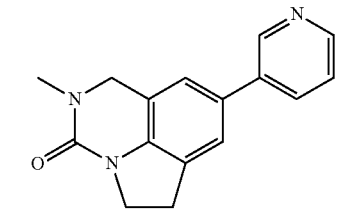

2-Methyl-8-pyridin-3-yl-1,2,5,6-tetrahydro-3H-pyrrolo[3,2,1-ij]chinazolin-3-one

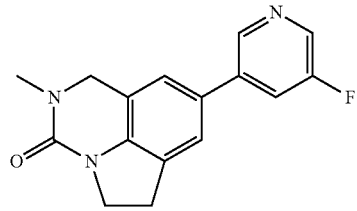

8-(5-Fluoropyridin-3-yl)-2-methyl-1,2,5,6-tetrahydro-3H-pyrrolo[3,2,1-ij)chinazolin-3-one

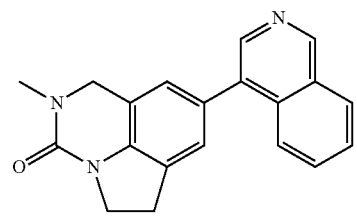

8-Isoquinolin-4-yl-2-methyl-1,2,5,6-tetrahydro-3H-pyrrolo[3,2,1-ij]chinazolin-3-one

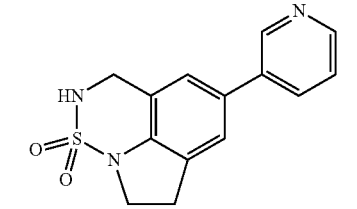

5-Pyridin-3-yl-2,3,7,8-tetrahydro-[1,2,6]thiadiazino[4,3,2-hi]indole 1,1-dioxid

-continued

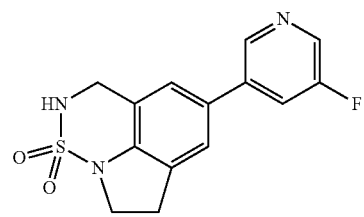

5-(5-Fluoropyridin-3-yl)-2,3,7,8-
tetrahydro[1,2,6]thiadiazino[4,3,2[hi]indole 1,1-dioxid

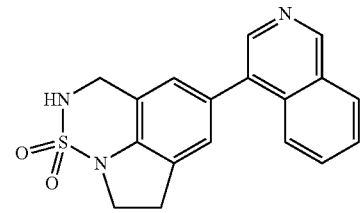

5-Isoquinolin-4-yl-2,3,7,8-tetrahydro[1,2,6]thiadiazino[4,3,2-hi]indole
1,1-dioxid

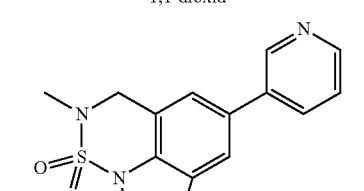

2-Methyl-5-pyridin-3-yl-2,3,7,8-
tetrahydro[1,2,6]thiadiazino[4,3,2-hi]indole 1,1-dioxid

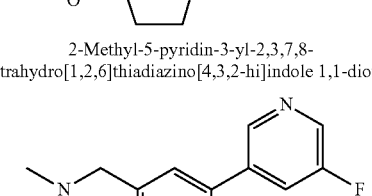

5-(5-Fluoropyridin-3-yl)-2-methyl-2,3,7,8-
tetrahydro[1,2,6]thiadiazino[4,3,2-hi]indole 1,1-dioxid

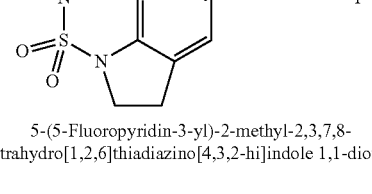

5-Isoquinolin-4-yl-2-methyl-2,3,7,8-
tetrahydro[1,2,6]thiadiazino[4,3,2-hi]indole 1,1-dioxid

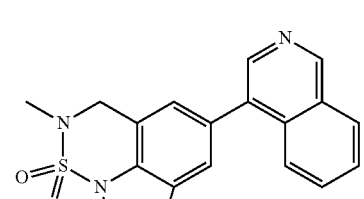

8-Pyridin-3-yl-1,2,5,6-tetrahydro-3H-pyrrolo[1,2,3-de]quinoxalin-3-one

-continued

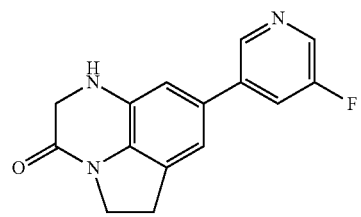

8-(5-Fluoropyridin-3-yl)-1,2,5,6-tetrahydro-3H-
pyrrolo[1,2,3-de]quinoxalin-3-one

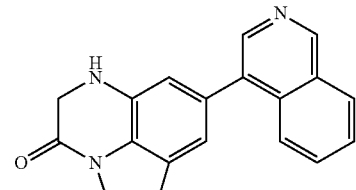

8-Isoquinolin-4-yl-1,2,5,6-tetrahydro-3H-
pyrrolo[1,2,3-de]quinoxalin-3-one

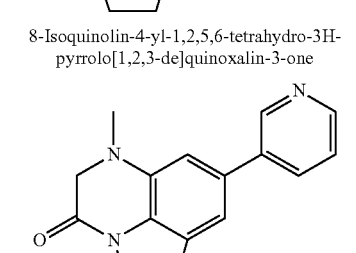

1-Methyl-8-pyridin-3-yl-1,2,5,6-tetrahydro-3H-
pyrrolo[1,2,3-de]quinoxalin-3-one

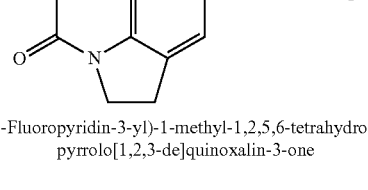

8-(5-Fluoropyridin-3-yl)-1-methyl-1,2,5,6-tetrahydro-3H-
pyrrolo[1,2,3-de]quinoxalin-3-one

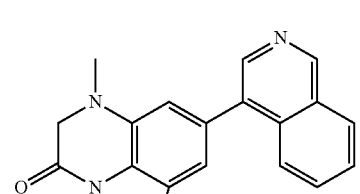

8-Isoquinolin-4-yl-1-methyl-1,2,5,6-tetrahydro-3H-
pyrrolo[1,2,3-de]quinoxalin-3-one

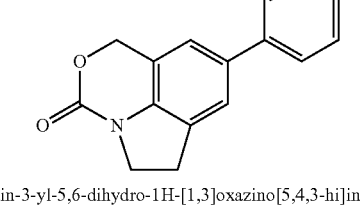

8-Pyridin-3-yl-5,6-dihydro-1H-[1,3]oxazino[5,4,3-hi]indol-3-one

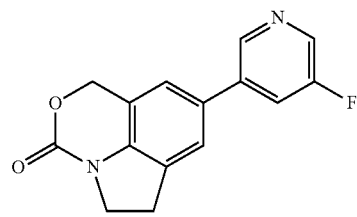

8-(5-Fluoropyridin-3-yl)-5,6-dihydro-1H-
[1,3]oxazino[5,4,3-hi]indol-3-one

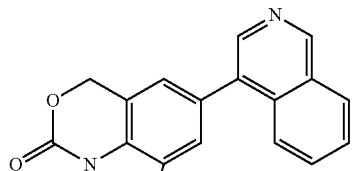

8-Isoquinolin-4-yl-5,6-dihydro-1H-[1,3]oxazino[5,4,3-hi]indol-3-one

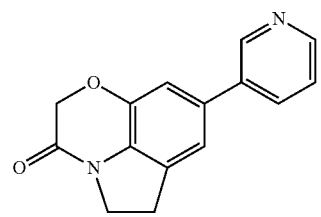

8-Pyridin-3-yl-5,6-dihydro[1,4]oxazino[2,3,4-hi]indol-3(2H)-one

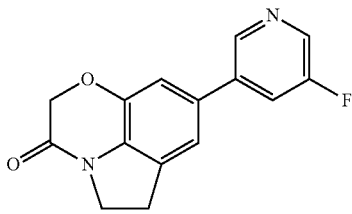

8-(5-Fluoropyridin-3-yl)-5,6-
dihydro[1,4]oxazino[2,3,4-hi]indol-3(2H)-one

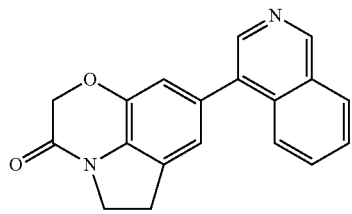

8-Isoquinolin-4-yl-5,6-dihydro[1,4]oxazino[2,3,4-hi]indol-3(2H)-one

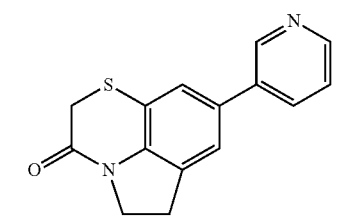

8-Pyridin-3-yl-5,6-dihydro[1,4]thiazino[2,3,4-hi]indol-3(2H)-one

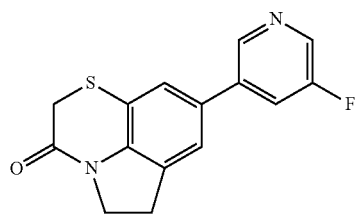

8-(5-Fluoropyridin-3-yl)-5,6-
dihydro[1,4]thiazino[2,3,4-hi]indol-3(2H)-one

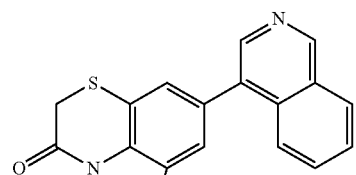

8-Isoquinolin-4-yl-5,6-dihydro[1,4]thiazino[2,3,4-hi]indol-3(2H)-one

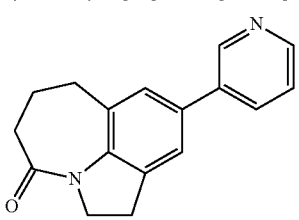

9-Pyridin-3-yl-1,2,6,7-tetrahydroazepino[3,2,1-hi]indol-4(5H)-one

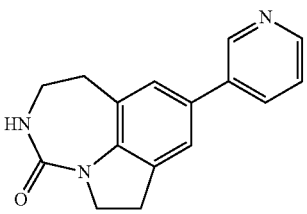

6-Pyridin-3-yl-3,4,8,9-tetrahydro[1,3]diazepino[6,7,1-hi]indol-1(2H)-one

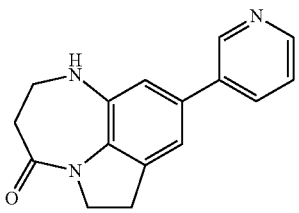

9-Pyridin-3-yl-2,3,6,7-tetrahydro[1,4]diazepino[3,2,1-hi]indol-4(1H)-one

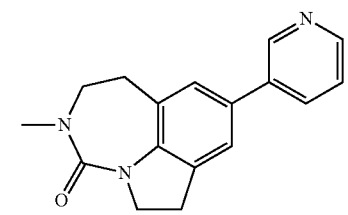

2-Methyl-6-pyridin-3-yl-3,4,8,9-
tetrahydro[1,3]diazepino[6,7,1-hi]indol-1(2H)-one

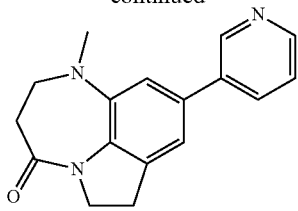

1-Methyl-9-pyridin-3-yl-2,3,6,7-tetrahydro[1,4]diazepino[3,2,1-hi]indol-4(1H)-one

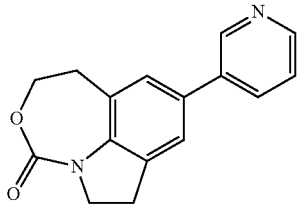

6-Pyridin-3-yl-3,4,8,9-tetrahydro[1,3]oxazepino[5,4,3-hi]indol-1-one

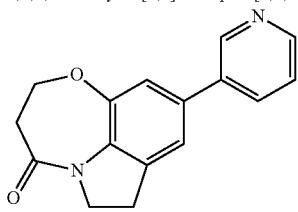

9-Pyridin-3-yl-2,3,6,7-tetrahydro-4H-[1,4]oxazepino[2,3,4-hi]indol-4-one

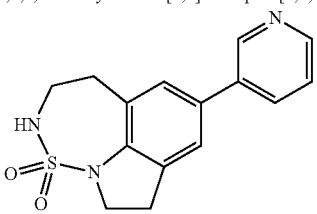

6-Pyridin-3-yl-3,4,8,9-tetrahydro-2H-[1,2,7]thiadiazepino[4,3,2-hi]indol 1,1-dioxid

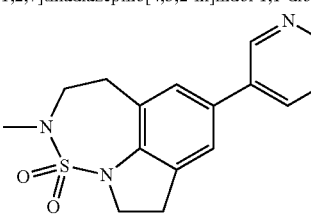

2-Methyl-6-pyridin-3-yl-3,4,8,9-tetrahydro-2H-[1,2,7]thiadiazepino[4,3,2-hi]indole 1,1-dioxid

Example 15

8-Chloro-6-pyridin-3-yl-3,4-dihydro-1H-quinoline-2-thione

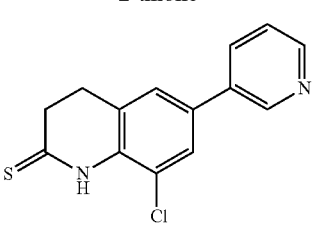

A mixture of 8-chloro-6-pyridin-3-yl-3,4-dihydro-1H-quinolin-2-one (900 mg, 3.48 mmol) and Lawessons reagent (985 mg, 2.44 mmol) was refluxed in 50 ml toluene for 2 h. After evaporation of the solvent under reduced pressure, the residue was purified by flash chromatography on silica gel (ethyl acetate, $R_f$=0.26) and crystallization from acetone/diethylether. 8-Chloro-6-pyridin-3-yl-3,4-dihydro-1H-quinoline-2-thione was obtained as yellow needles (212 mg, 0.77 mmol, 22%), mp (acetone/diethylether) 175° C. $^1$H-NMR (500 MHz, DMSO-d$_6$): δ=2.91 (m, 2H), 3.00 (m, 2H), 7.46 (ddd, $^3$J=7.9 Hz, $^3$J=4.9 Hz, $^5$J=0.9 Hz, 1H), 7.66 (d, $^4$J=2.1 Hz, 1H), 7.76 (d, $^4$J=2.0 Hz, 1H), 8.09 (ddd, $^3$J=7.9 Hz, $^4$J=2.4 Hz, $^4$J=1.5 Hz, 1H), 8.56 (dd, $^3$J=4.9 Hz, $^4$J=1.5 Hz, 1H), 8.91 (dd, $^4$J=2.4 Hz, $^5$J=0.9 Hz, 1H), 11.31 (bs, 1H). $^{13}$C-NMR (125 MHz, DMSO-d$_5$): δ=25.6, 39.4, 120.5, 123.8, 125.2, 126.0, 129.7, 133.4, 133.6, 133.8, 133.9, 147.5, 148.8, 201.5. MS m/z=273.95 (M$^{35}$Cl$^+$), 275.95 (M$^{37}$Cl$^+$).

Example 16

9-Pyridin-3-yl-1,2,6,7-tetrahydro-5H-pyrido[3,2,1-ij]quinolin-3-one

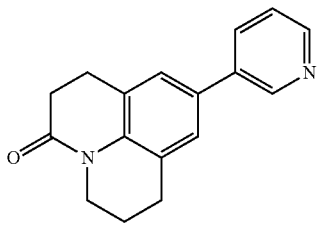 [SMILES: O=C1CCc2cc(-c3cccnc3)cc3c2N1CCC3]

The title compound was obtained via Suzuki coupling according to general procedure A from 9-bromo-1,2,6,7-tetrahydro-5H-pyrido[3,2,1-ij]quinolin-3-one (266 mg, 1.0 mmol) and 3-pyridineboronic acid (92 mg, 0.75 mmol) after flash chromatography on silica gel (hexanes/ethyl acetate, 2/3, $R_f$=0.12) and crystallization from acetone/diethylether as colorless needles (116 mg, 0.44 mmol, 59%), mp (acetone/diethylether) 123° C. $^1$H-NMR (500 MHz, CDCl$_3$): δ=1.97 (m, 2H), 2.69 (t, $^3$J=7.2 Hz, 2H), 2.86 (t, $^3$J=6.3 Hz, 2H), 2.95 (t, $^3$J=7.2 Hz, 2H), 3.90 (t, $^3$J=6.1 Hz, 2H), 7.20-7.24 (m, 2H), 7.33 (ddd, $^3$J=7.9 Hz, $^3$J=4.7 Hz, $^5$J=0.6 Hz, 1H), 7.81 (ddd, $^3$J=7.9 Hz, $^4$J=2.3 Hz, $^4$J=1.5 Hz, 1H), 8.55 (dd, $^3$J=4.8 Hz, $^4$J=1.5 Hz, 1H), 8.80 (m, 1H). $^{13}$C-NMR (125 MHz, CDCl$_3$): δ=21.4, 25.4, 27.4, 31.4, 41.0, 123.5, 124.4, 125.9, 126.2, 126.4, 131.9, 133.8, 135.9, 136.2, 148.0, 148.2, 169.4. MS m/z 265.18 (MH$^+$).

Example 17

8-(5-Methoxypyridin-3-yl)-1,2,5,6-tetrahydro-pyrrolo[3,2,1-ij]quinolin-4-one

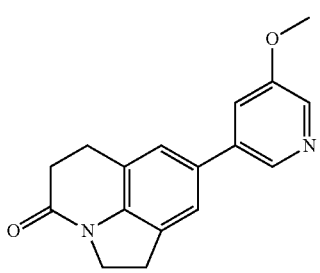 [SMILES: COc1cncc(-c2cc3c4c(c2)CCN4C(=O)CC3)c1]

The title compound was obtained via Suzuki coupling according to general procedure A from 8-bromo-1,2,5,6-tetrahydro-pyrrolo[3,2,1-ij]quinolin-4-one (252 mg, 1.0 mmol) and 5-methoxy-3-pyridineboronic acid (115 mg, 0.75 mmol) after flash chromatography on silica gel (ethyl acetate, $R_f$=0.09) as colorless needles (74 mg, 0.26 mmol, 35%), mp (ethyl acetate) 172° C. $^1$H-NMR (500 MHz, CDCl$_3$): δ=2.70 (t, $^3$J=7.7 Hz, 2H), 3.02 (t, $^3$J=7.7 Hz, 2H), 3.23 (t, $^3$J=8.4 Hz, 2H), 3.90 (s, 3H), 4.11 (t, $^3$J=8.4 Hz, 2H), 7.18 (s, 1H), 7.26 (s, 1H), 7.27 (dd, $^4$J=2.8 Hz, $^4$J=1.9 Hz, 1H), 8.25 (d, $^4$J=2.8 Hz, 1H), 8.37 (d, $^4$J=1.9 Hz, 1H). $^{13}$C-NMR (125 MHz, CDCl$_3$): δ=24.4, 27.7, 31.5, 45.4, 55.6, 118.8, 120.6, 122.4, 124.8, 129.8, 133.3, 135.6, 137.4, 140.5, 141.6, 155.7, 167.5. MS m/z 281.13 (MH$^+$).

Example 18

8-Isoquinolin-4-yl-1,2,5,6-tetrahydro-pyrrolo[3,2,1-ij]quinolin-4-one

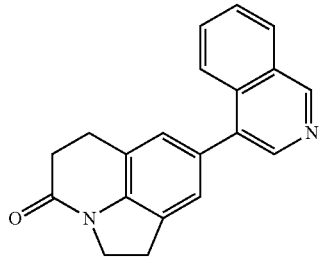 [SMILES: O=C1CCc2cc(-c3cncc4ccccc34)cc3c2N1CC3]

The title compound was obtained via Suzuki coupling according to general procedure A from 8-bromo-1,2,5,6-tetrahydro-pyrrolo[3,2,1-ij]quinolin-4-one (252 mg, 1.0 mmol) and 4-isoquinolineboronic acid (227 mg, 0.9 mmol) after flash chromatography on silica gel (hexanes/ethyl acetate, 2/3, $R_f$=0.13) as colorless needles (93 mg, 0.31 mmol, 34%), mp (hexanes/ethyl acetate) 185° C. $^1$H-NMR (500 MHz, CDCl$_3$): δ=2.75 (t, $^3$J=7.8 Hz, 2H), 3.05 (t, $^3$J=7.8 Hz, 2H), 3.28 (t, $^3$J=8.4 Hz, 2H), 4.16 (t, $^3$J=8.4 Hz, 2H), 7.13 (s, 1H), 7.20 (s, 1H), 7.62 (m, 1H), 7.67 (m, 1H), 7.91 (d, $^3$J=8.5 Hz, 1H), 8.02 (d, $^3$J=7.9 Hz, 1H), 8.44 (s, 1H), 9.22 (s, 1H). $^{13}$C-NMR (125 MHz, CDCl$_3$): δ=24.4, 27.8, 31.6, 45.4, 120.2, 124.7, 125.1, 127.1, 127.4, 127.9, 128.4, 129.3, 130.5, 132.2, 133.2, 134.2, 141.3, 142.8, 151.8, 167.6. MS m/z 301.15 (MH$^+$).

Example 19

9-(5-Methoxypyridin-3-yl)-1,2,6,7-tetrahydro-5H-pyrido[3,2,1-ij]quinolin-3-one

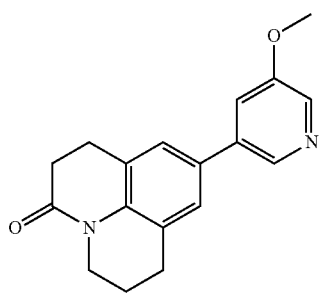 [SMILES: COc1cncc(-c2cc3c4c(c2)CCC(=O)N4CCC3)c1]

The title compound was obtained via Suzuki coupling according to general procedure A from 9-bromo-1,2,6,7-tetrahydro-5H-pyrido[3,2,1-ij]quinolin-3-one (266 mg, 1.0 mmol) and 5-methoxy-3-pyridineboronic acid (115 mg, 0.75 mmol) after flash chromatography on silica gel (hexanes/ethyl acetate, 2/3, $R_f$=0.08) and crystallization from acetone/diethylether as colorless needles (63 mg, 0.21 mmol, 28%), mp (acetone/diethylether) 150° C. $^1$H-NMR (500 MHz, CDCl$_3$): δ=1.98 (m, 2H), 2.69 (m, 2H), 2.86 (t, $^3$J=6.3 Hz, 2H), 2.95 (m, 2H), 3.90 (t, $^3$J=6.0 Hz, 2H), 3.91 (s, 3H), 7.20 (s, 1H), 7.21 (s, 1H), 7.31 (dd, $^4$J=2.8 Hz, $^4$J=1.9 Hz, 1H), 8.26 (d, $^4$J=2.8 Hz, 1H), 8.41 (d, $^4$J=1.9 Hz, 1H). $^{13}$C-NMR (125 MHz, CDCl$_3$): δ=21.4, 25.4, 27.5, 31.4, 40.0, 55.7, 118.7, 124.5, 125.9, 126.1, 126.5, 131.7, 135.8, 136.3, 136.6, 140.4, 155.8, 169.4. MS m/z 295.06 (MH$^+$).

Example 20

9-Isoquinolin-4-yl-1,2,6,7-tetrahydro-5H-pyrido[3,2,1-ij]quinolin-3-one

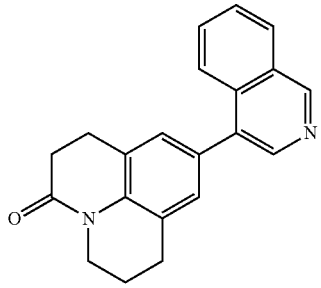 [SMILES: O=C1CCc2cc(-c3cncc4ccccc34)cc3c2N1CCC3]

The title compound was obtained via Suzuki coupling according to general procedure A from 9-bromo-1,2,6,7-tetrahydro-5H-pyrido[3,2,1-ij]quinolin-3-one (266 mg, 1.0 mmol) and 4-isoquinolineboronic acid (227 mg, 0.9 mmol) after flash chromatography on silica gel (hexanes/ethyl acetate, 2/3, $R_f$=0.10) and crystallization from acetone/diethylether as colorless needles (173 mg, 0.55 mmol, 61%), mp (acetone/diethylether) 159° C. $^1$H-NMR (500 MHz, CDCl$_3$): δ=2.01 (m, 2H), 2.72 (m, 2H), 2.87 (t, $^3$J=6.3 Hz, 2H), 2.97 (m, 2H), 3.95 (t, $^3$J=6.0 Hz, 2H), 7.14 (s, 1H), 7.15 (s, 1H), 7.62 (m, 1H), 7.68 (m, 1H), 7.94 (d, $^3$J=8.5 Hz, 1H), 8.03 (d, $^3$J=7.9 Hz, 1H), 8.45 (s, 1H), 9.23 (s, 1H). $^{13}$C-NMR (125 MHz, CDCl$_3$): δ=21.4, 25.3, 27.4, 31.5, 40.0, 124.7, 125.5, 125.6, 127.1, 127.4, 127.9, 128.4, 129.3, 130.5, 131.1, 132.6, 134.2, 136.0, 142.8, 151.9, 169.5. MS m/z 315.01 (MH$^+$).

Example 21

6-Pyrimidin-5-yl-3,4-dihydro-1H-quinolin-2-one

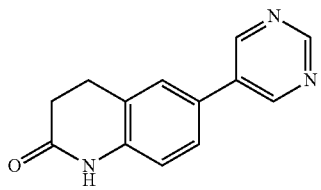 [SMILES: O=C1CCc2cc(-c3cncnc3)ccc2N1]

The title compound was obtained via Suzuki coupling according to general procedure A from 6-Bromo-3,4-dihydro-1H-quinolin-2-one (226 mg, 1.0 mmol) and 5-pyrimidineboronic acid (103 mg, 0.83 mmol) after crystallization from ethanol as colorless needles (75 mg, 0.33 mmol, 40%), mp (ethanol) 233° C. $^1$H-NMR (500 MHz, CDCl$_3$): δ=2.50 (t, $^3$J=7.6 Hz, 2H), 2.95 (t, $^3$J=7.6 Hz, 2H), 6.98 (d, $^3$J=8.2 Hz, 1H), 7.59 (dd, $^3$J=8.2 Hz, $^4$J=1.6 Hz, 1H), 7.66 (d, $^4$J=1.6 Hz, 1H), 9.08 (s, 2H), 9.11 (s, 1H), 10.22 (s, 1H). $^{13}$C-NMR (125 MHz, CDCl$_3$): δ=24.8, 30.2, 115.7, 124.5, 125.6, 126.2, 127.1, 132.9, 139.1, 154.0, 156.6, 170.2. MS m/z 225.74 (MH$^+$).

Example 22

8-Pyridin-3-yl-1,2,5,6-tetrahydro-pyrrolo[3,2,1-ij]quinoline-4-thione

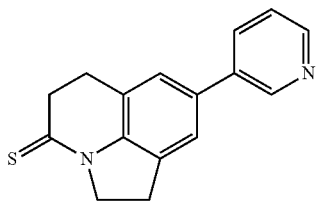 [SMILES: S=C1CCc2cc(-c3cccnc3)cc3c2N1CC3]

A mixture of 8-pyridin-3-yl-1,2,5,6-tetrahydro-pyrrolo[3,2,1-ij]quinoline-4-one (900 mg, 3.60 mmol) and Lawessons reagent (1.45 g, 3.60 mmol) was refluxed in a mixture of 50 ml toluene and 5 ml THF for 2 h. After evaporation of the solvent under reduced pressure, the residue was purified by flash chromatography on silica gel (hexanes/ethyl acetate, 1/1, R$_f$=0.25). 8-Pyridin-3-yl-1,2,5,6-tetrahydro-pyrrolo[3,2,1-ij]quinoline-4-thione was obtained as a yellow solid (155 mg, 0.58 mmol, 26%), mp (HCl salt, THF) 283° C. $^1$H-NMR (500 MHz, CDCl$_3$): δ=2.96 (t, $^3$J=7.9 Hz, 2H), 3.25 (t, $^3$J=7.6 Hz, 2H), 3.29 (t, $^3$J=8.0 Hz, 2H), 4.42 (t, $^3$J=8.2 Hz, 2H), 7.23 (s, 1H), 7.33 (s, 1H), 7.34 (ddd, $^3$J=7.9 Hz, $^3$J=4.7 Hz, $^5$J=0.6 Hz, 1H), 7.81 (ddd, $^3$J=7.9 Hz, $^4$J=2.5 Hz, $^4$J=1.9 Hz, 1H), 8.57 (dd, $^3$J=4.7 Hz, $^4$J=1.6 Hz, 1H), 8.59 (d, $^4$J=2.2 Hz, 1H). $^{13}$C-NMR (125 MHz, CDCl$_3$): δ=23.5, 27.1, 40.3, 52.0, 122.7, 123.0, 123.6, 125.1, 131.7, 134.2, 135.2, 136.4, 139.6, 148.1, 148.5, 192.5. MS m/z 267.10 (MH$^+$).

According to Example 22 starting from substituted 8-pyridin-3-yl-1,2,5,6-tetrahydro-pyrrolo[3,2,1-ij]quinolin-4-one derivatives (see Schemes 1-19) the following compounds can be synthesized:

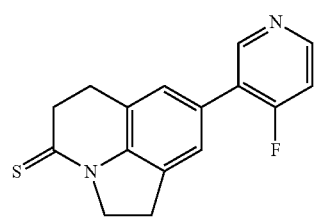

8-(4-Fluoropyridin-3-yl)-1,2,5,6-tetrahydro-4H-pyrrolo[3,2,1-ij]quinolin-4-thione

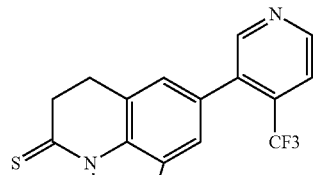

8-[4-(Trifluoromethyl)pyridin-3-yl]-1,2,5,6-tetrahydro-4H-pyrrolo[3,2,1-ij]quinoline-4-thione

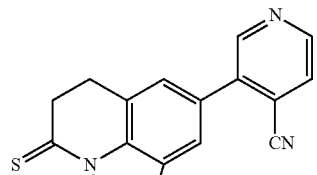

3-(4-Thioxo-1,2,5,6-tetrahydro-4H-pyrrolo[3,2,1-ij]quinolin-8-yl)pyridin-4-carbonitrile

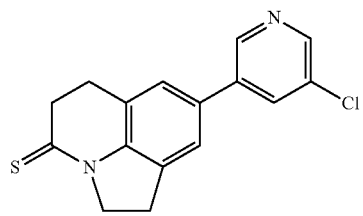

8-(5-Chloropyridin-3-yl)-1,2,5,6-tetrahydro-4H-pyrrolo[3,2,1-ij]quinolin-4-thione

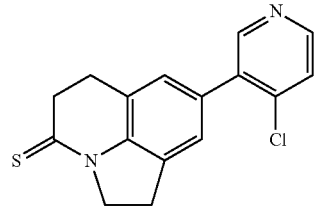

8-(4-Chloropyridin-3-yl)-1,2,5,6-tetrahydro-4H-pyrrolo[3,2,1-ij]quinolin-4-thione

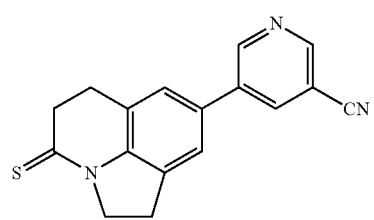

5-(4-Thioxo-1,2,5,6-tetrahydro-4H-pyrrolo[3,2,1-ij]quinolin-8-yl)pyridin-3-carbonitrile

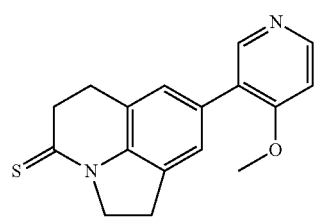

8-(4-Methoxypyridin-3-yl)-1,2,5,6-tetrahydro-4H-pyrrolo[3,2,1-ij]quinolin-4-thione -continued

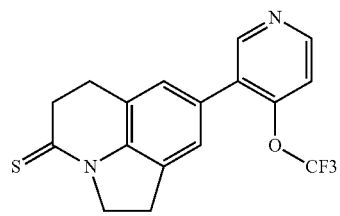

8-(4-Trifluoromethoxypyridin-3-yl)-1,2,5,6-tetrahydro-4H-pyrrolo[3,2,1-ij]quinolin-4-thione

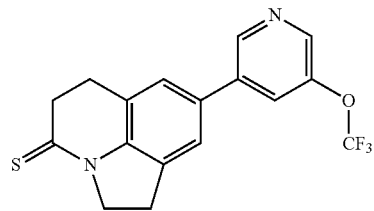

8-(5-Trifluoromethoxypyridin-3-yl)-1,2,5,6-tetrahydro-4H-pyrrolo[3,2,1-ij]quinolin-4-thione

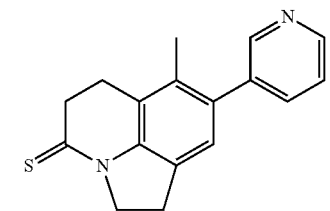

7-Methyl-8-pyridin-3-yl-1,2,5,6-tetrahydro-4H-pyrrolo[3,2,1-ij]quinolin-4-thione

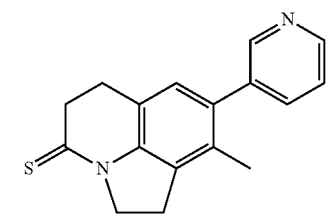

9-Methyl-8-pyridin-3-yl-1,2,5,6-tetrahydro-4H-pyrrolo[3,2,1-ij]quinolin-4-thione

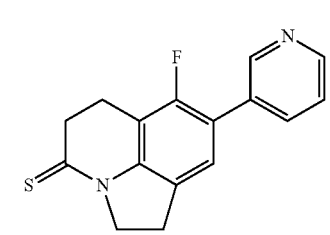

7-Fluoro-8-pyridin-3-yl-1,2,5,6-tetrahydro-4H-pyrrolo[3,2,1-ij]quinolin-4-one

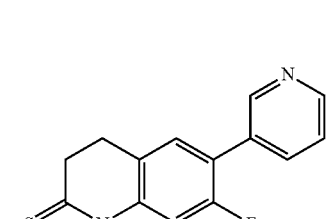

9-Fluoro-8-pyridin-3-yl-1,2,5,6-tetrahydro-4H-pyrrolo[3,2,1-ij]quinolin-4-thione -continued

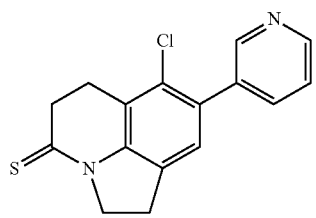

7-Chloro-8-pyridin-3-yl-1,2,5,6-tetrahydro-4H-pyrrolo[3,2,1-ij]quinolin-4-thione

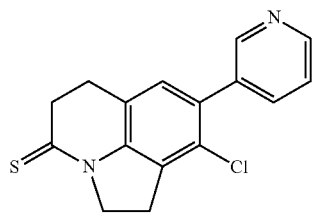

9-Chloro-8-pyridin-3-yl-1,2,5,6-tetrahydro-4H-pyrrolo[3,2,1-ij]quinolin-4-thione

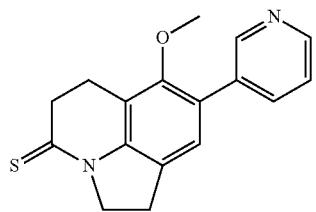

7-Methoxy-8-pyridin-3-yl-1,2,5,6-tetrahydro-4H-pyrrolo[3,2,1-ij]quinolin-4-thione

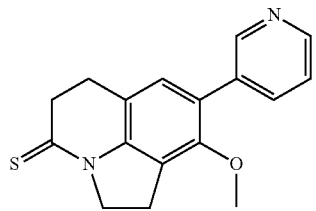

9-Methoxy-8-pyridin-3-yl-1,2,5,6-tetrahydro-4H-pyrrolo[3,2,1-ij]quinolin-4-thione

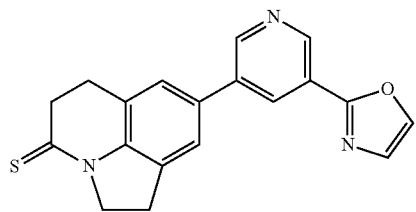

8-[5-(1,3-Oxazol-2-yl)pyridin-3-yl]-1,2,5,6-tetrahydro-4H-pyrrolo[3,2,1-ij]quinolin-4-thione

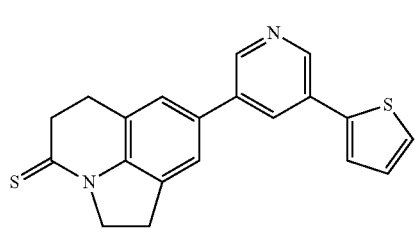

8-(5-Thiophen-2-ylpyridin-3-yl)-1,2,5,6-tetrahydro-4H-pyrrolo[3,2,1-ij]quinolin-4-thione -continued

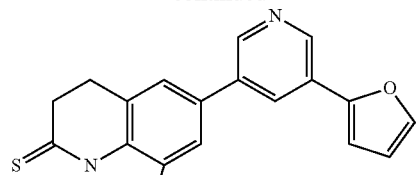

8-(5-Furan-2-ylpyridin-3-yl)-1,2,5,6-tetrahydro-4H-
pyrrolo[3,2,1-ij]quinolin-4-thione

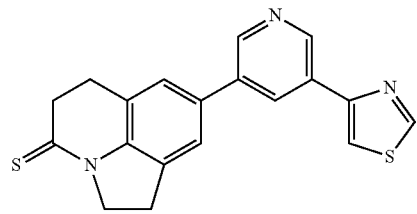

8-[5-(1,3-Thiazol-4-yl)pyridin-3-yl]-1,2,5,6-tetrahydro-4H-
pyrrolo[3,2,1-ij]quinolin-4-thione

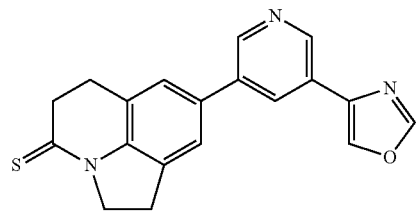

8-[5-(1,3-Oxazol-4-yl)pyridin-3-yl]-1,2,5,6-tetrahydro-4H-
pyrrolo[3,2,1-ij]quinolin-4-thione

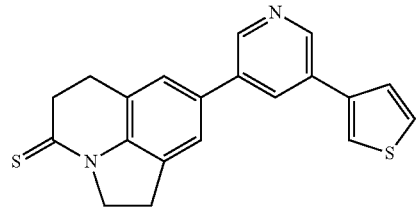

8-(5-Thiophen-3-ylpyridin-3-yl)-1,2,5,6-tetrahydro-4H-
pyrrolo[3,2,1-ij]quinolin-4-thione

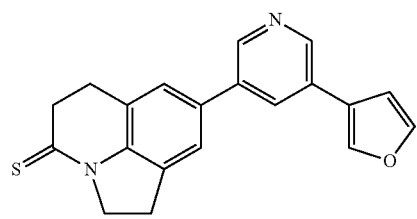

8-(5-Furan-3-ylpyridin-3-yl)-1,2,5,6-tetrahydro-4H-
pyrrolo[3,2,1-ij]quinolin-4-thione

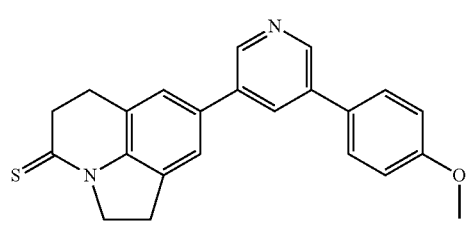

8-[5-(4-Methoxyphenyl)pyridin-3-yl]-1,2,5,6-tetrahydro-4H-
pyrrolo[3,2,1-ij]quinolin-4-thione

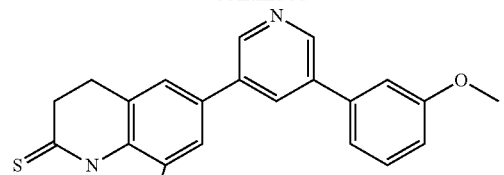

8-[5-(3-Methoxyphenyl)pyridin-3-yl]-1,2,5,6-tetrahydro-
4H-pyrrolo[3,2,1-ij]quinolin-4-thione

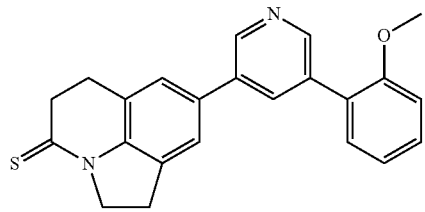

8-[5-(2-Methoxyphenyl)pyridin-3-yl]-1,2,5,6-tetrahydro-
4H-pyrrolo[3,2,1-ij]quinolin-4-thione

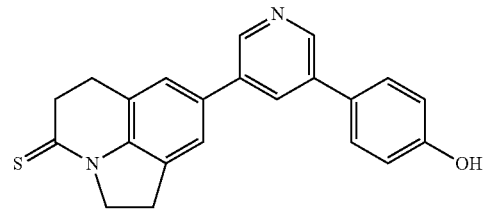

8-[5-(4-Hydroxyphenyl)pyridin-3-yl]-1,2,5,6-tetrahydro-
4H-pyrrolo[3,2,1-ij]quinolin-4-thione

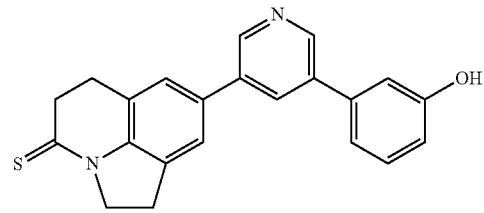

8-[5-(3-Hydroxyphenyl)pyridin-3-yl]-1,2,5,6-tetrahydro-
4H-pyrrolo[3,2,1-ij]quinolin-4-thione

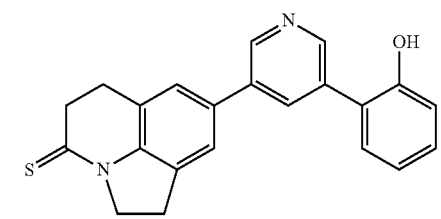

8-[5-(2-Hydroxyphenyl)pyridin-3-yl]-1,2,5,6-tetrahydro-
4H-pyrrolo[3,2,1-ij]quinolin-4-thione

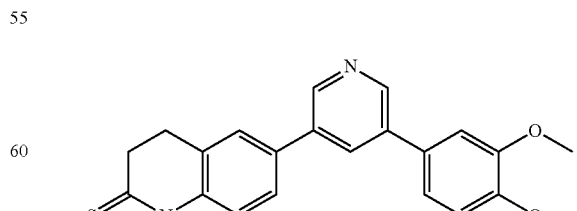

8-[5-(3,4-Dimethoxyphenyl)pyridin-3-yl]-1,2,5,6-tetrahydro-
4H-pyrrolo[3,2,1-ij]quinolin-4-thione

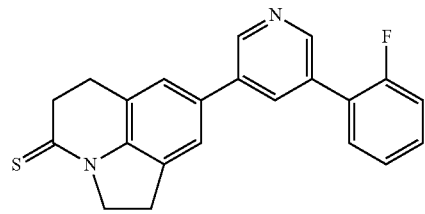

8-[5-(2-Fluorophenyl)pyridin-3-yl]-1,2,5,6-tetrahydro-
4H-pyrrolo[3,2,1-ij]quinolin-4-thione

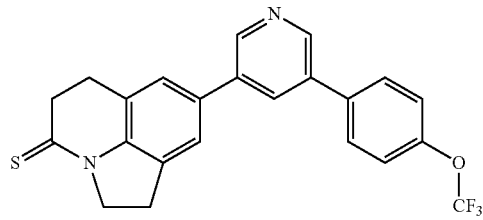

8-[5-(4-Trifluoromethoxyphenyl)pyridin-3-yl]-1,2,5,6-
tetrahydro-4H-pyrrolo[3,2,1-ij]quinolin-4-thione

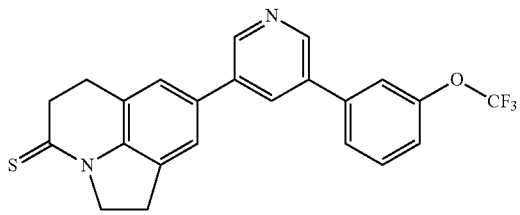

8-[5-(3-Trifluoromethoxyphenyl)pyridin-3-yl]-1,2,5,6-
tetrahydro-4H-pyrrolo[3,2,1-ij]quinolin-4-thione

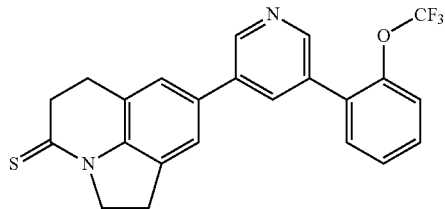

8-[5-(2-Trifluoromethoxyphenyl)pyridin-3-yl]-1,2,5,6-
tetrahydro-4H-pyrrolo[3,2,1-ij]quinolin-4-thione

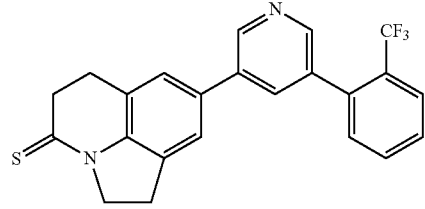

8-[5-(2-Trifluoromethylphenyl)pyridin-3-yl]-1,2,5,6-tetrahydro-
4H-pyrrolo[3,2,1-ij]quinolin-4-thione

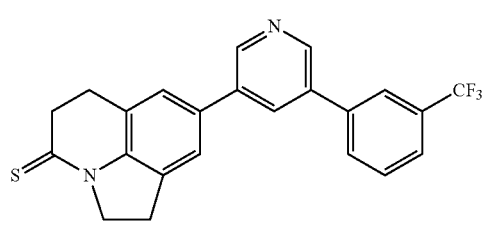

8-[5-(3-Trifluoromethylphenyl)pyridin-3-yl]-1,2,5,6-tetrahydro-
4H-pyrrolo[3,2,1-ij]quinolin-4-thione

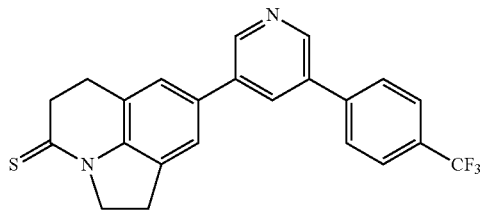

8-[5-(4-Trifluoromethylphenyl)pyridin-3-yl]-1,2,5,6-tetrahydro-
4H-pyrrolo[3,2,1-ij]quinolin-4-thione

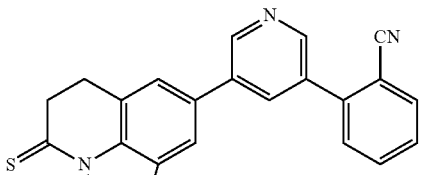

8-[5-(2-Cyanophenyl)pyridin-3-yl]-1,2,5,6-tetrahydro-4H-
pyrrolo[3,2,1-ij]quinolin-4-thione

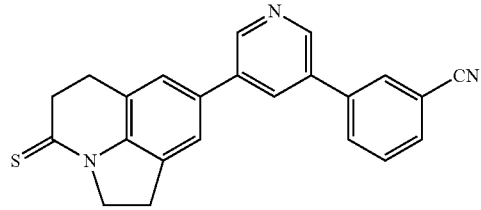

8-[5-(3-Cyanophenyl)pyridin-3-yl]-1,2,5,6-tetrahydro-4H-
pyrrolo[3,2,1-ij]quinolin-4-thione

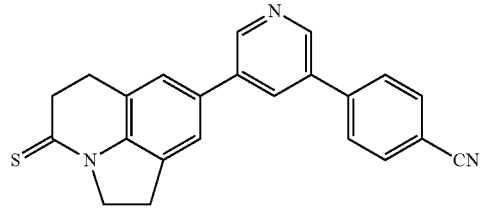

8-[5-(4-Cyanophenyl)pyridin-3-yl]-1,2,5,6-tetrahydro-4H-
pyrrolo[3,2,1-ij]quinolin-4-thione

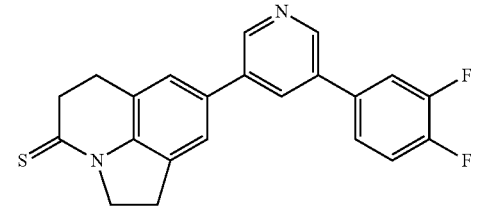

8-[5-(3,4-Difluorophenyl)pyridin-3-yl]-1,2,5,6-tetrahydro-4H-
pyrrolo[3,2,1-ij]quinolin-4-thione

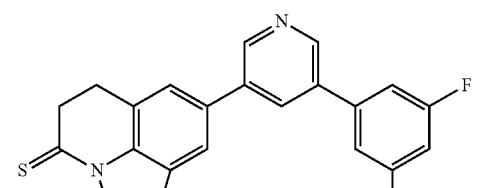

8-[5-(3,5-Difluorophenyl)pyridin-3-yl]-1,2,5,6-tetrahydro-4H-
pyrrolo[3,2,1-ij]quinolin-4-thione

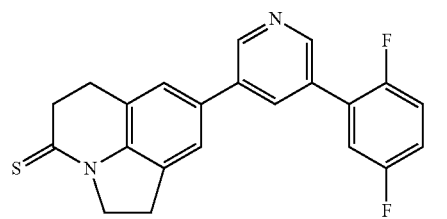

8-[5-(2,5-Difluorophenyl)pyridin-3-yl]-1,2,5,6-tetrahydro-4H-pyrrolo[3,2,1-ij]quinolin-4-thione

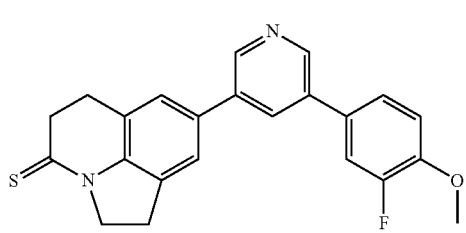

8-[5-(3,4-Fluoro-4-methoxyphenyl)pyridin-3-yl]-1,2,5,6-tetrahydro-4H-pyrrolo[3,2,1-ij]quinolin-4-thione

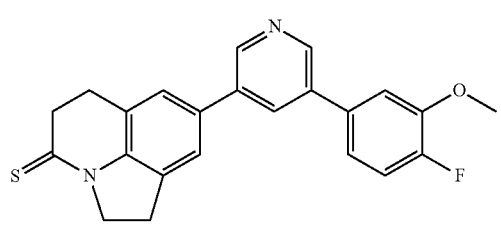

8-[5-(4-Fluoro-3-methoxyphenyl)pyridin-3-yl]-1,2,5,6-tetrahydro-4H-pyrrolo[3,2,1-ij]quinolin-4-thione According to Example 22 further tricyclic carbonyl compounds, as described in Example 14, can be derivatized to the corresponding thio analogues.

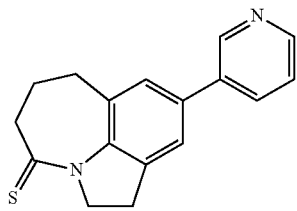

9-Pyridin-3-yl-1,2,6,7-tetrahydroazepino[3,2,1-hi]indol-4(5H)-thione

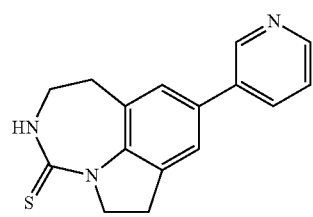

6-Pyridin-3-yl-3,4,8,9-tetrahydro[1,3]diazepino[6,7,1-hi]indol-1(2H)-thione

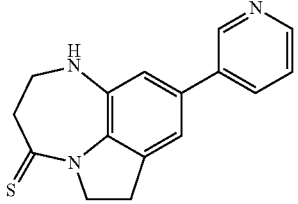

9-Pyridin-3-yl-2,3,6,7-tetrahydro[1,4]diazepino[3,2,1-hi]indol-4(1H)-thione

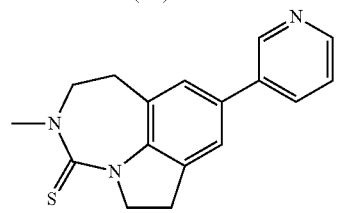

2-Methyl-6-pyridin-3-yl-3,4,8,9-tetrahydro[1,3]diazepino[6,7,1-hi]indol-1(2H)-thione

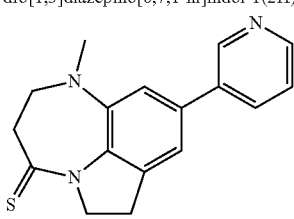

1-Methyl-9-pyridin-3-yl-2,3,6,7-tetrahydro[1,4]diazepino[3,2,1-hi]indol-4(1H)-thione

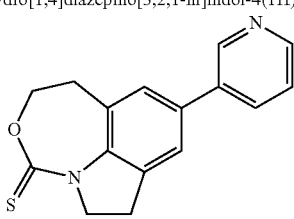

6-Pyridin-3-yl-3,4,8,9-tetrahydro[1,3]oxazepino[5,4,3-hi]indol-1-thione

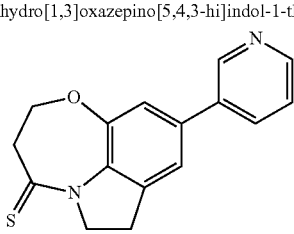

9-Pyridin-3-yl-2,3,6,7-tetrahydro-4H-[1,4]oxazepino[2,3,4-hi]indol-4-thione

Further thio analogues which can be synthesized according to Example 22 starting from the carbonyl compounds described in Example 35:

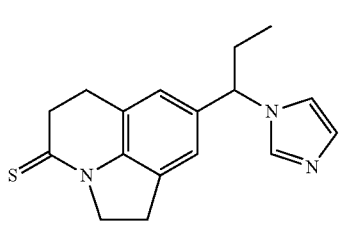

8-[1-(1H-Imidazol-1-yl)propyl]-1,2,5,6-tetrahydro-4H-pyrrolo[3,2,1-ij]quinolin-4-thione -continued

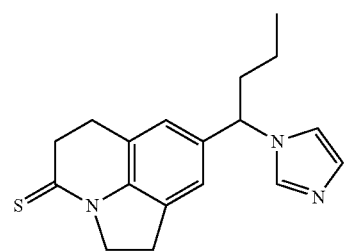

8-[1-(1H-Imidazol-1-yl)butyl]-1,2,5,6-tetrahydro-4H-pyrrolo[3,2,1-ij]quinolin-4-thione

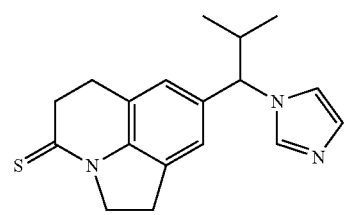

8-[1-(1H-Imidazol-1-yl)-2-methylpropyl]-1,2,5,6-tetrahydro-4H-pyrrolo[3,2,1-ij]quinolin-4-thione

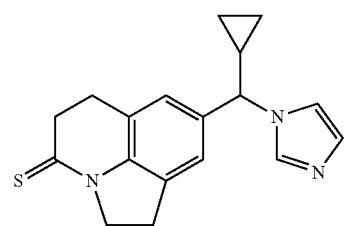

8-[Cyclopropyl(1H-imidazol-1-yl)methyl]-1,2,5,6-tetrahydro-4H-pyrrolo[3,2,1-ij]quinolin-4-thione

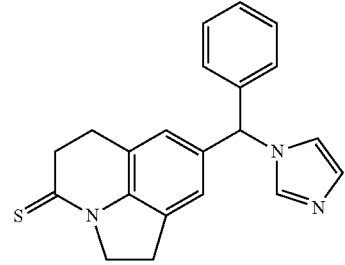

8-[1H-Imidazol-1-yl(phenyl)methyl]-1,2,5,6-tetrahydro-4H-pyrrolo[3,2,1-ij]quinolin-4-thione

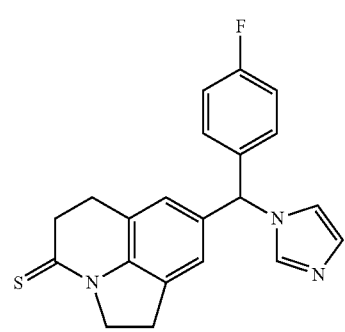

8-[(4-Fluorophenyl)(1H-imidazol-1-yl)methyl]-1,2,5,6-tetrahydro-4H-pyrrolo[3,2,1-ij]quinolin-4-thione -continued

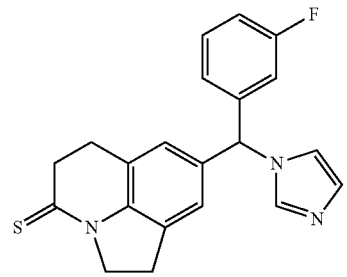

8-[(3-Fluorophenyl)(1H-imidazol-1-yl)methyl]-1,2,5,6-tetrahydro-4H-pyrrolo[3,2,1-ij]quinolin-4-thione

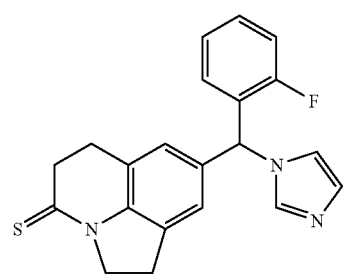

8-[(2-Fluorophenyl)(1H-imidazol-1-yl)methyl]-1,2,5,6-tetrahydro-4H-pyrrolo[3,2,1-ij]quinolin-4-thione

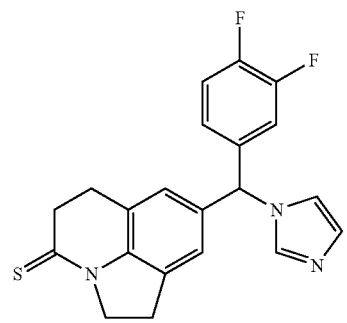

8-[(3,4-Difluorophenyl)(1H-imidazol-1-yl)methyl]-1,2,5,6-tetrahydro-4H-pyrrolo[3,2,1-ij]quinolin-4-thione

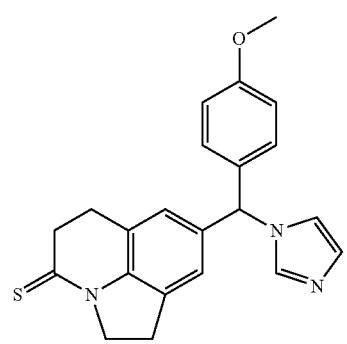

8-[(4-Methoxyphenyl)(1H-imidazol-1-yl)methyl]-1,2,5,6-tetrahydro-4H-pyrrolo[3,2,1-ij]quinolin-4-thione -continued

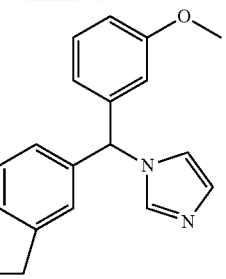

8-[(3-Methoxyphenyl)(1H-imidazol-1-yl)methyl]-1,2,5,6-
tetrahydro-4H-pyrrolo[3,2,1-ij]quinolin-4-thione

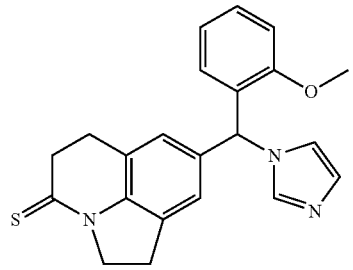

8-[(2-Methoxyphenyl)(1H-imidazol-1-yl)methyl]-1,2,5,6-
tetrahydro-4H-pyrrolo[3,2,1-ij]quinolin-4-thione

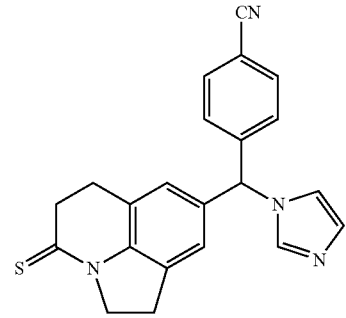

8-[(4-Cyanoxyphenyl)(1H-imidazol-1-yl)methyl]-1,2,5,6-
tetrahydro-4H-pyrrolo[3,2,1-ij]quinolin-4-thione

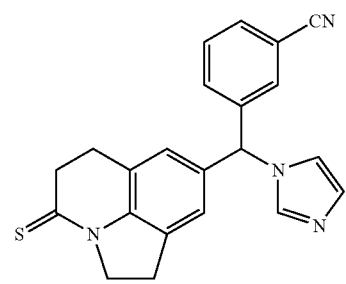

8-[(3-Cyanoxyphenyl)(1H-imidazol-1-yl)methyl]-1,2,5,6-
tetrahydro-4H-pyrrolo[3,2,1-ij]quinolin-4-thione

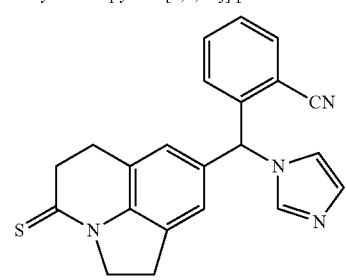

8-[(2-Cyanoxyphenyl)(1H-imidazol-1-yl)methyl]-1,2,5,6-
tetrahydro-4H-pyrrolo[3,2,1-ij]quinolin-4-thione Example 23

8-(5-Hydroxypyridin-3-yl)-1,2,5,6-tetrahydro-pyr-
rolo[3,2,1-ij]quinolin-4-one

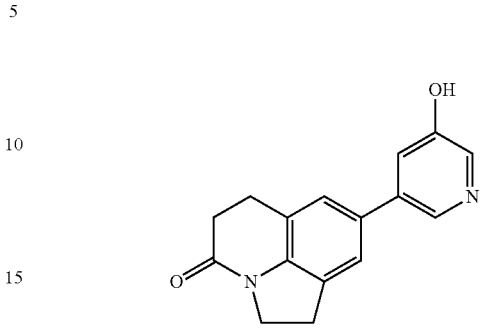

A solution of 8-(5-methoxypyridin-3-yl)-1,2,5,6-tetrahy-dro-pyrrolo[3,2,1-ij]quinolin-4-one (95 mg, 0.34 mmol) in 35 ml concentrated hydrobromic acid was heated under reflux for 18 h. After cooling to room temperature, the reaction mixture was neutralized with saturated NaHCO$_3$ solution and extracted with ethyl acetate (3×100 ml). The crude product which was obtained after evaporation of the solvent was purified by flash chromatography on silica gel (ethyl acetate, R$_f$=0.11) and crystallization from ethanol, yielding the hydroxy compound as a colorless solid (75 mg, 0.28 mmol, 83%), mp (HCl salt, THF)>300° C. $^1$H-NMR (500 MHz, DMSO-d$_6$): δ=2.57 (t, $^3$J=7.7 Hz, 2H), 2.97 (t, $^3$J=7.7 Hz, 2H), 3.18 (t, $^3$J=8.3 Hz, 2H), 3.96 (t, $^3$J=8.3 Hz, 2H), 7.28 (dd, $^4$J=2.5 Hz, $^4$J=1.9 Hz, 1H), 7.31 (s, 1H), 7.37 (s, 1H), 8.06 (d, $^4$J=2.5 Hz, 1H), 8.25 (d, $^4$J=1.9 Hz, 1H). MS m/z 267.94 (MH$^+$).

Example 24

6,6-Dimethyl-8-pyridin-3-yl-1,2,5,6-tetrahydro-pyr-
rolo[3,2,1-ij]quinolin-4-one

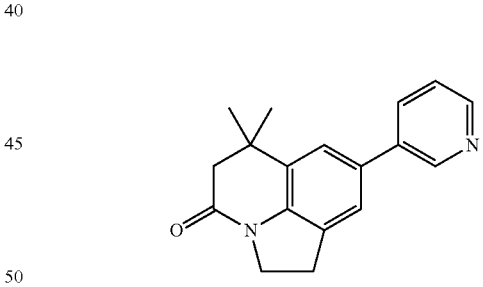

The title compound was obtained via Suzuki coupling according to general procedure A from 8-bromo-6,6-dim-ethyl-1,2,5,6-tetrahydro-pyrrolo[3,2,1-ij]quinolin-4-one (280 mg, 1.0 mmol) (prepared previously from 3,3-dimethy-lacryloylchloride and indoline as described for 8-bromo-1,2,5,6-tetrahydro-pyrrolo[3,2,1-ij]quinolin-4-one and 9-bromo-1,2,6,7-tetrahydro-5H-pyrido[3,2,1-ij]quinolin-3-one) and 3-pyridineboronic acid (92 mg, 0.75 mmol) after flash chromatography on silica gel (hexanes/ethyl acetate, 1/9, R$_f$=0.09) and crystallization from acetone as colorless needles (48 mg, 0.17 mmol, 23%), mp (acetone) 180° C. $^1$H-NMR (500 MHz, CDCl$_3$): δ=1.35 (s, 6H), 2.55 (s, 2H), 3.27 (t, $^3$J=8.3 Hz, 2H), 4.14 (t, $^3$J=8.3 Hz, 2H), 7.25 (d, $^4$J=1.3 Hz, 1H), 7.28 (d, $^4$J=1.6 Hz, 1H), 7.33 (ddd, $^3$J=7.9 Hz, $^3$J=4.7 Hz, $^5$J=1.0 Hz, 1H), 7.80 (ddd, $^3$J=7.9 Hz, $^4$J=2.2 Hz, $^4$J=1.6 Hz, 1H), 8.55 (dd, $^3$J=4.7 Hz, $^4$J=1.6 Hz, 1H), 8.78 (dd, $^4J$=2.5 Hz, $^5J$=1.0 Hz, 1H). $^{13}$C-NMR (125 MHz, CDCl$_3$): δ=28.0, 35.0, 45.1, 46.8, 121.5, 122.5, 123.5, 130.1, 130.2, 134.0, 134.1, 137.0, 140.2, 148.1, 148.2, 167.2. MS m/z 279.14 (MH$^+$).

Example 25

8-(5-Ethoxypyridin-3-yl)-1,2,5,6-tetrahydro-pyrrolo[3,2,1-ij]quinolin-4-one

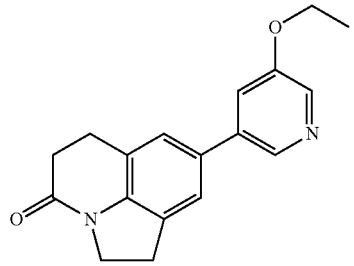 [SMILES: CCOc1cncc(-c2cc3c4c(c2)CCN4C(=O)CC3)c1]

The title compound was obtained via Suzuki coupling according to general procedure B from 8-(4,4,5,5-Tetramethyl-[1,3,2]dioxaborolan-2-yl)-1,2,5,6-tetrahydro-pyrrolo[3,2,1-ij]quinolin-4-one (300 mg, 1.0 mmol) and 3-bromo-5-ethoxypyridine (242 mg, 1.2 mmol) after flash chromatography on silica gel (hexanes/ethyl acetate, 1/9, R$_f$=0.10) and crystallization from acetone/diethylether as colorless needles (132 mg, 0.45 mmol, 45%), mp (acetone/diethyl-ether) 172° C. $^1$H-NMR (500 MHz, CDCl$_3$): δ=1.46 (t, $^3J$=7.3 Hz, 3H), 2.72 (t, $^3J$=7.7 Hz, 2H), 3.03 (t, $^3J$=7.7 Hz, 2H), 3.24 (t, $^3J$=8.5 Hz, 2H), 4.11-4.16 (m, 4H) 7.19 (s, 1H), 7.27 (s, 1H), 7.28 (dd, $^4J$=2.5 Hz, $^4J$=1.9 Hz, 1H), 8.24 (d, $^4J$=2.5 Hz, 1H), 8.37 (d, $^4J$=1.9 Hz, 1H). $^{13}$C-NMR (125 MHz, CDCl$_3$): δ=14.8, 24.5, 27.7, 31.6, 45.5, 64.0, 119.5, 120.6, 122.4, 124.8, 129.8, 133.4, 136.1, 137.4, 140.4, 141.6, 155.1, 167.6. MS m/z 295.16 (MH$^+$).

Example 26

8-(5-Trifluoromethylpyridin-3-yl)-1,2,5,6-tetrahydro-pyrrolo[3,2,1-ij]quinolin-4-one

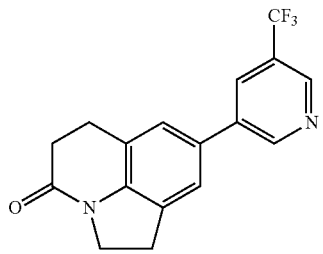 [SMILES: O=C1CCc2cc(-c3cncc(C(F)(F)F)c3)cc3c2N1CC3]

The title compound was obtained via Suzuki coupling according to general procedure B from 8-(4,4,5,5-Tetramethyl-[1,3,2]dioxaborolan-2-yl)-1,2,5,6-tetrahydro-pyrrolo[3,2,1-ij]quinolin-4-one (329 mg, 1.1 mmol) and 3-bromo-5-(trifluoromethyl)pyridine (249 mg, 1.1 mmol) after flash chromatography on silica gel (hexanes/ethyl acetate, 1/1, R$_f$=0.14) and crystallization from acetone/diethylether as colorless needles (248 mg, 0.78 mmol, 71%), mp (acetone/diethylether) 212° C. $^1$H-NMR (500 MHz, CDCl$_3$): δ=2.73 (t, $^3J$=7.7 Hz, 2H), 3.05 (t, $^3J$=7.9 Hz, 2H), 3.27 (t, $^3J$=8.5 Hz, 2H), 4.15 (t, $^3J$=8.5 Hz, 2H), 7.23 (s, 1H), 7.30 (s, 1H), 8.01 (m, 1H), 8.81 (d, $^4J$=1.3 Hz, 1H), 8.95 (d, $^4J$=1.9 Hz, 1H). MS m/z 318.95 (MH$^+$).

Example 27

8-(5-Fluoropyridin-3-yl)-1,2,5,6-tetrahydro-pyrrolo[3,2,1-ij]quinolin-4-one

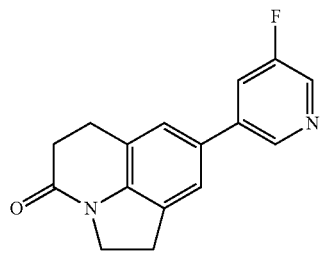 [SMILES: O=C1CCc2cc(-c3cncc(F)c3)cc3c2N1CC3]

The title compound was obtained via Suzuki coupling according to general procedure B from 8-(4,4,5,5-Tetramethyl-[1,3,2]dioxaborolan-2-yl)-1,2,5,6-tetrahydro-pyrrolo[3,2,1-ij]quinolin-4-one (359 mg, 1.2 mmol) and 3-bromo-5-fluoropyridine (211 mg, 1.2 mmol) after flash chromatography on silica gel (hexanes/ethyl acetate, 1/1, R$_f$=0.09) and crystallization from acetone/diethylether as colorless needles (202 mg, 0.75 mmol, 63%), mp (acetone/diethyl-ether) 158° C. $^1$H-NMR (500 MHz, CDCl$_3$): δ=2.72 (t, $^3J$=7.7 Hz, 2H), 3.04 (t, $^3J$=7.9 Hz, 2H), 3.25 (t, $^3J$=8.5 Hz, 2H), 4.14 (t, $^3J$=8.8 Hz, 2H), 7.20 (s, 1H), 7.28 (s, 1H), 7.51 (m, 1H), 8.41 (d, $^4J$=2.5 Hz, 1H), 8.60 (s, 1H). $^{13}$C-NMR (125 MHz, CDCl$_3$): δ=24.5, 27.7, 31.5, 45.5, 120.7 (q, $^2J_{C,F}$=18.3 Hz), 120.8, 122.5, 124.9, 130.1, 131.9, 136.2 (q, $^2J_{C,F}$=22.9 Hz) 138.4, 142.1, 143.9, 159.7 (q, $^1J_{C,F}$=257 Hz), 167.5. MS m/z 269.38 (MH$^+$).

Example 28

8-Imidazol-1-yl-1,2,5,6-tetrahydro-pyrrolo[3,2,1-ij]quinolin-4-one

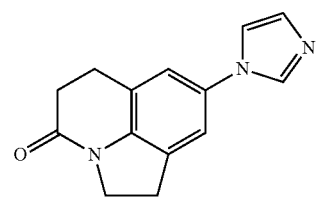 [SMILES: O=C1CCc2cc(-n3ccnc3)cc3c2N1CC3]

Imidazole (628 mg, 9.23 mmol), 8-bromo-1,2,5,6-tetrahydro-pyrrolo[3,2,1-ij]quinolin-4-one (2.12 g, 8.39 mmol), potassium carbonate (1.28 g, 9.23 mmol) and copper(II)sulfate (160 mg, 1.0 mmol) were mixed and heated at 180° C. for 10 h under an atmosphere of dry nitrogen. After being cooled to room temperature, the reaction mixture was poured into 150 ml water and extracted with ethyl acetate (3×100 ml). After drying over MgSO$_4$ and evaporating of the solvent, the crude product was purified by two subsequent crystallizations from acetone to yield a colorless solid (674 mg, 2.82 mg, 34%). mp (acetone) 124° C. $^1$H-NMR (500 MHz, CDCl$_3$):

δ=2.70 (t, $^3J$=7.7 Hz, 2H), 3.01 (t, $^3J$=7.7 Hz, 2H), 3.23 (t, $^3J$=8.5 Hz, 2H), 4.13 (t, $^3J$=8.5 Hz, 2H), 7.01 (s, 1H), 7.08 (s, 1H), 7.18 (m, 2H), 7.75 (s, 1H). MS m/z 239.95 (MH$^+$).

Example 29

8-Pyridin-4-yl-1,2,5,6-tetrahydro-pyrrolo[3,2,1-ij]quinolin-4-one

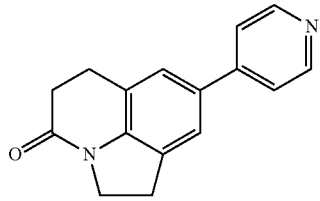 [SMILES: O=C1CCc2cc(-c3ccncc3)cc3c2N1CC3]

The title compound was obtained via Suzuki coupling according to general procedure B from 8-bromo-1,2,5,6-tetrahydro-pyrrolo[3,2,1-ij]quinolin-4-one (627 mg, 3.50 mmol) and 4-pyridineboronic acid (369 mg, 3.0 mmol) after crystallization from ethanol as yellow crystals (225 mg, 0.90 mmol, 30%), mp (ethanol) 174° C. $^1$H-NMR (500 MHz, DMSO-d$_6$): δ=2.58 (t, $^3J$=7.7 Hz, 2H), 2.98 (t, $^3J$=7.9 Hz, 2H), 3.19 (t, $^3J$=8.5 Hz, 2H), 3.98 (t, $^3J$=8.8 Hz, 2H), 7.50 (s, 1H), 7.55 (s, 1H), 7.62 (d, $^3J$=5.3 Hz, 2H), 8.55 (d, $^3J$=5.1 Hz, 2H). $^{13}$C-NMR (125 MHz, DMSO-d$_6$): δ=23.7, 27.1, 31.0, 45.2, 120.5, 120.7, 121.8, 124.2, 129.9, 131.9, 142.4, 147.2, 150.0, 166.8. MS m/z 251.71 (MH$^+$).

Example 30

8-Pyrimidin-5-yl-1,2,5,6-tetrahydro-pyrrolo[3,2,1-ij]quinolin-4-one

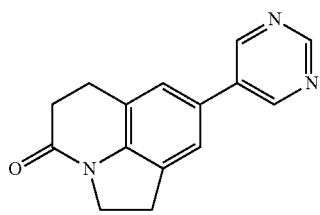 [SMILES: O=C1CCc2cc(-c3cncnc3)cc3c2N1CC3]

The title compound was obtained via Suzuki coupling according to general procedure B from 8-bromo-1,2,5,6-tetrahydro-pyrrolo[3,2,1-ij]quinolin-4-one (627 mg, 3.50 mmol) and 5-pyrimidineboronic acid (372 mg, 3.0 mmol) after crystallization from acetone as a yellow crystals (324 mg, 1.29 mmol, 43%), mp (acetone) 186° C. $^1$H-NMR (500 MHz, DMSO-d$_6$): δ=2.59 (t, $^3J$=7.7 Hz, 2H), 2.98 (t, $^3J$=7.9 Hz, 2H), 3.20 (t, $^3J$=8.5 Hz, 2H), 3.98 (t, $^3J$=8.5 Hz, 2H), 7.49 (s, 1H), 7.54 (s, 1H), 9.05 (s, 2H), 9.10 (s, 1H). $^{13}$C-NMR (125 MHz, DMSO-d$_6$): δ=23.7, 27.1, 31.0, 45.2, 120.8, 121.9, 124.3, 128.4, 130.0, 133.5, 142.1, 154.2, 156.5, 166.8. MS m/z 251.85 (MH$^+$).

Example 31

8-(Pyridine-4-carbonyl)-1,2,5,6-tetrahydro-pyrrolo[3,2,1-ij]quinolin-4-one

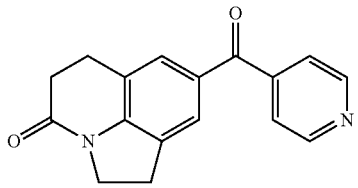 [SMILES: O=C(c1ccncc1)c1cc2c3c(c1)CCN3C(=O)CC2]

To a molten mixture of AlCl$_3$ (8.0 g, 60.0 mmol) and NaCl (2.34 g, 40.0 mmol) at 150° C. was added 1,2,5,6-tetrahydro-pyrrolo[3,2,1-ij]quinolin-4-one (1.79 g, 10.0 mmol) and thereafter isonicotinoylchloride hydrochloride salt (1.96 g, 11.0 mmol) portionwise. After stirring for 15 min and cooling to room temperature, excess aluminum chloride was decomposed by the addition of a chilled mixture of 10 ml concentrated hydrochloric acid and 200 ml water. Neutralization with NaHCO$_3$ solution and subsequent extraction with ethyl acetate (3×100 ml), followed by drying over MgSO$_4$ and removal of the solvent gave the crude product. Purification by crystallization from acetone gave the acylation product (751 mg, 2.70 mmol, 27%) as a yellow solid, mp (acetone) 184° C. $^1$H-NMR (500 MHz, CDCl$_3$): δ=2.70 (t, $^3J$=7.7 Hz, 2H), 2.99 (t, $^3J$=7.8 Hz, 2H), 3.21 (t, $^3J$=8.2 Hz, 2H), 4.12 (t, $^3J$=8.2 Hz, 2H), 7.49 (m, 3H), 7.55 (s, 1H), 8.76 (d, $^3J$=5.1 Hz, 2H). $^{13}$C-NMR (125 MHz, CDCl$_3$): δ=24.1, 27.2, 31.3, 45.7, 119.9, 122.6, 126.1, 129.0, 129.4, 131.4, 145.3, 146.3, 150.2, 167.8, 193.9. MS m/z 279.07 (MH$^+$).

Example 32

8-(Pyridine-3-carbonyl)-1,2,5,6-tetrahydro-pyrrolo[3,2,1-ij]quinolin-4-one

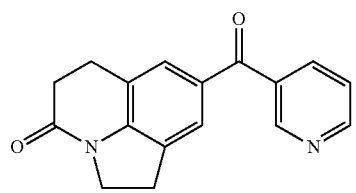 [SMILES: O=C(c1cccnc1)c1cc2c3c(c1)CCN3C(=O)CC2]

To a molten mixture of AlCl$_3$ (8.0 g, 60.0 mmol) and NaCl (2.34 g, 40.0 mmol) at 150° C. was added 1,2,5,6-tetrahydro-pyrrolo[3,2,1-ij]quinolin-4-one (1.79 g, 10.0 mmol) and thereafter nicotinoylchloride hydrochloride salt (1.96 g, 11.0 mmol) portionwise. After stirring for 15 min and cooling to room temperature, excess aluminum chloride was decomposed by the addition of a chilled mixture of 10 ml concentrated hydrochloric acid and 200 ml water. Neutralization with NaHCO$_3$ solution and subsequent extraction with ethyl acetate (3×100 ml), followed by drying over MgSO$_4$ and removal of the solvent gave the crude product. Purification by crystallization from ethanol gave the acylation product (624 mg, 2.24 mmol, 22%) as a yellow solid, mp (ethanol) 147° C. $^1$H-NMR (500 MHz, CDCl$_3$): δ=2.72 (t, $^3$J=7.9 Hz, 2H), 3.02 (t, $^3$J=7.9 Hz, 2H), 3.23 (t, $^3$J=8.6 Hz, 2H), 4.14 (t, $^3$J=8.6 Hz, 2H), 7.44 (ddd, $^3$J=7.9 Hz, $^3$J=4.7 Hz, $^5$J=1.0 Hz, 1H), 7.53 (s, 1H), 7.58 (s, 1H), 8.06 (m, 1H), 8.78 (dd, $^3$J=5.0 Hz, $^4$J=1.9 Hz, 1H), 8.92 (dd, $^4$J=1.9 Hz, $^5$J=0.8 Hz, 1H). $^{13}$C-NMR (125 MHz, CDCl$_3$): δ=24.2, 27.3, 31.4, 45.8, 199.9, 123.4, 126.1, 128.9, 129.4, 132.3, 134.0, 137.0, 146.1, 150.4, 152.4, 167.8, 193.6. MS m/z 278.79 (MH$^+$).

Example 33

8-(5-Phenylpyridin-3-yl)-1,2,5,6-tetrahydro-pyrrolo [3,2,1-ij]quinolin-4-one

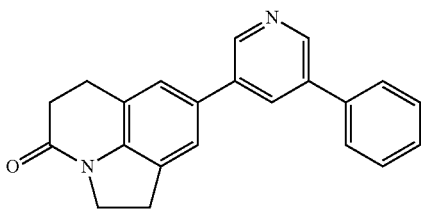 [SMILES: O=C1CCc2cc(-c3cncc(-c4ccccc4)c3)cc3c2N1CC3]

The title compound was obtained via Suzuki coupling according to general procedure B from 8-(4,4,5,5-Tetramethyl-[1,3,2]dioxaborolan-2-yl)-1,2,5,6-tetrahydro-pyrrolo [3,2,1-ij]quinolin-4-one (325 mg, 1.07 mmol) and 3-bromo-5-phenylpyridine (301 mg, 1.28 mmol) after flash chromatography on silica gel (hexanes/ethyl acetate, 2/3, R$_f$=0.09) as colorless plates (150 mg, 0.46 mmol, 43%), mp (hexanes/ethyl acetate) 189° C. $^1$H-NMR (500 MHz, CDCl$_3$): δ=2.73 (t, $^3$J=7.7 Hz, 2H), 3.05 (t, $^3$J=7.9 Hz, 2H), 3.26 (t, $^3$J=8.5 Hz, 2H), 4.14 (t, $^3$J=8.5 Hz, 2H), 7.26 (s, 1H), 7.34 (s, 1H), 7.42 (m, 1H), 7.49 (m, 2H), 7.63 (dd, $^3$J=6.9 Hz, $^4$J=1.6 Hz, 2H), 7.98 (m, 1H), 8.75 (d, $^4$J=1.9 Hz, 1H), 8.78 (d, $^4$J=1.9 Hz, 1H). $^{13}$C-NMR (125 MHz, CDCl$_3$): δ=24.5, 27.8, 31.6, 45.5, 120.7, 122.4, 124.8, 127.2, 128.3, 129.1, 129.9, 132.7, 133.3, 136.7, 136.8, 137.7, 141.7, 146.5, 146.6, 167.5. MS m/z 326.86 (MH$^+$).

Example 34

8-(5-Isopropoxypyridin-3-yl)-1,2,5,6-tetrahydro-pyrrolo[3,2,1-ij]quinolin-4-one

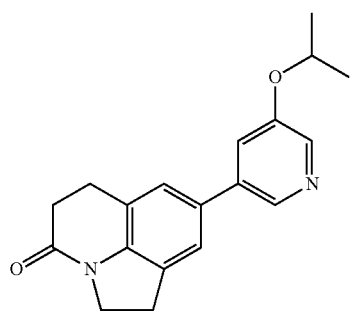 [SMILES: CC(C)Oc1cncc(-c2cc3c4c(c2)CCN4C(=O)CC3)c1]

The title compound was obtained via Suzuki coupling according to general procedure B from 8-(4,4,5,5-Tetramethyl-[1,3,2]dioxaborolan-2-yl)-1,2,5,6-tetrahydro-pyrrolo [3,2,1-ij]quinolin-4-one (359 mg, 1.20 mmol) and 3-bromo-5-(1-methylethoxy)pyridine (281 mg, 1.30 mmol) after flash chromatography on silica gel (hexanes/ethyl acetate, 3/7, R$_f$=0.07) as colorless plates (196 mg, 0.63 mmol, 53%), mp (hexanes/ethyl acetate) 155° C. $^1$H-NMR (500 MHz, CDCl$_3$): δ=1.38 (d, $^3$J=6.3 Hz, 6H), 2.72 (t, $^3$J=7.6 Hz, 2H), 3.03 (t, $^3$J=7.9 Hz, 2H), 3.24 (t, $^3$J=8.5 Hz, 2H), 4.13 (t, $^3$J=8.5 Hz, 2H), 4.65 (sep, $^3$J=6.3 Hz, 1H), 7.19 (s, 1H), 7.26 (s, 1H), 7.30 (m, 1H), 8.21 (d, $^4$J=2.8 Hz, 1H), 8.35 (d, $^4$J=1.6 Hz, 1H). $^{13}$C-NMR (125 MHz, CDCl$_3$): δ=22.0, 24.5, 27.7, 31.6, 45.5, 70.8, 120.6, 121.2, 122.4, 124.8, 129.9, 133.2, 136.8, 137.6, 139.9, 141.7, 154.2, 167.6. MS m/z 308.87 (MH$^+$).

Example 35

8-(1-Imidazol-1-yl-ethyl)-1,2,5,6-tetrahydro-pyrrolo [3,2,1-ij]quinolin-4-one

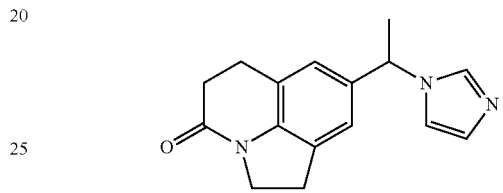

To a solution of 1,2,5,6-tetrahydro-pyrrolo[3,2,1-ij]quinolin-4-one (1.79 g, 10.0 mmol) and AlCl$_3$ (9.31 g, 70.0 mmol) in 50 ml dry dichloromethane was added dropwise acetyl chloride (1.18 g, 15.0 mmol) at room temperature. The mixture was then refluxed for 18 h, cooled to ambient temperature and quenched by addition of a cold mixture of 10 ml concentrated hydrochloric acid and 20 ml water. Extraction with ethyl acetate (3×100 ml), followed by drying over MgSO$_4$ and removal of the solvent in vacuo gave the crude product. This was dissolved in 50 ml methanol and sodium boron hydride (452 mg, 12.0 mmol) was added portionwise at 0° C. After 1 h stirring, water was added and the mixture was extracted with ethyl acetate (3×100 ml). Drying over MgSO$_4$ and removal of the solvent gave the alcohol as crude product. A solution of the obtained alcohol in 10 ml dry THF was added to a solution of thionylbis(imidazole) (prepared previously by reaction of imidazole (4.52 g, 66.4 mmol) with thionyl chloride (1.97 g, 16.6 mmol) in 30 mL THF and filtration to remove precipitated imidazole hydrochloride) at 0° C. The reaction mixture was stirred for one hour at 0° C. and an additional 18 h at ambient temperature. Water was added and the mixture extracted with ethyl acetate (3×100 ml), the combined organic extracts washed with water and brine, and the solvent was removed in vacuo after drying over MgSO$_4$. The crude product was purified by two subsequent crystallizations from acetone to yield 8-(1-Imidazol-1-yl-ethyl)-1,2,5,6-tetrahydro-pyrrolo[3,2,1-ij]quinolin-4-one (488 mg, 1.83 mmol, 18%) as pale yellow crystals, mp (acetone) 197° C. $^1$H-NMR (500 MHz, CDCl$_3$): δ=1.82 (d, $^3$J=6.9 Hz, 3H), 2.65 (t, $^3$J=7.7 Hz, 2H), 2.92 (t, $^3$J=7.7 Hz, 2H), 3.14 (t, $^3$J=8.5 Hz, 2H), 4.07 (t, $^3$J=8.5 Hz, 2H), 5.27 (q, $^3$J=6.9 Hz, 1H), 6.79 (s, 1H), 6.85 (s, 1H), 6.91 (s, 1H), 7.07 (s, 1H), 7.58 (s, 1H). $^{13}$C-NMR (125 MHz, CDCl$_3$): δ=22.3, 24.4, 27.7, 31.5, 45.4, 56.6, 117.9, 120.4, 121.2, 123.5, 129.3, 129.6, 135.9, 136.9, 141.4, 167.5. MS m/z 267.94 (MH$^+$).

According to Example 35 starting from 1,2,5,6-tetrahydro-pyrrolo[3,2,1-ij]quinolin-4-one the following compounds can be synthesized by reacting with various carboxylic acid halogenides (see Schemes 1-19):

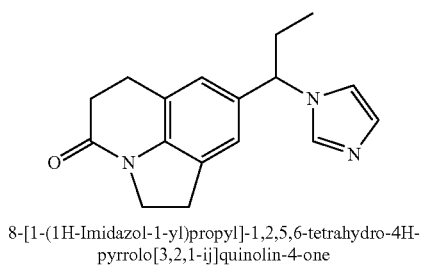

8-[1-(1H-Imidazol-1-yl)propyl]-1,2,5,6-tetrahydro-4H-pyrrolo[3,2,1-ij]quinolin-4-one

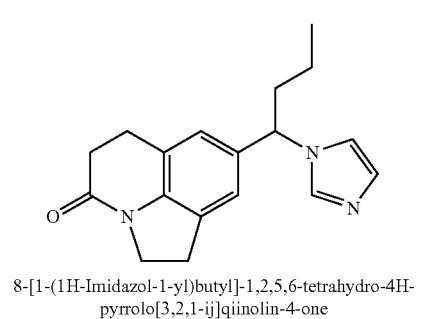

8-[1-(1H-Imidazol-1-yl)butyl]-1,2,5,6-tetrahydro-4H-pyrrolo[3,2,1-ij]qiinolin-4-one

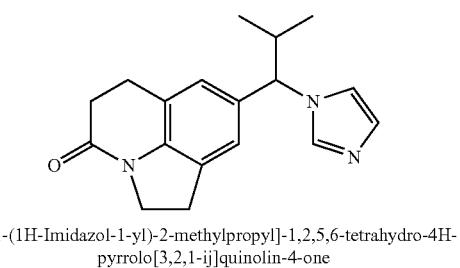

8-[1-(1H-Imidazol-1-yl)-2-methylpropyl]-1,2,5,6-tetrahydro-4H-pyrrolo[3,2,1-ij]quinolin-4-one

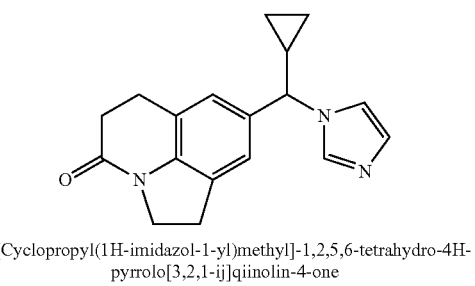

8-[Cyclopropyl(1H-imidazol-1-yl)methyl]-1,2,5,6-tetrahydro-4H-pyrrolo[3,2,1-ij]qiinolin-4-one

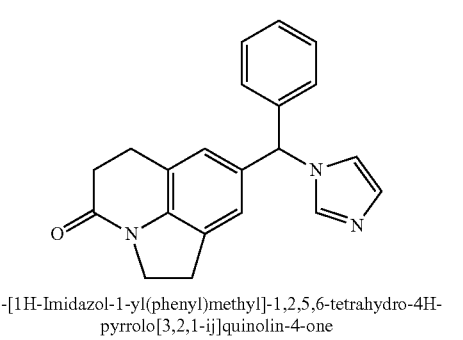

8-[1H-Imidazol-1-yl(phenyl)methyl]-1,2,5,6-tetrahydro-4H-pyrrolo[3,2,1-ij]quinolin-4-one -continued

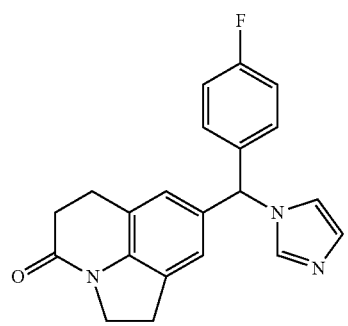

8-[(4-Fluorophenyl)(1H-imidazol-1-yl)methyl]-1,2,5,6-tetrahydro-4H-pyrrolo[3,2,1-ij]quinolin-4-one

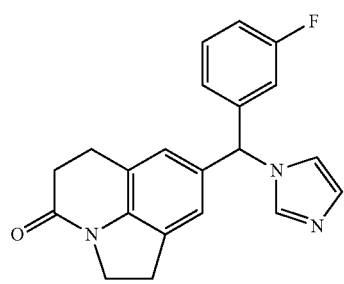

8-[(3-Fluorophenyl)(1H-imidazol-1-yl)methyl]-1,2,5,6-tetrahydro-4H-pyrrolo[3,2,1-ij]quinolin-4-one

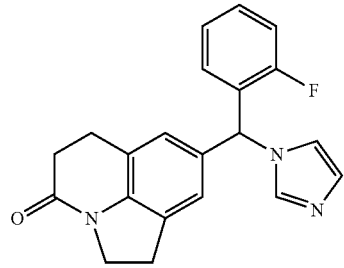

8-[(2-Fluorophenyl)(1H-imidazol-1-yl)methyl]-1,2,5,6-tetrahydro-4H-pyrrolo[3,2,1-ij]quinolin-4-one

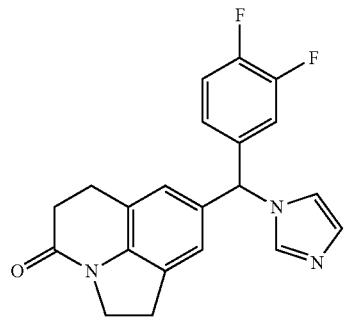

8-[(3,4-Difluorophenyl)(1H-imidazol-1-yl)methyl]-1,2,5,6-tetrahydro-4H-pyrrolo[3,2,1-ij]quinolin-4-one 135
-continued

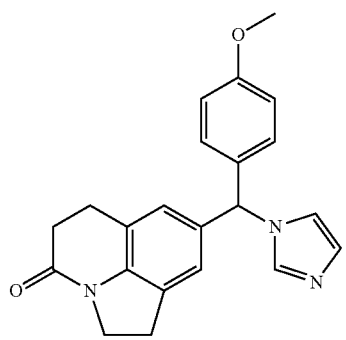

8-[(4-Methoxyphenyl)(1H-imidazol-1-yl)methyl]-1,2,5,6-
tetrahydro-4H-pyrrolo[3,2,1-ij]quinolin-4-one

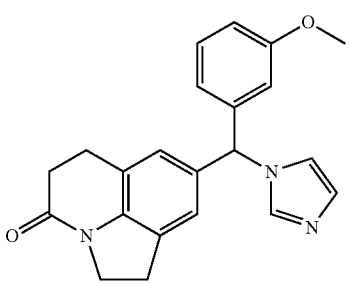

8-[(3-Methoxyphenyl)(1H-imidazol-1-yl)methyl]-1,2,5,6-
tetrahydro-4H-pyrrolo[3,2,1-ij]quinolin-4-one

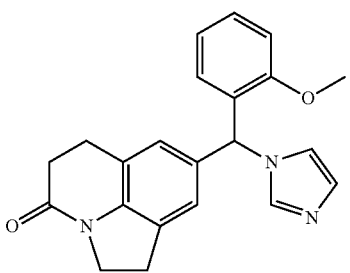

8-[(2-Methoxyphenyl)(1H-imidazol-1-yl)methyl]-1,2,5,6-
tetrahydro-4H-pyrrolo[3,2,1-ij]quinolin-4-one

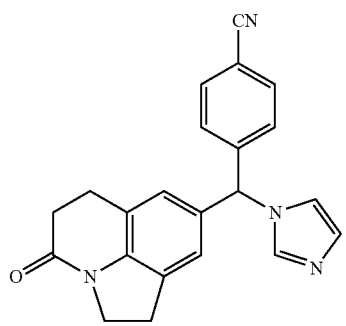

8-[(4-Cyanoxyphenyl)(1H-imidazol-1-yl)methyl]-1,2,5,6-
tetrahydro-4H-pyrrolo[3,2,1-ij]quinolin-4-one 136
-continued

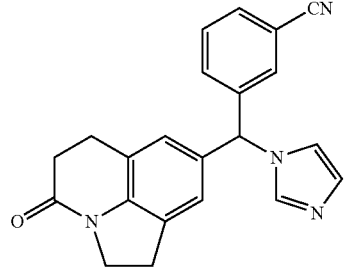

8-[(3-Cyanoxyphenyl)(1H-imidazol-1-yl)methyl]-1,2,5,6-
tetrahydro-4H-pyrrolo[3,2,1-ij]quinolin-4-one

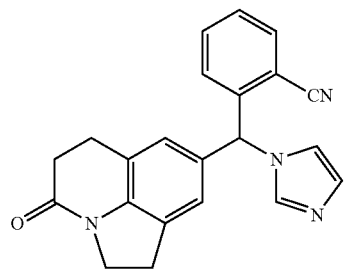

8-[(2-Cyanoxyphenyl)(1H-imidazol-1-yl)methyl]-1,2,5,6-
tetrahydro-4H-pyrrolo[3,2,1-ij]qiinolin-4-one Example 36

8-[5-(4-Fluorophenyl)-pyridin-3-yl]-1,2,5,6-tetrahy-
dro-pyrrolo[3,2,1-ij]quinolin-4-one

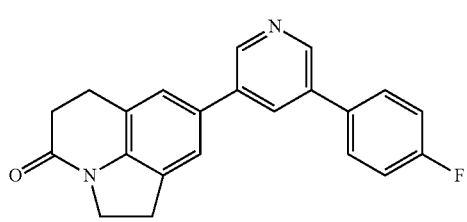 [SMILES: O=C1CCc2cc(-c3cncc(-c4ccc(F)cc4)c3)cc3c2N1CC3]

The title compound was obtained via Suzuki coupling according to general procedure B from 8-(4,4,5,5-Tetramethyl-[1,3,2]dioxaborolan-2-yl)-1,2,5,6-tetrahydro-pyrrolo[3,2,1-ij]quinolin-4-one (463 mg, 1.55 mmol) and 3-bromo-5-(4-fluorophenyl)pyridine (440 mg, 1.75 mmol) (prepared previously by Suzuki coupling according to general procedure B from 3,5-dibromopyridine and 4-fluorophenylboronic acid) after flash chromatography on silica gel (hexanes/ethyl acetate, 2/3, $R_f$=0.05) as colorless needles (189 mg, 0.55 mmol, 35%), mp (hexanes/ethyl acetate) 233° C. $^1$H-NMR (500 MHz, CDCl$_3$): δ=2.73 (t, $^3$J=7.7 Hz, 2H), 3.05 (t, $^3$J=7.7 Hz, 2H), 3.26 (t, $^3$J=8.5 Hz, 2H), 4.14 (t, $^3$J=8.5 Hz, 2H), 7.18 (m, 2H), 7.26 (s, 1H), 7.33 (s, 1H), 7.58 (m, 2H), 7.93 (m, 1H), 8.73 (d, $^4$J=2.2 Hz, 1H), 8.74 (d, $^4$J=1.9 Hz, 1H). $^{13}$C-NMR (125 MHz, CDCl$_3$): δ=24.5, 27.7, 31.6, 45.5, 116.1 (d, $^2$J$_{C,F}$=22.0 Hz), 120.8, 122.4, 124.8, 128.9 (d, $^3$J$_{C,F}$=8.3

Hz), 130.0, 132.5, 133.1, 133.8, 133.8, 136.8, 141.8, 146.2, 146.6, 163.0 (d, $^1J_{C,F}$=248 Hz), 167.5. MS m/z 344.84 (MH$^+$).

Example 37

8-[5-(3-Fluorophenyl)-pyridin-3-yl]-1,2,5,6-tetrahydro-pyrrolo[3,2,1-ij]quinolin-4-one

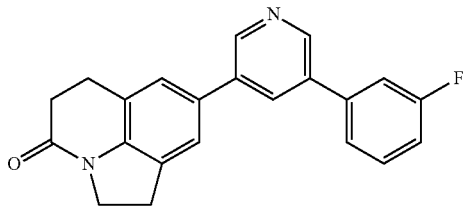 [SMILES: O=C1CCc2cc(-c3cncc(-c4cccc(F)c4)c3)cc3c2N1CC3]

The title compound was obtained via Suzuki coupling according to general procedure B from 8-(4,4,5,5-Tetramethyl-[1,3,2]dioxaborolan-2-yl)-1,2,5,6-tetrahydro-pyrrolo [3,2,1-ij]quinolin-4-one (360 mg, 1.20 mmol) and 3-bromo-5-(3-fluorophenyl)pyridine (378 mg, 1.50 mmol) (prepared previously by Suzuki coupling according to general procedure B from 3,5-dibromopyridine and 3-fluorophenylboronic acid) after flash chromatography on silica gel (hexanes/ethyl acetate, 2/3, R$_f$ 0.08) as colorless needles (97 mg, 0.28 mmol, 23%), mp (hexanes/ethyl acetate) 181° C. $^1$H-NMR (500 MHz, CDCl$_3$): δ=2.73 (t, $^3$J=7.9 Hz, 2H), 3.05 (t, $^3$J=7.9 Hz, 2H), 3.27 (t, $^3$J=8.5 Hz, 2H), 4.14 (t, $^3$J=8.5 Hz, 2H), 7.12 (m, 1H), 7.26 (s, 1H), 7.31-7.35 (m, 2H), 7.40-7.48 (m, 2H), 7.96 (m, 1H), 8.76 (d, $^4$J=2.0 Hz, 1H), 8.77 (d, $^4$J=2.2 Hz, 1H). $^{13}$C-NMR (125 MHz, CDCl$_3$): δ=24.5, 27.7, 31.6, 45.5, 120.8, 114.2 (d, $^2J_{C,F}$=22.0 Hz), 115.2 (d, $^2J_{C,F}$=21.9 Hz), 122.5, 122.9, 124.8, 130.0, 130.7 ($^3J_{C,F}$=8.3 Hz), 132.7, 133.0, 135.5, 136.9, 139.9 ($^3J_{C,F}$=7.3 Hz), 141.9, 146.2, 147.0, 163.3 (d, $^1J_{C,F}$=247 Hz), 167.5. MS m/z 344.80 (MH$^+$).

Example 38

8-[5-(4-Methoxyphenyl)pyridin-3-yl]-1,2,5,6-tetrahydropyrrolo[3,2,1-ij]-quinolin-4-on

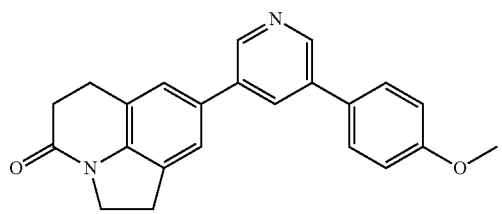 [SMILES: COc1ccc(-c2cncc(-c3cc4c5c(c3)CCN5C(=O)CC4)c2)cc1]

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (389 mg, 1.30 mmol) and 3-bromo-5-(4-methoxyphenyl)pyridine (315 mg, 1.19 mmol) (synthesized by Suzuki coupling according to general procedure B from 3,5-dibromopyridine and 4-methoxyphenylboronic acid) after flash chromatography (ethyl acetate, R$_f$=0.08) as a colorless crystalline solid (182 mg, 0.51 mmol, 43%). $^1$H-NMR (500 MHz, CDCl$_3$): δ=2.73 (t, $^3$J=7.7 Hz, 2H), 3.05 (t, $^3$J=7.7 Hz, 2H), 3.26 (t, $^3$J=8.5 Hz, 2H), 3.86 (s. 3H), 4.14 (t, $^3$J=8.5 Hz, 2H), 7.02 (d, $^3$J=8.8 Hz. 2H), 7.26 (s, 1H), 7.33 (s, 1H), 7.56 (d, $^3$J=8.8 Hz, 2H), 7.92 (m, 1H), 8.70 (d, $^4$J=2.0 Hz, 1H), 8.74 (d, $^4$J=2.2 Hz, 1H), $^{13}$C-NMR (125 MHz, CDCl$_3$): δ=24.5, 27.8, 31.6, 45.5, 55.4, 114.6, 120.7, 122.4, 124.8, 128.3, 129.9, 130.2, 132.1, 133.5, 136.2, 136.6, 141.7, 146.2, 147.3, 159.9, 167.6, MS m/z 357.09 (MH$^+$).

Example 39

8-[5-(3-Methoxyphenyl)pyridin-3-yl]-1,2,5,6-tetrahydropyrrolo[3,2,1-ij]-quinolin-4-one

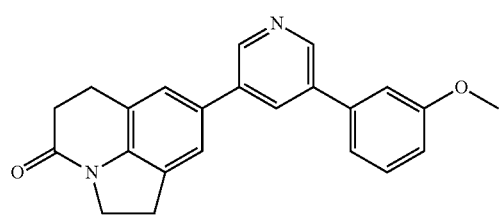 [SMILES: COc1cccc(-c2cncc(-c3cc4c5c(c3)CCN5C(=O)CC4)c2)c1]

The title compound was obtained according to general procedure B from 8-(4,4,5,5-tetramethyl-[1,3,2]dioxaborolan-2-yl)-1,2,5,6-tetrahydropyrrolo[3,2,1-ij]quinolin-4-one (329 mg, 1.10 mmol) and 3-bromo-5-(3-methoxyphenyl)pyridine (270 mg, 1.02 mmol) (synthesized by Suzuki coupling according to general procedure B from 3,5-dibromopyridine and 4-methoxyphenylboronic acid) after flash chromatography (ethyl acetate, R$_f$=0.09) as a colorless crystalline solid (62 mg, 0.17 mmol, 17%). $^1$H-NMR (500 MHz, CDCl$_3$): δ=2.73 (t, $^3$J=7.7 Hz, 2H), 3.05 (t, $^3$J=7.7 Hz, 2H), 3.27 (t, $^3$J=8.3 Hz, 2H), 3.88 (s, 3H), 4.14 (t, $^3$J=8.2 Hz, 2H), 6.96 (dd, $^3$J=8.2 Hz, $^4$J=2.5 Hz, 1H), 7.15 (m, 1H), 7.21 (m, 1H), 7.26 (s, 1H), 7.34 (s, 1H), 7.41 (m, 1H), 7.96 (m, 1H), 8.75 (d, $^4$J=2.2 Hz, 1H), 8.77 (d, $^4$J=2.2 Hz, 1H), $^{13}$C-NMR (125 MHz, CDCl$_3$): δ=24.5, 27.8, 31.6, 45.5, 55.4, 113.2, 113.4, 119.7, 120.7, 122.4, 124.8, 130.0, 130.2, 132.6, 133.4, 136.5, 136.7, 139.3, 141.7, 146.7, 146.9, 160.2, 167.6.

Example 40

8-[5-(2-Fluorophenyl)pyridin-3-yl]-1,2,5,6-tetrahydropyrrolo[3,2,1-ij]quinolin-4-one

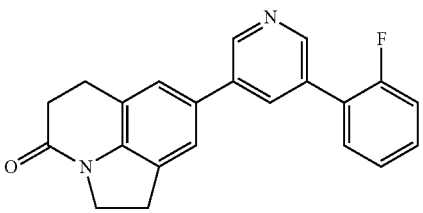 [SMILES: O=C1CCc2cc(-c3cncc(-c4ccccc4F)c3)cc3c2N1CC3]

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (389 mg, 1.30 mmol) and 3-bromo-5-(2-fluorophenyl)pyridine (311 mg, 1.23 mmol) (synthesized by Suzuki coupling according to general procedure B from 3,5-dibromopyridine and 2-fluorophenylboronic acid) after flash chromatography (hexane/ethyl acetate, 2/3, R$_f$=0.09) as a crystalline solid (239 mg, 0.69 mmol, 56%). $^1$H-NMR (500 MHz, CDCl$_3$): δ=2.72 (t, $^3$J=7.7 Hz, 2H), 3.04 (t, $^3$J=7.7 Hz, 2H), 3.26 (t, $^3$J=8.3 Hz, 2H), 4.13 (t, $^3$J=8.5 Hz, 2H), 7.20 (m, 1H), 7.25 (s, 1H), 7.26 (m, 1H), 7.33 (s, 1H), 7.39 (m, 1H), 7.48 (m, 1H), 7.98 (m, 1H), 8.72 (m, 1H), 8.76 (d, $^4$J=2.2 Hz, 1H), MS m/z 344.98 (MH$^+$).

Example 41

8-[5-(3-Trifluoromethylphenyl)pyridin-3-yl]-1,2,5,6-tetrahydropyrrolo[3,2,1-ij]quinolin-4-one

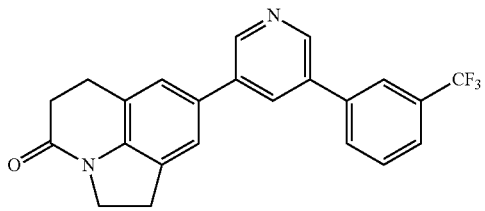 [SMILES: O=C1CCc2cc(-c3cncc(-c4cccc(C(F)(F)F)c4)c3)cc3c2N1CC3]

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (344 mg, 1.15 mmol) and 3-bromo-5-(3-trifluoromethylphenyl)pyridine (330 mg, 1.09 mmol) (synthesized by Suzuki coupling according to general procedure B from 3,5-dibromopyridine and 3-trifluoromethylphenylboronic acid) after flash chromatography (hexane/ethyl acetate, 2/3, R$_f$=0.05) as a colorless crystalline solid (276 mg, 0.70 mmol, 64%). $^1$H-NMR (500 MHz, CDCl$_3$): δ=2.72 (t, $^3$J=7.7 Hz, 2H), 3.05 (t, $^3$J=7.8 Hz, 2H), 3.26 (t, $^3$J=8.2 Hz, 2H), 4.14 (t, $^3$J=8.2 Hz, 2H), 7.26 (s, 1H), 7.34 (s, 1H), 7.61 (dd, $^3$J=7.9 Hz, $^3$J=7.9 Hz, 1H), 7.68 (d, $^3$J=7.9 Hz, 1H), 7.80 (d, $^3$J=7.9 Hz, 1H), 7.85 (s, 1H), 7.96 (m, 1H), 8.77 (d, $^4$J=1.9 Hz, 1H), 8.79 (d, $^4$J=2.2 Hz, 1H), MS m/z 394.94 (MH$^+$).

Example 42

8-[5-(3,4-Difluorophenyl)pyridin-3-yl]-1,2,5,6-tetrahydropyrrolo[3,2,1-ij]quinolin-4-one

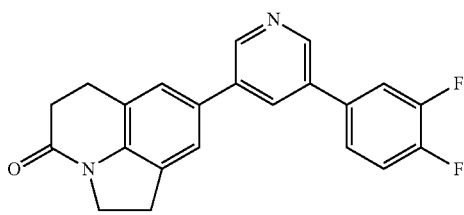 [SMILES: O=C1CCc2cc(-c3cncc(-c4ccc(F)c(F)c4)c3)cc3c2N1CC3]

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (449 mg, 1.50 mmol) and 3-bromo-5-(3,4-difluorophenyl)pyridine (367 mg, 1.34 mmol) (synthesized by Suzuki coupling according to general procedure B from 3,5-dibromopyridine and 3,4-difluorophenylboronic acid) after flash chromatography (hexane/ethyl acetate, 1/4, R$_f$=0.07) as a colorless crystalline solid (110 mg, 0.30 mmol, 22%). $^1$H-NMR (500 MHz, CDCl$_3$): δ=2.73 (t, $^3$J=7.6 Hz, 2H), 3.05 (t, $^3$J=7.6 Hz, 2H), 3.26 (t, $^3$J=8.5 Hz, 2H), 4.14 (t, $^3$J=8.8 Hz, 2H), 7.25 (s, 1H), 7.27-7.36 (m, 3H), 7.43 (m, 1H), 789 (m, 1H), 8.70 (d, $^4$J=2.2 Hz, 1H), 8.76 (d, $^4$J=2.2 Hz, 1H), MS m/z 363.11 (MH$^+$).

Example 43

8-[5-(3-Trifluoromethoxyphenyl)pyridin-3-yl]-1,2,5,6-tetrahydropyrrolo-[3,2,1-ij]-quinolin-4-one

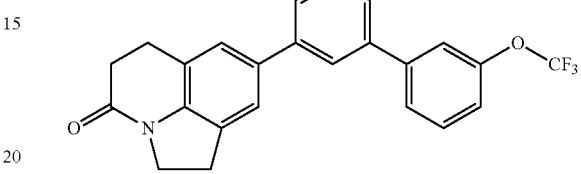

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (382 mg, 1.20 mmol) and 3-bromo-5-(3-trifluoromethoxyphenyl)pyridine (370 mg, 1.16 mmol) (synthesized by Suzuki coupling according to general procedure B from 3,5-dibromopyridine and 3-trifluoromethoxyphenylboronic acid) after flash chromatography (hexane/ethyl acetate, 1/4, R$_f$=0.11) as a colorless crystalline solid (332 mg, 0.81 mmol, 70%). $^1$H-NMR (500 MHz, CDCl$_3$): δ=2.73 (t, $^3$J=7.7 Hz, 2H), 3.06 (t, $^3$J=7.7 Hz, 2H), 3.27 (t, $^3$J=8.5 Hz, 2H), 4.15 (t, $^3$J=8.5 Hz, 2H), 7.25-7.29 (m, 2H), 7.34 (s, 1H), 7.46 (s, 1H), 7.51-7.57 (m, 2H), 7.94 (m, 1H), 8.76 (d, $^4$J=2.2 Hz, 1H), 8.79 (d, $^4$J=2.2 Hz, 1H).

Example 44

8-[5-(2-Methoxyphenyl)pyridin-3-yl]-1,2,5,6-tetrahydropyrrolo[3,2,1-ij]-quinolin-4-one

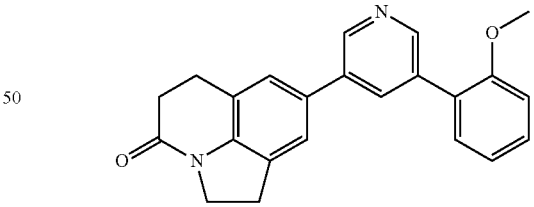

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (512 mg, 1.71 mmol) and 3-bromo-5-(2-methoxyphenyl)pyridine (430 mg, 1.63 mmol) (synthesized by Suzuki coupling according to general procedure B from 3,5-dibromopyridine and 2-methoxyphenylboronic acid) after flash chromatography (hexane/ethyl acetate, 1/4, R$_f$=0.10) as a colorless crystalline solid (106 mg, 0.29 mmol, 18%). $^1$H-NMR (500 MHz, CDCl$_3$): δ=2.72 (t, $^3$J=7.6 Hz, 2H), 3.04 (t, $^3$J=7.6 Hz, 2H), 3.26 (t, $^3$J=8.5 Hz, 2H), 3.84 (s, 3H), 4.13 (t, $^3$J=8.5 Hz, 2H), 7.02 (d, ³J=8.2 Hz, 1H), 7.07 (m, 1H), 7.25 (s, 1H), 7.32 (s, 1H), 7.35-7.40 (m, 2H), 7.95 (m, 1H), 8.71 (m, 2H).

Example 45

8-[5-(3,5-Difluorophenyl)pyridin-3-yl]-1,2,5,6-tetrahydropyrrolo[3,2,1-ij]-quinolin-4-one

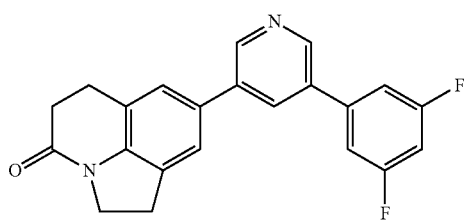 [SMILES: O=C1CCc2cc(-c3cncc(-c4cc(F)cc(F)c4)c3)cc3c2N1CC3]

The title compound was obtained according to general procedure B from 8-(4,4,5,5-tetramethyl-[1,3,2]dioxaborolan-2-yl)-1,2,5,6-tetrahydro-pyrrolo[3,2,1-ij]quinolin-4-one (404 mg, 1.35 mmol) and 3-bromo-5-(3,5-difluorophenyl) pyridine (315 mg, 2.0 mmol) (synthesized by Suzuki coupling according to general procedure B from 3,5-dibromopyridine and 3,5-difluorophenylboronic acid) after flash chromatography (hexane/ethyl acetate, 3/7, $R_f$=0.10) as a colorless crystalline solid (104 mg, 0.29 mmol, 21%). ¹H-NMR (500 MHz, CDCl₃): δ=2.73 (t, ³J=7.6 Hz, 2H), 3.06 (t, ³J=7.6 Hz, 2H), 3.27 (t, ³J=8.5 Hz, 2H), 4.15 (t, ³J=8.5 Hz, 2H), 6.87 (m, 1H), 7.14 (m, 2H), 7.26 (s, 1H), 7.33 (s, 1H), 7.93 (m, 1H), 8.73 (d, ⁴J=2.2 Hz, 1H), 8.80 (d, ⁴J=1.9 Hz, 1H).

According to Examples 36-45 using the general procedures A or B and the appropriate starting compounds (see Schemes 1-19) also the following compounds are synthesized:

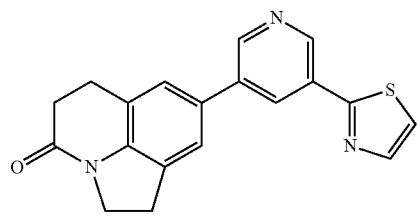

8-[5-(1,3-Thiazol-2-yl)pyridin-3-yl]-1,2,5,6-tetrahydro-4H-pyrrolo[3,2,1-ij]quinolin-4-one

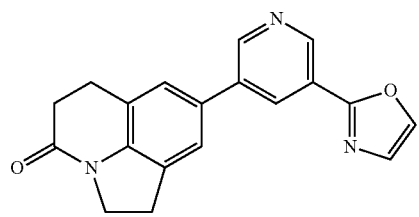

8-[5-(1,3-Oxazol-2-yl)pyridin-3-yl]-1,2,5,6-tetrahydro-4H-pyrrolo[3,2,1-ij]quinolin-4-one

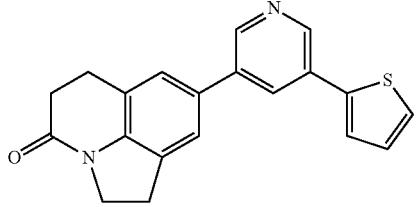

8-(5-Thiophen-2-ylpyridin-3-yl)-1,2,5,6-tetrahydro-4H-pyrrolo[3,2,1-ij]quinolin-4-one

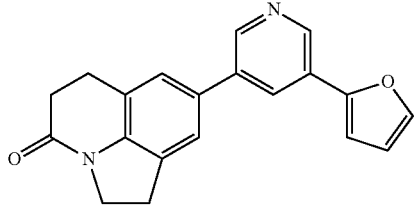

8-(5-Furan-2-ylpyridin-3-yl)-1,2,5,6-tetrahydro-4H-pyrrolo[3,2,1-ij]quinolin-4-one

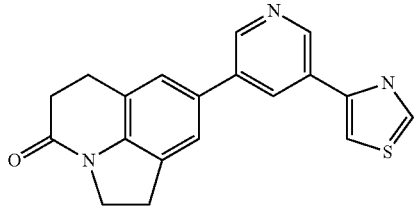

8-[5-(1,3-Thiazol-4-yl)pyridin-3-yl]-1,2,5,6-tetrahydro-4H-pyrrolo[3,2,1-ij]quinolin-4-one

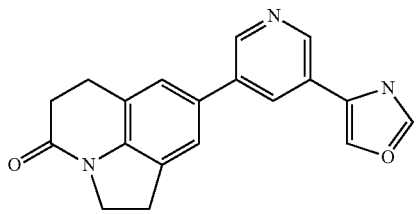

8-[5-(1,3-Oxazol-4-yl)pyridin-3-yl]-1,2,5,6-tetrahydro-4H-pyrrolo[3,2,1-ij]quinolin-4-one

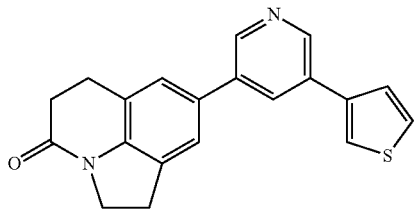

8-(5-Thiophen-3-ylpyridin-3-yl)-1,2,5,6-tetrahydro-4H-pyrrolo[3,2,1-ij]quinolin-4-one

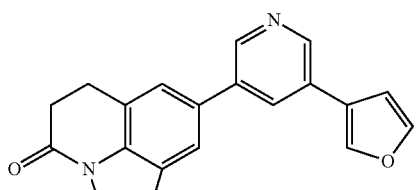

8-(5-Furan-3-ylpyridin-3-yl)-1,2,5,6-tetrahydro-4H-pyrrolo[3,2,1-ij]quinolin-4-one -continued

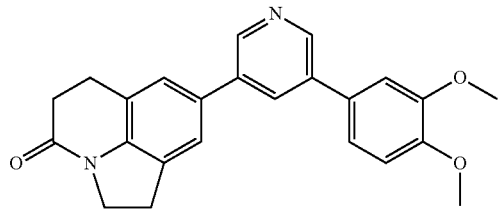

8-[5-(3,4-Dimethoxyphenyl)pyridin-3-yl]-1,2,5,6-tetrahydro-
4H-pyrrolo[3,2,1-ij]quinolin-4-one

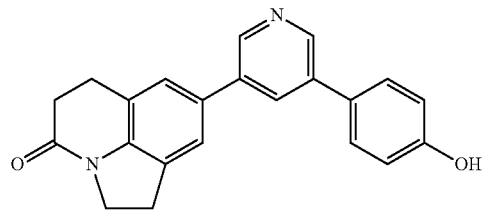

8-[5-(4-Hydroxyphenyl)pyridin-3-yl]-1,2,5,6-tetrahydro-
4H-pyrrolo[3,2,1-ij]quinolin-4-one

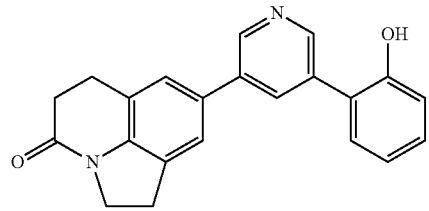

8-[5-(2-Hydroxyphenyl)pyridin-3-yl]-1,2,5,6-tetrahydro-
4H-pyrrolo[3,2,1-ij]quinolin-4-one

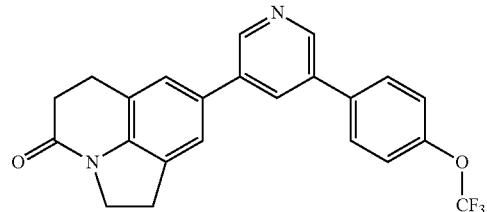

8-[5-(4-Trifluoromethoxyphenyl)pyridin-3-yl]-1,2,5,6-
tetrahydro-4H-pyrrolo[3,2,1-ij]quinolin-4-one

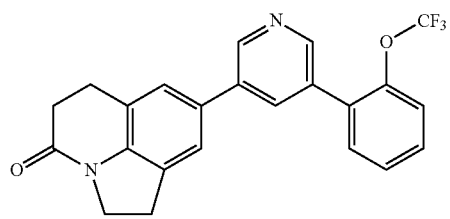

8-[5-(2-Trifluoromethoxyphenyl)pyridin-3-yl]-1,2,5,6-
tetrahydro-4H-pyrrolo[3,2,1-ij]quinolin-4-one

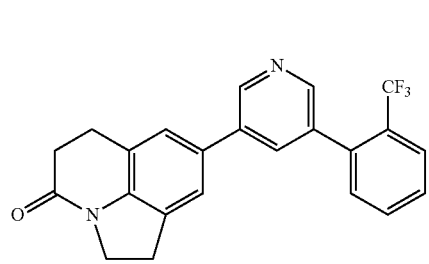

8-[5-(2-Trifluoromethylphenyl)pyridin-3-yl]-1,2,5,6-tetrahydro-
4H-pyrrolo[3,2,1-ij]quinolin-4-one -continued

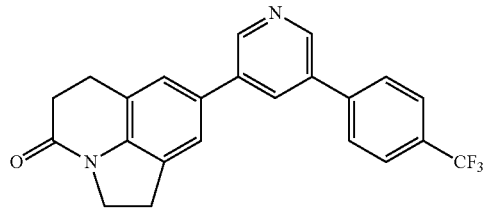

8-[5-(4-Trifluoromethylphenyl)pyridin-3-yl]-1,2,5,6-tetrahydro-
4H-pyrrolo[3,2,1-ij]quinolin-4-one

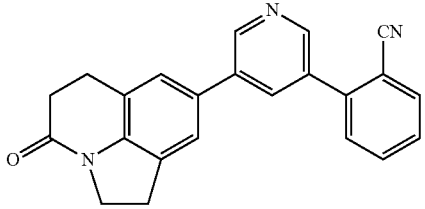

8-[5-(2-Cyanophenyl)pyridin-3-yl]-1,2,5,6-tetrahydro-4H-
pyrrolo[3,2,1-ij]quinolin-4-one

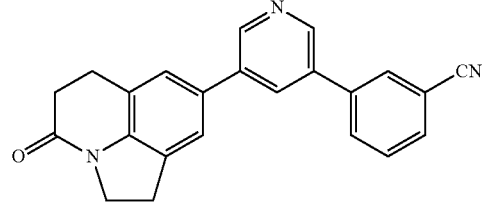

8-[5-(3-Cyanophenyl)pyridin-3-yl]-1,2,5,6-tetrahydro-4H-
pyrrolo[3,2,1-ij]quinolin-4-one

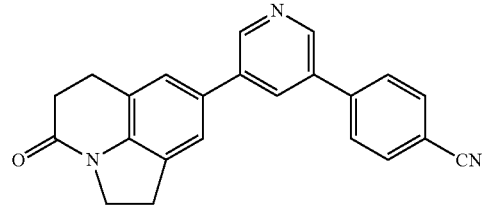

8-[5-(4-Cyanophenyl)pyridin-3-yl]-1,2,5,6-tetrahydro-4H-
pyrrolo[3,2,1-ij]quinolin-4-one

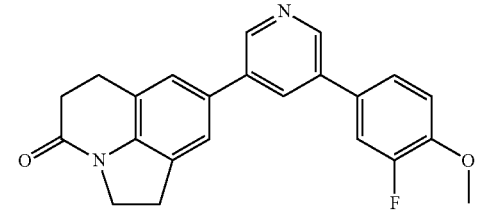

8-[5-(3,4-Fluoro-4-methoxyphenyl)pyridin-3-yl]-1,2,5,6-
tetrahydro-4H-pyrrolo[3,2,1-ij]quinolin-4-one

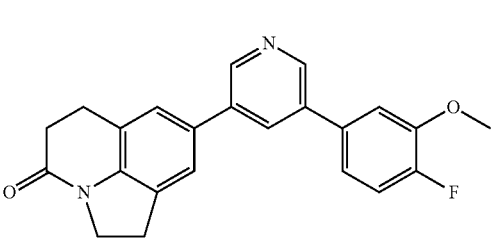

8-[5-(4-Fluoro-3-methoxyphenyl)pyridin-3-yl]-1,2,5,6-
tetrahydro-4H-pyrrolo[3,2,1-ij]quinolin-4-one

Example 46

8-Fluoro-6-pyridin-3-yl-3,4,4a,8a-tetrahydro-1H-quinolin-2-one

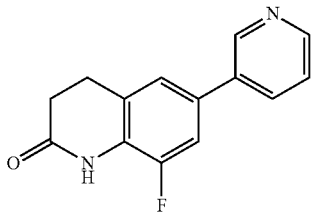 [SMILES: O=C1CCc2cc(-c3cccnc3)cc(F)c2N1]

The title compound was obtained via Suzuki coupling according to general procedure C from 6-Bromo-8-fluoro-3,4,4a,8a-tetrahydro-1H-quinolin-2-one (321 mg, 1.32 mmol) and 3-pyridineboronic acid (210 mg, 1.71 mmol) after flash chromatography on silica gel (dichloromethane/methanol, 20/1, $R_f$=0.25) as white solid (274 mg, 1.13 mmol, 86%), mp 203° C. $^1$H-NMR (500 MHz, CDCl$_3$): δ=2.72 (t, $^3$J=7.9 Hz, 2H), 3.09 (t, $^3$J=7.9 Hz, 2H), 7.20 (s, 1H), 7.21 (d, $^3$J$_{H,F}$=11.0 Hz, 1H), 7.36 (dd, $^3$J=4.8, 7.9 Hz, 1H), 7.76 (s, br, 1H), 7.81 (dt, $^3$J=7.9 Hz, $^4$J=2.3 Hz, 1H), 8.60 (dd, $^3$J=4.8 Hz, $^4$J=2.0 Hz, 1H), 8.80 (d, $^4$J=2.0 Hz, 1H). $^{13}$C-NMR (125 MHz, CDCl$_3$): δ=25.5, 30.5, 120.8, 112.5, 112.6, 121.9, 122.0, 123.6, 134.0, 135.2, 147.9, 148.8, 149.0, 150.9, 169.8. MS m/z 243 (MH$^+$).

Example 47

7-Fluoro-6-pyridin-3-yl-3,4,4a,8a-tetrahydro-1H-quinolin-2-one

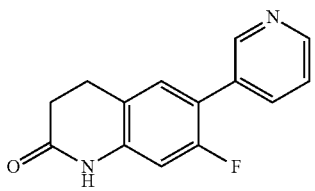 [SMILES: O=C1CCc2cc(-c3cccnc3)c(F)cc2N1]

The title compound was obtained via Suzuki coupling according to general procedure C from 6-Bromo-7-fluoro-3,4,4a,8a-tetrahydro-1H-quinolin-2-one (130 mg, 0.53 mmol) and 3-pyridineboronic acid (86 mg, 0.7 mmol) after flash chromatography on silica gel (dichloromethane/methanol, 20/1, $R_f$=0.27) as white solid (107 mg, 0.44 mmol, 83%), mp 228° C. $^1$H-NMR (500 MHz, CDCl$_3$): δ=2.70 (t, $^3$J=7.9 Hz, 2H), 3.02 (t, $^3$J=7.9 Hz, 2H), 6.69 (d, $^3$J$_{H,F}$=10.8 Hz, 1H), 7.23 (d, $^4$J$_{H,F}$=7.9 Hz, 1H), 7.36 (dd, $^3$J=4.8, 7.9 Hz, 1H), 7.83 (dt, $^3$J=7.9 Hz, $^4$J=2.3 Hz, 1H), 8.59 (dd, $^3$J=4.8 Hz, $^4$J=2.0 Hz, 1H), 8.76 (d, $^4$J=2.0 Hz, 1H), 8.92 (s, 1H). $^{13}$C-NMR (125 MHz, CDCl$_3$): δ=24.8, 30.6, 103.5, 103.7, 119.9, 123.3, 129.5, 131.2, 136.0, 138.6, 148.6, 149.4, 159.0, 171.6. MS m/z 243 (MH$^+$).

Example 48

8-Fluoro-6-isoquinolin-4-yl-3-yl-3,4,4a,8a-tetrahydro-1H-quinolin-2-one

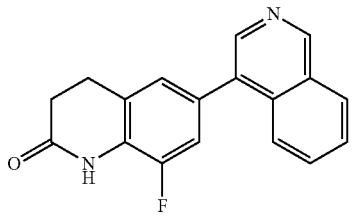 [SMILES: O=C1CCc2cc(-c3cncc4ccccc34)cc(F)c2N1]

The title compound was obtained via Suzuki coupling according to general procedure C from 6-Bromo-8-fluoro-3,4,4a,8a-tetrahydro-1H-quinolin-2-one (169 mg, 0.69 mmol) and isoquinolin-4-yl boronic acid (144 mg, 0.83 mmol) after flash chromatography on silica gel (dichloromethane/methanol, 20/1, $R_f$=0.32) as white solid (172 mg, 0.59 mmol, 85%), mp 202° C. $^1$H-NMR (500 MHz, CDCl$_3$): δ=2.75 (t, $^3$J=7.9 Hz, 2H), 3.11 (t, $^3$J=7.9 Hz, 2H), 7.13 (s, 1H), 7.17 (d, $^3$J$_{H,F}$=10.7 Hz, 1H), 7.64-7.73 (m, 2H), 7.74 (s, br, 1H), 7.90 (d, $^3$J=8.2 Hz, 1H), 8.06 (d, $^3$J=7.9 Hz, 1H), 8.45 (s, 1H), 9.27 (s, 1H). $^{13}$C-NMR (125 MHz, CDCl$_3$): δ=25.5, 30.5, 124.3, 124.9, 125.4, 126.0, 127.4, 128.1, 128.4, 130.9, 131.6, 132.1, 134.0, 142.8, 149.5, 152.4. MS m/z 293 (MH$^+$).

Example 49

7-Fluoro-6-isoquinolin-4-yl-3-yl-3,4,4a,8a-tetrahydro-1H-quinolin-2-one

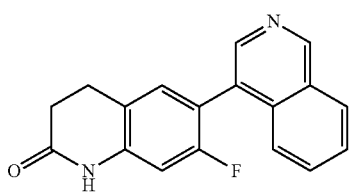 [SMILES: O=C1CCc2cc(-c3cncc4ccccc34)c(F)cc2N1]

The title compound was obtained via Suzuki coupling according to general procedure C from 6-Bromo-7-fluoro-3,4,4a,8a-tetrahydro-1H-quinolin-2-one (169 mg, 0.69 mmol) and isoquinolin-4-yl boronic acid (144 mg, 0.83 mmol) after flash chromatography on silica gel (dichloromethane/methanol, 20/1, $R_f$=0.32) as white solid (160 mg, 0.55 mmol, 79%), mp 281° C. $^1$H-NMR (500 MHz, CDCl$_3$): δ=2.73 (t, $^3$J=7.9 Hz, 2H), 3.03 (t, $^3$J=7.9 Hz, 2H), 6.74 (d, $^3$J$_{H,F}$=9.8 Hz, 1H), 7.23 (d, $^4$J$_{H,F}$=7.4 Hz, 1H), 7.62-7.70 (m, 3H), 8.05 (d, $^3$J=8.0 Hz, 1H), 8.48 (s, 1H), 8.62 (s, 1H), 9.29 (s, 1H). $^{13}$C-NMR (125 MHz, CDCl$_3$): δ=24.8, 30.7, 103.2, 117.5, 118.6, 119.7, 124.7, 127.1, 127.3, 127.9, 128.3, 130.7, 134.5, 143.6, 152.7, 159.4, 171.4. MS m/z 293 (MH+).

Example 50

7-Hydroxy-6-pyridin-3-yl-3,4,4a,8a-tetrahydro-1H-quinolin-2-one

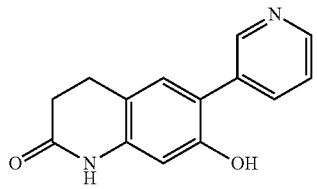 [SMILES: O=C1CCc2cc(-c3cccnc3)c(O)cc2N1]

The title compound was obtained via Suzuki coupling according to general procedure C from 6-Bromo-7-hydroxy-3,4,4a,8a-tetrahydro-1H-quinolin-2-one (500 mg, 2.07 mmol) and 3-pyridineboronic acid (305 mg, 2.48 mmol) after flash chromatography on silica gel (dichloromethane/methanol, 5/1, $R_f$=0.27) as white solid (72 mg, 0.30 mmol, 15%), mp 298° C. $^1$H-NMR (500 MHz, CDCl$_3$): δ=2.44 (t, $^3$J=7.9 Hz, 2H), 2.81 (t, $^3$J=7.9 Hz, 2H), 6.55 (s, 1H), 7.13 (s, 1H), 7.37 (dd, $^3$J=4.8, 7.9 Hz, 1H), 7.89 (dt, $^3$J=7.9 Hz, $^4$J=2.3 Hz, 1H), 8.42 (dd, $^3$J=4.8 Hz, $^4$J=2.0 Hz, 1H), 8.70 (d, $^4$J=2.0 Hz, 1H), 9.68 (s, 1H). $^{13}$C-NMR (125 MHz, CDCl$_3$): δ=23.9, 30.7, 102.7, 114.6, 117.8, 122.9, 129.1, 133.9, 135.9, 138.9, 146.8, 149.3, 153.5, 170.2. MS m/z 241 (MH+).

Example 51

8-Fluoro-6-pyridin-3-yl-3,4,4a,8a-tetrahydro-1H-quinolin-2-thione

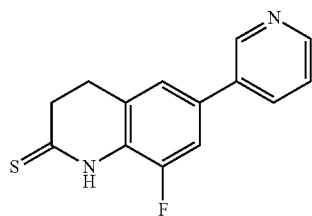 [SMILES: Fc1cc(-c2cccnc2)cc2c1NC(=S)CC2]

The title compound was obtained according to general procedure D from 8-Fluoro-6-pyridin-3-yl-3,4,4a,8a-tetrahydro-1H-quinolin-2-one (450 mg, 1.86 mmol) and Lawesson's reagent (451 mg, 1.11 mmol) after flash chromatography on silica gel (dichloromethane/methanol, 10/1, $R_f$=0.22) as white solid (302 mg, 1.17 mmol, 63%), mp 235° C. $^1$H-NMR (500 MHz, CDCl$_3$): δ=2.91 (t, $^3$J=7.9 Hz, 2H), 3.01 (t, $^3$J=7.9 Hz, 2H), 7.48 (dd, $^3$J=4.8, 7.9 Hz, 1H), 7.53 (s, 1H), 7.59 (d, $^3$J$_{H,F}$=11.0 Hz, 1H), 8.11 (dt, $^3$J=7.9 Hz, $^4$J=2.3 Hz, 1H), 8.57 (dd, $^3$J=4.8 Hz, $^4$J=2.0 Hz, 1H), 8.93 (d, $^4$J=2.0 Hz, 1H), 12.16 (s, 1H). $^{13}$C-NMR (125 MHz, CDCl$_3$): δ=24.1, 30.5, 112.5, 121.9, 123.9, 129.6, 133.4, 133.5, 133.9, 147.3, 148.6, 149.6, 159.7, 200.7. MS m/z 259 (MH+).

Example 52

7-Fluoro-6-pyridin-3-yl-3,4,4a,8a-tetrahydro-1H-quinolin-2-thione

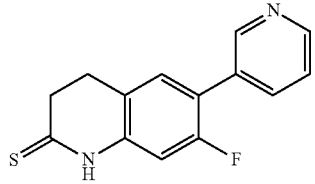 [SMILES: Fc1cc2c(cc1-c1cccnc1)CCC(=S)N2]

The title compound was obtained according to general procedure D from 7-Fluoro-6-pyridin-3-yl-3,4,4a,8a-tetrahydro-1H-quinolin-2-one (640 mg, 2.64 mmol) and Lawesson's reagent (641 mg, 1.59 mmol) after flash chromatography on silica gel (dichloromethane/methanol, 10/1, $R_f$=0.22) as white solid (317 mg, 1.23 mmol, 66%), mp 248° C. $^1$H-NMR (500 MHz, CDCl$_3$): δ=2.85 (t, $^3$J=7.9 Hz, 2H), 2.99 (t, $^3$J=7.9 Hz, 2H), 7.03 (d, $^3$J$_{H,F}$=11.0 Hz, 1H), 7.48-7.51 (m, 2H), 7.94 (dt, $^3$J=7.9 Hz, $^4$J=2.3 Hz, 1H), 8.57 (dd, $^3$J=4.8 Hz, $^4$J=2.0 Hz, 1H), 8.74 (d, $^4$J=2.0 Hz, 1H), 12.33 (s, 1H). $^{13}$C-NMR (125 MHz, CDCl$_3$): δ=23.1, 30.5, 103.6, 119.8, 119.9, 121.9, 123.6, 129.8, 130.6, 135.9, 137.7, 148.7, 157.9, 200.4. MS m/z 259 (MH+).

Example 53

7-(Pyridin-3-yl)-2H-benzo[b][1,4]oxazin-3(4H)-one

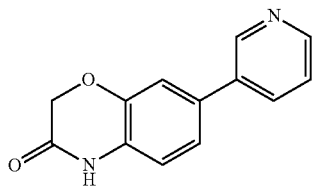 [SMILES: O=C1COc2cc(-c3cccnc3)ccc2N1]

The title compound was obtained via Suzuki coupling according to general procedure A from 7-bromo-2H-benzo[b][1,4]oxazin-3(4H)-one (342 mg, 1.5 mmol) and 3-pyridineboronic acid (242 mg, 1.95 mmol) after flash chromatography on silica gel (dichloromethane/methanol, 95/5, $R_f$=0.08) as pale yellow solid (121 mg, 0.53 mmol, 36%), mp (dichloromethane/methanol) 256° C. $^1$H-NMR (500 MHz, DMSO-d$_6$): δ=4.62 (s, 2H), 7.00 (d, $^3$J=8.2 Hz, 1H); 7.32-7.34 (m, 2H), 7.44 (ddd, $^3$J=7.9 Hz, $^3$J=4.7 Hz, $^5$J=0.8 Hz, 1H), 8.02 (m, 1H), 8.52 (dd, $^3$J=4.7 Hz, $^4$J=1.6 Hz, 1H), 8.85 (d, $^4$J=2.5 Hz, 1H), 10.82 (s, 1H). $^{13}$C-NMR (125 MHz, DMSO-d$_6$): δ=66.7, 114.3, 116.3, 120.7, 123.7, 127.2, 131.9, 133.5, 134.6, 143.7, 147.2, 148.1, 164.6. MS m/z 227.7 (MH+).

Example 54

6-(Pyridin-3-yl)benzo[d]oxazol-2(3H)-one

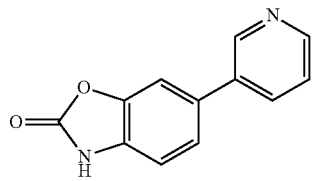 [SMILES: O=c1[nH]c2ccc(-c3cccnc3)cc2o1]

The title compound was obtained via Suzuki coupling according to general procedure C from 6-bromobenzo[d]oxazol-2(3H)-one (428 mg, 2.0 mmol) and 3-pyridineboronic acid (320 mg, 2.6 mmol) with Cs$_2$CO$_3$ as base instead of Na$_2$CO$_3$ after flash chromatography on silica gel (dichloromethane/methanol, 95/5, R$_f$=0.19) and flash chromatography on silica gel (ethyl acetate, R$_f$=0.27) as colorless solid (99 mg, 0.47 mmol, 23%), mp (ethyl acetate) 265° C. $^1$H-NMR (500 MHz, DMSO-d$_6$): δ=7.20 (d, $^3$J=8.2 Hz, 1H), 7.46 (ddd, $^3$J=7.9 Hz, $^3$J=4.7 Hz, $^5$J=0.6 Hz, 1H), 7.51 (dd, $^3$J=8.0 Hz, $^4$J=1.7 Hz, 1H), 7.71 (d, $^4$J=1.9 Hz, 1H), 8.06 (m, 1H), 8.54 (dd, $^3$J=4.7 Hz, $^4$J=1.6 Hz, 1H), 8.88 (d, $^4$J=2.5 Hz, 1H), 11.73 (s, 1H). $^{13}$C-NMR (125 MHz, DDMSO-d$_6$): δ=108.0, 110.1, 122.5, 123.7, 130.4, 131.1, 133.8, 135.1, 144.0, 147.4, 148.1, 154.3.

Example 55

7-(Isoquinolin-4-yl)-2H-benzo[b][1,4]oxazin-3(4H)-one

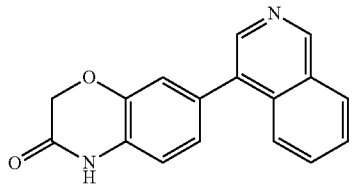 [SMILES: O=C1COc2cc(-c3cncc4ccccc34)ccc2N1]

The title compound was obtained via Suzuki coupling according to general procedure A from 7-bromo-2H-benzo[b][1,4]oxazin-3(4H)-one (242 mg, 1.95 mmol) and 4-isoquinolineboronic acid (337 mg, 1.95 mmol) after flash chromatography on silica gel (dichloromethane/methanol, 97/3, R$_f$=0.13) as off-white solid (177 mg, 0.64 mmol, 43%), mp (dichloromethane/methanol) 266° C. $^1$H-NMR (500 MHz, DMSO-d$_6$): δ=4.66 (s, 2H), 7.08 (d, $^3$J=8.5 Hz, 1H), 7.12-7.13 (m, 2H), 7.73 (m, 1H), 7.80 (m, 1H), 7.89 (d, $^3$J=8.5 Hz, 1H), 8.21 (d, $^3$J=8.2 Hz, 1H), 8.41 (s, 1H), 9.32 (s, 1H), 10.88 (s, 1H). $^{13}$C-NMR (125 MHz, DMSO-d$_6$): δ=66.7, 115.9, 117.4, 123.9, 124.0, 127.1, 127.4, 127.9, 128.0, 131.0, 131.1, 131.7, 133.1, 142.3, 143.3, 151.7, 164.7. MS m/z 276.6 (MH$^+$).

Example 56

6-(Isoquinolin-4-yl)-3,4-dihydroquinoxalin-2(1H)-one

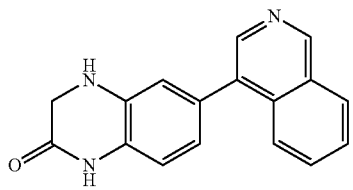 [SMILES: O=C1CNc2cc(-c3cncc4ccccc34)ccc2N1]

The title compound was obtained via Suzuki coupling according to general procedure A from 6-bromo-3,4-dihydroquinoxalin-2(1H)-one (340 mg, 1.5 mmol) and 4-isoquinolineboronic acid (337 mg, 1.95 mmol) after flash chromatography on silica gel (dichloromethane/methanol, 95/5, R$_f$=0.19) and crystallization from ethanol as yellow solid (148 mg, 0.54 mmol, 36%), mp (ethanol)>300° C. $^1$H-NMR (500 MHz, DMSO-d$_6$): δ=3.82 (d, $^4$J=1.8 Hz, 2H), 6.14 (s, 1H), 6.75 (dd, $^3$J=7.9 Hz, $^4$J=1.6 Hz, 1H), 6.82 (d, $^4$J=1.8 Hz, 1H), 6.90 (d, $^3$J=7.9 Hz, 1H), 7.71 (m, 1H), 7.78 (m, 1H), 7.93 (d, $^3$J=8.5 Hz, 1H), 8.19 (d, $^3$J=8.2 Hz, 1H), 8.37 (s, 1H), 9.28 (s, 1H), 10.42 (s, 1H). $^{13}$C-NMR (125 MHz, DMSO-d$_6$): δ=46.1, 114.4, 115.0, 119.2, 124.2, 126.0, 127.3, 127.9, 127.9, 130.7, 130.7, 132.7, 133.2, 134.9, 142.0, 151.4, 165.9. MS m/z 276.0 (MH$^+$).

Example 57

4-Methyl-6-(pyridin-3-yl)-3,4-dihydroquinoxalin-2(1H)-one

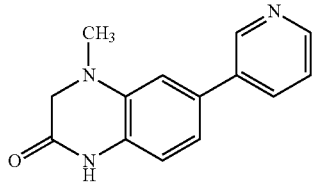 [SMILES: CN1CC(=O)Nc2ccc(-c3cccnc3)cc21]

The title compound was obtained via Suzuki coupling according to general procedure A from 6-bromo-4-methyl-3,4-dihydroquinoxalin-2(1H)-one (342 mg, 1.42 mmol) and 3-pyridineboronic acid (229 mg, 1.86 mmol) after flash chromatography on silica gel (dichloromethane/methanol, 97/3, R$_f$=0.09) and crystallization from acetone as pale yellow solid (55 mg, 0.23 mmol, 16%), mp (acetone)>300° C. $^1$H-NMR (500 MHz, DMSO-d$_5$): δ=2.87 (s, 3H), 3.70 (s, 2H), 6.90 (d, $^3$J=7.9 Hz, 1H), 6.98 (s, 1H), 7.06 (d, $^3$J=7.9 Hz, 1H), 7.43 (dd, $^3$J=7.6 Hz, $^3$J=5.0 Hz, 1H), 8.02 (dd, $^3$J=7.6 Hz, $^4$J=1.6 Hz, 1H), 8.51 (d, $^3$J=4.7 Hz, 1H), 8.86 (d, $^4$J=2.2 Hz, 1H), 10.52 (s, 1H). $^{13}$C-NMR (125 MHz, DMSO-d$_6$): δ=36.8, 54.0, 109.7, 115.1, 117.0, 123.6, 127.4, 131.9, 133.6, 135.8, 136.7, 147.3, 147.7, 165.9. MS m/z 240.0 (MH$^+$).

Example 58

6-(Pyridin-3-yl)-1H-benzo[d][1,3]oxazin-2(4H)-one

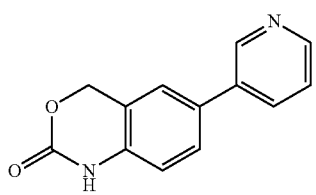 [SMILES: O=C1Nc2ccc(-c3cccnc3)cc2CO1]

The title compound was obtained via Suzuki coupling according to general procedure C from 6-bromo-1H-benzo[d][1,3]oxazin-2(4H)-one (342 mg, 1.5 mmol) and 3-pyridineboronic acid (240 mg, 1.95 mmol) after flash chromatography on silica gel (dichloromethane/methanol, 97/3, R$_f$=0.12) and crystallization from acetone as colorless solid (85 mg, 0.38 mmol, 25%), mp (acetone) 211° C. $^1$H-NMR (500 MHz, DMSO-d$_6$): δ=5.35 (s, 2H), 7.00 (d, $^3$J=8.2 Hz, 1H), 7.46 (dd, $^3$J=8.2 Hz, $^3$J=4.7 Hz, 1H), 7.61 (s, 1H), 7.64 (dd, $^3$J=8.0 Hz, $^4$J=2.0 Hz, 1H), 8.01 (m, 1H), 8.53 (dd, $^3$J=4.7 Hz, $^4$J=1.6 Hz, 1H), 8.85 (d, $^4$J=1.9 Hz, 1H), 10.29 (s, 1H).

$^{13}$C-NMR (125 MHz, DMSO-d$_6$): δ=67.4, 114.2, 119.2, 122.9, 123.7, 125.1, 127.2, 131.0, 133.4, 136.4, 147.1, 148.0, 151.5.

Example 59

6-(Isoquinolin-4-yl)-1H-benzo[d][1,3]oxazin-2(4H)-one

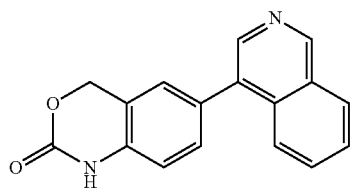 [SMILES: O=C1Nc2ccc(-c3cncc4ccccc34)cc2CO1]

The title compound was obtained via Suzuki coupling according to general procedure C from 6-bromo-1H-benzo[d][1,3]oxazin-2(4H)-one (255 mg, 1.12 mmol) and 4-isoquinolineboronic acid (232 mg, 1.34 mmol) after flash chromatography on silica gel (dichloro-methane/methanol, 98/2, R$_f$=0.06) and crystallization from acetone as colorless solid (74 mg, 0.27 mmol, 24%), mp (acetone) 215° C. $^1$H-NMR (500 MHz, DMSO-d$_6$): δ=5.38 (s, 2H), 7.08 (d, $^3$J=8.2 Hz, 1H), 7.41 (s, 1H), 7.44 (dd, $^3$J=8.2 Hz, $^4$J=1.9 Hz, 1H), 7.73 (m, 1H), 7.79 (m, 1H), 7.88 (d, $^3$J=8.5 Hz, 1H), 8.21 (d, $^3$J=8.2 Hz, 1H), 8.41 (s, 1H), 9.32 (s, 1H), 10.34 (s, 1H). $^{13}$C-NMR (125 MHz, DMSO-d$_6$): δ=67.39, 113.8, 118.9, 124.0, 125.9, 127.4, 127.9, 128.0, 130.2, 130.2, 131.0, 131.8, 133.1, 136.3, 142.3, 151.6, 151.7.

Example 60

8-(1-(1H-imidazol-1-yl)propyl)-1,2,5,6-tetrahydro-pyrrolo[3,2,1-ij]quinolin-4-one

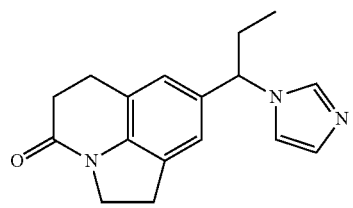 [SMILES: CCC(c1cc2c3c(c1)CCN3C(=O)CC2)n1ccnc1]

To a solution of 1,2,5,6-tetrahydro-pyrrolo[3,2,1-ij]quinolin-4-one (1.73 g, 10.0 mmol) and AlCl$_3$ (4.0 g, 30.0 mmol) in 80 ml dry dichloromethane was added dropwise propionyl chloride (1.31 mL, 15.0 mmol) at room temperature. The mixture was refluxed overnight, cooled to ambient temperature and quenched by addition of a cold mixture of 10 ml concentrated hydrochloric acid and 20 ml water. Extraction with dichloromethane (3×75 ml), followed by drying over MgSO$_4$ and removal of the solvent in vacuo gave the crude product, which was purified by flash chromatography on silica gel (hexanes/ethyl acetate, 3/7, R$_f$=0.16) to yield a green solid (1.20 g, 5.20 mmol). This was dissolved in 26 ml methanol and sodium boron hydride (236 mg, 6.21 mmol) was added portionwise at 0° C. After stirring for 1 h, water was added and the mixture was extracted with ethyl acetate (3×75 ml). Drying over MgSO$_4$ and removal of the solvent gave the alcohol as crude product. A solution of the obtained alcohol in 10 ml dry THF was added to a solution of thionylbis (imidazole) (prepared previously by reaction of imidazole (1.47 g, 21.6 mmol) with thionyl chloride (0.39 mL, 5.4 mmol) in 20 mL THF and filtration to remove precipitated imidazole hydrochloride) at 0° C. The reaction mixture was stirred for one hour at 0° C. and an additional 18 h at ambient temperature. Water was added and the mixture extracted with ethyl acetate (3×75 ml), the combined organic extracts washed with water and brine, and the solvent was removed in vacuo after drying over MgSO$_4$. The crude product was purified by flash chromatography on silica gel (ethyl acetate/methanol, 9/1, R$_f$=0.1) to yield 8-(1-(1H-imidazol-1-yl)propyl)-1,2,5,6-tetrahydropyrrolo[3,2,1-ij]quinolin-4-one (200 mg, 0.71 mmol, 7%) as a white solid, mp (ethyl acetate/methanol) 195° C. $^1$H-NMR (500 MHz, CDCl$_3$): δ=0.93 (t, $^3$J=7.2, 3H), 2.13-2.25 (m, 2H), 2.65 (t, $^3$J=7.9, 2H), 2.93 (t, $^3$J=7.9, 2H), 3.14 (t, $^3$J=8.5, 2H), 4.06 (t, $^3$J=8.5, 2H), 4.90-4.94 (t, $^3$J=7.6, 1H), 6.82 (s, 1H), 6.90 (s, 1H), 6.92 (s, 1H), 7.06 (s, 1H), 7.59 (s, 1H). $^{13}$C-NMR (125 MHz, CDCl$_3$): δ=11.4, 24.6, 27.9, 29.0, 31.7, 45.6, 63.6, 117.8, 120.6, 121.9, 124.3, 129.6, 129.8, 135.8, 136.4, 141.7, 167.7. MS m/z 282.07 (MH$^+$).

Example 61

8-((1H-imidazol-1-yl)(phenyl)methyl)-1,2,5,6-tetrahydropyrrolo[3,2,1-ij]quinolin-4-one

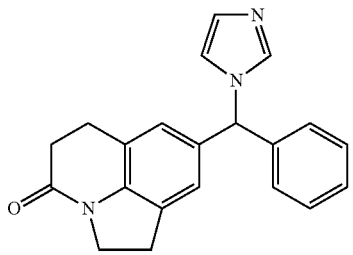 [SMILES: O=C1CCc2cc(C(c3ccccc3)n3ccnc3)cc3c2N1CC3]

To a solution of 1,2,5,6-tetrahydro-pyrrolo[3,2,1-ij]quinolin-4-one (1.94 g, 10.8 mmol) and AlCl$_3$ (3.99 g, 29.9 mmol) in 50 ml dry dichloromethane was added dropwise benzoyl chloride (3.14 g, 22.3 mmol) at 0° C. The mixture was then refluxed overnight, cooled to ambient temperature and quenched by, addition of a cold mixture of 10 ml concentrated hydrochloric acid and 20 ml water. Extraction with ethyl acetate (3×100 ml), followed by drying over MgSO$_4$ and removal of the solvent in vacuo gave the crude product, which was purified by flash chromatography on silica gel (hexanes/ethyl acetate, 1/1, R$_f$=0.14) to yield yellow crystals (1.82 g, 6.57 mmol). These were dissolved in 50 ml methanol and sodium boron hydride (378 mg, 10.0 mmol) was added portionwise at 0° C. After stirring for 1 h, water was added and the mixture was extracted with ethyl acetate (3×100 ml). Drying over MgSO$_4$ and removal of the solvent gave the alcohol as crude product. A solution of the obtained alcohol in 10 ml dry THF was added to a solution of thionylbis(imidazole) (prepared previously by reaction of imidazole (2.72 g, 40.0 mmol) with thionyl chloride (0.73 mL, 10.0 mmol) in 30 mL THF and filtration to remove precipitated imidazole hydrochloride) at 0° C. The reaction mixture was stirred for one hour at 0° C. and an additional 18 h at ambient temperature. Water was added and the mixture extracted with ethyl acetate (3×100 ml), the combined organic extracts washed with water and brine, and the solvent was removed in vacuo after drying over MgSO₄. The crude product was purified by two subsequent crystallizations from acetone to yield 8-((1H-imidazol-1-yl)(phenyl)methyl)-1,2,5,6-tetrahydropyrrolo[3,2,1-ij]quinolin-4-one (385 mg, 1.17 mmol, 11%) as colorless needles, mp (acetone) 186° C. ¹H-NMR (500 MHz, CDCl₃): δ=2.67 (t, ³J=7.7 Hz, 2H), 2.92 (t, ³J=7.7 Hz, 2H), 3.14 (t, ³J=8.5 Hz, 2H), 4.09 (t, ³J=8.5 Hz, 2H), 6.45 (s, 1H), 6.75 (s, 1H), 6.81 (s, 1H), 6.85 (s, 1H), 7.09 (m, 3H), 7.33-7.39 (m, 3H), 7.41 (s, 1H). ¹³C-NMR (125 MHz, CDCl₃): δ=22.3, 24.4, 27.7, 31.5, 45.4, 56.6, 117.9, 120.4, 121.2, 123.5, 129.3, 129.6, 135.9, 136.9, 141.4, 167.5.

Example 62

8-((4-Fluorophenyl)(1H-imidazol-1-yl)methyl)-1,2,5,6-tetrahydropyrrolo-[3,2,1-ij]quinolin-4-one

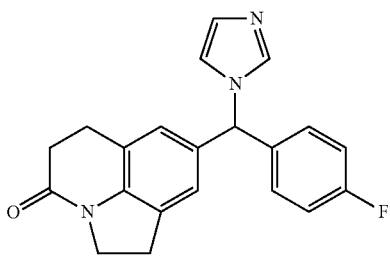 [SMILES: O=C1CCc2cc(C(c3ccc(F)cc3)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.33 g, 2.86 mmol) and 4-fluorobenzoyl chloride (0.68 mL, 5.72 mmol) after flash chromatography on silica gel (methanol/dichloromethane, 1/50, R$_f$=0.08) as a pale yellow solid (300 mg, 0.86 mmol, 30%). mp (methanol/dichloromethane) 203° C. ¹H-NMR (500 MHz, CDCl₃): δ=2.67 (t, ³J=7.8 Hz, 2H), 2.92 (t, ³J=7.8 Hz, 2H), 3.15 (t, ³J=8.5 Hz, 2H), 4.09 (t, ³J=8.5 Hz, 2H), 6.46 (s, 1H), 6.73 (s, 1H), 6.78 (s, 1H), 6.85 (s, 1H), 7.06 (s, 2H), 7.07 (s, 2H), 7.13 (s, 1H), 7.47 (s, 1H). ¹³C-NMR (125 MHz, CDCl₃): δ=24.4, 27.7, 31.4, 45.4, 64.5, 116.0 (d, ³J$_{C,F}$=21.8 Hz), 119.3, 120.5, 123.1, 125.5, 128.9, 129.6 (d, ³J$_{C,F}$=8.2 Hz), 129.8, 133.9, 135.0 (d, ⁴J$_{C,F}$=3.5 Hz), 137.0, 141.9, 162.5 (d, ¹J$_{C,F}$=248 Hz), 167.5. MS m/z 280.60 (M⁺-imidazole).

Example 63

8-((1H-imidazol-1-yl)(4-methoxyphenyl)methyl)-1,2,5,6-tetrahydropyrrolo-[3,2,1-ij]quinolin-4-one

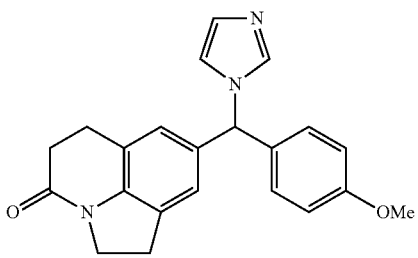 [SMILES: COc1ccc(C(c2cc3c4c(c2)CCN4C(=O)CC3)n2ccnc2)cc1]

The title compound was obtained according to general procedure E from 8-(tributylstannyl)-1,2,5,6-tetrahydro-pyrrolo[3,2,1-ij]quinolin-4-one (2.0 g, 4.33 mmol) and 4-methoxybenzoyl chloride (1.17 mL, 8.66 mmol) after flash chromatography on silica gel (methanol/dichloromethane, 1/50, R$_f$=0.05) as a colorless crystal (90 mg, 0.25 mmol, 6%). mp (methanol/dichloromethane) 55° C. ¹H-NMR (500 MHz, CDCl₃): δ=2.66 (t, ³J=7.8 Hz, 2H), 2.91 (t, ³J=7.8 Hz, 2H), 3.14 (t, ³J=8.5 Hz, 2H), 3.81 (s, 3H), 4.08 (t, ³J=8.5 Hz, 2H), 6.40 (s, 1H), 6.72 (s, 1H), 6.78 (s, 1H), 6.86 (m, 1H), 6.88 (m, 2H), 7.02 (m, 2H), 7.11 (s, 1H), 7.43 (s, 1H). ¹³C-NMR (125 MHz, CDCl₃): δ=24.4, 27.7, 31.4, 45.4, 55.3, 64.6, 114.3, 120.4, 123.0, 125.3, 129.2, 129.6, 131.1, 134.7, 141.6, 159.6, 167.5. MS m/z 292.60 (M⁺-imidazole).

Example 64

8-(1-(1H-imidazol-1-yl)-2-methylpropyl)-1,2,5,6-tetrahydropyrrolo[3,2,1-ij]-quinolin-4-one

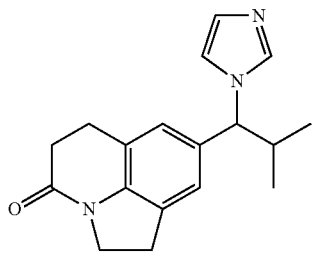 [SMILES: CC(C)C(c1cc2c3c(c1)CCN3C(=O)CC2)n1ccnc1]

The title compound was obtained according to general procedure E from 8-(tributylstannyl)-1,2,5,6-tetrahydro-pyrrolo[3,2,1-ij]quinolin-4-one (1.5 g, 3.24 mmol) and isobutyryl chloride (0.68 mL, 6.49 mmol) after flash chromatography on silica gel (methanol/dichloromethane, 1/50, R$_f$=0.1) as a pale yellow solid (35 mg, 0.12 mmol, 4%). mp (methanol/dichloromethane) 151° C. ¹H-NMR (500 MHz, CDCl₃): δ=0.91 (t, ³J=6.9 Hz, 6H), 2.54 (m, 1H), 2.66 (t, ³J=7.8 Hz, 2H), 2.94 (t, ³J=7.8 Hz, 2H), 3.16 (t, ³J=8.5 Hz, 2H), 4.07 (t, ³J=8.5 Hz, 2H), 4.55 (d, ³J=10.5 Hz, 1H), 6.92 (s, 1H), 6.99 (s, 1H), 7.01 (s, 2H), 7.06 (s, 1H), 7.68 (s, 1H). ¹³C-NMR (125 MHz, CDCl₃): δ=20.1, 20.5, 24.4, 27.7, 31.4, 32.5, 45.4, 69.5, 117.4, 120.4, 122.3, 124.7, 128.9, 129.6, 134.6, 136.1, 141.5, 167.5. MS m/z 228.60 (M⁺-imidazole).

Example 65

8-((3-Fluorophenyl)(1H-imidazol-1-yl)methyl)-1,2,5,6-tetrahydropyrrolo-[3,2,1-ij]quinolin-4-one

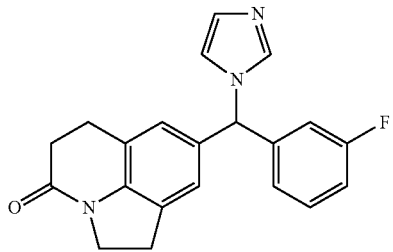 [SMILES: O=C1CCc2cc(C(c3cccc(F)c3)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.5 g, 3.24 mmol) and 3-fluorobenzoyl chloride (0.79 mL, 6.48 mmol) after flash chromatography on silica gel (methanol/dichloromethane, 1/50, $R_f$=0.07) as a pale yellow solid (159 mg, 0.46 mmol, 14%). mp (methanol/dichloromethane) 195° C. $^1$H-NMR (500 MHz, CDCl$_3$): δ=2.68 (t, $^3$J=7.8 Hz, 2H), 2.92 (t, $^3$J=7.8 Hz, 2H), 3.15 (t, $^3$J=8.5 Hz, 2H), 4.09 (t, $^3$J=8.5 Hz, 2H), 6.43 (s, 1H), 6.75 (s, 1H), 6.78 (m, 1H), 6.81 (s, 1H), 6.84 (s, 1H), 6.88 (m, 1H), 7.04 (m, 1H), 7.11 (s, 1H), 7.34 (m, 1H), 7.41 (s, 1H). $^{13}$C-NMR (125 MHz, CDCl$_3$): δ=24.4, 27.7, 31.4, 45.4, 64.4, 114.9 (d, $^2$J$_{C,F}$=22.8 Hz), 115.4 (d, $^2$J$_{C,F}$=21.1 Hz), 120.5, 123.3, 123.4, 123.6, 125.7, 129.7, 129.7, 130.5 (d, $^3$J$_{C,F}$=8.2 Hz), 133.6, 141.9, 142.0, 142.0, 163.0 (d, $^1$J$_{C,F}$=248 Hz), 167.5. MS m/z 280.60 (M$^+$-imidazole).

Example 66

8-((2-Fluorophenyl)(1H-imidazol-1-yl)methyl)-1,2,5,6-tetrahydropyrrolo-[3,2,1-ij]quinolin-4-one

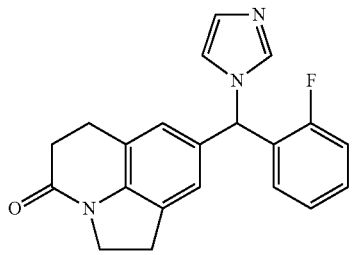 [SMILES: O=C1CCc2cc(C(c3ccccc3F)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.2 g, 2.60 mmol) and 2-fluorobenzoyl chloride (0.63 mL, 5.20 mmol) after flash chromatography on silica gel (methanol/dichloromethane, 1/50, $R_f$=0.06) as a pale yellow solid (105 mg, 0.30 mmol, 12%). mp (methanol/dichloromethane) 176° C. $^1$H-NMR (500 MHz, CDCl$_3$): δ=2.67 (t, $^3$J=7.8 Hz, 2H), 2.91 (t, $^3$J=7.8 Hz, 2H), 3.14 (t, $^3$J=8.5 Hz, 2H), 4.08 (t, $^3$J=8.5 Hz, 2H), 6.73 (s, 1H), 6.74 (s, 1H), 6.80 (s, 1H), 6.85 (s, 1H), 6.88 (m, 1H), 7.08-7.16 (m, 3H), 7.35 (m, 1H), 7.41 (s, 1H). $^{13}$C-NMR (125 MHz, CDCl$_3$): δ=24.3, 27.6, 31.4, 45.4, 58.5 (d, $^3$J$_{C,F}$=4.0 Hz), 115.8 (d, $^2$J$_{C,F}$=21.2 Hz), 119.3, 120.0, 123.0, 124.6 (d, $^4$J$_{C,F}$=3.5 Hz), 125.4, 127.0 (d, $^3$J$_{C,F}$=13.1 Hz), 128.7 (d, $^4$J$_{C,F}$=2.9 Hz), 129.5, 129.6, 130.3 (d, $^3$J$_{C,F}$=8.3 Hz), 133.0, 137.3, 141.8, 160.0 (d, $^1$J$_{C,F}$=249 Hz), 167.5. MS m/z 280.00 (M$^+$-imidazole).

Example 67

4-((2,4,5,6-Tetrahydro-4-oxo-1H-pyrrolo[3,2,1-ij]quinolin-8-yl)(1H-imidazol-1-yl)methyl)benzonitrile

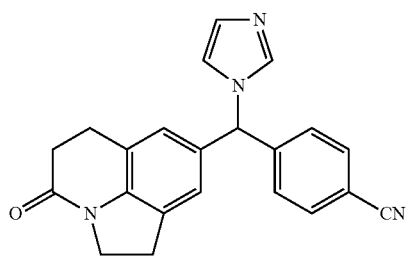 [SMILES: N#Cc1ccc(C(c2cc3c4c(c2)CCN4C(=O)CC3)n2ccnc2)cc1]

The title compound was obtained according to general procedure E from 8-(tributylstannyl)-1,2,5,6-tetrahydro-pyrrolo[3,2,1-ij]quinolin-4-one (1.5 g, 3.24 mmol) and 4-cyanobenzoyl chloride (1.07 g, 6.48 mmol) after flash chromatography on silica gel (methanol/dichloromethane, 1/50, $R_f$=0.08) as a white solid (302 mg, 0.85 mmol, 26%). mp (methanol/dichloromethane) 115° C. $^1$H-NMR (500 MHz, CDCl$_3$): δ=2.67 (t, $^3$J=7.8 Hz, 2H), 2.92 (t, $^3$J=7.8 Hz, 2H), 3.15 (t, $^3$J=8.5 Hz, 2H), 4.09 (t, $^3$J=8.5 Hz, 2H), 6.49 (s, 1H), 6.74 (s, 1H), 6.79 (s, 1H), 6.82 (s, 1H), 7.13 (s, 1H), 7.16 (d, $^3$J=8.3 Hz, 2H), 7.40 (s, 1H), 7.66 (d, $^3$J=8.3 Hz, 2H). $^{13}$C-NMR (125 MHz, CDCl$_3$): δ=24.3, 27.6, 31.3, 45.4, 64.5, 112.4, 118.1, 119.0, 120.7, 123.5, 126.0, 128.2, 130.0, 130.0, 132.6, 132.7, 137.1, 142.2, 144.8, 167.4. MS m/z 355.62 (MH$^+$).

Example 68

8-(Cyclopropyl(1H-imidazol-1-yl)methyl)-1,2,5,6-tetrahydropyrrolo[3,2,1-ij]quinolin-4-one

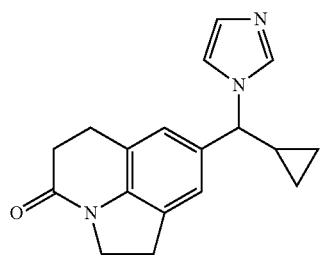 [SMILES: O=C1CCc2cc(C(C3CC3)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.5 g, 3.24 mmol) and cyclopropanecarbonyl chloride (0.59 mL, 6.49 mmol) after flash chromatography on silica gel (methanol/dichloromethane, 1/50, $R_f$=0.09) as a white solid (502 mg, 1.71 mmol, 53%). mp (methanol/dichloromethane) 147° C. $^1$H-NMR (500 MHz, CDCl$_3$): δ=0.42-0.50 (m, 2H), 0.76-0.85 (m, 2H), 1.46-1.54 (m, 1H), 2.66 (t, $^3$J=7.8 Hz, 2H), 2.93 (t, $^3$J=7.8 Hz, 2H), 3.15 (t, $^3$J=8.5 Hz, 2H), 4.08 (t, $^3$J=8.5 Hz, 2H), 4.30 (d, $^3$J=9.3 Hz, 1H), 6.82 (s, 1H), 6.90 (s, 1H), 6.95 (s, 2H), 7.07 (s, 1H), 7.67 (s, 1H). $^{13}$C-NMR (125 MHz, CDCl$_3$): δ=4.8, 5.3, 16.6, 24.4, 27.7, 31.5, 32.5, 45.4, 66.3, 118.3, 120.3, 121.8, 124.1, 129.3, 129.4, 135.6, 136.4, 141.4, 167.5. MS m/z 226.48 (M$^+$-imidazole).

Example 69

8-((1H-imidazol-1-yl)(3-methoxyphenyl)methyl)-1,2,5,6-tetrahydropyrrolo-[3,2,1-ij]quinolin-4-one

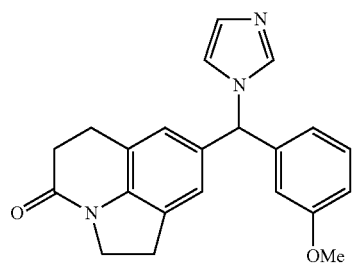 [SMILES: COc1cccc(C(c2cc3c4c(c2)CCN4C(=O)CC3)n2ccnc2)c1]

The title compound was obtained according to general procedure E from 8-(tributylstannyl)-1,2,5,6-tetrahydro-pyrrolo[3,2,1-ij]quinolin-4-one (1.5 g, 3.24 mmol) and 3-methoxybenzoyl chloride (0.98 mL, 6.48 mmol) after flash chromatography on silica gel (methanol/dichloromethane, 1/50, $R_f$=0.05) as a colorless crystal (402 mg, 1.12 mmol, 35%). mp (methanol/dichloromethane) 66° C. $^1$H-NMR (500 MHz, CDCl$_3$): δ=2.66 (t, $^3J$=7.8 Hz, 2H), 2.91 (t, $^3J$=7.8 Hz, 2H), 3.13 (t, $^3J$=8.5 Hz, 2H), 3.76 (s, 3H), 4.08 (t, $^3J$=8.5 Hz, 2H), 6.40 (s, 1H), 6.61 (t, $^4J$=2.0 Hz, 1H), 6.67 (d, $^3J$=7.6 Hz, 1H), 6.75 (s, 1H), 6.81 (s, 1H), 6.84 (m, 1H), 6.87 (dd, $^3J$=8.2 Hz, $^4J$=2.5 Hz, 1H), 7.08 (m, 1H), 7.27 (t, $^3J$=7.8 Hz, 1H), 7.40 (s, 1H). $^{13}$C-NMR (125 MHz, CDCl$_3$): δ=24.3, 27.6, 31.4, 45.4, 55.3, 64.8, 113.2, 114.0, 119.3, 120.1, 120.3, 123.2, 125.6, 129.4, 129.5, 129.9, 134.2, 137.3, 140.9, 141.6, 160.0, 167.5. MS m/z 360.60 (MH$^+$).

Example 70

8-(Cyclobutyl(1H-imidazol-1-yl)methyl)-1,2,5,6-tetrahydropyrrolo[3,2,1-ij]-quinolin-4-one

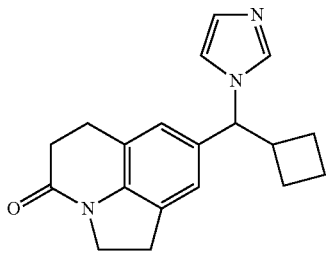 [SMILES: O=C1CCc2cc(C(C3CCC3)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.2 g, 2.60 mmol) and cyclobutanecarbonyl chloride (0.42 mL, 5.20 mmol) after flash chromatography on silica gel (methanol/dichloromethane, 1/50, $R_f$=0.09) as a white solid (401 mg, 1.30 mmol, 50%). mp (methanol/dichloromethane) 121° C. $^1$H-NMR (500 MHz, CDCl$_3$): δ=1.76-1.99 (m, 4H), 2.01-2.07 (m, 1H), 2.14-2.21 (m, 1H), 2.65 (t, $^3J$=7.8 Hz, 2H), 2.92 (t, $^3J$=7.8 Hz, 2H), 3.08 (m, 1H), 3.13 (t, $^3J$=8.5 Hz, 2H), 4.06 (t, $^3J$=8.5 Hz, 2H), 4.93 (d, $^3J$=10.4 Hz, 1H), 6.80 (s, 1H), 6.85 (s, 1H), 6.87 (s, 1H), 7.03 (s, 1H), 7.51 (s, 1H). $^{13}$C-NMR (125 MHz, CDCl$_3$): δ=17.5, 24.5, 26.3, 26.9, 27.8, 31.5, 39.8, 45.4, 67.3, 117.8, 120.3, 122.3, 124.7, 129.4, 129.5, 134.4, 136.2, 141.7, 167.3. MS m/z 240.10 (M$^+$-imidazole).

Example 71

8-(Furan-2-yl(1H-imidazol-1-yl)methyl)-1,2,5,6-tetrahydropyrrolo[3,2,1-ij]quinolin-4-one

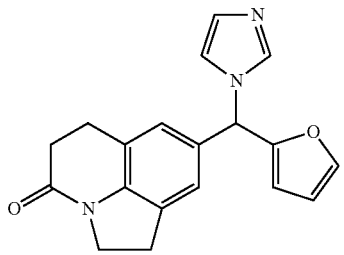 [SMILES: O=C1CCc2cc(C(c3ccco3)n3ccnc3)cc3c2N1CC3]

The title compound was obtained according to general procedure E from 8-(tributylstannyl)-1,2,5,6-tetrahydro-pyrrolo[3,2,1-ij]quinolin-4-one (1.2 g, 2.60 mmol) and furan-2-carbonyl chloride (0.51 mL, 5.20 mmol) after flash chromatography on silica gel (methanol/dichloromethane, 3/100, $R_f$=0.05) as a yellow solid (112 mg, 0.35 mmol, 13%). mp (methanol/dichloromethane) 152° C. $^1$H-NMR (500 MHz, CDCl$_3$): δ=2.67 (t, $^3J$=7.8 Hz, 2H), 2.92 (t, $^3J$=7.8 Hz, 2H), 3.15 (t, $^3J$=8.5 Hz, 2H), 4.08 (t, $^3J$=8.5 Hz, 2H), 6.17 (d, $^4J$=3.3 Hz, 1H), 6.38 (m, 2H), 6.78 (s, 1H), 6.84 (s, 1H), 6.89 (s, 1H), 7.08 (s, 1H), 7.45 (s, 2H). $^{13}$C-NMR (125 MHz, CDCl$_3$): δ=24.3, 27.6, 31.4, 45.4, 58.8, 110.2, 110.5, 118.7, 120.4, 122.3, 124.7, 129.4, 129.6, 132.6, 136.8, 141.8, 143.4, 151.4, 167.5. MS m/z 252.50 (M$^+$-imidazole).

Example 72

8-((1H-imidazol-1-yl)(thiophen-2-yl)methyl)-1,2,5,6-tetrahydropyrrolo[3,2,1-ij]quinolin-4-one

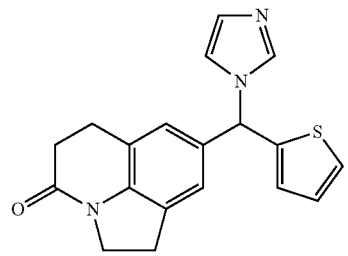

The title compound was obtained according to general procedure E from 8-(tributylstannyl)-1,2,5,6-tetrahydro-pyrrolo[3,2,1-ij]quinolin-4-one (1.2 g, 2.60 mmol) and thiophene-2-carbonyl chloride (0.56 mL, 5.20 mmol) after flash chromatography on silica gel (methanol/dichloromethane, 1/50, $R_f$=0.09) as a white solid (300 mg, 0.89 mmol, 34%). mp (methanol/dichloromethane) 170° C. $^1$H-NMR (500 MHz, CDCl$_3$): δ=2.67 (t, $^3J$=7.8 Hz, 2H), 2.92 (t, $^3J$=7.8 Hz, 2H), 3.15 (t, $^3J$=8.5 Hz, 2H), 4.08 (t, $^3J$=8.5 Hz, 2H), 6.61 (s, 1H), 6.82 (s, 1H), 6.86 (dt, $^3J$=3.5 Hz, $^4J$=1.0 Hz, 1H), 6.88 (s, 1H), 6.91 (m, 1H), 7.00 (dd, $^3J$=5.1 Hz, $^3J$=3.6 Hz, 1H), 7.09 (s, 1H), 7.34 (dd, $^3J$=5.1 Hz, $^4J$=1.2 Hz, 1H), 7.48 (s, 1H). $^{13}$C-NMR (125 MHz, CDCl$_3$): δ=24.3, 27.7, 31.4, 45.4, 60.5, 118.9, 120.4, 122.3, 124.7, 126.7, 127.0, 127.5, 129.5, 129.6, 134.8, 136.9, 141.8, 142.5, 167.5. MS m/z 268.46 (M$^+$-imidazole).

Example 73

3-((2,4,5,6-Tetrahydro-4-oxo-1H-pyrrolo[3,2,1-ij]quinolin-8-yl)(1H-imidazol-1-yl)methyl)benzonitrile

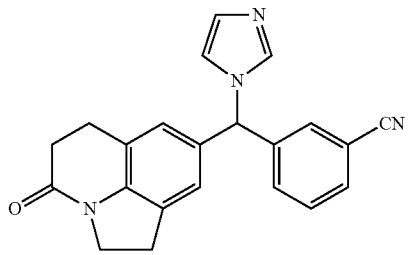 [SMILES: N#Cc1cccc(C(c2cc3c4c(c2)CCN4C(=O)CC3)n2ccnc2)c1]

The title compound was obtained according to general procedure E from 8-(tributylstannyl)-1,2,5,6-tetrahydro-pyrrolo[3,2,1-ij]quinolin-4-one (1.2 g, 2.60 mmol) and 3-cyanobenzoyl chloride (861 mg, 5.20 mmol) after flash chromatography on silica gel (methanol/dichloromethane, 1/50, $R_f$=0.05) as a white solid (62 mg, 0.18 mmol, 7%). mp (methanol/dichloromethane) 202° C. $^1$H-NMR (500 MHz, CDCl$_3$): δ=2.68 (t, $^3J$=7.8 Hz, 2H), 2.93 (t, $^3J$=7.8 Hz, 2H), 3.16 (t, $^3J$=8.5 Hz, 2H), 4.10 (t, $^3J$=8.5 Hz, 2H), 6.48 (s, 1H), 6.73 (s, 1H), 6.78 (s, 1H), 6.83 (s, 1H), 7.14 (s, 1H), 7.30 (d, $^3J$=7.9 Hz, 1H), 7.34 (s, 1H), 7.42 (s, 1H), 7.50 (t, $^3J$=8.0 Hz, 1H), 7.64 (d, $^3J$=7.7 Hz, 1H). $^{13}$C-NMR (125 MHz, CDCl$_3$): δ=24.3, 27.6, 31.3, 45.4, 64.2, 113.2, 118.1, 120.7, 123.4, 125.7, 129.8, 130.0, 131.1, 131.9, 132.0, 132.7, 141.2, 142.2, 167.5. MS m/z 287.20 (M$^+$-imidazole).

Example 74

8-(1,1-Di(1H-imidazol-1-yl)ethyl)-1,2,5,6-tetrahydropyrrolo[3,2,1-ij]quinolin-4-one

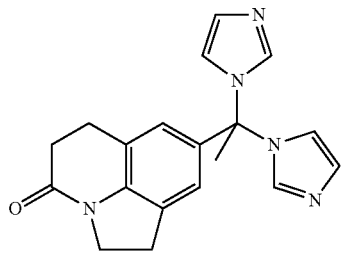 [SMILES: CC(c1cc2c3c(c1)CCN3C(=O)CC2)(n1ccnc1)n1ccnc1]

To a solution of imidazole (2.28 g, 33.4 mmol) in dichloromethane (15 mL) was added SOCl$_2$ (0.40 mL, 5.6 mmol) under an atmosphere of nitrogen at 0° C. The mixture was stirred for 30 min, then 8-acetyl-1,2,5,6-tetrahydropyrrolo[3,2,1-ij]quinolin-4-one (1.00 g, 4.60 mmol) was added. The mixture was stirred at ambient temperature for 96 h, then neutralized with aqueous NaHCO$_3$ and extracted with CHCl$_3$ (3×15 mL). The extracts were washed with water and brine, dried over MgSO$_4$ and concentrated in vacuo. The residue was purified by flash chromatograph on silica gel (methanol/dichloromethane, 1/20, $R_f$=0.05) to yield a pale yellow solid (330 mg, 0.99 mmol, 22%). mp (methanol/dichloromethane) 189° C. $^1$H-NMR (500 MHz, CDCl$_3$): δ=2.53 (s, 3H), 2.67 (t, $^3J$=7.8 Hz, 2H), 2.91 (t, $^3J$=7.8 Hz, 2H), 3.14 (t, $^3J$=8.5 Hz, 2H), 4.10 (t, $^3J$=8.5 Hz, 2H), 6.52 (s, 1H), 6.56 (s, 1H), 6.82 (s, 2H), 7.13 (s, 2H), 7.35 (s, 2H). $^{13}$C-NMR (125 MHz, CDCl$_3$): δ=24.4, 27.6, 30.3, 31.3, 45.5, 75.9, 118.0, 120.4, 121.2, 123.5, 129.8, 130.3, 135.6, 136.2, 142.8, 167.4.

Example 75

1,2,5,6-Tetrahydro-8-(hydroxy(pyridin-4-yl)methyl)pyrrolo[3,2,1-ij]quinolin-4-one

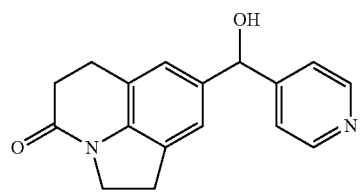 [SMILES: O=C1CCc2cc(C(O)c3ccncc3)cc3c2N1CC3]

To a solution of 8-(pyridine-4-carbonyl)-1,2,5,6-tetrahydro-pyrrolo[3,2,1-ij]quinolin-4-one (200 mg, 0.72 mmol) in methanol (8 mL) was added sodium boron hydride (27 mg, 0.72 mmol) at 0° C. The mixture was stirred at ambient temperature for 1 h before evaporation under reduced pressure. The resulting solid was washed with water and diethyl ether to yield a white solid (190 mg, 0.68 mmol, 94%). mp (diethyl ether) 252° C. $^1$H-NMR (500 MHz, DMSO-d$_6$): δ=2.67 (t, $^3J$=7.7 Hz, 2H), 2.87 (t, $^3J$=7.7 Hz, 2H), 3.08 (t, $^3J$=8.5 Hz, 2H), 3.90 (t, $^3J$=8.5 Hz, 2H), 5.63 (t, $^3J$=4.0 Hz, 1H), 6.00 (t, $^3J$=4.0 Hz, 1H), 7.02 (s, 1H), 7.08 (s, 1H), 7.36 (dd, $^3J$=4.5 Hz, $^4J$=1.6 Hz, 2H), 8.46 (dd, $^3J$=4.5 Hz, $^4J$=1.6 Hz, 2H). $^{13}$C-NMR (125 MHz, DMSO-d$_6$): δ=23.7, 27.0, 31.0, 44.9, 73.0, 119.6, 121.0, 121.2, 123.4, 128.7, 139.3, 140.3, 149.3, 154.3, 166.5.

Example 76

1,2,5,6-Tetrahydro-8-((pyridin-4-yl)methyl)pyrrolo[3,2,1-ij]quinolin-4-one

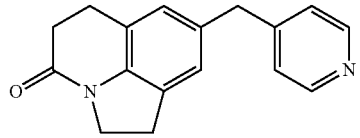 [SMILES: O=C1CCc2cc(Cc3ccncc3)cc3c2N1CC3]

To a suspension of 1,2,5,6-tetrahydro-8-(hydroxy(pyridin-4-yl)methyl)pyrrolo[3,2,1-ij]quinolin-4-one (125 mg, 0.45 mmol) in dry dichloromethane (5 mL) was added by syringe trifluoroacetic acid (0.34 mL, 4.46 mmol), triethylsilane (0.22 mL, 1.34 mmol) and trifluoromethanesulfuric acid (0.05 equivalent) under an atmosphere of nitrogen at 0° C. The resulting solution was stirred at ambient temperature for 48 h, before it was washed with aqueous NaHCO$_3$ and water, dried over MgSO$_4$ and concentrated in vacuo. The residue was purified by flash chromatography on silica gel (methanol/dichloromethane, 1/50, $R_f$=0.1) to yield a pale yellow solid (65 mg, 0.25 mmol, 55%). mp (methanol/dichloromethane) 199° C. $^1$H-NMR (500 MHz, CDCl$_3$): δ=2.66 (t, $^3J$=7.7 Hz, 2H), 2.93 (t, $^3J$=7.7 Hz, 2H), 3.15 (t, $^3J$=8.5 Hz, 2H), 3.89 (s, 2H) 4.07 (t, $^3J$=8.5 Hz, 2H), 6.80 (s, 1H), 6.88 (s, 1H), 7.09 (dd, $^3J$=4.5 Hz, $^4J$=1.4 Hz, 2H), 8.50 (dd, $^3J$=4.5 Hz, $^4J$=1.4 Hz, 2H). $^{13}$C-NMR (125 MHz, CDCl$_3$): δ=24.4, 27.7, 31.5, 41.0, 45.3, 120.3, 123.9, 124.0, 126.1, 129.4, 134.2, 140.1, 149.9, 150.2, 167.4.

Example 77

1,2,5,6-Tetrahydro-8-(hydroxy(phenyl)(pyridin-4-yl)methyl)pyrrolo[3,2,1-ij]-quinolin-4-one

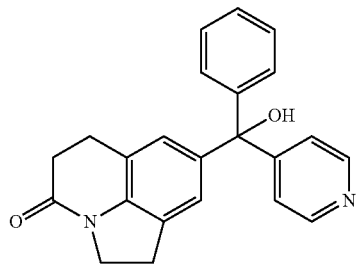 [SMILES: O=C1CCc2cc(C(O)(c3ccccc3)c3ccncc3)cc3c2N1CC3]

To a solution of 8-(pyridine-4-carbonyl)-1,2,5,6-tetrahydro-pyrrolo[3,2,1-ij]quinolin-4-one (200 mg, 0.72 mmol) in dry THF (5 mL) was added dropwise a solution of PhMgBr (2.16 mL, 1 M in THF, 2.16 mmol) under an atmosphere of nitrogen at −78° C. Then the mixture was stirred at the same temperature for 1 h, before it was warmed to ambient temperature. After being stirred for 15 h, the reaction was quenched with saturated aqueous NH$_4$Cl (5 mL), extracted with ethyl acetate (3×10 mL), dried over MgSO$_4$ and concentrated in vacuo. The residue was purified by flash chromatography on silica gel (methanol/dichloromethane, 1/30, R$_f$=0.1) to yield a pale yellow solid (120 mg, 0.34 mmol, 47%). mp (methanol/dichloromethane) 195° C. $^1$H-NMR (500 MHz, CDCl$_3$): δ=2.63 (t, $^3$J=7.7 Hz, 2H), 2.88 (t, $^3$J=7.7 Hz, 2H), 3.11 (t, $^3$J=8.3 Hz, 2H), 3.53 (s, 1H), 4.04 (t, $^3$J=8.3 Hz, 2H), 6.88 (s, 1H), 6.93 (s, 1H), 7.25-7.33 (m, 7H), 8.49 (d, $^3$J=3.2 Hz, 2H). $^{13}$C-NMR (125 MHz, CDCl$_3$): δ=24.4, 27.7, 31.5, 45.4, 81.2, 119.5, 122.6, 123.1, 125.3, 127.7, 127.8, 128.2, 128.7, 140.9, 141.4, 145.7, 149.4, 155.6, 167.6.

Example 78

1,2,5,6-Tetrahydro-8-(phenyl(pyridin-4-yl)methyl)pyrrolo[3,2,1-ij]quinolin-4-one

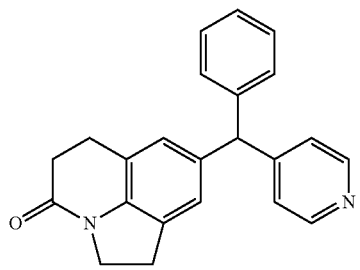 [SMILES: O=C1CCc2cc(C(c3ccccc3)c3ccncc3)cc3c2N1CC3]

To 1,2,5,6-tetrahydro-8-(hydroxy(phenyl)(pyridin-4-yl)methyl)pyrrolo[3,2,1-ij]quinolin-4-one (70 mg, 0.20 mmol) in dry dichloromethane (5 mL) was added by syringe trifluoroacetic acid (0.15 mL, 1.96 mmol), triethylsilane (95 μL, 0.59 mmol) and trifluoromethanesulfuric acid (0.05 equivalent) under an atmosphere of nitrogen at 0° C. The resulting solution was stirred at ambient temperature for 48 h before it was washed with aqueous NaHCO$_3$ and water, dried over MgSO$_4$ and concentrated in vacuo. The residue was purified by flash chromatography on silica gel (methanol/dichloromethane, 1/40, R$_f$=0.1) to yield a pale yellow solid (48 mg, 0.25 mmol, 72%). mp (methanol/dichloromethane) 168° C. $^1$H-NMR (500 MHz, CDCl$_3$): δ=2.66 (t, $^3$J=7.7 Hz, 2H), 2.90 (t, $^3$J=7.7 Hz, 2H), 3.13 (t, $^3$J=8.4 Hz, 2H), 4.07 (t, $^3$J=8.4 Hz, 2H), 5.43 (s, 1H), 6.73 (s, 1H), 6.79 (s, 1H), 7.04 (d, $^3$J=5.3 Hz, 2H), 7.08 (d, $^3$J=7.2 Hz, 2H), 7.26 (m, 1H), 7.32 (t, $^3$J=7.4 Hz, 2H), 8.52 (d, $^3$J=5.3 Hz, 2H). $^{13}$C-NMR (125 MHz, CDCl$_3$): δ=24.4, 27.7, 31.5, 45.3, 56.1, 120.1, 124.3, 124.5, 126.5, 126.9, 128.6, 129.2, 129.2, 137.6, 140.3, 142.2, 149.9, 152.9, 167.5.

Example 79

Example of Activity

The biological in vitro assay systems (A-C) described below were used for assessment of the inhibition of aldosterone synthase (CYP11B2) by compounds of the present invention.

The following abbreviations are used:
DMEM: Dulbecco's Modified Eagle Medium
DMSO: Dimethyl sulfoxide
EDTA: Ethylenediaminetetraacetic acid
EMMG: Edinburgh Minimal Medium with glycerol
EtOAc: Ethyl acetate
FCS: Fetal calf serum
HPLC: High pressure liquid chromatography
HPTLC: High performance thin layer chromatography A) Screening Assay in Transgenic Fission Yeast A fission yeast suspension (S. pombe PE1) with a cellular density of 3×10$^7$ cells/ml was prepared from a freshly grown culture using fresh EMMG (pH 7.4) modified according to Ehmer et al (Ehmer, P. B. et al, J Steroid Biochem Mol Biol 81, 173-179 (2002)). An amount of 492.5 μl of this cellular suspension was mixed with 5 μl of inhibitor solution (50 μM of the compound to be tested dissolved in ethanol or DMSO) and incubated for 15 min at 32° C. Controls were mixed with 5 μl of ethanol. The enzyme reaction was started by the addition of 2.5 μl of 11-deoxycorticosterone (20 μM, containing 1.25 nCi of [4-$^{14}$C]11-deoxycorticosterone, dissolved in ethanol), then it was shaken horizontally at 32° C. for 6 h. The test was stopped by extracting the sample with 500 μl of EtOAc. After a centrifugation step (10000×g, 2 min), the EtOAc was pipetted into a fresh cup and evaporated to dryness. The residue was redissolved in 10 μl of chloroform and the conversion of the substrate to corticosterone was analyzed by HPTLC (see below).

The spots for the substrate deoxycorticosterone and the resulting products corticosterone (and, if detectable, 18-hydroxycorticosterone and aldosterone) were quantified using the relevant analysis program AIDA. For the human aldosterone synthase expressed in S. pombe, only the product corticosterone and the substrate deoxycorticosterone were quantified. 18-Hydroxycorticosterone and aldosterone were not formed in detectable concentrations following an incubation period of 6 hours and therefore did not enter into the analysis. The conversion was calculated according to equation 1.

$$\% \ P = \frac{[PSL_B] - PSL_{HG}}{[PSL_{DOC} + PSL_B] - 2 \times PSL_{HG}} \times 100 \qquad \text{Equation 1}$$

% P=conversion (percentage of total steroid of the product)
PSL=photon-stimulated luminescence (luminescence index)
PSL$_B$=PSL for corticosterone (B)
PSL$_{DOC}$=PSL for deoxycorticosterone (DOC)
PSL$_{HG}$=PSL of the background The percentage inhibition that was caused by an inhibitor in the concentration employed in each case was calculated according to equation 2.

$$\% \ H = \left[1 - \frac{\% \ P_H}{\% \ P_K}\right] \times 100 \qquad \text{Equation 2}$$

wherein
% H=percentage inhibition
% P=percentage conversion of the substrate to products
% P$_H$=percentage conversion in the presence of an inhibitor
% P$_K$=percentage conversion of the control B) Test for CYP11B2 Inhibitors (V79 MZh Cells):
Maintenance of the Cells:

V79 MZh11B2 and V79 MZh11B1, which recombinantly express human aldosterone synthase (CYP11B2) or steroid 11-β-hydroxylase CYP11B1) and were prepared according to Denner et al. (Denner, K. et al., *Pharmacogenetics* 5:89-96 (1995)), were cultured in cell culture dishes of 60 or 90 mm diameter in a $CO_2$ incubator at 37° C. and in a water-saturated atmosphere containing 5% of $CO_2$. Both cell lines were cultured in DMEM⁺, which contained 10% of FCS and the antibiotics penicillin and streptomycin (1%) for protection from bacterial contamination. The cells were passaged every 2 to 3 days following treatment with trypsin/EDTA, since the doubling density, according to cell count, was 1 to 2 days. The cells were passaged up to 12 to 15 times in order to exclude possible cell changes. If needed, freshly thawed cells were employed.

| DMEM⁺ medium | |
|---|---|
| DMEM powder medium | 13.4 g |
| NaHCO₃ | 3.7 g |
| L-Glutamine (200 mM) | 20.0 ml |
| Penicillin (100 units/ml)/streptomycin (0.1 mg/ml) | 10.0 ml |
| Sodium pyruvate (100 mM) | 10.0 ml |
| Fetal calf serum (FCS) | 100 ml |
| H₂O, double-distilled | to 1 l |

The pH of the medium was adjusted to 7.2 to 7.3. FCS was added only after sterile filtration.

Inhibition Test:

V79 MZh11B2- and V79 MZh11B1 cells ($8 \cdot 10^5$ cells per well) were grown to confluence in 24-well cell culture plates with a 1.9 cm² culture area per hole (Nunc, Roskilde, Denmark). Before the test, the DMEM culture medium present was removed, and 450 µl of fresh DMEM with inhibitor were added to each hole in at least three different concentrations in order to determine the $IC_{50}$ value. After preincubation (60 min, 37° C.), the reaction was started by the addition of 50 µl of DMEM containing 2.5 µl of a solution of the substrate 11-deoxycorticosterone (20 µM, containing 1.25 nCi of [4-$^{14}$C]11-deoxycorticosterone, in ethanol). The plate was then kept in the $CO_2$ incubator at 37° C. and under 5% $CO_2$. The V79 MZh11B1 cells were incubated for 120 min, the V79 MZh11B2 cells for 40 min. Controls not containing inhibitor were treated in the same manner. The enzyme reactions were stopped by extraction of the supernatant with 500 µl of EtOAc. The samples were centrifuged (10000×g, 2 min), and the solution was removed and evaporated. The residue was taken up in 10 µl of chloroform and analyzed by HPTLC (see below).

In the case of V79 MZh11B1, conversion was calculated analogously to equation 1, wherein:
$PSL_B$=PSL for cortisol and/or corticosterone
$PSL_{Doc}$=PSL for deoxycortisol (RSS) and/or deoxycorticosterone For V79 MZh11B2, the conversion followed according to equation 3:

$$\% P = \frac{[PSL_B + PSL_{18OHB} + PSL_{Aldo}] - 3 \times PSL_{HG}}{[PSL_{DOC} + PSL_B + PSL_{18OHB} + PSL_{Aldo}] - 4 \times PSL_{HG}} \times 100 \quad \text{Equation 3}$$

wherein
% P=conversion (proportion of product in total steroid
PSL=photon-stimulated luminescence (luminescence index)
$PSL_B$=PSL for corticosterone (B)
$PSL_{18OHB}$=PSL for 18-hydroxycorticosterone (18OHB)
$PSL_{Aldo}$=PSL for aldosterone
$PSL_{DOC}$=PSL for 11-deoxycorticosterone (DOC)
$PSL_{HG}$=PSL of the background The percentage inhibition which was caused by an inhibitor in the concentration employed in each case was calculated according to equation 2.

Determination of the $IC_{50}$ Value:

The $IC_{50}$ value is defined as the concentration of the inhibitor at which the enzyme is inhibited to the extent of 50%. It was calculated by determining the percentage inhibition at least 3 different inhibitor concentrations, which must all lie in the linear range of the sigmoidal $IC_{50}$ curve (log C/% inhibition). The calculation was carried out by linear regression. The values determined were only used if they formed a straight line at a probability r of >0.95.

HPTLC Analysis and Phospho-Imaging of the Radiolabeled Steroids:

The resuspended residue from example A) or B)—containing the radiolabeled steroids—was applied to an HPTLC plate (20×10 cm, silica gel 60F$_{254}$) with a concentration zone (Merck, Darmstadt, Germany). The plate was developed twice using the mobile phase chloroform/methanol/water (300:20:1). Unlabeled 11-deoxycorticosterone and corticosterone were applied as a reference for the CYP11B1 reaction. For the CYP11B2 reaction, 11-deoxycorticosterone, corticosterone, 18-hydroxycorticosterone and aldosterone were used as a reference. The unlabeled references were detected at 260 nm. Subsequently, imaging plates (BAS MS2340, for $^{14}$C samples, Raytest, Straubenhardt, Germany) were exposed for 48 h with the HPTLC plates. The imaging plates were scanned using the Phosphoimager system Fuji FLA 3000 (Raytest, Straubenhardt, Germany) and the steroids were quantified.

Using the in vitro test systems (A, B) described above; exemplary compounds of the present invention show inhibitory effects of human aldosterone synthase (CYP11B2) in the range of from >80% to >98% inhibition [inhibitor concentration=2.5 µM, test system A (transgenic fission yeast *S. pombe* PE1); inhibitor concentration=0.5 µM, test system B (V79 MZh11B2)].

The determined $IC_{50}$ values of the compounds of the present invention using the in vitro test system B (V79 MZh11B2) described above lie in a concentration range of from $10^{-3}$ mol/l to $10^{-10}$ mol/l. The biological test data for exemplary compounds are summarized in Table 1 and Table 2.

TABLE 1

| | % | $IC_{50}$ (×10⁻⁹ mol/l)[b] | |
|---|---|---|---|
| Example | (0.5 µM)[a] hCYP11B2 | V79 11B2 hCYP11B2 | V79 11B1 hCYP11B1 |
| 1 | 88 | 28 | 6746 |
| 2 | 92 | 2.6 | 742 |
| 6 | 94 | 0.2 | 87 |
| 9 | 93 | 21 | 5972 |
| 12 | 97 | 3.8 | 1671 |

[a]inhibitor concentration employed (test system B)

[b]test system B, the selectivity of the test substances toward CYP11B1 results from the ratio IC₅₀(11B1)/IC₅₀(11B2)

TABLE 2

| Example | % (0.5 μM)[a] hCYP11B2 | % (0.5 μM)[a] hCYP11B1 |
|---------|------------------------|------------------------|
| 7       | 99                     | 97                     |
| 8       | 97                     | 49                     |
| 14      | 92                     | 49                     |
| 19      | 95                     | 51                     |
| 28      | 87                     | 24                     |

[a]inhibitor concentration employed (test system B)

C) Test for Selective CYP11B2 Inhibitors (NCI-H295R Cells):

The NCI-H295R cell line is commercially available and is often used as a model for the human adrenal cortex. The cell line was isolated for the first time in 1980 from an invasive adrenocortical tumor of a patient (Gazdar, A. F. et al., *Cancer Res.* 50:5488-5496 (1990)). The cells contain 5 steroidogenic CYP450 enzymes, among them CYP11B2 and CYP11B1. Since all steroidogenic CYP enzymes that occur in the adrenal cortex are expressed in this cell line, it is an important tool in the estimation of the selectivity of inhibitors in vitro.

The NCI-H295R cells were ordered through LGC-Promchem (Wesel). The DMEM:Ham's F12-medium, glutamine and penicillin/streptomycin were obtained from c.c.pro, Neustadt/W. ITS⁺Premix originated from BD Biosciences, Heidelberg and Ultroser SF from the company Pall BioSepra SA, (Cergy Saint Christophe, France).

The NCI-H295R cells were cultured in DMEM:Ham's F12 medium (1:1), 1.25% glutamine, 1% penicillin/streptomycin, 1% ITS⁺Premix, 2% Ultroser SF in 90 mm dishes (NUNC International, Wiesbaden) in a $CO_2$ incubator at 37° C. under 5% $CO_2$. Change of medium was carried out every 48 hours. The cell lines were cultured and passaged until a confluent cell layer was formed. The cell, material was obtained by trypsin treatment and the cell count was determined with the aid of a CASY®TT cell counter (150 μl capillary). By diluting the suspension with DMEM:Ham's F12, the cell density was adjusted to $1 \times 10^6$ cells/ml. 1 ml of the cell suspensions thus obtained was placed in each hole of a 24-well plate. It was possible to coat two 24-well plates using the cell material of two confluently grown culture dishes. After 24 hours, the cells had grown and could be employed after a further 24-hour stimulation phase for the test with potassium ion-containing solution (final concentration: 20 mM KCl).

Execution of the CYP11B2 Test (NCI-H295R):
Preincubation:

The medium was aspirated and replaced by 450 μl of DMEM:Ham's F12, to which the inhibitor was added in the appropriate concentration (final concentration of the inhibitor in the final volume (500 μl) of the test: 2.5 μM). It was then preincubated for 1 h. The control batches contained 1% ethanol.

Start of Test:

The reaction was initiated by the addition of the substrate, dissolved in 50 μl of DMEM:Ham's F12 (deoxycorticosterone (DOC) or corticosterone (B), final concentration of the substrate: 0.5 μM). The substrate solutions were in each case a mixture of unlabeled and [³H]-labeled substrates. The 24-well plate was then kept at 37° C. under 5% $CO_2$ in a $CO_2$ incubator. When using DOC as a substrate, the incubation period was 3 h, when using B it was 24 h.

Termination of Test:

After expiration of the incubation periods, the contents of the well were removed and inactivated by mixing with 1000 μl of dichloromethane in a 2 ml Eppendorf cup. They were shaken for 10 minutes and then centrifuged for phase separation, and the organic phase was transferred to a 1.5 ml Eppendorf cup. The solvent was evaporated overnight, and the residue was resuspended in 20 μl of acetonitrile/water (50:50). Separation of the steroids was carried out using an Agilent 1000 HPLC equipped with a radioactivity and UV detector. The stationary phase used was a C18 reverse-phase column (Nucleodur C18ec, 100-3, 2×125 mm, Macherey-Nagel). The steroids were eluted by means of a water/acetonitrile mixture (flow rate 0.7-0.8 ml/min). To enhance the radioactivity signals, a scintillation fluid (Quickszint Flow 302, Zinsser) was admixed in the ratio 1:2. By integration of the peak areas under the resulting chromatograms (determination using the HPLC evaluation software ChemStation®), it was possible to determine the conversion of the enzyme reaction.

The percentage inhibition caused by an inhibitor in the respective concentration employed is calculated according to equation 2:

$$\% H = \left[1 - \frac{\% P_H}{\% P_K}\right] \times 100 \qquad \text{Equation 2}$$

% H=percentage inhibition
% P=percentage conversion of the substrate to products
% $P_H$=percentage conversion with inhibitor
% $P_K$=percentage conversion of the control The $IC_{50}$ value was calculated by determining the percentage inhibition at least 3 different inhibitor concentrations, which must all lie in the linear range of the sigmoidal $IC_{50}$-curve (% inhibition/log C). Calculation was carried out by linear regression. The values determined were only used if the regression of the straight line was >0.95.

The CYP11B1 test was carried out in analogy to the CYP11B2 test as described above. The substrate solution was a mixture of unlabeled and [³H]-labeled deoxycortisol (RSS). The incubation period was 12 h.

The disclosure of all documents referred to in the present application, such as, for example, journal articles, books, patents, and patent applications, is hereby included in the specification by way of reference.

The invention claimed is:

1. A compound of formula (I):

$$(I)$$

wherein:
Z is C=O or C=S;
U is $CR^5R^6$, $NR^7$, O or S;
X is $CR^5R^6$, $NR^7$, O, or S;
A is $CR^8R^9$
b is 0 or 1;
n is 0;
m is 0 or 1;
provided that not more than one of U and X is $NR^7$, O, or S;

wherein, when m is 1, the bond between U and X is single bond;

Het is a ring system containing 1 or 2 rings, where the or at least one of the rings is aromatic and contains 5 or 6 ring atoms, of which at least one is nitrogen, and the other ring of the 2 rings can be saturated or unsaturated and comprises from 5 to 7 ring atoms; while the ring system can contain additional 1 to 5 heteroatoms selected from the group consisting of N, S, and O, provided that not more than two heteroatoms are selected from the group consisting of S and O; and the ring system can be substituted by from one to four substituents $R^{11}$, $R^1$ and $R^2$ form, together with the atoms to which they are bonded, an unsaturated nitrogen-containing five membered to seven membered ring comprising 1 or 2 unsaturated bonds and may, in addition to the nitrogen atom to which the $R^1$ group is bonded, also contain a hetero atom or a heteroatom-containing group selected from the group consisting of O, S and $NR^7$, and can be substituted by from one to four substituents $R^{12}$;

$R^3$ and $R^4$ are independently selected from the group consisting of H, $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylcarbonyl, $C_{1-4}$ alkoxycarbonyl, $C_{1-4}$ alkylsulfonyl, which in each case can be partially or completely halogenated with independent halogen atoms or can be substituted by from one to three substituents $R^a$, wherein $R^a$ is independently selected from the group consisting of optionally partially or completely halogenated $C_{1-4}$ alkyl, $C_{1-4}$ alkoxy, $C_{1-4}$ alkylthio, and $C_{1-4}$ alkylcarbonyl and also hydroxyl, nitro, and cyano, or can be partially or completely halogenated with independent halogen atoms; aryl $C_{1-4}$ alkyl, aryl $C_{0-4}$ alkylsulfonyl, heterocyclyl $C_{1-4}$ alkyl, which can in each case be substituted on the ring or at least on one ring by from one to four substituents $R^b$, wherein $R^b$ is selected from the group consisting of $C_{1-4}$ alkyl, $C_{1-4}$ alkoxy, $C_{1-4}$ alkylthio, $C_{1-4}$ alkylcarbonyl, $C_{1-4}$ alkylsulfonyl, whose alkyl moieties may be partially or completely halogenated with independent halogen atoms, halogen, hydroxyl, nitro, cyano, $—NR^c_2$, $—CONR^c_2$, and $SO_2NR^c_2$, wherein $R^c$ is independently selected from the group consisting of H and $C_{1-4}$ alkyl; halogen, hydroxyl, nitro, cyano, $—NR^c_2$, $—CONR^c_2$, and $—SO_2NR^c_2$;

$R^5$ and $R^6$ are independently selected from the group consisting of H, $C_{1-4}$ alkyl, $C_{3-7}$ cycloalkyl, hydroxyl $C_{1-4}$ alkyl, $C_{1-4}$ alkoxy, $C_{1-4}$ alkoxycarbonyl, $C_{1-4}$ alkylthio, whose alkyl moieties can be partially or completely halogenated with independent halogen atoms; halogen, hydroxyl, nitro, cyano, $—NR^c_2$, and $NR^cCOR^d$, and $R^d$ is selected from the group consisting of $C_{1-4}$ alkyl, $C_{3-7}$ cycloalkyl, $C_{1-4}$ alkoxy, whose alkyl moieties can be partially or completely halogenated with independent halogen atoms, and wherein $R^5$ or $R^6$ may be bonded to a carbon atom forming part of a double bond, $R^7$ is selected from the group consisting of H, $C_{1-4}$ alkyl, and $C_{3-7}$ cycloalkyl, which in each case can be substituted by from one to three substituents $R^a$, or can be partially or completely halogenated with independent halogen atoms; and aryl $C_{1-4}$ alkyl, which can be substituted on the ring or at least on one ring by from one to four substituents $R^b$;

$R^8$ is phenyl;

$R^9$ is H or hydroxyl;

$R^{10}$ is selected from the group consisting of H; $C_{1-4}$ alkyl, $C_{3-7}$ cycloalkyl, which in each case can be substituted by from one to three substituents $R^a$, or can be partially or completely halogenated with independent halogen atoms; aryl, aryl $C_{1-4}$ alkyl, heterocyclyl, and heterocyclyl $C_{1-4}$ alkyl, each of which can be substituted on the or at least one ring by from one to four substituents $R^b$;

$R^{11}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylthio, $C_{1-4}$ alkylcarbonyl, $C_{1-4}$ alkoxycarbonyl, $C_{1-4}$ alkylsulfonyl, which can in each case be substituted by from one to three substituents $R^a$, or can be partially or completely halogenated with independent halogen atoms; aryl, heterocyclyl, aryl $C_{0-4}$ alkylsulfonyl, aryl $C_{1-4}$ alkyl, and heterocyclyl $C_{1-4}$ alkyl, which can in each case be substituted on the ring or at least on one ring by from one to four substituents $R^b$, halogen, hydroxyl, nitro, cyano, $—NR^c_2$, $—CONR^c_2$, and $—SO_2NR^c_2$; and $R^{12}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, which can in each case be substituted by from one to three substituents $R^a$, or can be partially or completely halogenated with independent halogen atoms; aryl, heterocyclyl, aryl $C_{1-4}$ alkyl, and heterocyclyl $C_{1-4}$ alkyl, which can in each case be substituted on the ring or at least on one ring by from one to four substituents $R^b$; optionally partially or completely halogenated $C_{1-4}$ alkoxy, hydroxyl, halogen, nitro, cyano, and $NR^c_2$ when $R^{12}$ is bonded to a carbon atom;

or a pharmaceutically acceptable salt thereof.

2. A compound according to claim 1, wherein Z is C=O, or a pharmaceutically acceptable salt thereof.

3. A compound according to claim 1, wherein U is S or $CR^5R^6$, wherein $R^5$ and $R^6$ are independently selected from H and $C_{1-4}$ alkyl, X is $CH_2$, or a pharmaceutically acceptable salt thereof.

4. A compound according to claim 1, wherein the unsaturated nitrogen containing ring is an unsubstituted 5- or 6-membered ring having one or two unsaturated bond(s) and no further heteroatom, or a pharmaceutically acceptable salt thereof.

5. A compound according to claim 1, wherein Het is for pyridinyl, isoquinolinyl, pyrimidinyl or imidazolyl, optionally substituted with a substituent $R^{11}$, wherein $R^{11}$ is defined as in claim 1, or a pharmaceutically acceptable salt thereof.

6. A compound according to claim 1 selected from

8-Pyridin-3-yl-1,2,5,6-tetrahydropyrrolo[3,2,1-ij]quinolin-4-one

9-Pyridin-3-yl-1,2,6,7-tetrahydro-5H-pyrido[3,2,1-ij]quinolin-3-one 8-(5-Methoxypyridin-3-yl)-1,2,5,6-tetrahydropyrrolo[3,2,1-ij]quinolin-4-one 8-Isoquinolin-4-yl-1,2,5,6-tetrahydropyrrolo[3,2,1-ij]quinolin-4-one 9-(5-Methoxypyridin-3-yl)-1,2,6,7-tetrahydro-5H-pyrido[3,2,1-ij]quinolin-3-one 9-Isoquinolin-4-yl-1,2,6,7-tetrahydro-5H-pyrido[3,2,1-ij]quinolin-3-one 8-Pyridin-3-yl-1,2,5,6-tetrahydropyrrolo[3,2,1-ij]quinoline-4-thione 8-(5-Hydroxypyridin-3-yl)-1,2,5,6-tetrahydro-pyrrolo[3,2,1-ij]quinolin-4-one 6,6-Dimethyl-8-pyridin-3-yl-1,2,5,6-tetrahydropyrrolo[3,2,1-ij]quinolin-4-one 8-(5-Ethoxypyridin-3-yl)-1,2,5,6-tetrahydropyrrolo[3,2,1-ij]quinolin-4-one 8-(5-Trifluoromethylpyridin-3-yl)-1,2,5,6-tetrahydropyrrolo[3,2,1-ij]quinolin-4-one 8-(5-Fluoropyridin-3-yl)-1,2,5,6-tetrahydropyrrolo[3,2,1-ij]quinolin-4-one 8-Imidazol-1-yl-1,2,5,6-tetrahydropyrrolo[3,2,1-ij]quinolin-4-one 8-Pyridin-4-yl-1,2,5,6-tetrahydropyrrolo[3,2,1-ij]quinolin-4-one 8-Pyrimidin-5-yl-1,2,5,6-tetrahydropyrrolo[3,2,1-ij]quinolin-4-one 8-(Pyridin-4-carbonyl)-1,2,5,6-tetrahydropyrrolo[3,2,1-ij]quinolin-4-one 8-(Pyridin-3-carbonyl)-1,2,5,6-tetrahydropyrrolo[3,2,1-ij]quinolin-4-one 8-(5-Phenylpyridin-3-yl)-1,2,5,6-tetrahydropyrrolo[3,2,1-ij]quinolin-4-one 8-(5-Isopropoxypyridin-3-yl)-1,2,5,6-tetrahydropyrrolo[3,2,1-ij]quinolin-4-one 8-(1-Imidazol-1-yl-ethyl)-1,2,5,6-tetrahydropyrrolo[3,2,1-ij]quinolin-4-one 8-[5-(4-Fluorophenyl)pyridin-3-yl]-1,2,5,6-tetrahydropyrrolo[3,2,1-ij]quinolin-4-one 8-[5-(3-Fluorophenyl)pyridin-3-yl]-1,2,5,6-tetrahydropyrrolo[3,2,1-ij]quinolin-4-one 8-[5-(4-Methoxyphenyl)pyridin-3-yl]-1,2,5,6-tetrahydropyrrolo[3,2,1-ij]quinolin-4-one 8-[5-(3-Methoxyphenyl)pyridin-3-yl]-1,2,5,6-tetrahydropyrrolo[3,2,1-ij]quinolin-4-one 8-[5-(2-Fluorophenyl)pyridin-3-yl]-1,2,5,6-tetrahydropyrrolo[3,2,1-ij]quinolin-4-one 8-[5-(3-Trifluoromethylphenyl)pyridin-3-yl]-1,2,5,6-tetrahydropyrrolo[3,2,1-ij]quinolin-4-one 8-[5-(3,4-Difluorophenyl)pyridin-3-yl]-1,2,5,6-tetrahydropyrrolo[3,2,1-ij]quinolin-4-one 8-[5-(3-Trifluoromethoxyphenyl)pyridin-3-yl]-1,2,5,6-tetrahydropyrrolo[3,2,1-ij]-quinolin-4-one 8-[5-(2-Methoxyphenyl)pyridin-3-yl]-1,2,5,6-tetrahydropyrrolo[3,2,1-ij]quinolin-4-one or a pharmaceutically acceptable salt thereof.

7. A compound of formula (I):

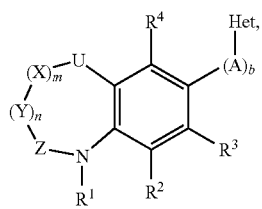

(I)

wherein:

Z is C=O or C=S;

U is $CR^5R^6$, $NR^7$, O or S;

X is $CR^5R^6$, $NR^7$, O, or S;

b is 0;

n is 0;

m is 0 or 1;

provided that not more than one of U and X is $NR^7$, O, or S;

wherein, when m is 1, the bond between U and X is single bond;

Het is a ring system containing 2 rings, where at least one of the rings is aromatic and contains 5 or 6 ring atoms, of which at least one is nitrogen, and the other ring can be saturated or unsaturated and comprises from 5 to 7 ring atoms; while the ring system can contain additional 1 to 5 heteroatoms selected from the group consisting of N, S, and O, provided that not more than two heteroatoms are selected from the group consisting of S and O; and the ring system can be substituted by from one to four substituents $R^{11}$, $R^1$ is selected from the group consisting of H; $C_{1-4}$ alkyl; $C_{2-4}$ alkenyl; $C_{3-7}$ cycloalkyl; $C_{1-4}$ alkylcarbonyl; and $C_{1-4}$ alkoxycarbonyl; each of which can be substituted by from one to three substituents $R^a$, wherein $R^a$ is independently selected from the group consisting of optionally partially or completely halogenated $C_{1-4}$ alkyl, $C_{1-4}$ alkoxy, $C_{1-4}$ alkylthio, and $C_{1-4}$ alkylcarbonyl and also hydroxyl, nitro, and cyano, or can be partially or completely halogenated with independent halogen atoms; aryl $C_{1-4}$ alkyl and heterocyclyl $C_{1-4}$ alkyl, which can in each case be substituted on the ring or at least on one ring by from one to four substituents $R^b$, wherein $R^b$ is selected from the group consisting of $C_{1-4}$ alkyl, $C_{1-4}$ alkoxy, $C_{1-4}$ alkylthio, $C_{1-4}$ alkylcarbonyl, $C_{1-4}$ alkylsulfonyl, whose alkyl moieties may be partially or completely halogenated with independent halogen atoms, halogen, hydroxyl, nitro, cyano, —$NR^c_2$, —$CONR^c_2$, and $SO_2NR^c_2$, wherein $R^c$ is independently selected from the group consisting of H and $C_{1-4}$ alkyl;

$R^2$, $R^3$ and $R^4$ are independently selected from the group consisting of H, $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylcarbonyl, $C_{1-4}$ alkoxycarbonyl, $C_{1-4}$ alkylsulfonyl, which in each case can be substituted by from one to three substituents $R^a$, or can be partially or completely halogenated with independent halogen atoms; aryl $C_{1-4}$ alkyl, aryl $C_{0-4}$ alkylsulfonyl, heterocyclyl $C_{1-4}$ alkyl, which can in each case be substituted on the ring or at least on one ring by from one to four substituents $R^b$; halogen, hydroxyl, nitro, cyano, —$NR^c_2$, —$CONR^c_2$, and —$SO_2NR^c_2$;

$R^5$ and $R^6$ are independently selected from the group consisting of H, $C_{1-4}$ alkyl, $C_{3-7}$ cycloalkyl, hydroxyl $C_{1-4}$ alkyl, $C_{1-4}$ alkoxy, $C_{1-4}$ alkoxycarbonyl, $C_{1-4}$ alkylthio, whose alkyl moieties can be partially or completely halogenated with independent halogen atoms; halogen, hydroxyl, nitro, cyano, —$NR^c_2$, and $NR^cCOR^d$, and $R^d$ is selected from the group consisting of $C_{1-4}$ alkyl, $C_{3-7}$ cycloalkyl, $C_{1-4}$ alkoxy, whose alkyl moieties can be partially or completely halogenated with independent halogen atoms, and wherein $R^5$ or $R^6$ may be bonded to a carbon atom forming part of a double bond, $R^7$ is selected from the group consisting of H, $C_{1-4}$ alkyl, and $C_{3-7}$ cycloalkyl, which in each case can be substituted by from one to three substituents $R^a$, or can be partially or completely halogenated with independent halogen atoms; and aryl $C_{1-4}$ alkyl, which can be substituted on the ring or at least on one ring by from one to four substituents $R^b$;

$R^{10}$ is selected from the group consisting of H; $C_{1-4}$ alkyl, $C_{3-7}$ cycloalkyl, which in each case can be substituted by from one to three substituents $R^a$, or can be partially or completely halogenated with independent halogen atoms; aryl, aryl $C_{1-4}$ alkyl, heterocyclyl, and heterocyclyl $C_{1-4}$ alkyl, each of which can be substituted on the or at least one ring by from one to four substituents $R^b$;

$R^{11}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylthio, $C_{1-4}$ alkylcarbonyl, $C_{1-4}$ alkoxycarbonyl, $C_{1-4}$ alkylsulfonyl, which can in each case be substituted by from one to three substituents $R^a$, or can be partially or completely halogenated with independent halogen atoms; aryl, heterocyclyl, aryl $C_{0-4}$ alkylsulfonyl, aryl $C_{1-4}$ alkyl, and heterocyclyl $C_{1-4}$ alkyl, which can in each case be substituted on the ring or at least on one ring by from one to four substituents $R^b$, halogen, hydroxyl, nitro, cyano, $-NR^c_2$, $-CONR^c_2$, and $-SO_2NR^c_2$; and $R^{12}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, which can in each case be substituted by from one to three substituents $R^a$, or can be partially or completely halogenated with independent halogen atoms; aryl, heterocyclyl, aryl $C_{1-4}$ alkyl, and heterocyclyl $C_{1-4}$ alkyl, which can in each case be substituted on the ring or at least on one ring by from one to four substituents $R^b$; optionally partially or completely halogenated $C_{1-4}$ alkoxy, hydroxyl, halogen, nitro, cyano, and $NR^c_2$ when $R^{12}$ is bonded to a carbon atom;

or a pharmaceutically acceptable salt thereof.

8. A compound according to claim 7, wherein Z is C=O, or a pharmaceutically acceptable salt thereof.

9. A compound according to claim 7, wherein $R^1$ is H or $C_{1-4}$ alkyl, or a pharmaceutically acceptable salt thereof.

10. A compound according to claim 7, wherein U is S or $CR^5R^6$, wherein $R^5$ and $R^6$ are independently selected from H and $C_{1-4}$ alkyl, X is $CH_2$, or a pharmaceutically acceptable salt thereof.

11. A compound according to claim 7, wherein Het is isoquinolinyl optionally substituted with a substituent $R^{11}$, wherein $R^{11}$ is defined as in claim 7, or a pharmaceutically acceptable salt thereof.

12. A compound according to claim 7 selected from
6-Isoquinolin-4-yl-3,4-dihydro-1H-quinolin-2-one,
6-Isoquinolin-4-yl-1-methyl-3,4-dihydro-1H-quinolin-2-one,
or a pharmaceutically acceptable salt thereof.

13. A compound of formula (I):

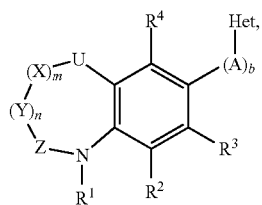

(I)

wherein:
Z is C=S;
U is $CR^5R^6$, $NR^7$, O or S;
X is $CR^5R^6$, $NR^7$, O, or S;
b is 0;
n is 0;
m is 0 or 1;
provided that not more than one of U and X is $NR^7$, O, or S;
wherein, when m is 1, the bond between U and X is single bond;
Het is a ring system containing one ring which is aromatic and contains 5 or 6 ring atoms, of which at least one is nitrogen, and the ring system can be substituted by from one to four substituents $R^{11}$;
$R^1$ is selected from the group consisting of H; $C_{1-4}$ alkyl; $C_{2-4}$ alkenyl; $C_{3-7}$ cycloalkyl; $C_{1-4}$ alkylcarbonyl; and $C_{1-4}$ alkoxycarbonyl; each of which can be substituted by from one to three substituents $R^a$, wherein $R^a$ is independently selected from the group consisting of optionally partially or completely halogenated $C_{1-4}$ alkyl, $C_{1-4}$ alkoxy, $C_{1-4}$ alkylthio, and $C_{1-4}$ alkylcarbonyl and also hydroxyl, nitro, and cyano, or can be partially or completely halogenated with independent halogen atoms; aryl $C_{1-4}$ alkyl and heterocyclyl $C_{1-4}$ alkyl, which can in each case be substituted on the ring or at least on one ring by from one to four substituents $R^b$, wherein $R^b$ is selected from the group consisting of $C_{1-4}$ alkyl, $C_{1-4}$ alkoxy, $C_{1-4}$ alkylthio, $C_{1-4}$ alkylcarbonyl, $C_{1-4}$ alkylsulfonyl, whose alkyl moieties may be partially or completely halogenated with independent halogen atoms, halogen, hydroxyl, nitro, cyano, $-NR^c_2$, $-CONR^c_2$, and $SO_2NR^c_2$, wherein $R^c$ is independently selected from the group consisting of H and $C_{1-4}$ alkyl;

$R^2$, $R^3$ and $R^4$ are independently selected from the group consisting of H, $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylcarbonyl, $C_{1-4}$ alkoxycarbonyl, $C_{1-4}$ alkylsulfonyl, which in each case can be substituted by from one to three substituents $R^a$, or can be partially or completely halogenated with independent halogen atoms; aryl $C_{1-4}$ alkyl, aryl $C_{0-4}$ alkylsulfonyl, heterocyclyl $C_{1-4}$ alkyl, which can in each case be substituted on the ring or at least on one ring by from one to four substituents $R^b$; halogen, hydroxyl, nitro, cyano, $-NR^c_2$, $-CONR^c_2$, and $-SO_2NR^c_2$;

$R^5$ and $R^6$ are independently selected from the group consisting of H, $C_{1-4}$ alkyl, $C_{3-7}$ cycloalkyl, hydroxyl $C_{1-4}$ alkyl, $C_{1-4}$ alkoxy, $C_{1-4}$ alkoxycarbonyl, $C_{1-4}$ alkylthio, whose alkyl moieties can be partially or completely halogenated with independent halogen atoms; halogen, hydroxyl, nitro, cyano, $-NR^c_2$, and $NR^cCOR^d$, and $R^d$ is selected from the group consisting of $C_{1-4}$ alkyl, $C_{3-7}$ cycloalkyl, $C_{1-4}$ alkoxy, whose alkyl moieties can be partially or completely halogenated with independent halogen atoms, and wherein $R^5$ or $R^6$ may be bonded to a carbon atom forming part of a double bond, $R^7$ is selected from the group consisting of H, $C_{1-4}$ alkyl, and $C_{3-7}$ cycloalkyl, which in each case can be substituted by from one to three substituents $R^a$, or can be partially or completely halogenated with independent halogen atoms; and aryl $C_{1-4}$ alkyl, which can be substituted on the ring or at least on one ring by from one to four substituents $R^b$;

$R^{10}$ is selected from the group consisting of H; $C_{1-4}$ alkyl, $C_{3-7}$ cycloalkyl, which in each case can be substituted by from one to three substituents $R^a$, or can be partially or completely halogenated with independent halogen atoms; aryl, aryl $C_{1-4}$ alkyl, heterocyclyl, and heterocyclyl $C_{1-4}$ alkyl, each of which can be substituted on the or at least one ring by from one to four substituents $R^b$;

$R^{11}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, $C_{1-4}$ alkoxy, $C_{1-4}$ alkylthio, $C_{1-4}$ alkylcarbonyl, $C_{1-4}$ alkoxycarbonyl, $C_{1-4}$ alkylsulfonyl, which can in each case be substituted by from one to three substituents $R^a$, or can be partially or completely halogenated with independent halogen atoms; aryl, heterocyclyl, aryl $C_{0-4}$ alkylsulfonyl, aryl $C_{1-4}$ alkyl, and heterocyclyl $C_{1-4}$ alkyl, which can in each case be substituted on the ring or at least on one ring by from one to four substituents $R^b$, halogen, hydroxyl, nitro, cyano, $-NR^c_2$, $-CONR^c_2$, and $-SO_2NR^c_2$; and $R^{12}$ is independently selected from the group consisting of $C_{1-4}$ alkyl, $C_{2-4}$ alkenyl, $C_{2-4}$ alkynyl, $C_{3-7}$ cycloalkyl, $C_{5-7}$ cycloalkenyl, which can in each case be substituted by from one to three substituents $R^a$, or can be partially or completely halogenated with independent halogen atoms; aryl, heterocyclyl, aryl $C_{1-4}$ alkyl, and heterocyclyl $C_{1-4}$ alkyl, which can in each case be substituted on the ring or at least on one ring by from one to four substituents $R^b$; optionally partially or completely halogenated $C_{1-4}$ alkoxy, hydroxyl, halogen, nitro, cyano, and $NR^c{}_2$ when $R^{12}$ is bonded to a carbon atom;

or a pharmaceutically acceptable salt thereof.

14. A compound according to claim 13, wherein $R^1$ is H or $C_{1-4}$ alkyl, or a pharmaceutically acceptable salt thereof.

15. A compound according to claim 13, wherein U is S or $CR^5R^6$, wherein $R^5$ and $R^6$ are independently selected from H and $C_{1-4}$ alkyl, X is $CH_2$, or a pharmaceutically acceptable salt thereof.

16. A compound according to claim 13, wherein Het is for pyridinyl, pyrimidinyl or imidazolyl, optionally substituted with a substituent $R^{11}$, wherein $R^{11}$ is defined as in claim 12, or a pharmaceutically acceptable salt thereof.

17. A compound according to claim 13 selected from
    8-Chloro-6-pyridin-3-yl-3,4-dihydro-1H-quinoline-2-thione,
    8-Fluoro-6-pyridin-3-yl-3,4-dihydro-1H-quinolin-2-thione,
    7-Fluoro-6-pyridin-3-yl-3,4-dihydro-1H-quinolin-2-thione,
    or a pharmaceutically acceptable salt thereof.

\* \* \* \* \*